(12) United States Patent
Evans et al.

(10) Patent No.: US 10,301,268 B2
(45) Date of Patent: May 28, 2019

(54) ANALOGS OF FEXARAMINE AND METHODS OF MAKING AND USING

(71) Applicants: Salk Institute for Biological Studies, La Jolla, CA (US); The University of Sydney, Sydney (AU)

(72) Inventors: Ronald M. Evans, La Jolla, CA (US); Michael Downes, San Diego, CA (US); Annette Atkins, San Diego, CA (US); Sungsoon Fang, La Jolla, CA (US); Jae Myoung Suh, San Diego, CA (US); Thomas J. Baiga, Escondido, CA (US); Ruth T. Yu, La Jolla, CA (US); John F. W. Keana, Eugene, OR (US); Christopher Liddle, Tura Beach (AU)

(73) Assignees: The Salk Institute for Biological Studies, La Jolla, CA (US); University of Sydney, Sydney (AU)

(*) Notice: Subject to any disclaimer, the term of this patent is extended or adjusted under 35 U.S.C. 154(b) by 0 days.

(21) Appl. No.: 15/263,033

(22) Filed: Sep. 12, 2016

(65) Prior Publication Data

US 2017/0066724 A1    Mar. 9, 2017

Related U.S. Application Data

(63) Continuation-in-part of application No. PCT/US2015/020552, filed on Mar. 13, 2015.

(60) Provisional application No. 61/952,763, filed on Mar. 13, 2014, provisional application No. 62/061,607, filed on Oct. 8, 2014, provisional application No. 62/252,045, filed on Nov. 6, 2015.

(51) Int. Cl.
  *C07D 231/56*    (2006.01)
  *C07C 233/63*    (2006.01)
  *C07B 59/00*    (2006.01)

(52) U.S. Cl.
  CPC .......... *C07D 231/56* (2013.01); *C07B 59/001* (2013.01); *C07B 59/002* (2013.01); *C07C 233/63* (2013.01); *C07B 2200/05* (2013.01); *C07C 2601/14* (2017.05); *C07C 2602/42* (2017.05)

(58) Field of Classification Search
  CPC .......... C07B 2200/05; C07D 231/56
  See application file for complete search history.

(56) References Cited

U.S. PATENT DOCUMENTS

| | | | | |
|---|---|---|---|---|
| 6,221,335 B1* | 4/2001 | Foster | ................ | C07B 59/002 424/1.81 |
| 6,603,008 B1* | 8/2003 | Ando | ................ | C07D 405/14 546/269.7 |
| 10,077,268 B2 | 9/2018 | Evans et al. | | |
| 2005/0054634 A1 | 3/2005 | Busch et al. | | |
| 2006/0069070 A1 | 3/2006 | Fiorucci et al. | | |
| 2006/0128764 A1 | 6/2006 | Downes et al. | | |
| 2008/0207594 A1 | 8/2008 | Mussmann et al. | | |
| 2008/0299118 A1 | 12/2008 | Hartman et al. | | |
| 2008/0300235 A1 | 12/2008 | Harnish et al. | | |
| 2009/0163474 A1 | 6/2009 | Zhang et al. | | |
| 2009/0215748 A1 | 8/2009 | Harnish et al. | | |
| 2011/0039824 A1 | 2/2011 | Lundquist, IV et al. | | |
| 2011/0294767 A1 | 12/2011 | Gedulin et al. | | |

(Continued)

FOREIGN PATENT DOCUMENTS

| | | |
|---|---|---|
| WO | WO 2002/076945 A1 | 10/2002 |
| WO | WO 2003/099821 A1 | 12/2003 |

(Continued)

OTHER PUBLICATIONS

Kushner, D.J. et al. "Pharmacological uses and perspectives of heavy water and deuterated compounds" Can. J. Physiol. Pharmacol. 77: 79-88 (1999) (Year: 1999).*

(Continued)

*Primary Examiner* — Andrew S Rosenthal
(74) *Attorney, Agent, or Firm* — Klarquist Sparkman, LLP

(57) ABSTRACT

Novel compounds having a formula

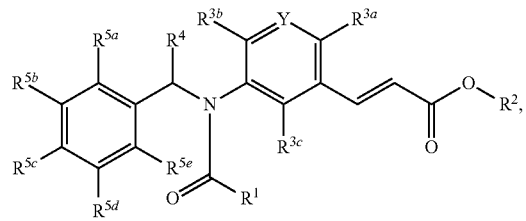

embodiments of a method of making the same, and of a composition comprising them are disclosed herein. Also disclosed are embodiments of a method of treating or preventing a metabolic disorder in a subject, comprising administering to a subject (e.g., via the gastrointestinal tract) a therapeutically effective amount of one or more of the disclosed compounds, thereby activating FXR receptors in the intestines, and treating or preventing a metabolic disorder in the subject. Additionally disclosed are embodiments of a method of treating or preventing inflammation in an intestinal region of a subject, comprising administering to the subject (e.g., via the gastrointestinal tract) a therapeutically effective amount of one or more of the disclosed compounds, thereby activating FXR receptors in the intestines, and thereby treating or preventing inflammation in the intestinal region of the subject.

31 Claims, 59 Drawing Sheets
(44 of 59 Drawing Sheet(s) Filed in Color)
Specification includes a Sequence Listing.

(56) References Cited

U.S. PATENT DOCUMENTS

| | | | |
|---|---|---|---|
| 2017/0066724 | A1 | 3/2017 | Evans et al. |
| 2018/0000768 | A1 | 1/2018 | Fang et al. |

FOREIGN PATENT DOCUMENTS

| | | | | |
|---|---|---|---|---|
| WO | WO 2004/045511 | | 6/2004 | |
| WO | WO-2004045511 | A2 * | 6/2004 | ............ A61K 31/16 |
| WO | WO 2007/070796 | A1 | 6/2007 | |
| WO | WO 2008/051942 | A2 | 5/2008 | |
| WO | WO 2008/073825 | A1 | 6/2008 | |
| WO | WO 2010/036362 | A1 | 4/2010 | |
| WO | WO 2011/150286 | A2 | 12/2011 | |
| WO | WO 2013/020108 | A2 | 2/2013 | |
| WO | WO 2013/040441 | A1 | 3/2013 | |
| WO | WO 2014/179734 | A1 | 11/2014 | |
| WO | WO 2014/184271 | A1 | 11/2014 | |
| WO | WO 2015/012400 | A1 | 1/2015 | |
| WO | WO 2015/138986 | | 9/2015 | |
| WO | WO 2017/078927 | A1 | 5/2017 | |
| WO | WO 2017/078928 | A1 | 5/2017 | |

OTHER PUBLICATIONS

O'Driscoll, C. "Heavyweight drugs" (http://www.concertpharma. com/news/documents/CIHeavyweightdrugsMarch2009.pdf) Chemistry & Industry Mar. 9, 2009 (Year: 2009).*

Maltais, F. et al. "In Vitro and In Vivo Isotope Effects with Hepatitis C Protease Inhibitors: Enhanced Plasma Exposure of Deuterated Telaprevir versus Telaprevir in Rats" J. Med. Chem. 2009, 52, 7993-8001 (Year: 2009).*

CAS Registry No. 938197-65-0; STN Entry Date Jun. 21, 2007; 2-Propenoic acid, 3-[3-[[[4-(3-butoxy-3-oxo-1-propen-1-yl)phenyl]methyl](cyclohexylcarbonyl)amino]phenyl]-, methyl ester CAS Registry No. 938197-65-0.

CAS Registry No. 1348506-83-1; STN Entry Date Dec. 4, 2011; 2-Propenoic acid, 3-[3-[[[4-[(1E)-2-(2-fluorophenyl)ethenyl]phenyl]methyl](1-oxohexyl)amino]phenyl]-, methyl ester, (2E)—CAS Registry No. 1348506-83-1.

CAS Registry No. 1350073-50-5; STN Entry Date Dec. 7, 2011; 2-Propenoic acid, 3-[3-[[(3'-methoxy[1,1'-biphenyl]-4-yl)methyl](1-oxohexyl)amino]phenyl]-, methyl ester, (2E)—CAS Registry No. 1350073-50-5.

CAS Registry No. 1025915-35-8; STN Entry Date Jun. 6, 2008; Acetamide, N-[3-[(acetyloxy)methyl]phenyl]-N-[[3-chloro-4-(tetradecyloxy)phenyl]methyl]-XCAS Registry No. 1025915-35-8.

Fang et al., "Intestinal FXR agonism promotes adipose tissue browning and reduces obesity and insulin resistance," Nature Medicine 21(2):159-165, published online Jan. 5, 2015.

Ghorbani et al., "Appearance of brown adipocytes in white adipose tissue during CL 316,243-induced reversal of obesity and diabetes in Zucker fa/fa rats," International Journal of Obesity 21:465-475, 1997, Jun. 1997.

Hambruch et al., "Synthetic Farnesoid X Receptor Agonists Induce High-Density Lipoprotein-Mediated Transhepatic Cholesterol Efflux in Mice and Monkeys and Prevent Atherosclerosis in Cholesteryl Ester Transfer Protein Transgenic Low-Density Lipoprotein Receptor (−/−) Mice," The Journal of Pharmacology and Experimental Therapeutics 343:556-567, 2012, Dec. 1, 2012.

Hawa et al., "Adult-Onset Autoimmune Diabetes in Europe Is Prevalent With a Broad Clinical Phenotype," Diabetes Care 36:908-913, 2013, published online Dec. 17, 2012.

International Search Report dated Jun. 1, 2015 from International Application No. PCT/US2015/020582 (10 pages).

International Search Report dated Jun. 26, 2015 from International Application No. PCT/US2015/020552 (9 pages).

International Search Report dated May 2, 2016 from International Application No. PCT/US2016/022082 (5 pages).

Lundquist et al., "Improvement of Physiochemical Properties of the Tetrahydroazepinoindole Series of Farnesoid X Receptor (FXR) Agonists: Beneficial Modulation of Lipids in Primates," Journal of Medical Chemistry 53:1774-1787, 2010, Jan. 22, 2010.

Mudaliar et al., "Farnesoid-X Receptor Agonists—A New Therapeutic Class for Diabetes and NAFLD—First Clinical Data," Diabetologia 52:S78, 2009, Aug. 14, 2009.

Schuster et al., "Pharmacophore-Based Discovery of FXR Agonists. Part I: Model Development and Experimental Validation," Bioorganic & Medicinal Chemistry 19:7168-7180, 2011, published online Oct. 4, 2011.

Tang et al., "Conformation-Induced Remote Meta-C—H Activation of Amines," Nature 507:215-220, published online Mar. 12, 2014.

Written Opinion dated Jun. 1, 2015 from International Application No. PCT/US2015/020582 (9 pages).

Written Opinion dated Jun. 26, 2015 from International Application No. PCT/US2015/020552 (10 pages).

Written Opinion dated May 2, 2016 from International Application No. PCT/US2016/022082 (8 pages).

Foster, "Deuterium isotope effects in the metabolism of drugs and xenobiotics: Implications for drug design," Advances in Drug Design 14:1-40, 1985.

International Search Report from International Application No. PCT/US2016/057532 dated Jan. 16, 2017.

International Search Report from International Application No. PCT/US2016/057527 dated Feb. 6, 2017.

Written Opinion from International Application No. PCT/US2016/057532 dated Jan. 16, 2017.

Written Opinion from International Application No. PCT/US2016/057527 dated Feb. 6, 2017.

Crawley, "Farnesoid X receptor modulators: a patent review," Expert Opinion on Therapeutic Patents 20(8):1047-1057, 2010.

Downes et al., "A Chemical, Genetic, and Structural Analysis of the Nuclear Bile Acid Receptor FXR," Molecular Cell 11:1079-1092, Apr. 2003.

Partial European Search Report dated Sep. 22, 2017, from European Application No. 15761517.0.

Richter et al., "Optimization of a novel class of benzimidazole-based farnesoid X receptor (FXR) agonists to improve physicochemical and ADME properties," Bioorganic & Medicinal Chemistry Letters 21:1134-1140, 2011.

Stojancevic et al., "The impact of farnesoid X receptor activation on intestinal permeability in inflammatory bowel disease," Canadian Journal of Gastroenterology 26(9):631-637, Sep. 2012.

Deuterium in https://www.britannica.com/science/deuterium (retrieved from the internet Oct. 8, 2018).

Goodman and Gilman's The Pharmacological Basis of Therapeutics (Tenth Edition), McGraw Hill, Chapter I, pp. 3-29, 2001.

Meier, Juris J., "GLP-1 Receptor Agonists for Individualized Treatment of Type 2 Diabetes mellitus," Nat Rev Endocrinol. 8:728-742, 2012.

Mudalair et al., "Efficacy and Safety of the Farnesoid X Receptor Agonist Obeticholic Acid in Patients With Type 2 Diabetes and Nonalcoholic Fatty Liver Disease," Gastroenterol. 145:574-584, 2013.

Oslowski et al., "Thioredoxin-Interacting Protein Mediates ER Stress-Induced in β Cell Death through Initiation of the Inflammasome," Cell Metabolism 16:265-273, 2012.

Stenstrom et al., "Latent Autoimmune Diabetes in Adults: Definition, Prevalence, β-Cell Function, and Treatment," Diabetes 54: S68-S72, 2005.

EP 15760948.8 Extended Search Report dated Jul. 17, 2017 (7 pages).

Cariou et al., "The Farnesoid X Receptor Modulates Adiposity and Peripheral Insulin Sensitivity in Mice," J Biol Chem. 281:11039-11049, 2006.

Cernea et al., "-Cell Protection and Therapy for Latent Autoimmune Diabetes in Adults," Diabetes Care 32:5246-5252, 2009.

Cipriani et al., "FXR activation reverses insulin resistance and lipid abnormalities and protects against liver steatosis in Zucker (fa/fa) obese rats," J Lipid Res. 51:771-784, 2010.

Düfer et al., "Bile Acids Acutely Stimulate Insulin Secretion of Mouse b-Cells via Farnesoid X Receptor Activation and KATP Channel Inhibition," Diabetes 61:1479-1489, 2012.

(56) References Cited

OTHER PUBLICATIONS

Düfer et al., "The significance of the nuclear farnesoid X receptor (FXR) in β cell function," *Islets* 4:333-338, 2012.

Jacinto and Fang, "Essential roles of bile acid receptors FXR and TGR5 as metabolic regulators," *Animal Cells Systems* 18:359-364, 2014.

Li et al., "Protective effects of 1-alpha-hydroxyvitamin D3 on residual beta-cell function in patients with adult-onset latent autoimmune diabetes (LADA)," *Diabetes Metab Res Rev.* 25:411-416, 2009.

Popescu et al., "The nuclear receptor FXR is expressed in pancreatic b-cells and protects human islets from lipotoxicity," *FEBS Lett.* 584:2845-2851, 2010.

Renga et al., "The bile acid sensor FXR regulates insulin transcription and secretion," *Biochim Biophys Acta* 1802:363-372, 2010.

Seyer et al., "Hepatic glucose sensing is required to preserve β cell glucose competence," *J Clin Invest.* 123:1662-1676, 2013.

Zhang et al., "Activation of the nuclear receptor FXR improves hyperglycemia and hyperlipidemia in diabetic mice," *Proc Natl Acad Sci. USA* 103:1006-1011, 2006.

Zhao et al., "Dipeptidyl Peptidase 4 Inhibitor Sitagliptin Maintains β-Cell Function in Patients With Recent-Onset Latent Autoimmune Diabetes in Adults: One Year Prospective Study," *J Clin Endocrinol Metab.* 99:E876-E880, 2014.

EP 16765500.0 Extended European Search Report dated Nov. 7, 2018 (19 pages).

\* cited by examiner

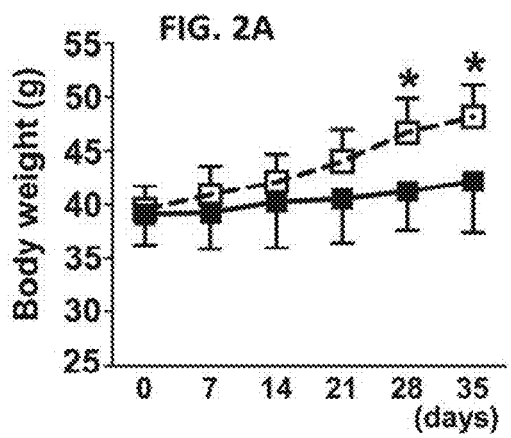
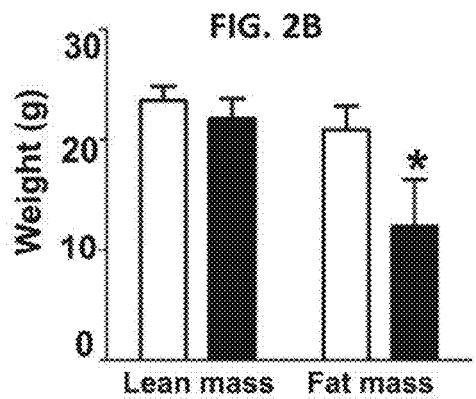
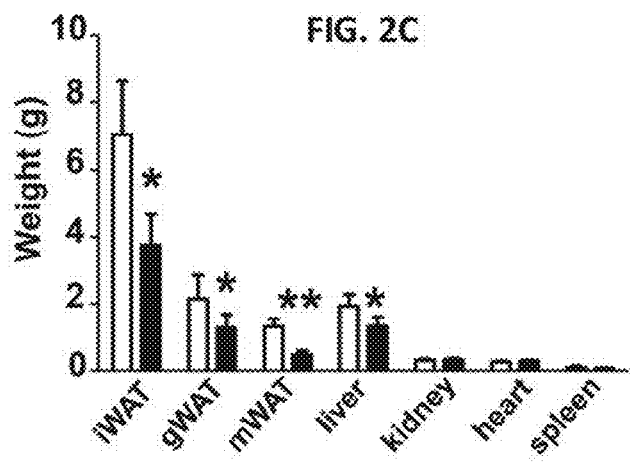
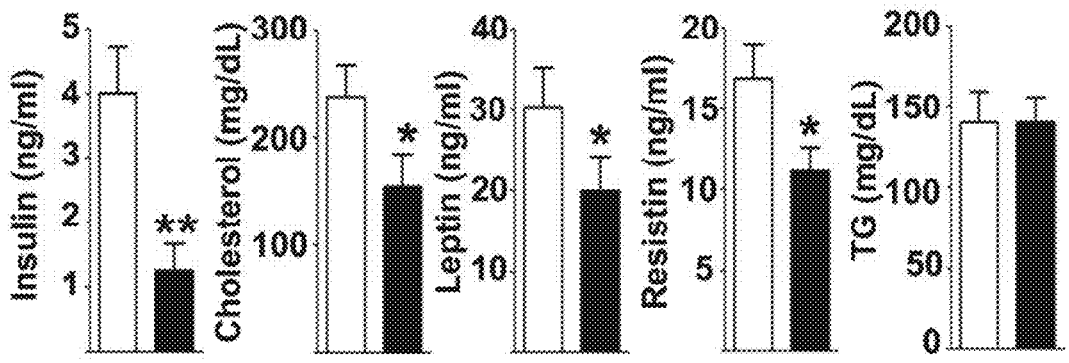

FIG. 5E
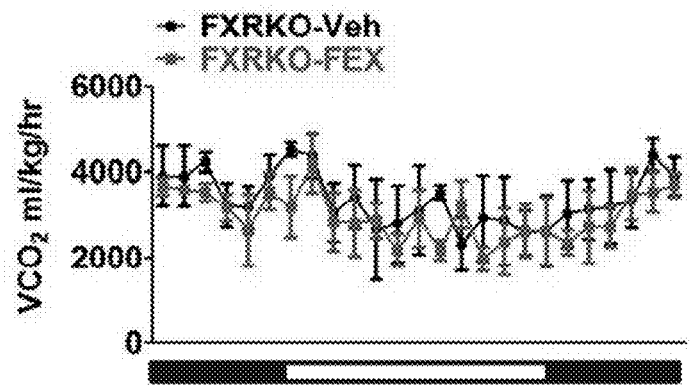
FIG. 5F
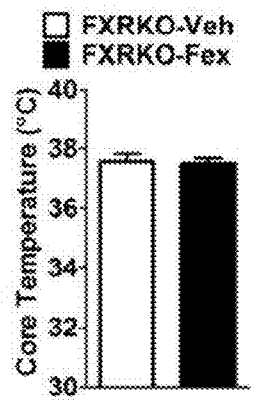
FIG. 5G
FIG. 5H
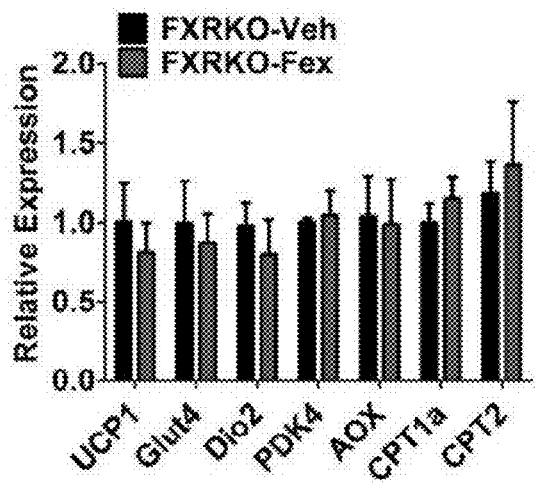
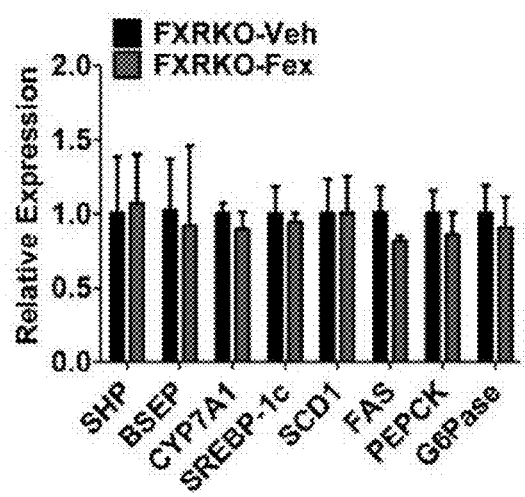
FIG. 5I
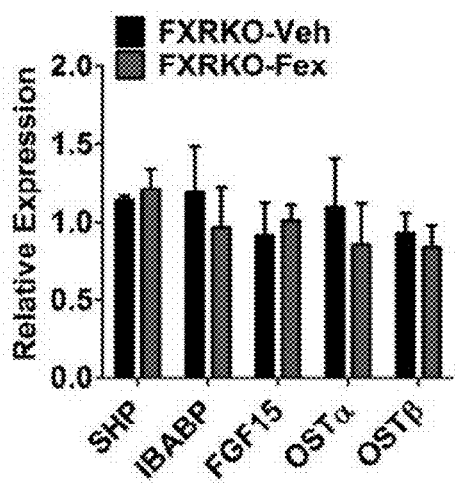

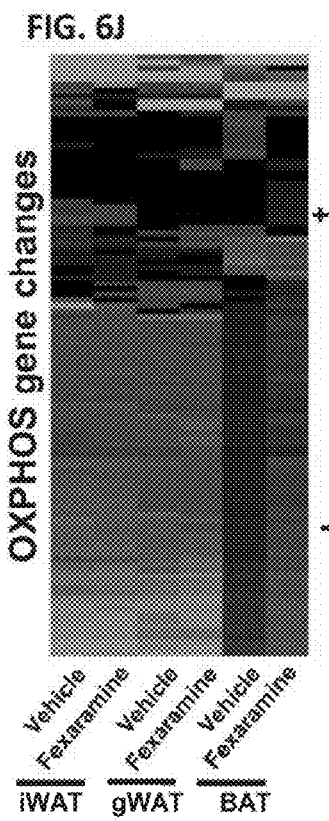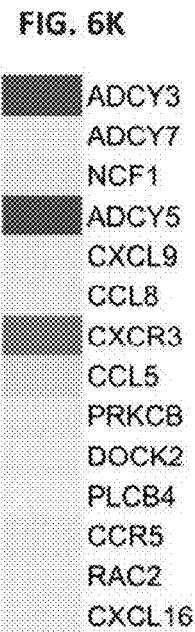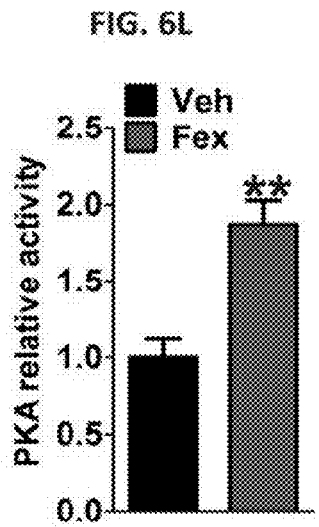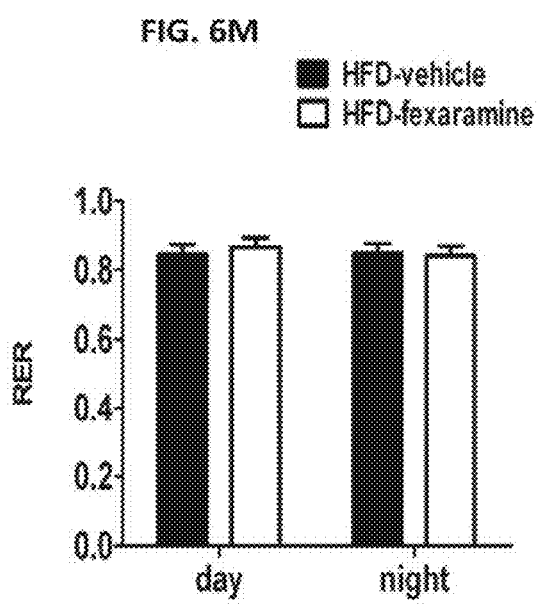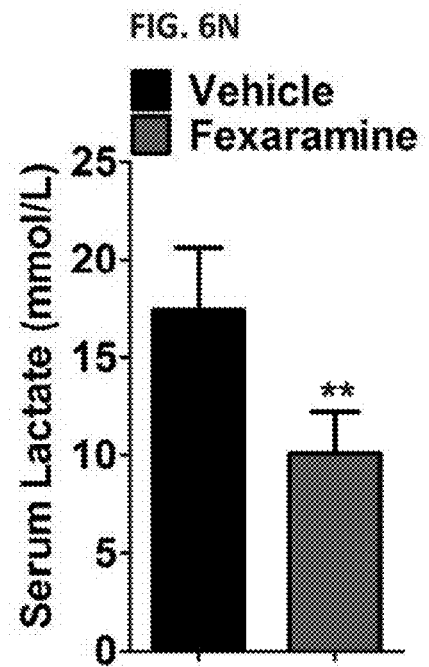

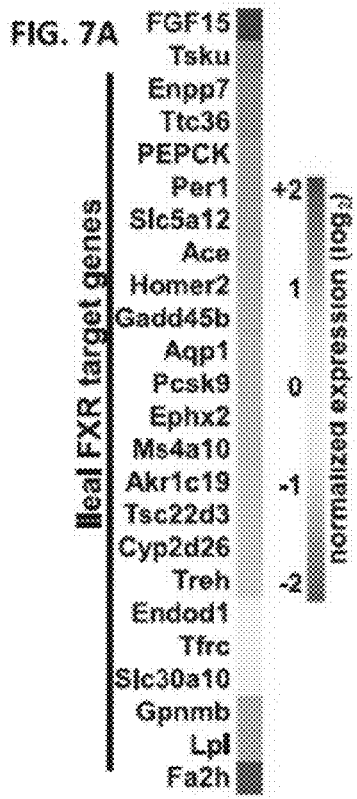
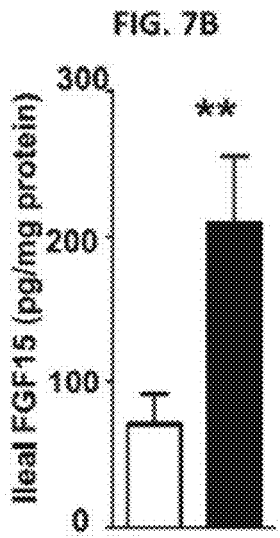
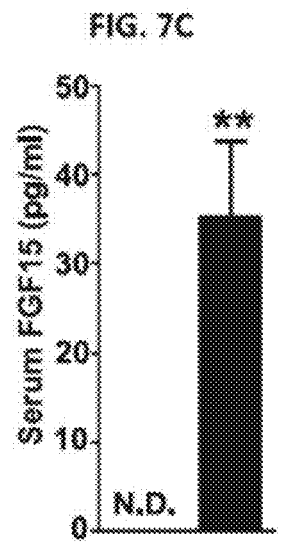
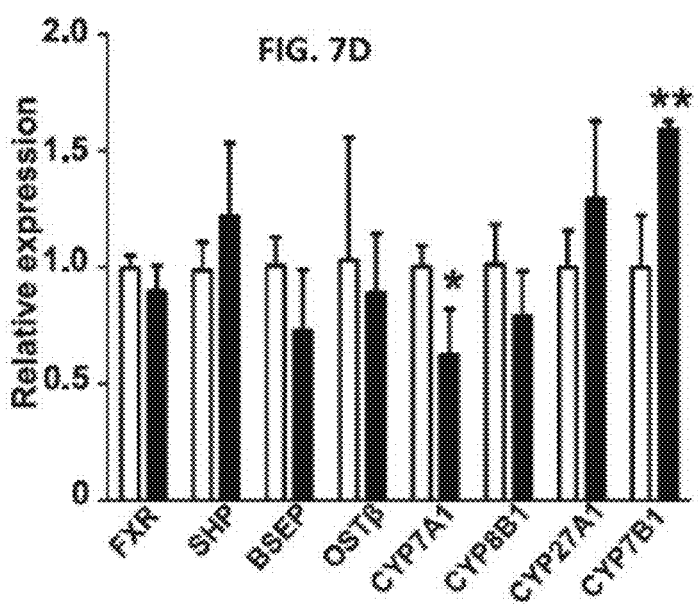

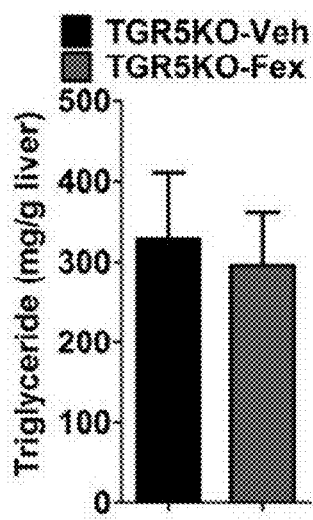
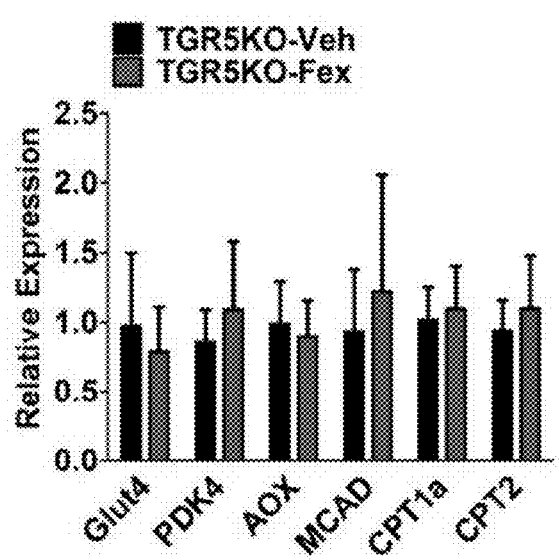
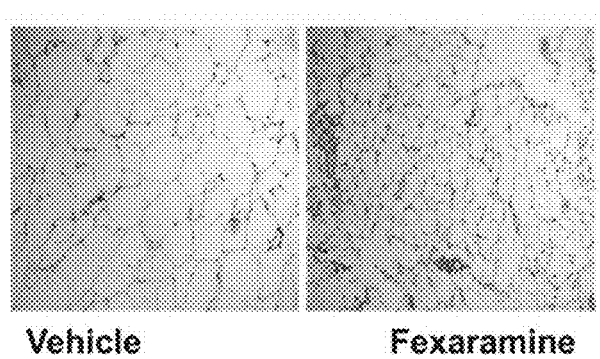
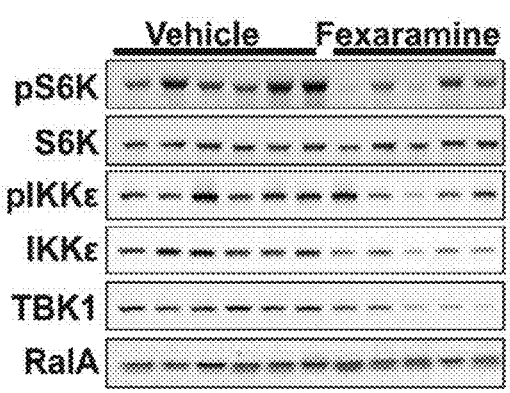
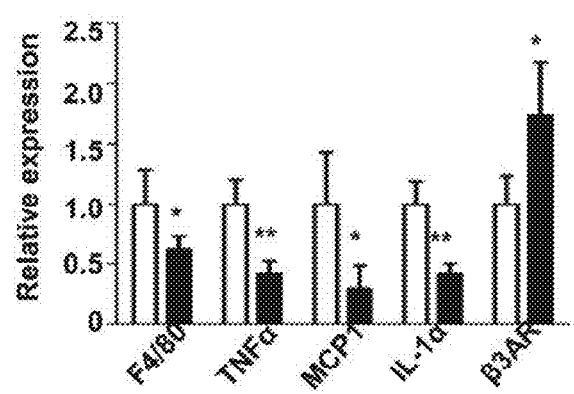

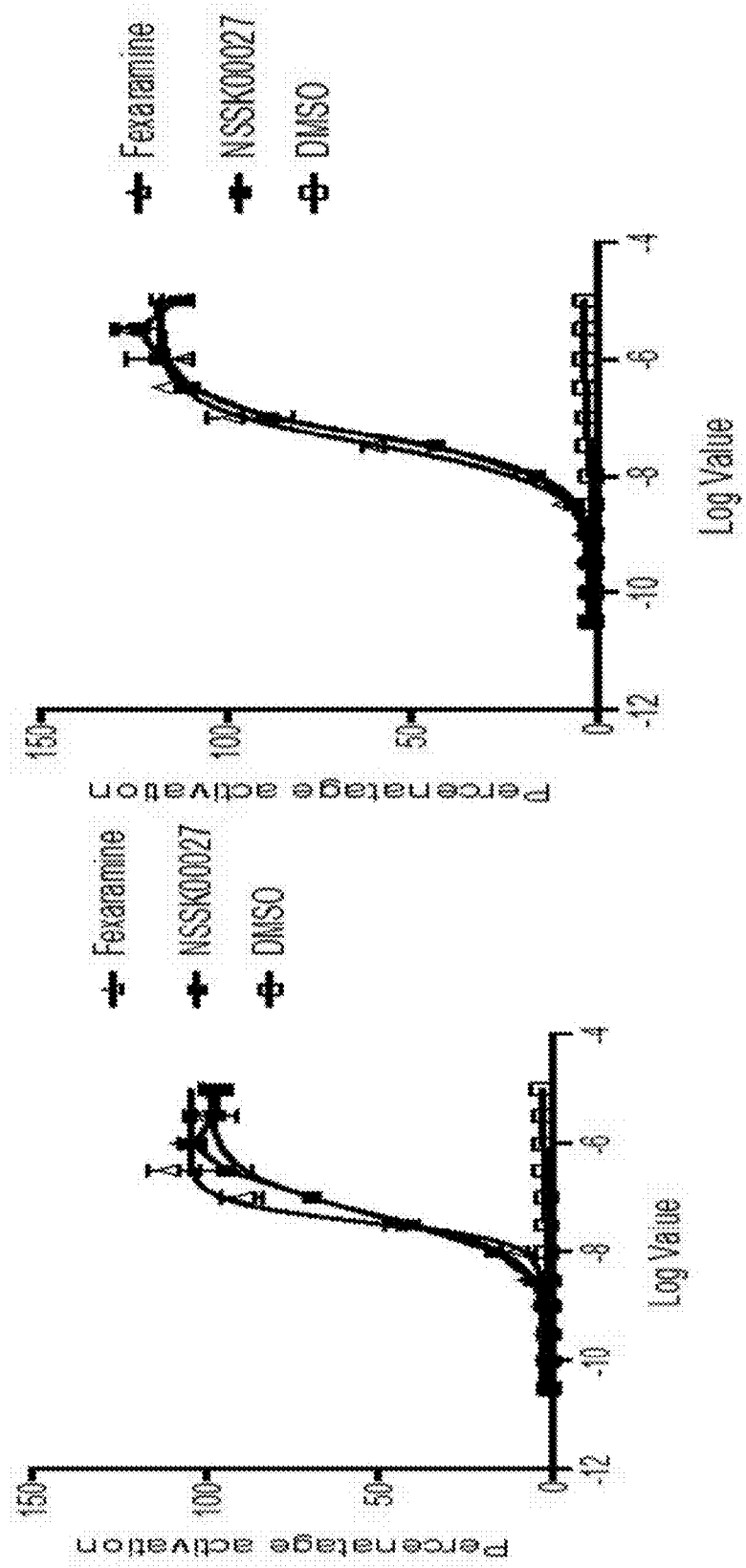

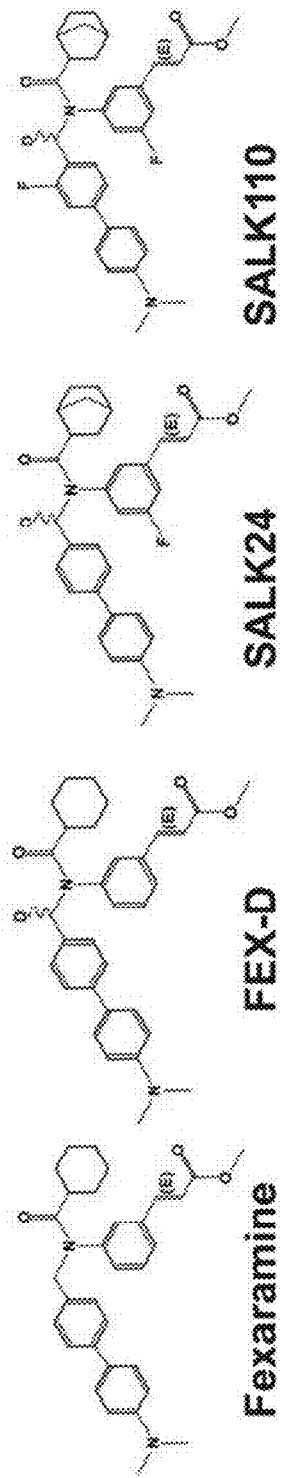
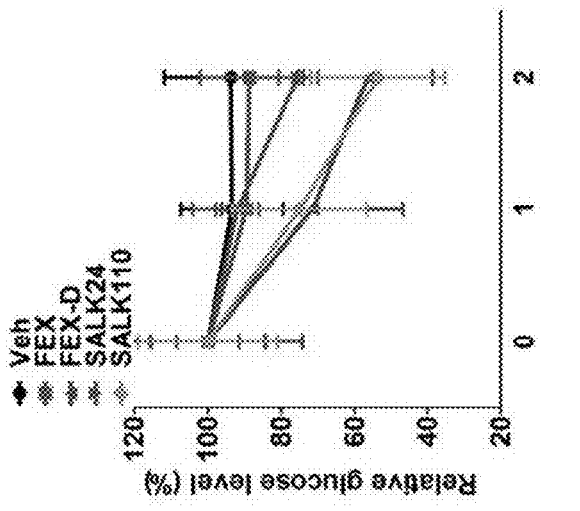
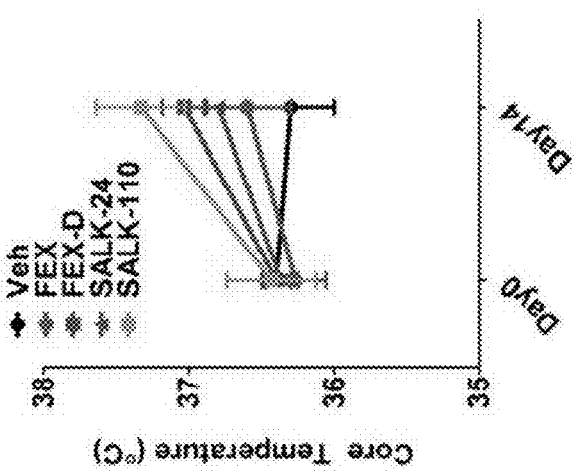
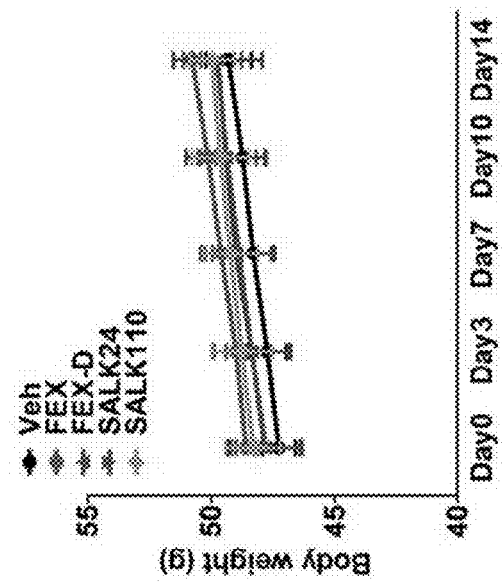
FIG. 29A
FIG. 29B
FIG. 29C
FIG. 29D islets from chronic treated-ob/ob mice

FIG. 32

Results Summary

| Compound ID | Assay Conc. (μM) | Mean P$_{app}$, A-B (10$^{-6}$ cm/s) | Mean P$_{app}$, B-A (10$^{-6}$ cm/s) | Mean (B-A/A-B) Efflux Ratio | Mean % Recovery | A-B Permeability Ranking |
|---|---|---|---|---|---|---|
| Fexaramine | 10 | 0.597 | 0.770 | NA | 149.7% | Lower |
| Salk Control | 10 | 0.110 | 0.274 | NA | 96.2% | Lower |
| Salk 00024 | 10 | 0.0294 | 0.230 | NA | 192.0% | Lower |
| Salk 00027 | 10 | 0.0295 | 0.0280 | NA | 138.2% | Lower |
| Salk 00089 | 10 | 0.0962 | 0.0640 | NA | 67.1% | Lower |
| Salk 00096 | 10 | 0.0104 | 0.0399 | NA | 69.9% | Lower |
| Salk 00110 | 10 | 0.115 | 0.351 | NA | 118.3% | Lower |
| Controls: | | | | | | |
| Warfarin | 10 | 42.8 | 29.8 | 0.695 | 101.0% | Higher as expected |
| Ranitidine | 10 | 0.274 | 0.922 | 3.36 | 92.7% | Lower as expected |
| Talinolol | 10 | 0.422 | 4.41 | 10.5 | 92.4% | Effuxd as expected |

Notes: Permeability Ranking: lower is < 1x10$^{-6}$ cm/s; higher is > 1x10$^{-6}$ cm/s.
An efflux ratio >2 indicates potential for the compound to be a substrate for Pgp or other active transporter.

ANALOGS OF FEXARAMINE AND METHODS OF MAKING AND USING

CROSS-REFERENCE TO RELATED APPLICATIONS

This application is a continuation-in-part of International Application No. PCT/US2015/020552, filed Mar. 13, 2015, which claims the benefit of U.S. Provisional Application No. 61/952,763 filed Mar. 13, 2014 and 62/061,607 filed Oct. 8, 2014. This application also claims the benefit of U.S. Provisional Application No. 62/252,045, filed Nov. 6, 2015. Each of these prior applications is incorporated herein by reference.

ACKNOWLEDGMENT OF GOVERNMENT SUPPORT

This invention was made with government support under Grant No. R24-DK090962 awarded by the National Institute of Health (NIH). The government has certain rights in the invention.

FIELD

This disclosure concerns new fexaramine analogs and a method for using the analogs to treat or prevent gastrointestinal (GI) inflammatory conditions, intestinal permeability conditions, intestinal altered microbiome conditions, cholestatic disorders, bile disorders, intestinal absorption disorders, and metabolic disorders, including obesity and diabetes.

PARTIES TO JOINT RESEARCH AGREEMENT

Salk Institute for Biological Studies and The University of Sydney are parties to a joint research agreement governing inventions disclosed herein.

BACKGROUND

Metabolic syndrome, a western diet-induced, pro-inflammatory disease affecting up to 25% of Americans, is characterized by central obesity, impaired glucose tolerance, dyslipidemia, insulin resistance, and type II diabetes. Secondary complications associated with metabolic syndrome include atherosclerosis, stroke, fatty liver disease, blindness, gallbladder disease, cancer, polycystic ovary disease and others. Consequently there is interest in reducing food intake, losing weight, and reducing elevated blood glucose. There is also an interest in combating obesity and related conditions using methods that do not require drastic lifestyle or dietary changes. In addition, inflammatory gastrointestinal conditions resulting from various types of pathology affect millions of people. Thus, effective and targeted treatments for various inflammatory gastrointestinal (GI) conditions are also needed.

Farnesoid X receptor (FXR) is a ligand-activated transcriptional receptor expressed in diverse tissues including the adrenal gland, kidney, stomach, duodenum, jejunum, ileum, colon, gall bladder, liver, macrophages, and white and brown adipose tissue (Forman et al., *Cell* 81:687-693 (1995). FXR has been reported to contribute to the regulation of whole body metabolism including bile acid/cholesterol, glucose and lipid metabolism. Synthetic ligands for FXR have been identified and applied to animal models of metabolic disorders, but these known synthetic ligands have shown limited efficacy and, in certain cases, exacerbated phenotypes.

Bile acids (BAs) function as endogenous ligands for FXR such that enteric and systemic release of BAs induces FXR-directed changes in gene expression networks (Lee et al., *Trends Biochem Sci* 31:572-580, 2006; Repa et al., *Science* 289:1524-1529, 2000; Zollner et al., *J Hepatol* 39:480-488, 2003; Fang et al., *J Biol Chem* 283:35086-35095, 2008; Kemper et al., *Cell Metab* 10:392-404, 2009; Makishima et al., *Science* 284:1362-1365, 1999; Stedman et al., *Proc Natl Acad Sci USA* 103:11323-11328, 2006). The complex role of FXR in metabolic homeostasis is evident in studies on whole body FXR knockout (FXR KO) mice. On a normal chow diet, FXR KO mice develop metabolic defects including hyperglycemia and hypercholesterolemia, but conversely, exhibit improved glucose homeostasis compared to control mice when challenged with a high fat diet (Sinal et al., *Cell* 102:731-744, 2000; Prawitt et al., *Diabetes* 60:1861-1871, 2011). Similar contrary effects are seen with systemic FXR agonists, with beneficial effects observed when administered to chow-fed mice and exacerbated weight gain and glucose intolerance observed when administered to diet-induced obesity (DIO) mice (Zhang et al., *Proc Natl Acad Sci USA* 103:1006-1011, 2006; Watanabe et al., *J Biol Chem* 286:26913-26920, 2011). In the liver, FXR activation suppresses hepatic BA synthesis, alters BA composition, reduces the BA pool size (Wang et al., *Dev Cell* 2:721-731, 2002; Fang et al., *Mol Cell Biol* 27:1407-1424, 2007; Lu et al., *Mol Cell* 6:507-515, 2000), and contributes to liver regeneration (Huang et al., *Science* 312:233-236, 2006) as well as lipid and cholesterol homeostasis (Zhang et al., *Genes Dev* 18:157-169, 2004; Ma et al., *J Clin Invest* 116:1102-1109, 2006). Consistent with this, activation of hepatic FXR by the synthetic bile acid 6α-ethyl chenodeoxycholic acid (6-eCDCA) is beneficial in the treatment of diabetes, non-alcoholic fatty liver disease (NAFLD), and primary biliary cirrhosis (PBC) (Stanimirov et al., *Acta Gastroenterol Belg* 75:389-398, 2012; Mudaliar et al., *Gastroenterology* 145:574-582 e571, 2013).

FXR is also widely expressed in the intestine where it regulates production of the endocrine hormone FGF15 (FGF19 in humans), which, in conjunction with hepatic FXR, is thought to control BA synthesis, transport and metabolism (Kim et al., *J Lipid Res* 48:2664-2672, 2007; Song et al., *Hepatology* 49:97-305, 2009; Inagak et al., *Cell Metab* 2:217-225, 2005). Intestinal FXR activity is also known to be involved in reducing overgrowth of the microbiome during feeding (Li et al., *Nat Commun* 4:2384, 2013; Inagaki et al., *Proc Natl Acad Sci USA* 103:3920-3925, 2006).

SUMMARY

In view of the above, there is an ongoing need for methods and compositions for the treatment and prevention of metabolic disorders, including obesity and metabolic syndrome. As well as other disorders such as gastrointestinal (GI) inflammatory conditions, intestinal permeability conditions, intestinal altered microbiome conditions, cholestatic disorders, intestinal absorption disorders, and bile disorders. There is also a need for methods and compositions that produce beneficial clinical effects, while reducing side effects, such as those resulting from systemic administration of a particular therapy (such as systemic FXR-directed therapies). There also is a need for compositions that specifically target intestinal FXR, which can result in a beneficial anti-inflammatory effect in the intestines. Disclosed embodiments of the present disclosure address these needs, and provide novel compounds and compositions that target intestinal FXR. In some examples, the compounds are gut-selective, non-bile acid FXR agonists.

Certain disclosed compounds have the following general formula

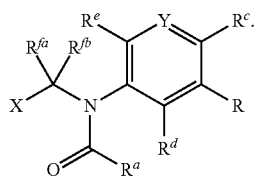

With reference to the general formula, R is selected from

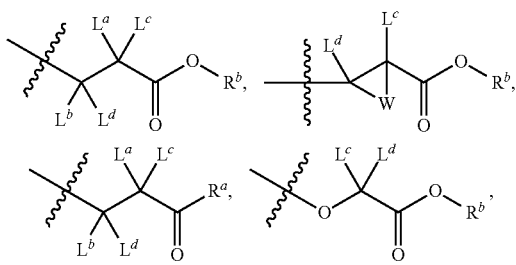

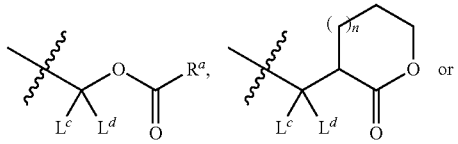

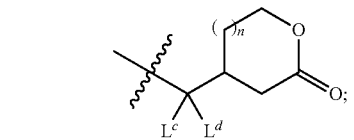

$R^a$ is selected from aryl, heteroaryl, alkyl, alkenyl, cycloalkyl, heterocyclic, or polycyclic; $R^b$ is selected from hydrogen, alkyl, alkenyl, or cycloalkyl; Y is $CR^g$, N or N—O (N-oxide); $R^c$, $R^d$, $R^e$ and $R^g$ are each independently selected from hydrogen, deuterium, halide, alkyl, alkenyl, alkoxy, alkylthio, amino, sulfonyl, aminosulfonyl, aminocarbonyl, acyl, hydroxyl or nitro; $R^{fa}$ and $R^{fb}$ are each independently selected from hydrogen, deuterium, halide or alkyl; $L^a$ and $L^b$ are each independently selected from hydrogen, deuterium, alkyl or cycloalkyl, or together form a pi-bond; $L^c$ and $L^d$ are each independently selected from hydrogen, deuterium, alkyl or cycloalkyl; W is selected from O or $—(C(L^c)(L^d))_s$—; s is 1, 2, 3, 4, 5 or 6; n is 0 or 1; and X is aryl, heterocyclic or heteroaryl.

Also with reference to the general formula the following provisos apply:

if W is $CH_2$ and $L^c$ and $L^d$ are both H, then X is not a benzopyran;

if R is

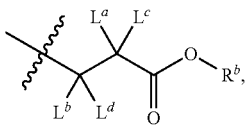

$L^c$ and $L^d$ are both H, and $L^a$ and $L^b$ are both H or together form a pi-bond, then X is not a benzopyran;

X is not substituted with —$R^x$-$L^x$-$R^{x2}$, where $R^x$ is selected from O, $NR^{x3}$, sulfonyl or S;

$R^{x3}$ is selected from H, alkyl, alkenyl, alkynyl, cycloalkyl, cycloalkenyl, or aryl;

$L^x$ is selected from a bond, alkylene, alkenylene, alkynylene, cycloalkyl, cycloalkenyl, heterocyclic, aryl, heteroaryl or $CR^{x4}R^{x5}$;

$R^{x4}$ and $R^{x5}$ are each independently selected from H, D, halogen, alkyl, alkenyl, alkynyl, cycloalkyl, cycloalkenyl, —C(O)$OR^{x6}$, or —C(O)$NR^{x6}R^{x7}$;

$R^{x6}$ and $R^{x7}$ are each independently selected from H, alkyl, alkenyl, alkynyl, cycloalkyl or cycloalkenyl;

$R^{x2}$ is selected from —C(O)$L^{x2}R^{x8}$ or a carboxyl bioisostere;

$L^{x2}$ is a bond or $NR^{x3}$;

$R^{x8}$ is H, alkyl, alkenyl, alkynyl, cycloalkyl, cycloalkenyl, —$OR^{x9}$, $N(R^{x9})_2$, —C(O)$R^{x9}$, —S(O)$_2R^{x9}$, —C(O)$OR^{x9}$, —S(O)$_2N(R^{x9})_2$ or C(O)$N(R^{x9})_2$; and each $R^{x9}$ is independently selected from H, alkyl, alkenyl, alkynyl, cycloalkyl or cycloalkenyl; and if R is

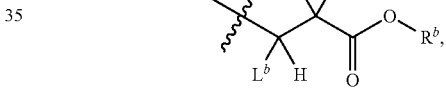

Y is CH, $R^c$, $R^d$, $R^e$ and $R^{fa}$ are all hydrogen, and $L^a$ and $L^b$ are both H or together form a pi-bond, then if $R^a$ is cyclohexyl, $R^b$ is methyl, and $R^{fb}$ is H then X is not phenyl, 4-biphenyl, 4-bromophenyl, 3-bromophenyl, 2-bromophenyl, 4-tert-butylphenyl, 3-methoxyphenyl, 3,5-dimethoxyphenyl, 3-(trifluoromethyl)phenyl, 4-(3,4-difluorophenyl)phenyl, 4-(3-acetylphenyl)phenyl, 4-(4-methylthiophenyl)phenyl, 4-(4-methoxyphenyl)phenyl, 4-(3-methoxyphenyl)phenyl, 4-(2-methoxyphenyl)phenyl, 4-(3,5-dichlorophenyl)phenyl, 4-(4-tert-butylphenyl)phenyl, 4-(3-ethoxyphenyl)phenyl, 4-(3-chlorophenyl)phenyl, 4-(3-methylphenyl)phenyl, 4-(4-methylphenyl)phenyl, 4-(2-methoxy-5-chlorophenyl)phenyl, 4-(3-chloro-4-fluorophenyl)phenyl, 4-(4-trifluoromethoxyphenyl)phenyl, 4-(3-trifluoromethoxyphenyl)phenyl, 4-(2,6-dimethoxyphenyl)phenyl, 4-(4-dimethylaminophenyl)phenyl,

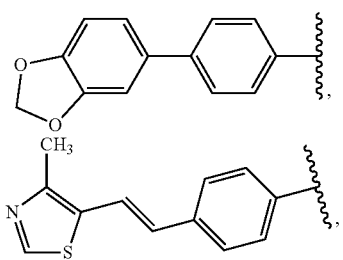

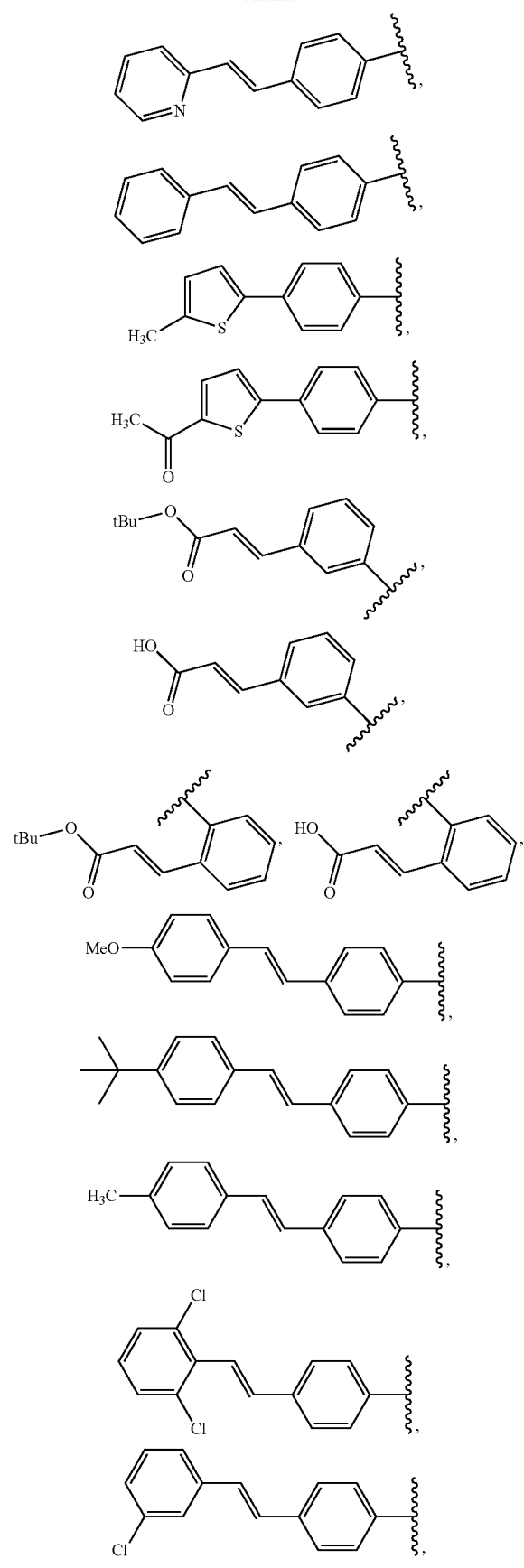
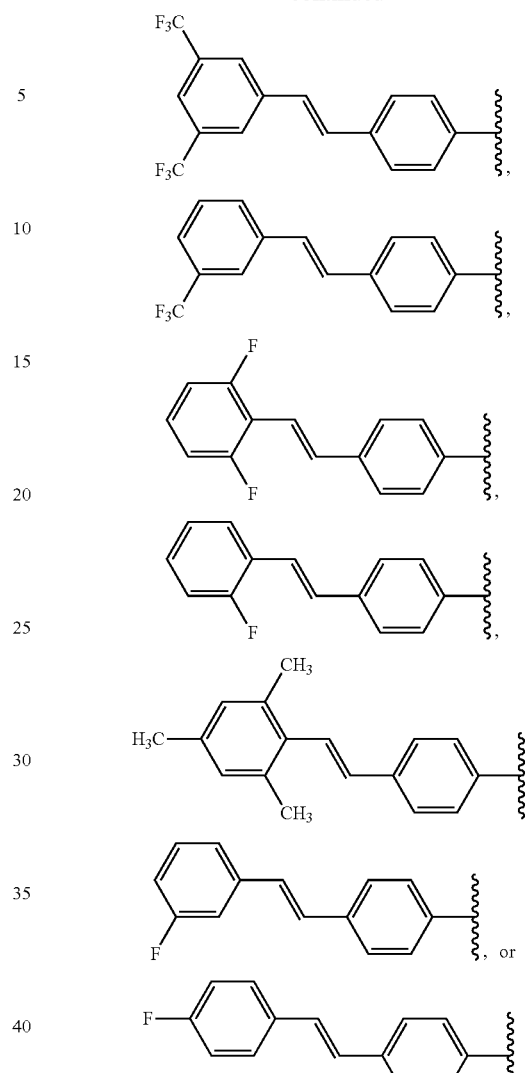
if $R^a$ is cyclohexyl, $R^{fb}$ is H and X is
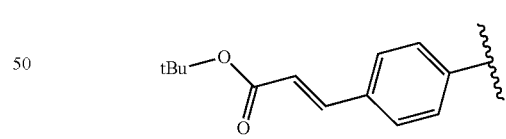
then $R^b$ is not methyl, ethyl or tert-butyl;
if $R^b$ is methyl, $R^{fb}$ is H and X is
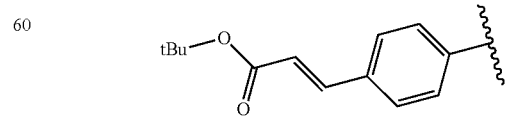
then $R^a$ is not cyclopropyl, cyclobutyl, cyclopentyl, or cyclohexyl;

if $R^a$ is cyclohexyl, $R^{fb}$ is H and X is

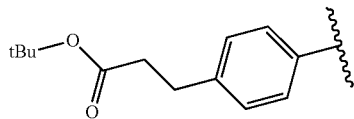 [SMILES: *c1ccc(CCC(=O)OC(C)(C)C)cc1]

then $R^b$ is not methyl or tert-butyl;
if $R^a$ is cyclohexyl, $R^b$ is methyl, $R^{fb}$ is H and X is

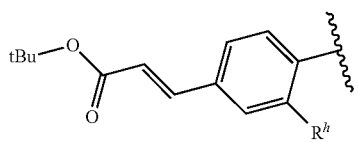

then $R^h$ is not hydroxyl, (trimethylsilyl)ethoxymethyl-O, methoxy, O-benzyl, $OCH_2CO_2Et$, $OC(O)CH_3$, $OC(O)Ph$ or $OSO_2CH_3$; and
if $R^a$ is cyclohexyl, $R^b$ is methyl, $R^{fb}$ is H and X is

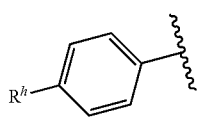

then $R^h$ is not $-CH=CHC(O)OMe$, $-CH=CHC(O)OEt$, $-CH=CHC(O)NMe_2$, $-CH=CHC(O)NH^tBu$, $-CH=CHC(O)O^tBu$, $-CH=CHC(O)O^iPr$, $-CH=CHC(O)OCH_2Ph$, $-CH=CHC(O)OH$, $-CH=CHCH_2OMe$, $-CH=CHCH_2OEt$ or $-CH=CHCH_2OPh$.

In some embodiments, the compounds $L^c$ and $L^d$ are both H, and $L^a$ and $L^b$ together form a pi-bond.

Certain other disclosed compounds have the following general formula

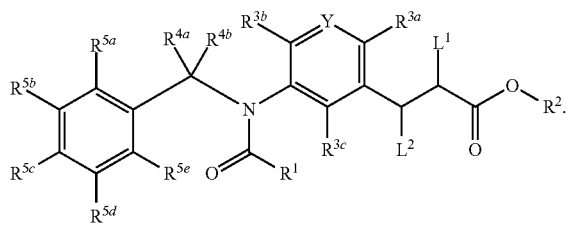

With reference to the general formula, $R^1$ is selected from aryl, heteroaryl, heterocyclic, alkyl, alkenyl, cycloalkyl, cycloalkenyl or polycyclic; $R^2$ is selected from alkyl, alkenyl, or cycloalkyl; Y is selected from N, N—O or C—$R^{3d}$; $R^{3a}$, $R^{3b}$, $R^{3c}$ and $R^{3d}$ are each independently selected from hydrogen, deuterium, halide, alkyl, alkenyl, alkoxy, alkylthio, amino, sulfonyl, aminosulfonyl, aminocarbonyl, acyl, hydroxyl or nitro; $R^{4a}$ and $R^{4b}$ are each independently selected from hydrogen, deuterium, halide or alkyl; $L^1$ and $L^2$ are independently selected from hydrogen, deuterium, alkyl, cycloalkyl, or together form a pi-bond; and $R^{5a}$, $R^{5b}$, $R^{5c}$, $R^{5d}$ and $R^{5e}$ are each independently selected from hydrogen, deuterium, halide, alkyl, alkenyl, alkoxy, alkylthio, amino, sulfonyl, aminosulfonyl, aminocarbonyl, acyl, aryl, heteroaryl, cycloalkyl, heterocyclyl, hydroxyl or nitro; or any two adjacent groups selected together form an aryl, heteroaryl, cycloalkyl or heterocyclic ring; and none of $R^{5a}$, $R^{5b}$, $R^{5c}$, $R^{5d}$ or $R^{5e}$ is $-R^x-L^x-R^{x2}$, where $R^x$ is selected from O, $NR^{x3}$, sulfonyl or S; $R^{x3}$ is selected from H, alkyl, alkenyl, alkynyl, cycloalkyl, cycloalkenyl, or aryl; $L^x$ is selected from a bond, alkylene, alkenylene, alkynylene, cycloalkyl, cycloalkenyl, heterocyclic, aryl, heteroaryl or $CR^{x4}R^{x5}$; $R^{x4}$ and $R^{x5}$ are each independently selected from H, D, halogen, alkyl, alkenyl, alkynyl, cycloalkyl, cycloalkenyl, $-C(O)OR^{x6}$, or $-C(O)NR^{x6}R^{x7}$; $R^{x6}$ and $R^{x7}$ are each independently selected from H, alkyl, alkenyl, alkynyl, cycloalkyl or cycloalkenyl; $R^{x2}$ is selected from $-C(O)L^{x2}R^{x8}$ or a carboxyl bioisostere; $L^{x2}$ is a bond or $NR^{x3}$; $R^{x8}$ is H, alkyl, alkenyl, alkynyl, cycloalkyl, cycloalkenyl, $-OR^{x9}$, $N(R^{x9})_2$, $-C(O)R^{x9}$, $-S(O)_2R^{x9}$, $-C(O)OR^{x9}$, $-S(O)_2N(R^{x9})_2$ or $-C(O)N(R^{x9})_2$; and each $R^{x9}$ is independently selected from H, alkyl, alkenyl, alkynyl, cycloalkyl or cycloalkenyl. For certain embodiments where $L^1$ and $L^2$ are both hydrogen or together form a pi-bond, Y is N or C-halogen; or $R^1$ is polycyclic; or $R^4$ is D, or $R^{5a}$ is F, Cl or I; or $R^{5d}$ and $R^{5e}$ together form an aryl, heteroaryl, cycloalkyl or heterocyclic ring; or $R^{5b}$ and $R^{5c}$ together form an aryl, cycloalkyl, nitrogen-containing heterocyclic or nitrogen-containing heteroaryl ring; or any combination thereof.

In some embodiments, Y is C—$R^{3d}$, and $R^{3d}$ or $R^{5a}$ or both are halogen, and in certain examples the halogen is fluorine. In other embodiments, Y is N.

In certain embodiments, $R^1$ is polycyclic. Exemplary $R^1$ polycyclics are selected from

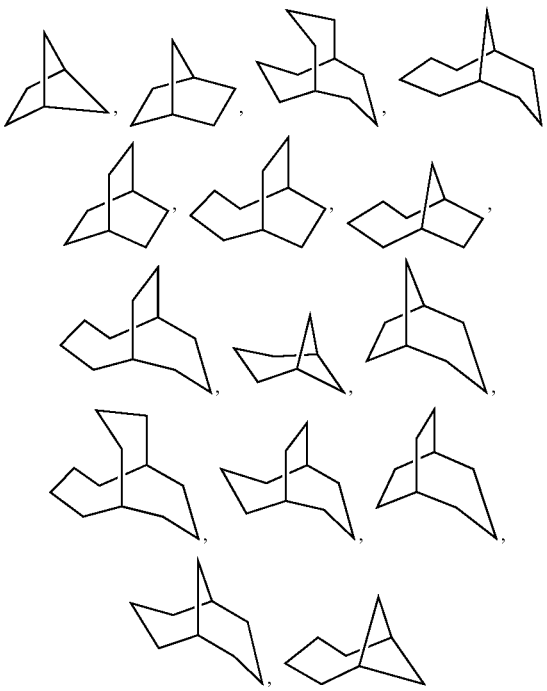

or adamantyl. In other examples, the polycyclic is selected from [2.1.1], [2.2.1], [3.3.3], [4.3.1], [2.2.2], [4.2.2], [4.2.1], [4.3.2], [3.1.1], [3.2.1], [4.3.3], [3.3.2], [3.2.2], [3.3.1], [4.1.1], or adamantyl. In certain working embodiments, the polycyclic is

In some embodiments, $R^{5c}$ is a nitrogen-containing heteroaryl ring, and the compound has a formula

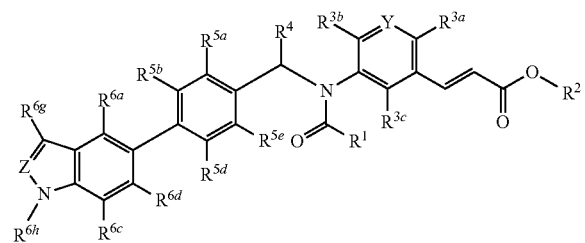

where Z is selected from N, CH, or C-alkyl; $R^{6a}$, $R^{6c}$, $R^{6d}$ and $R^{6g}$ each is independently selected from H, D, halogen or alkyl; and $R^{6h}$ is selected from H, D, alkyl, cycloalkyl, aryl or heteroaryl. In some examples, Z is N, and/or $R^{6a}$, $R^{6c}$, $R^{6d}$ and $R^{6g}$ are all H. In particular embodiments, $R^{6h}$ is methyl.

In other embodiments, $R^{5c}$ comprises phenyl, leading to compounds having a formula

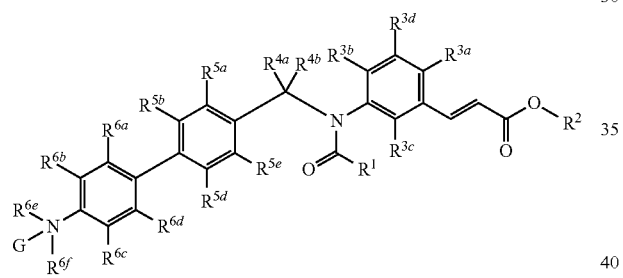

where $R^{6a}$, $R^{6b}$, $R^{6c}$ and $R^{6d}$ each is independently selected from H, D, halogen or alkyl; G is a lone pair of electrons, or an oxygen; $R^{6e}$ and $R^{6f}$ each is independently selected from alkyl, H or cycloalkyl; and where $R^{3d}$ or $R^{5a}$ or both are halogen, or $R^4$ is D, or $R^1$ is polycyclic, or any combination thereof. In some examples, $R^{6e}$ and $R^{6f}$ are both methyl.

In any of the above embodiments, $R^4$ may be deuterium, and/or $R^2$ may be methyl. In certain embodiments, $R^1$ is cyclohexyl.

In particular embodiments, the compound is selected from

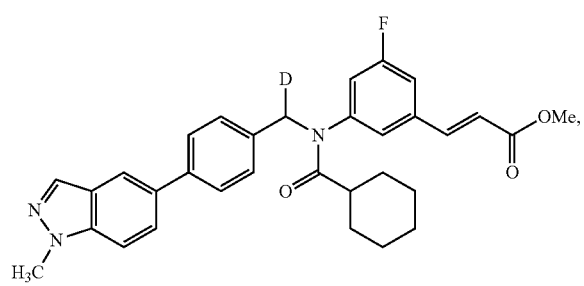

NSSK00096

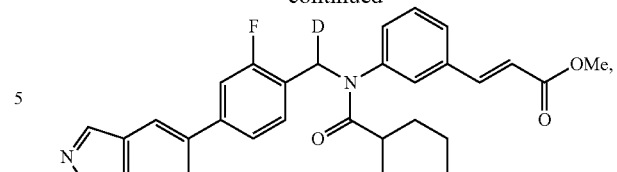

NSSK00089

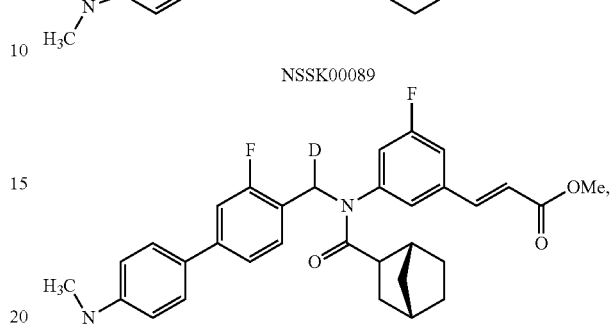

NSSK00110

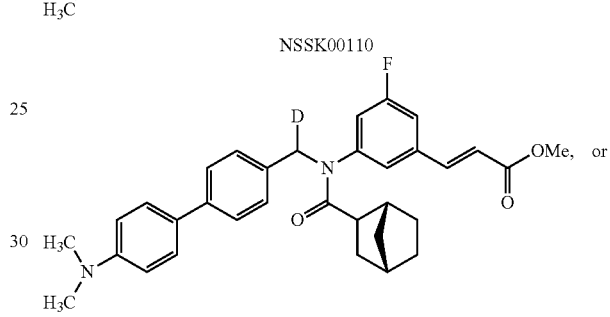

NSSK00024

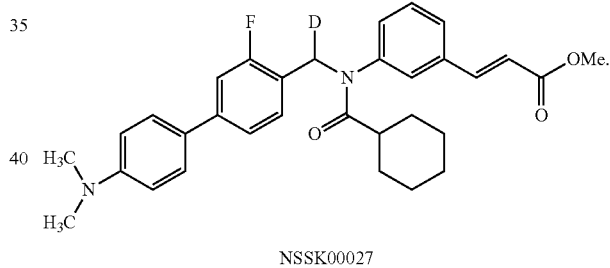

NSSK00027

Compositions comprising the disclosed compounds also are disclosed. In some embodiments, the composition comprises a first disclosed compound, and an additional component, such as a pharmaceutically exceptable excipient, an additional therapeutic compound, or a combination thereof. In certain examples, the additional therapeutic compound is a second disclosed compound. In some embodiments, the composition may include an enteric coating.

Also disclosed herein are embodiments of a method for treating or preventing a metabolic disorder in a subject. Such methods can include administering to the subject a therapeutically effective amount of one or more of the disclosed compounds, or one or more of the disclosed compositions (such as 1, 2, 3, 4, or 5 of such compounds and/or compositions). The compounds are substantially absorbed in the gastrointestinal tract, thereby activating FXR receptors in the intestines to treat or prevent a metabolic disorder in the subject. The method also may improve glucose and/or lipid homeostasis in the subject. In other embodiments, the method further includes administering to the subject a statin, an insulin sensitizing drug, (such as sitagliptin, vildagliptin, saxagliptin, linagliptin, anaglptin, teneligliptin, alogliptin, gemiglptin, or dutoglpitin), meglinitide, sulfonylurea, peroxisome proliferator-activated receptor (alpha-glucosidase inhibitor, amylin agonist, dipeptidyl-peptidase 4 (DPP-4) inhibitor PPAR)-gamma agonist (e.g., a thiazolidinedione (TZD) [such as ioglitazone, rosiglitazone, rivoglitazone, or troglitazone], aleglitazar, farglitazar, muraglitazar, or tesaglitazar), a glucagon-like peptide (GLP) agonist, anti-inflammatory agent (e.g., oral corticosteroid), nicotinamide nibonucleoside and analogs thereof, or a combination thereof.

In some examples, absorption of the compounds is substantially limited to the intestines. In other examples, the compound substantially enhances FXR target gene expression in the intestines while not substantially enhancing FXR target gene expression in the liver or kidney.

In some embodiments, administering the compounds reduces or prevents diet-induced weight gain and/or increases a metabolic rate in the subject. Increasing the metabolic rate may include enhancing oxidative phosphorylation in the subject.

In some embodiments, administering the compounds results in no substantial change in food intake and/or fat consumption in the subject, and/or no substantial change in appetite in the subject. Administering the compounds can protect against diet-induced weight gain, reduce inflammation, enhance thermogenesis, enhance insulin sensitivity in the liver, reduce hepatic steatosis, promote browning of white adipose tissue (WAT), promote activation of brown adipose tissue (BAT), decrease blood glucose, increase weight loss, or any combination thereof. In particular embodiments, administering the compounds enhances insulin sensitivity in the liver and promotes BAT activation.

Exemplary metabolic disorders include but are not limited to: obesity (such as a BMI of greater than 25, at least 30, at least 35, or at least 40, such as 25 to 30, 35 to 40, or over 40), diabetes, insulin resistance, dyslipidemia (such as an elevated serum lipids and/or triglycerides, such as a serum LDL of at least 100 mg/dL, such as at least 130 mg/dL, at least 160 mg/dL or at least 200 mg/dL, such as 100 to 129 mg/dL, 130 to 159 mg/dL, 160 to 199 mg/dL or greater than 200 mg/dL, and/or such as a serum triglyceride of at least of at least 151 mg/dL, such as at least 200 mg/dL, or at least 500 mg/dL, such as 151 to 199 mg/dL, 200 to 499 mg/dL or greater than 499 mg/dL) or any combination thereof. In particular examples, the metabolic disorder is non-insulin dependent diabetes mellitus.

Embodiments of a method for treating or preventing inflammation in an intestinal region of a subject are also disclosed. Administering to a subject a therapeutically effective amount of one or more of the disclosed compounds, or one or more of the disclosed compositions, such as 1, 2, 3, 4, or 5 of such compounds and/or compositions, activates FXR receptors in the intestines, thereby treating or substantially preventing inflammation in the intestinal region of the subject. In some embodiments, the method further includes administering a therapeutically effective amount of an antibiotic (such as metronidazole, vancomycin, and/or fidaxomicin) to the subject, such as to treat or substantially prevent inflammation associated with pseudomembranous colitis in the subject. In other embodiments, the method comprises administering to the subject a therapeutically effective amount of an oral corticosteroid and/or other anti-inflammatory or immunomodulatory therapy in combination with the compound, and/or in combination with an antibiotic.

Intestinal inflammation may be associated with a clinical condition selected from necrotizing enterocolitis, gastritis, ulcerative colitis, Crohn's disease, inflammatory bowel disease, irritable bowel syndrome, gastroenteritis, radiation induced enteritis, pseudomembranous colitis, chemotherapy induced enteritis, gastro-esophageal reflux disease (GERD), peptic ulcer, non-ulcer dyspepsia (NUD), celiac disease, intestinal celiac disease, post-surgical inflammation, gastric carcinogenesis, infectious colitis, or any combination thereof. In certain examples, the one or more FXR target genes comprises IBABP, OSTα, Per1, FGF15, FGF19, or combinations thereof.

Embodiments of a method for treating or preventing cholestatic disorders in subject (such as an adult or pediatric subject) are also disclosed. Administering to a subject a therapeutically effective amount of one or more of the disclosed compounds, or one or more of the disclosed compositions, such as 1, 2, 3, 4, or 5 of such compounds, can be used to treat or prevent a cholestatic disorder in subject. Cholestasis is a condition where bile cannot flow (or flow is significantly reduced) from the liver to the duodenum, for example due to a mechanical blockage (e.g., gallstone, malignancy, or congenital defect), or as a result of a defect in bile formation (e.g., due to a genetic defect, side effect of medication). Examples of such disorders include, but are not limited to, primary biliary cirrhosis (PBC), primary sclerosing cholangitis (PSC), overlap syndrome (PBC plus autoimmune hepatitis), cholestasis resulting from a drug (e.g., one or more of androgen, birth control pills, gold salts, nitrofurantoin, anabolic steroids, chlorpromazine, prochlorperazine, sulindac, cimetidine, estrogen, statins, and antibiotics such as TMP/SMX, flucoxacillin and erythromycin), drug-induced cholestatic hepatitis, total parenteral nutrition (TPN)-induced cholestasis, ICU/sepsis-related cholestasis, obstetric cholestasis, graft vs. host disease, prolonged cholestasis due to hepatitis A, B or C infection, cholestasis due to cystic fibrosis, alcoholic hepatitis, progressive familial intrahepatic cholestasis (PFIC) syndromes, Alagille syndrome, biliary atresia, or any combination thereof. In some embodiments, the method further includes administering a therapeutically effective amount of another therapeutic agent (such as ursodeoxycholic acid, phenobarbital, methotrexate, fat-soluble vitamins, or combinations thereof) to the subject, such as to treat or substantially prevent one or more cholestatic disorders in the subject.

Embodiments of a method for treating or preventing intestinal permeability conditions in subject are also disclosed. Administering to a subject a therapeutically effective amount of one or more of the disclosed compounds, or one or more of the disclosed compositions, such as 1, 2, 3, 4, or 5 of such compounds, can be used to treat or prevent an intestinal permeability condition in subject. Intestinal permeability is a condition where the gut wall exhibits excessive permeability (which some in the field call leaky gut syndrome). Examples of such disorders include, but are not limited to, Crohn's disease, ulcerative colitis, infectious colitis, celiac disease, type 1 diabetes, inflammatory bowel disease, irritable bowel syndrome, or any combination thereof. In some embodiments, the method further includes administering a therapeutically effective amount of another therapeutic agent (such as glutamine, prebiotics, probiotics, *Escherichia coli* Nissle 1917, or combinations thereof) to the subject, such as to treat or substantially prevent one or more intestinal permeability disorders in the subject.

Embodiments of a method for treating or preventing disorder that causes or results from an altered intestinal microbiome in subject are also disclosed. Administering to a subject a therapeutically effective amount of one or more of the disclosed compounds, or one or more of the disclosed compositions, such as 1, 2, 3, 4, or 5 of such compounds, can be used to treat or prevent a disorder resulting altered intestinal microbiome in subject. An altered intestinal microbiome is a condition where the abundance and/or types of bacteria (such as *Bacteriodes. E. coli, Lactobacillus*, and *Bifidobacteria* species) and other microbes (such as yeast) in the intestine are abnormal. Examples of disorders that can have an altered gut microbiome include, but are not limited to, celiac disease, the intestinal permeability conditions described herein, the intestinal inflammation disorders described herein, alcoholic hepatitis, necrotizing enterocolitis, Crohn's disease, ulcerative colitis, intestinal lesions (such as those in a cystic fibrosis patient), cirrhosis, or any combination thereof. In some embodiments, the method further includes administering a therapeutically effective amount of another therapeutic agent (such as a fecal microbiota transplant, immunosuppressant, antibiotic, mesalamine, steroid, altered diet, or combinations thereof) to the subject, such as to treat or substantially prevent one or more disorders resulting from or that causes an altered intestinal microbiome in the subject.

Embodiments of a method for treating an inborn error of metabolism in subject are also disclosed. Administering to a subject a therapeutically effective amount of one or more of the disclosed compounds, or one or more of the disclosed compositions, such as 1, 2, 3, 4, or 5 of such compounds, can be used to treat or prevent an inborn error of metabolism in subject. An inborn error of metabolism is a genetic condition resulting in accumulation of substance which interfere with normal function or the reduced ability to synthesize essential compounds, (such as a reduction in bile acid production, lipid production, or lipid storage). One example of an inborn error of metabolism is cerebrotendinous xanthomatosis (CTX). In some embodiments, the method further includes administering a therapeutically effective amount of another therapeutic agent (such as chenodeoxycholic acid (CDCA), an HMG-CoA reductase inhibitor ("statins" such as simvastatin) or combinations thereof) to the subject, such as to treat an inborn error of metabolism in the subject.

Embodiments of a method for treating or preventing a bile disorder in subject are also disclosed. Administering to a subject a therapeutically effective amount of one or more of the disclosed compounds, or one or more of the disclosed compositions, such as 1, 2, 3, 4, or 5 of such compounds, can be used to treat or prevent a bile disorder in subject. Bile disorders include mechanical biliary obstructions, disorders that result from bile acid malabsorption, and bile acid synthesis disorders. Examples of bile disorders that can be treated with the disclosed compounds include, but are not limited to, benign biliary stricture, malignant biliary obstruction, bile acid diarrhea, or any combination thereof. In some embodiments, the method further includes administering a therapeutically effective amount of another therapeutic agent (such as bile acid sequestrant, cholestyramine, colestipol, farnesoid X receptor agonist (such as obeticholic acid), or combinations thereof) to the subject, such as to treat or prevent a bile disorder in the subject.

Embodiments of a method for treating or preventing a malabsorption disorder (e.g., intestinal malabsorption), such as short bowel syndrome (or symptoms arising from such, such as diarrhea, steatorrhea, malnutrition, fatigue, vitamin deficiency), environmental enteropathy, or tropical sprue, in subject are also disclosed. Administering to a subject a therapeutically effective amount of one or more of the disclosed compounds, or one or more of the disclosed compositions, such as 1, 2, 3, 4, or 5 of such compounds, can be used to treat a malabsorption disorder in subject. Short bowel syndrome is a malabsorption disorder causes by surgical removal of the small intestine or dysfunction of a large segment of bowel. Short bowel syndrome can be caused by a birth defect, Crohn's disease, volvulus, tumors, injury, necrotizing enterocolitis, or surgery. Environmental enteropathy is a malabsorption disease believed to be due to frequent intestinal infections, which can result in chronic malnutrition and growth stunting. Tropical sprue is a malabsorption disease found in tropical regions, with abnormal flattening of the villi and inflammation of the small intestine. In some embodiments, the method further includes administering a therapeutically effective amount of another therapeutic agent (such as an anti-diarrheal medicine such as loperamide or codeine, vitamin supplement (such as $B_{12}$ and folic acid), mineral supplement, L glutamine, proton pump inhibitors, lactase, tedulutide (a glucagon-like peptide-2 analog), total parenteral nutrition, antibiotic (e.g., tetracycline or sulfamethoxazole/trimethoprim) or combinations thereof) to the subject, such as to treat or prevent a malabsorption disorder in the subject.

Embodiments of a method for treating or preventing a cell proliferation disease (e.g., cancer, such as adenocarcinoma, such as cancer of the colon, jejunum, and/or ileum), for example in an intestinal region of a subject, are also disclosed. Administering to a subject a therapeutically effective amount of one or more of the disclosed compounds, or one or more of the disclosed compositions, such as 1, 2, 3, 4, or 5 of such compounds and/or compositions, activates FXR receptors in the intestines, thereby treating or substantially preventing a cell proliferation disease, for example in the intestinal region of the subject. In some embodiments, the method further includes administering a therapeutically effective amount of another therapeutic agent, (such as a chemotherapeutic, a biologic, a radiotherapeutic, or combinations thereof) to the subject, such as to treat or substantially prevent a cell proliferation disease in the subject.

Embodiments of a method for treating or preventing alcoholic liver disease (e.g., fatty liver (steatosis), cirrhosis, alcoholic hepatitis), nonalcoholic steatohepatitis (NASH), or nonalcoholic fatty liver disease (NAFLD), in a subject, are also disclosed. Administering to a subject a therapeutically effective amount of one or more of the disclosed compounds, or one or more of the disclosed compositions, such as 1, 2, 3, 4, or 5 of such compounds and/or compositions, can treat or substantially preventing alcoholic liver disease, NASH, or NAFLD. In some embodiments, the method further includes administering a therapeutically effective amount of another therapeutic agent, (such as a corticosteroid, anti-tumor necrosis factor (TNF) or combinations thereof) to the subject, such as to treat or substantially prevent alcoholic liver disease, NASH, or NAFLD in the subject.

In any of the above embodiments, the method may increase HSL phosphorylation and β3-adrenergic receptor expression (such as an increase of at least 20%, at least 25%, at least 30%, at least 40%, at least 50%, at least 75%, or at least 100%). Additionally, the serum concentration of the compound in the subject may remain below its $EC_{50}$ following administration of the compound.

Also disclosed herein are embodiments of a method for making the disclosed compounds. In some embodiments, the method comprises reacting an aldehyde with a first amine to form an imine, reacting the imine with a reducing agent to form a second amine, and reacting the second amine with an activated carboxylic acid derivative or a carboxylic acid to form an amide. In certain embodiments, the method further comprising reacting the aldehyde with a boronic acid, and/or reacting the amide with a vinyl ester. In other embodiments, the method further comprises reacting the first amine with a vinyl ester, and/or reacting the amide with a boronic acid. The reducing agent may be a deuterated reducing agent to produce compounds comprising deuterium.

The foregoing and other objects and features of the disclosure will become more apparent from the following detailed description, which proceeds with reference to the accompanying figures.

BRIEF DESCRIPTION OF THE DRAWINGS

This application contains at least one drawing executed in color. Copies of any patent(s) issuing from this application, or patent application publication(s), with color drawing(s) will be provided by the Office upon request and payment of the necessary fee.

FIG. 1A shows FXR target SHP gene expression in FXR abundant tissues including liver, kidney and intestine from 8 week-old mice that were treated with vehicle or fexaramine (100 mg/kg) via oral (PO) or intraperitoneal (IP) injection for three days. FXR target gene expression was analyzed by qPCR. Gene expression was normalized against a vehicle-treated group.

FIG. 1B shows that PO administration of fexaramine (solid bars), but not vehicle (open bars), substantially enhances FXR target gene expression in the intestine, and not in the liver or kidney.

FIG. 1C shows that IP injection of fexaramine increases FXR target gene expression in the liver and kidney, in addition to the intestines. Data represent the mean±SD. Statistical analysis was performed with the Student's t test. $*p<0.05$, $**p<0.01$

FIGS. 2A-2G are graphs illustrating the reduction of diet-induced obesity and improvement in metabolic homeostasis with fexaramine. Mice were fed a high fat diet (HFD) for 14 weeks and then administered daily oral injections of vehicle (open boxes) or fexaramine (100 mg/kg) (solid boxes) for 5 weeks with HFD. Data represent the mean±STD. Statistical analysis was performed with the Student's t test ($*p<0.05$, $**p<0.01$).

FIG. 2A is a line chart illustrating changes in body weight of mice fed a high fat diet (HFD) for 14 weeks and then administered daily oral injections of vehicle (open boxes) or fexaramine (100 mg/kg) (solid boxes) for 5 weeks with HFD. n=8 per group.

FIG. 2B shows mice body weight composition by MRI at the completion of the study.

FIG. 2C shows the wet weight of inguinal fat (iWAT), gonadal fat (gWAT), mesenteric fat (mWAT), liver, kidney, heart and spleen at the completion of the study.

FIG. 2D shows the serum levels (samples were collected after 8 hours-fasting for parameter analysis) of insulin, cholesterol, leptin, resistin and triglycerides.

FIG. 2E shows the serum levels of cytokines at the completion of the study.

FIG. 2F is a line graph representing glucose tolerance testing (GTT), which revealed that fexaramine treatment improved glucose clearance.

FIG. 2G is a line graph representing insulin tolerance testing (ITT), which showed that fexaramine treatment improved insulin sensitivity.

FIG. 3A is a line graph showing hourly composite carbon dioxide production.

FIG. 3B is a line graph showing hourly composite oxygen consumption.

FIG. 3C is a glucose tolerance test.

FIG. 3D is a bar graph showing core body temperature.

FIGS. 5A-5I show that FXR is required for fexaramine's effects (A) Body weights, (B) glucose tolerance test, (C) insulin tolerance test, (D) oxygen consumption, (E) carbon dioxide production, (F) core body temperature, (G) brown adipose tissue gene expression, (H) liver gene expression, and (I) FXR target gene expressions in ileum of 14 week HFD fed FXR-null mice treated with vehicle or fexaramine (100 mg/kg) for 5 week with HFD. Data represent the mean±SD. Statistical analysis was performed with the Student's t test. $*p<0.05$, $**p<0.01$.

FIGS. 6A-6J demonstrate that fexaramine increases OXPHOS to enhance metabolic rate in brown adipose tissue. Mice were fed HFD for 14 weeks and then administered vehicle or fexaramine (100 mg/kg) daily by oral administration for 5 weeks with HFD. Data represent the mean±STD. Statistical analysis was performed with the Student's t test (*p<0.05, **p<0.01).

FIG. 6A is a bar chart showing daily food intake during the first week treatment.

FIG. 6B is a line chart showing carbon dioxide production.

FIG. 6C is a line chart showing oxygen consumption.

FIG. 6D is a bar chart showing daytime and nighttime cumulative ambulatory counts.

FIG. 6E is a bar chart showing core body temperature.

FIG. 6F shows hematoxyin and eosin staining of brown adipose tissue (BAT) for histological analysis.

FIG. 6G is a bar chart showing relative gene expression of nuclear receptors and other genes encoding proteins involved in mitochondrial biogenesis, glucose transport and FA oxidation in BAT.

FIG. 6H is a set of digital images of gel electrophoreses showing protein expression levels of total and phosphorylated p38 in BAT. RalA levels are shown as a loading control.

FIG. 6I is a bar chart showing the relative levels of phosphorylated p38 in BAT after vehicle (open bar) or Fexaramine administration (solid bar).

FIG. 6J is a chart showing changes in relative expression of OXPHOS genes based on RNA-sequencing transcriptomic analysis in inguinal fat (iWAT), gonadal fat (gWAT) and brown fat (BAT) after vehicle or fexaramine treatment.

FIG. 6K is a heatmap depiction of changes in genes involved in chemokine and cytokine signaling in BAT after vehicle or fexaramine treatment.

FIG. 6L is a bar graph showing PKA activity in BAT. Data represent the mean±SD. Statistical analysis was performed with the Student's t test. *p<0.05, **p<0.01.

FIG. 6M is a bar chart showing the effect of fexaramine on respiratory exchange ratio (RER). Mice were fed on HFD for 14 weeks, and then administered daily oral injections of vehicle or fexaramine (100 mg/kg) for 5 weeks with HFD. No changes were observed in respiratory exchange ratio by fexaramine treatment.

FIG. 6N is a bar graph showing the effect of fexaramine administration on serum lactate concentrations. Mice were fed on HFD for 14 weeks, and then administered daily oral injections of vehicle or fexaramine (100 mg/kg) for 5 weeks with HFD. Serum lactate levels were found to be significantly decreased with fexaramine treatment. Data represent the mean±STD. Statistical analysis was performed with the Student's t test (*p<0.05, **p<0.01).

FIGS. 7A-7H show a comparative expression chart and bar charts illustrating that fexaramine increased endogenous FGF15 signaling and changes in BA composition. Mice were fed HFD for 14 weeks and then administered daily oral injections of vehicle or fexaramine (100 mg/kg) for 5 weeks with HFD. In the bar graphs, open bars represent vehicle treatment and solid bars represent fexaramine treatment, and data represent the mean±STD. Statistical analysis was performed with the Student's t test (*p<0.05, **p<0.01).

FIG. 7A is a heatmap depicting changes in expression of ileal FXR target genes following PO fexaramine administration.

FIG. 7B is a bar chart showing FGF15 protein levels from ileal extract.

FIG. 7C is a bar chart showing FGF15 protein levels in the serum.

FIG. 7D is a bar chart showing changes in the expression of hepatic genes involved in bile acid metabolism.

FIG. 7E is a bar chart showing total serum bile acid (BA) levels.

FIG. 7F is a bar chart showing composition ratios of bile acids. The ratio of unconjugated to conjugated cholic acid was remarkably increased by fexaramine.

FIG. 7G is a bar chart showing changes in intestinal permeability.

FIG. 7H is a bar chart showing changes in expression of intestinal genes involved in mucosal defense.

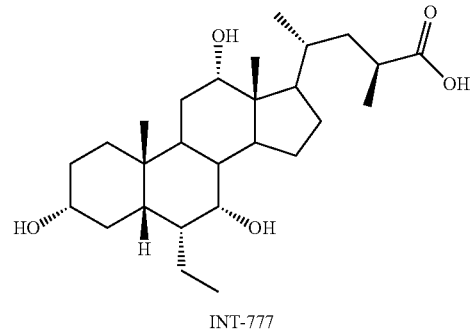 [SMILES: CC[C@H]1[C@@H](O)C2C3CCC([C@H](C)C[C@H](C)C(=O)O)[C@@]3(C)[C@@H](O)CC2[C@@]2(C)CC[C@@H](O)C[C@@H]12]

INT-777

FIGS. 10A-10F show that systemic TGR5 activation is required to affect glucose homeostasis. HFD-fed mice were treated with vehicle, the intestinally-restricted TGR5 ligand L755-0379 (A, L755, 100 mg/kg, EC50 300 nM) or the systemic ligand RO5527239 (B, RO, 100 mg/kg. EC50 70 nM) via per os for 14 days. C, Plasma L755 concentrations in portal and tail veins after PO administration. D, Body weight curve. E, Glucose tolerance test. F, Serum insulin levels after a glucose challenge. Data represent the mean±SD. Statistical analysis was performed with the Student's t test. *p<0.05, **p<0.01.

Figure 11A:
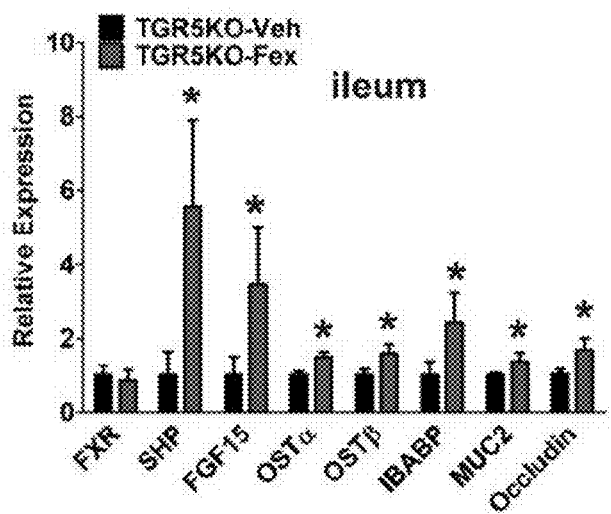

FIGS. 11A-11N show that TGR5 is required for a subset of fexaramine's effects. HFD-fed TGR5-null mice were treated with vehicle or fexaramine (100 mg/kg os daily for 5 weeks with HFD, n=10). (A) Heal FXR target gene expressions (B) Serum BA levels (C) Fasting glucose levels (D) Glucose tolerance test (E) Core body temperature (F) Oxygen consumption rate (G) Carbon dioxide production (H) Gene expression in BAT (I) Body weight curve (J) Body composition by MRI (K) Insulin Tolerance Test (L) Hepatic gene expression (M) Hepatic TG levels (N) and Gene expression in soleus of TGR5 knockout mice with and without fexaramine treatment. Data represent the mean±SD. Statistical analysis was performed with the Student's t test. *p<0.05, **p<0.01.

FIGS. 12A-12H demonstrate that fexaramine reduces inflammation and increases lipolysis in adipose tissues. Mice were fed on HFD for 14 weeks and subsequently subjected to daily PO injection of vehicle or fexaramine (100 mg/kg) for 5 weeks with HFD. In the bar graphs, open bars are vehicle, solid bars of fexaramine, and data represent the mean±STD. Statistical analysis was performed with the Student's t test (*p<0.05, **p<0.01).

FIG. 12A shows histological sections of mesenteric white adipose tissues from vehicle and fexaramine-treated mice.

FIG. 12B is a set of photographs of gel electrophoreses showing protein expression levels of TBK1, and total and phosphorylated IKKε and S6K, in gonadal adipose tissues (gWAT) from vehicle or fexaramine-treated mice.

FIG. 12C is a bar chart showing relative gene expression levels of β-3-adrenergic receptor and various cytokines in gonadal adipose tissue.

Figure 12D:
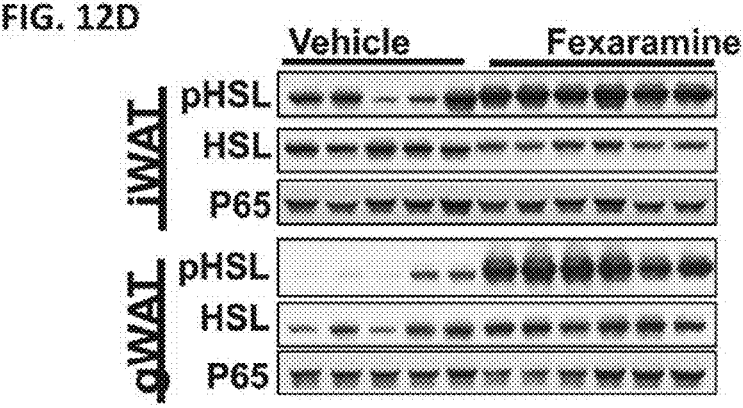

FIG. 12D is a set of photographs of gel electrophoreses showing protein expression levels of total and phosphorylated HSL (p-HSL) and p65 in gonadal and inguinal adipose tissues.

Figure 12E:
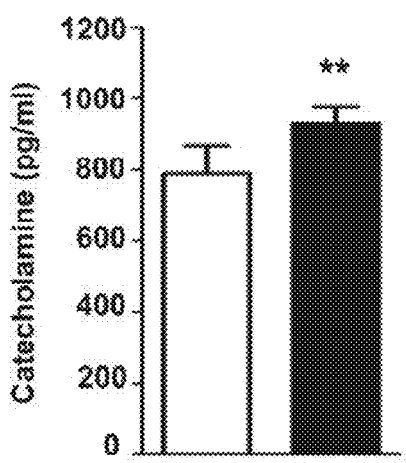

FIG. 12E is a bar chart showing serum levels of catecholamines, in vehicle or fexaramine-treated mice.

Figure 12F:
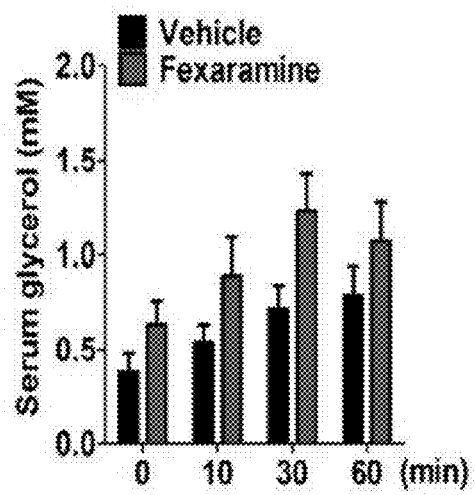

FIG. 12F is a bar chart showing serum glycerol levels, in vehicle or fexaramine-treated mice. Isoproterenol (1 μg/kg) was injected at 0 minutes and free glycerol levels were measured at the indicated time points.

Figure 12G:
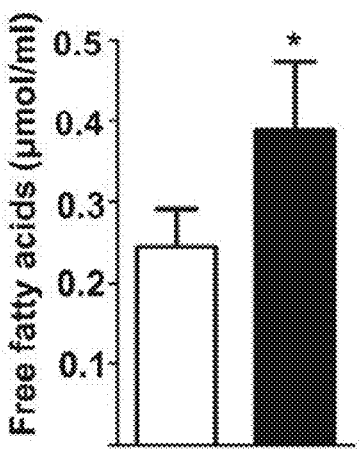

FIG. 12G is a bar chart showing serum levels of free fatty acids in vehicle or fexaramine-treated mice. Data represent the mean±STD. Statistical analysis was performed with the Student's t test (*p<0.05, **p<0.01).

Figure 12H:
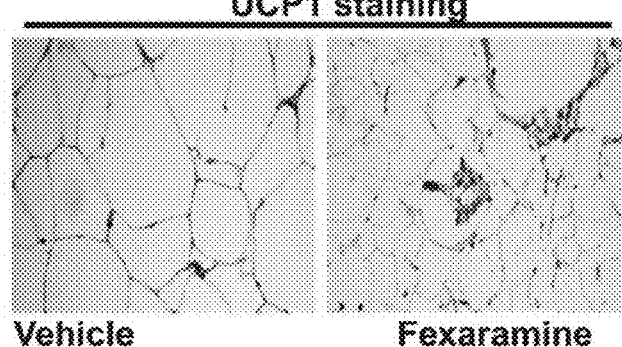

FIG. 12H shows UCP1 staining of brown fat-like cells in inguinal adipose tissues (iWAT) from vehicle or fexaramine-treated mice (Magnification: 100×).

Figure 12I:
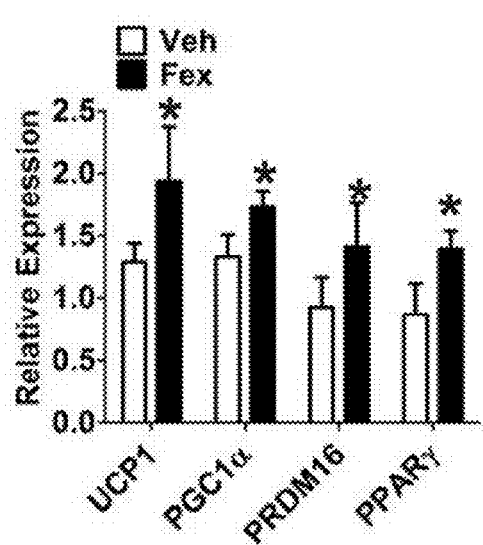
Figure 12J:
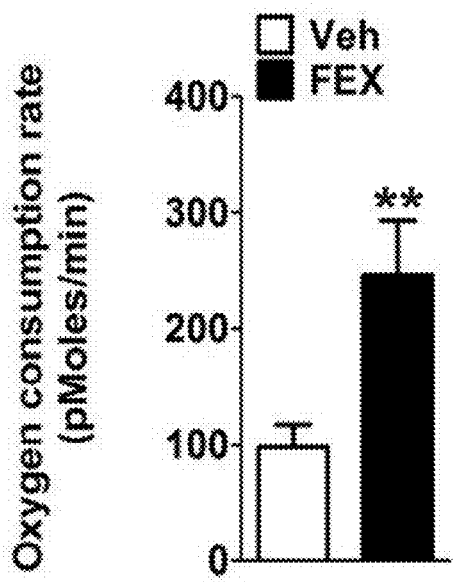

FIGS. 12I and 12J show that fexaramine enhances OXPHOS in iWAT. Mice fed a HFD for 14 weeks were maintained on a HFD and treated with vehicle or fexaramine (100 mg/kg/day os for 5 week). (I) Changes in genes associated with the browning of adipose tissue and (J) oxygen consumption rate of the stromal vascular fraction (SVF) from inguinal fat (iWAT). Data represent the mean±SD. Statistical analysis was performed with the Student's t test. *p<0.05, **p<0.01.

Figure 13:
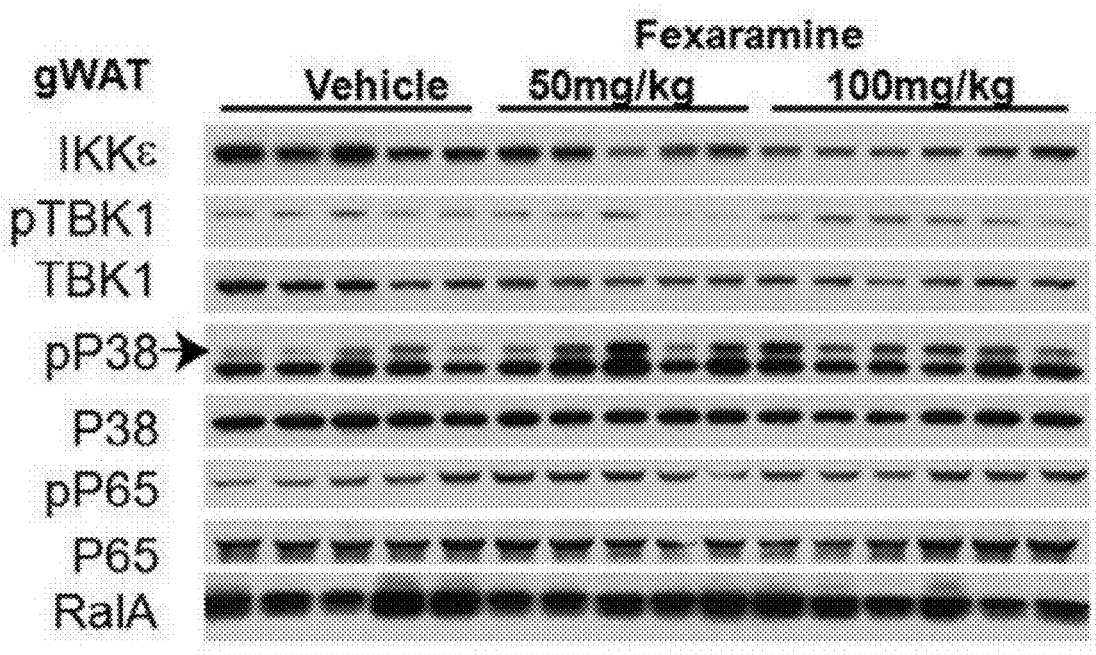

FIG. 13 is a set of digital images of gel electrophoreses (Western blots) showing the level of expression of various proteins in gonadal white adipose tissue (gWAT). Mice fed a HFD for 14 weeks were maintained on a HFD and treated with vehicle or fexaramine (50 mg or 100 mg/kg/day os for 5 week).

Figure 14:
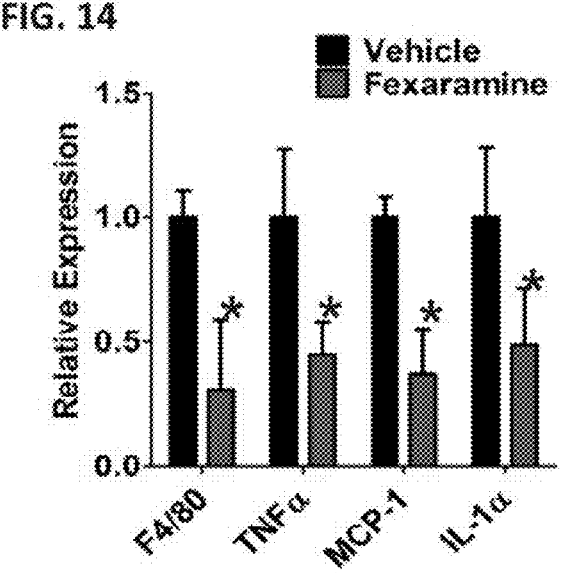

FIG. 14 is a bar chart showing that fexaramine reduces brown adipose tissue (BAT) inflammation. Mice fed a HFD for 14 weeks were maintained on a HFD and treated with vehicle or fexaramine (100 mg/kg/day os for 5 week). Expression of inflammatory cytokines in BAT. Data represent the mean±SD. Statistical analysis was performed with the Student's t test. *p<0.05, **p<0.01.

FIGS. 15A-15H are a set of histology stains and bar charts demonstrating that fexaramine induced less weight gain and improved glucose homeostasis relative to mice that did not receive fexaramine. Mice were fed HFD for 14 weeks and then subjected to daily PO injection of vehicle or fexaramine (100 mg/kg) for 5 weeks with HFD.

Figure 15A:
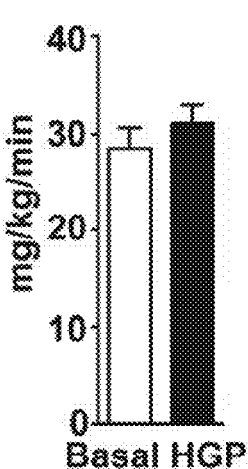

FIG. 15A is a bar chart showing basal hepatic glucose production (HGP).

Figure 15B:
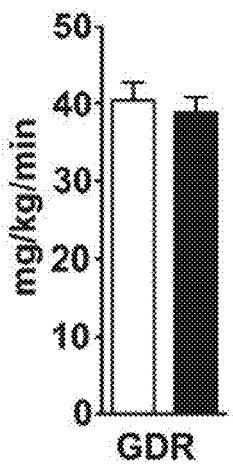

FIG. 15B is a bar chart showing glucose disposal rate (GDR).

Figure 15C:
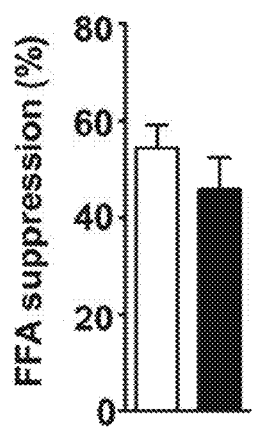

FIG. 15C is a bar chart showing percentage free fatty acid (FFA) suppression by insulin.

Figure 15D:
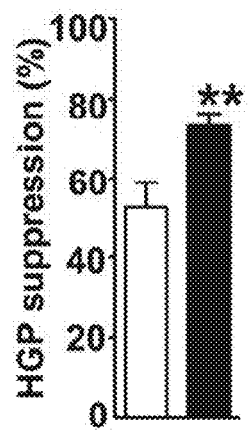

FIG. 15D is a bar chart showing HGP suppression by insulin, as measured by hyperinsulinemic-euglycemic clamps.

Figure 15E:
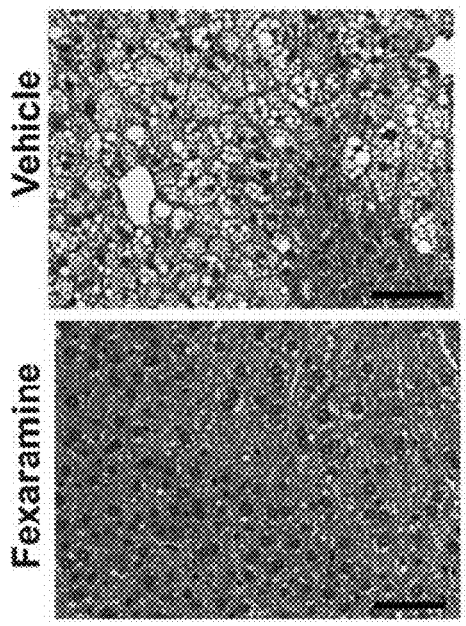

FIG. 15E shows hematoxylin and eosin staining for liver histology.

Figure 15F:
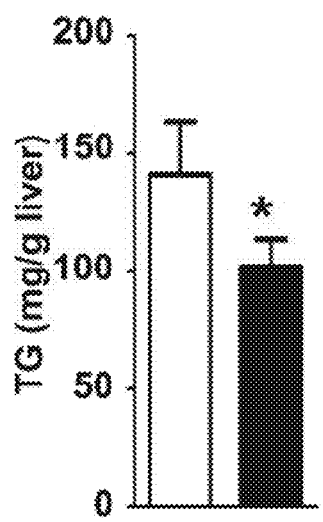

FIG. 15F is a bar chart showing triglyceride levels in the liver.

Figure 15G:
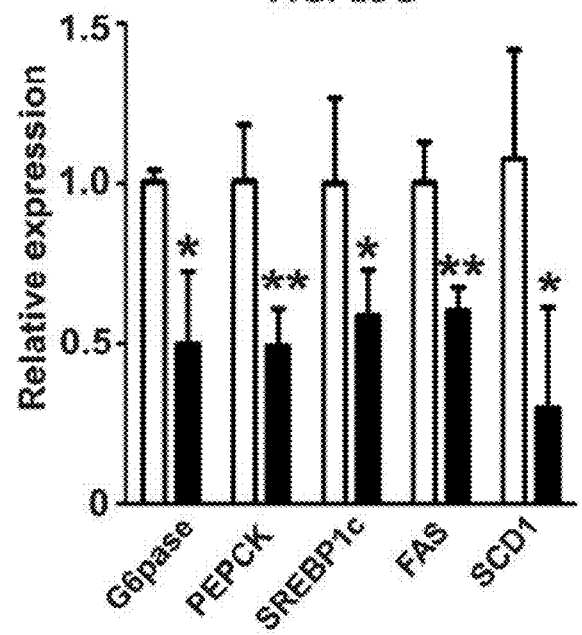

FIG. 15G is a bar chart showing hepatic gene expression levels for genes involved in gluconeogenesis and lipogenesis.

Figure 15H:
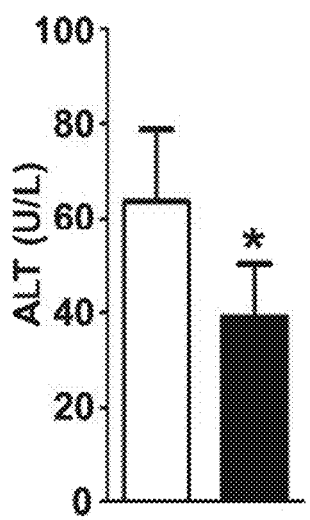

FIG. 15H is a bar chart showing serum levels of alanine aminotransferase (ALT).

Figure 15I:
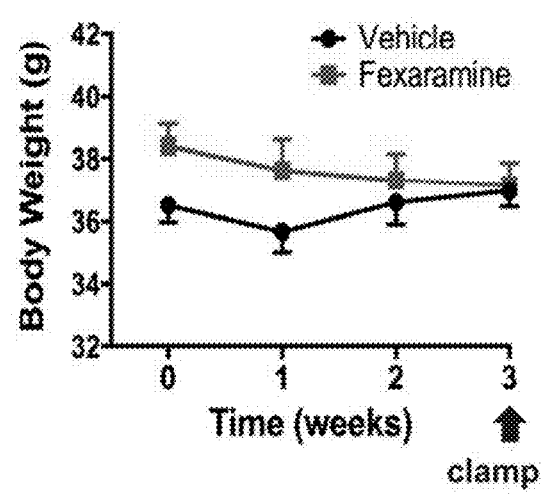
Figure 15J:
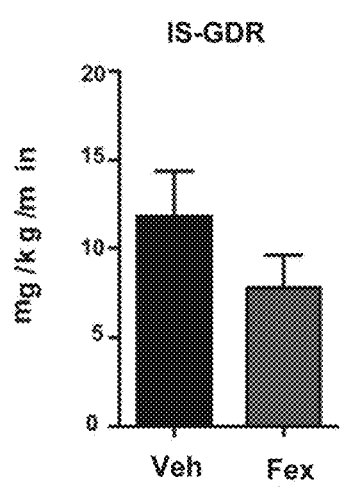
Figure 15K:
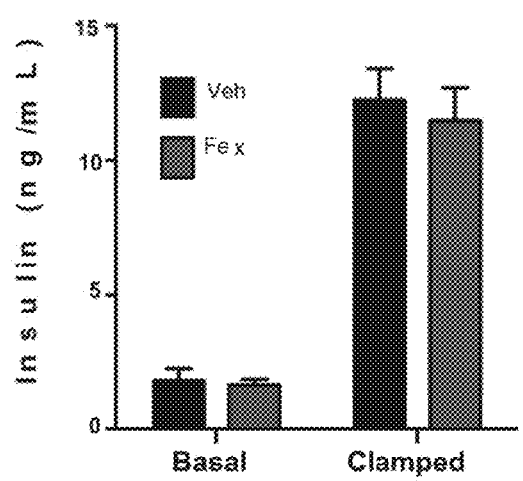

FIGS. 15I-15K are a line graph and two bar graphs showing the effect of fexaramine treatment on body weight, insulin-stimulated GDR, and fasting insulin levels. Mice were fed HFD for 14 weeks, and then administered daily oral injections of vehicle or fexaramine (100 mg/kg) for 3 weeks with HFD. The mice treated with fexaramine were initially heavier (by 2-3 grams). Three weeks after treatment, a clamp study was performed on the mice. Data represent the mean±STD. Statistical analysis was performed with the Student's t test (*p<0.05, **p<0.01).

FIG. 15I is a line graph showing the changes in body weight for the two groups of mice.

FIG. 15J is a bar chart showing the insulin-stimulated GDR (IS-GDR).

FIG. 15K is a bar chart showing the fasting insulin levels.

Figure 16B:
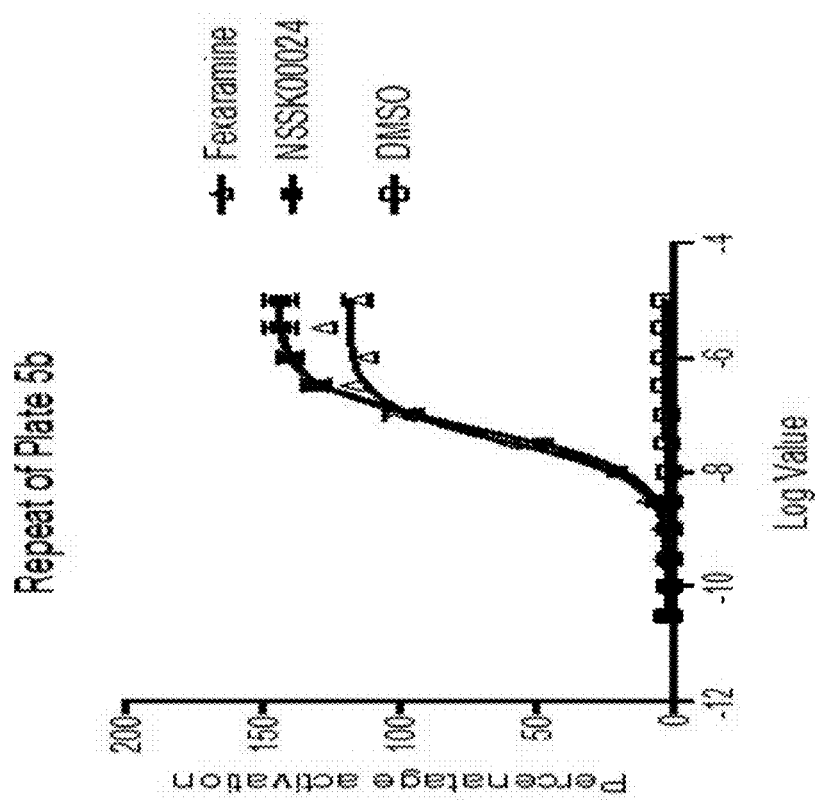
Figure 16A:
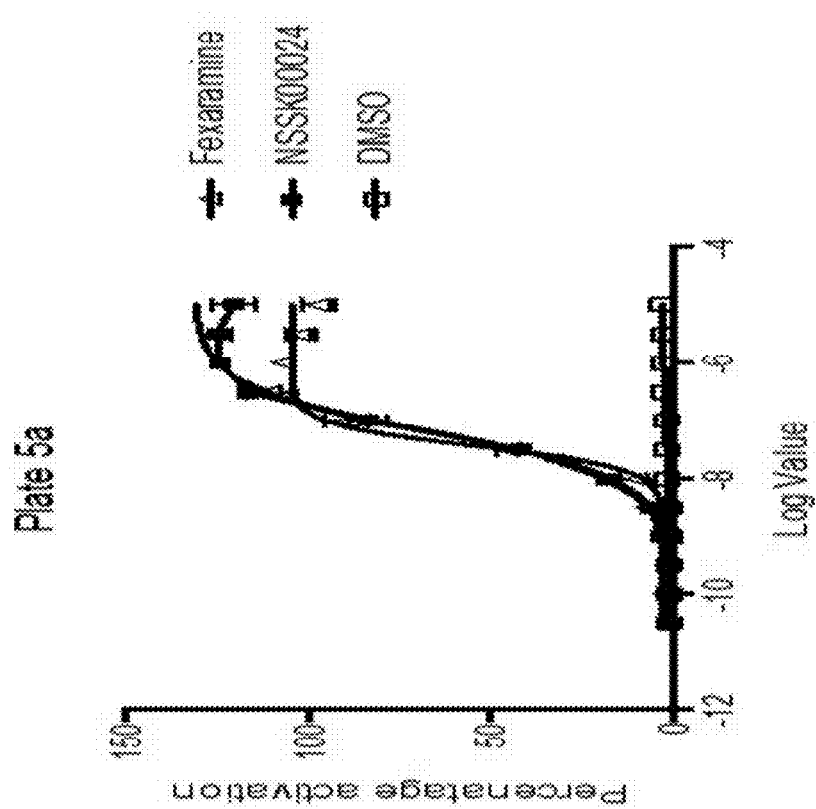
Figure 16C:
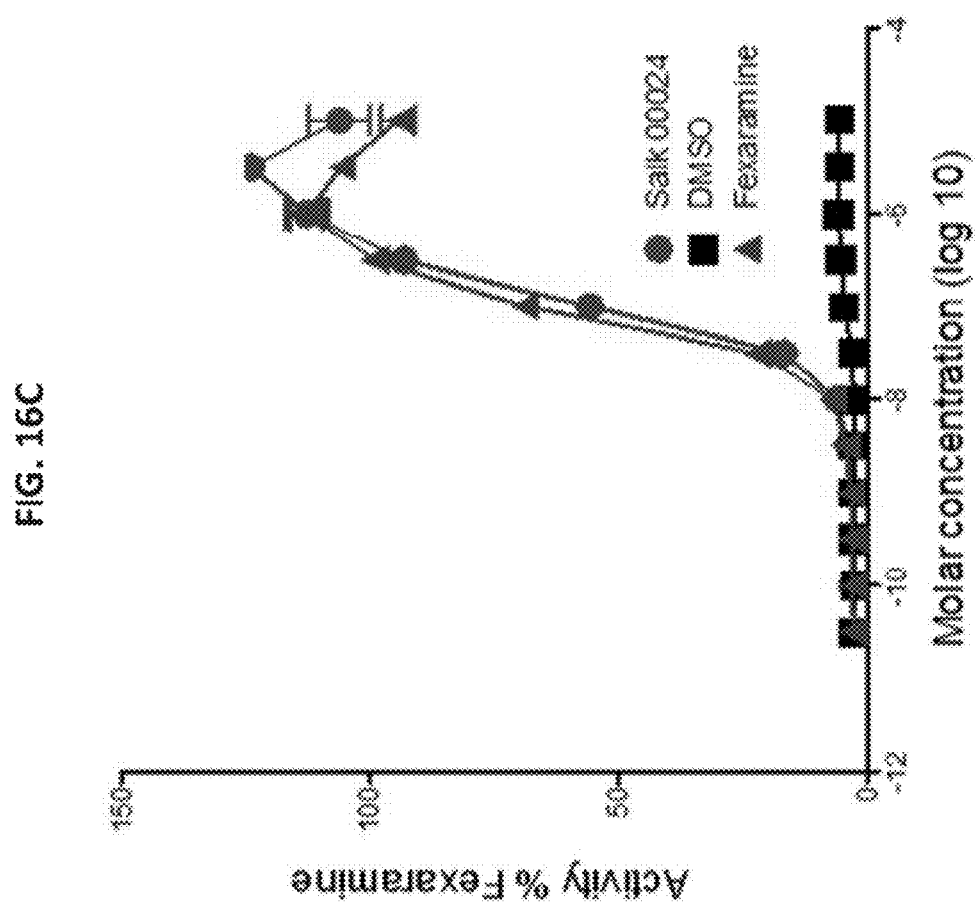

FIGS. 16A, 16B and 16C are graphs of percentage activation of FXR versus the log value of concentration for duplicate runs of NSSK00024, fexaramine and DMSO.

Figure 17C:
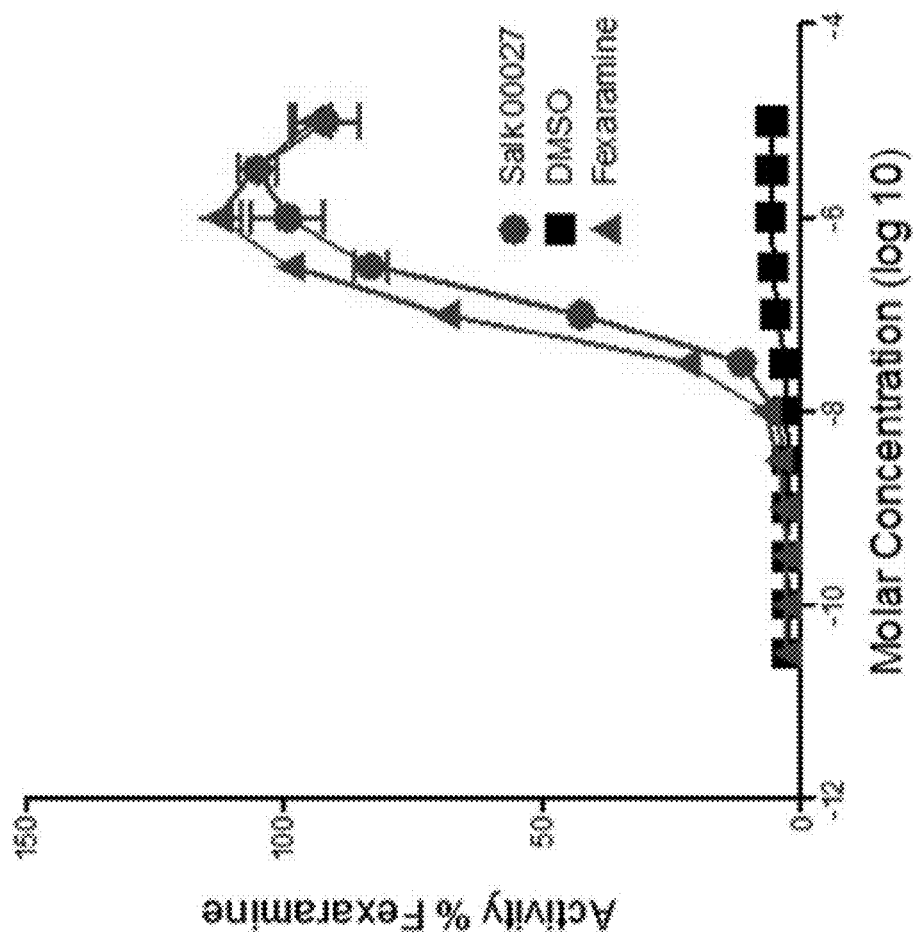

FIGS. 17A, 17B and 17C are graphs of percentage activation of FXR versus the log value of concentration for duplicate runs of NSSK00027, fexaramine and DMSO.

Figure 18B:
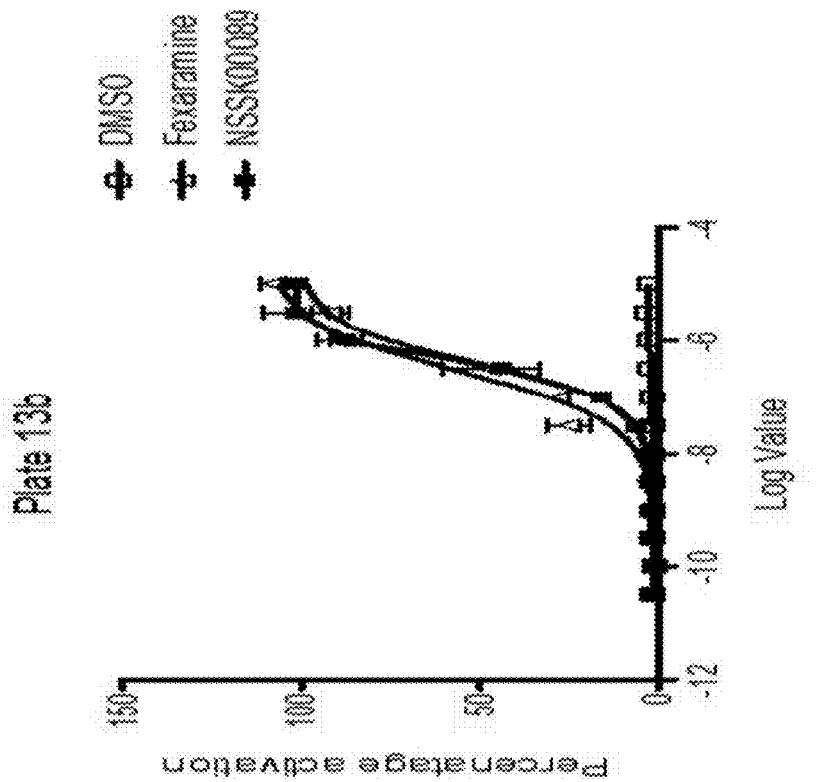
Figure 18A:
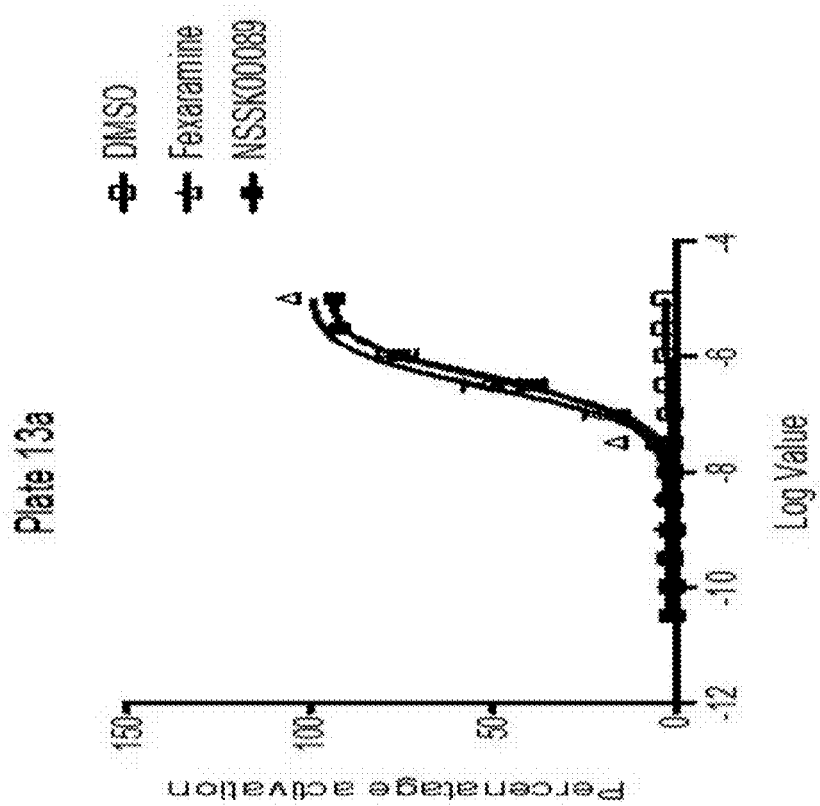
Figure 18C:
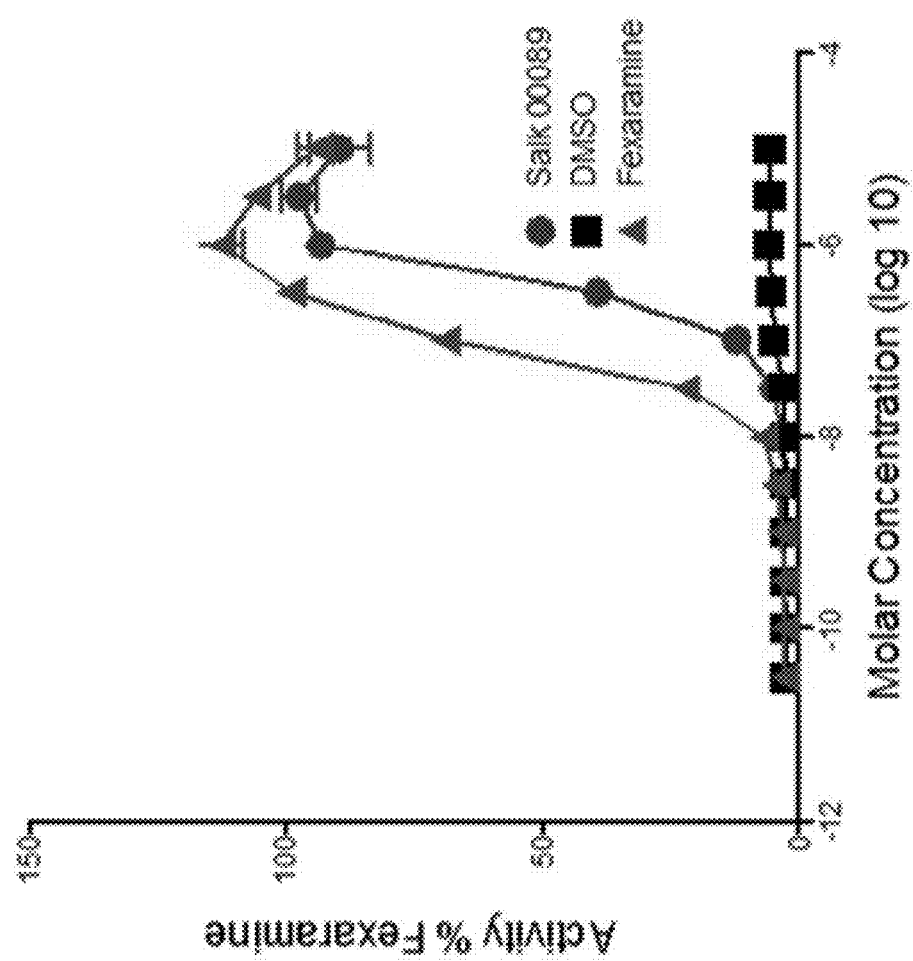

FIGS. 18A, 18B and 18C are graphs of percentage activation of FXR versus the log value of concentration for duplicate runs of NSSK00089, fexaramine and DMSO.

Figure 19A:
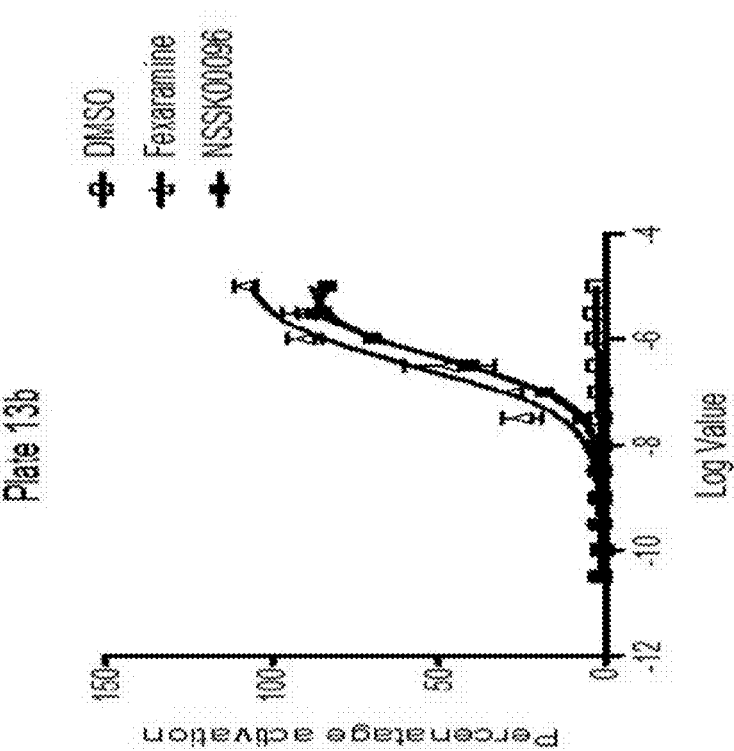
Figure 19B:
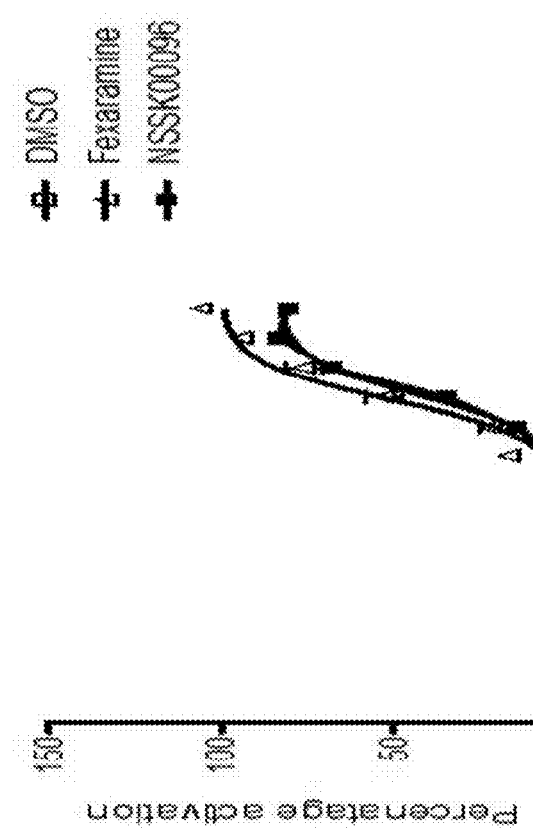
Figure 19C:
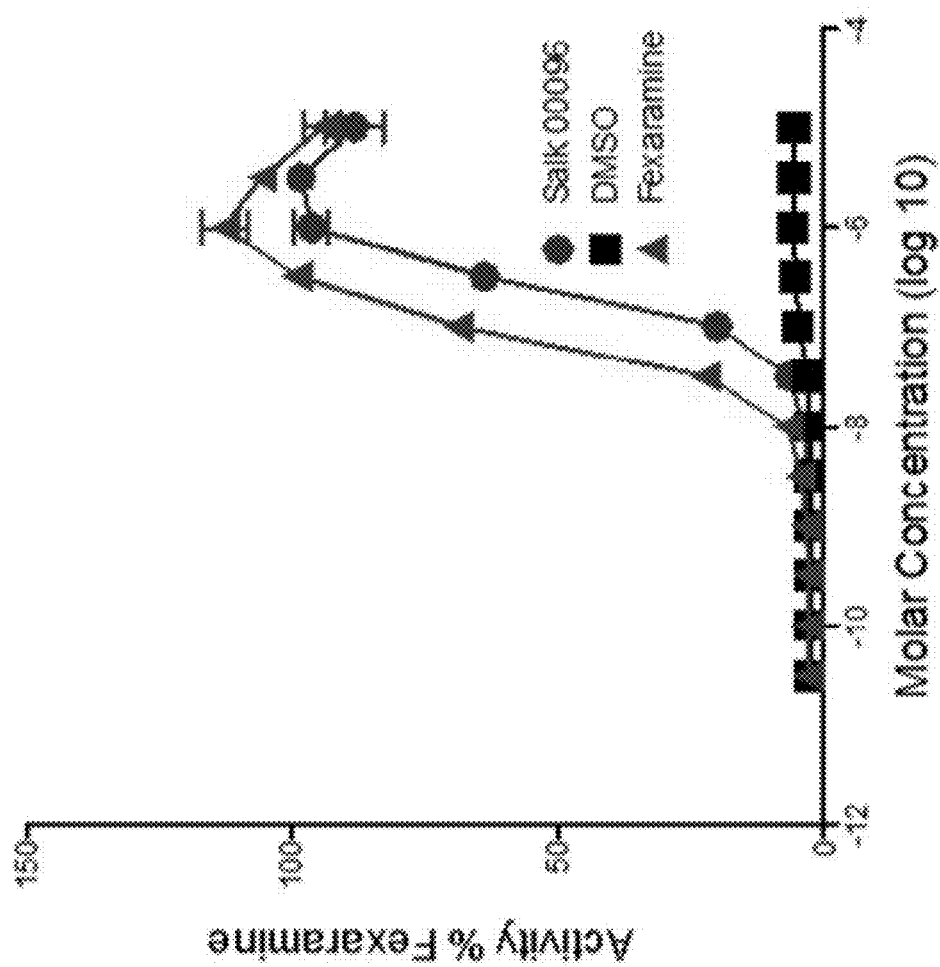

FIGS. 19A, 19B and 19C are graphs of percentage activation of FXR versus the log value of concentration for duplicate runs of NSSK00096, fexaramine and DMSO.

Figure 20A:
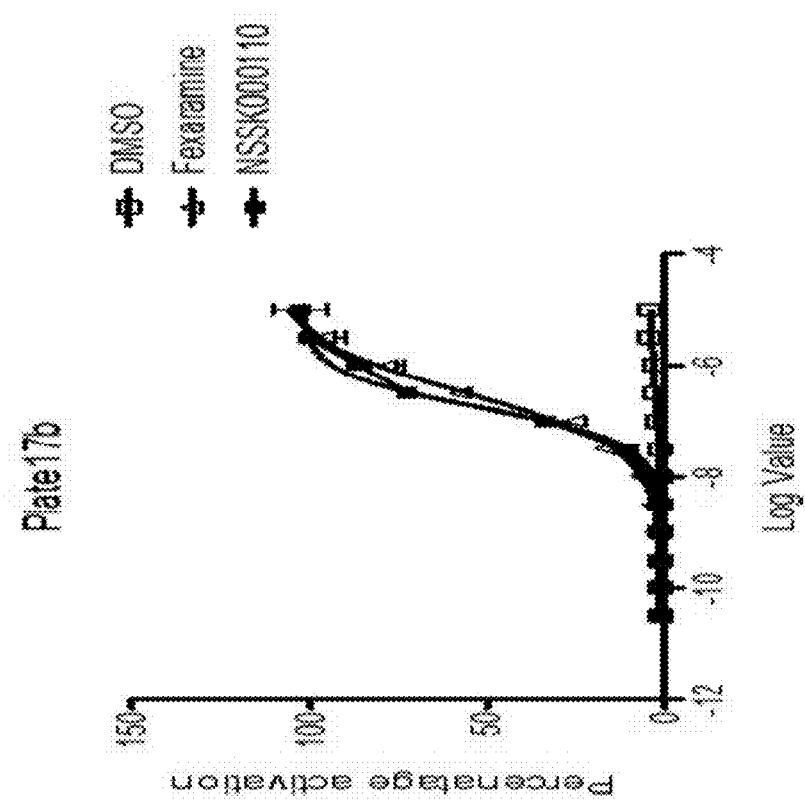
Figure 20B:
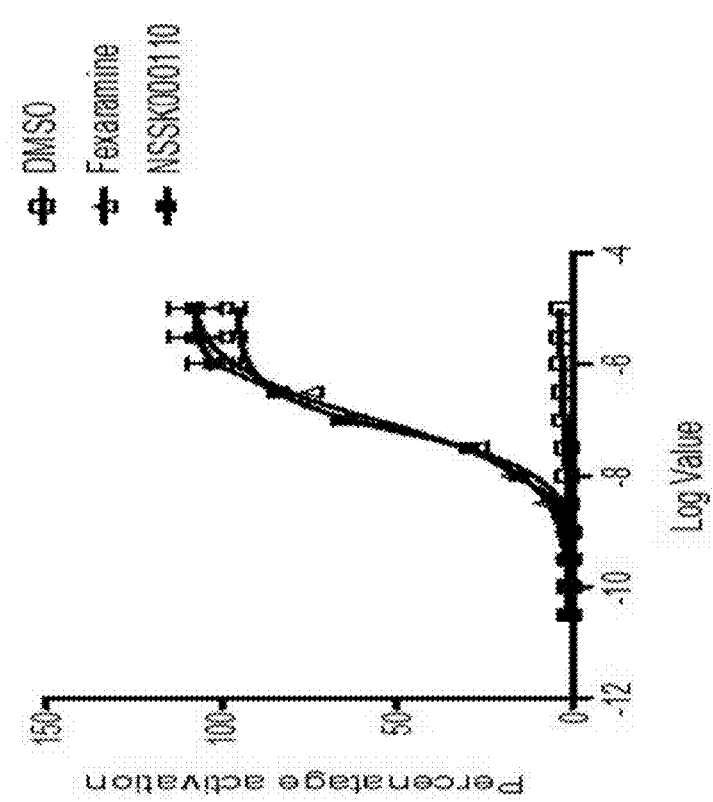
Figure 20C:
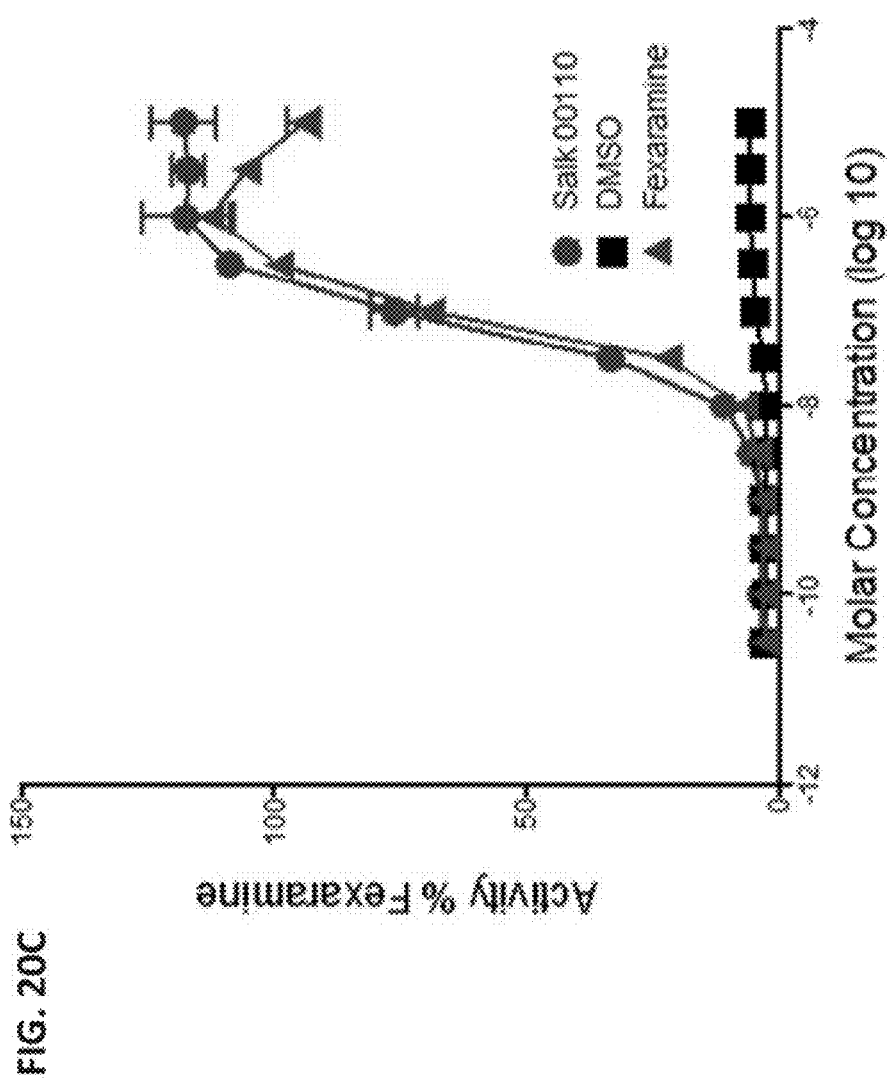

FIGS. 20A, 20B and 20C are graphs of percentage activation of FXR versus the log value of concentration for duplicate runs of NSSK00110, fexaramine and DMSO.

Figure 21:
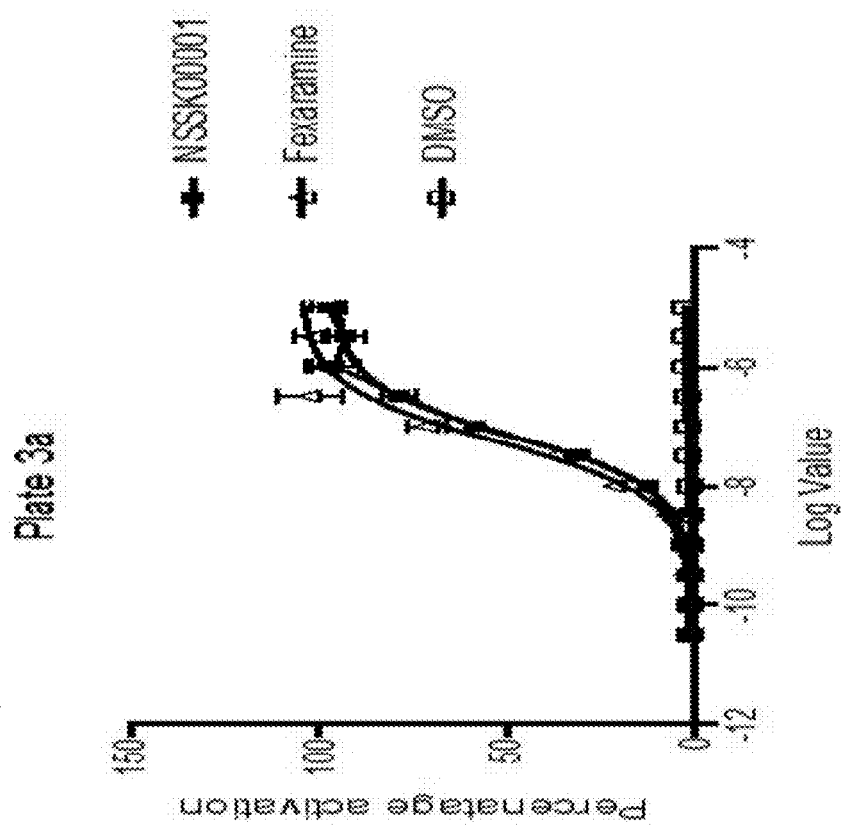

FIG. 21 is a graph of percentage activation of FXR versus the log value of concentration for NSSK00001, fexaramine and DMSO.

Figure 22:
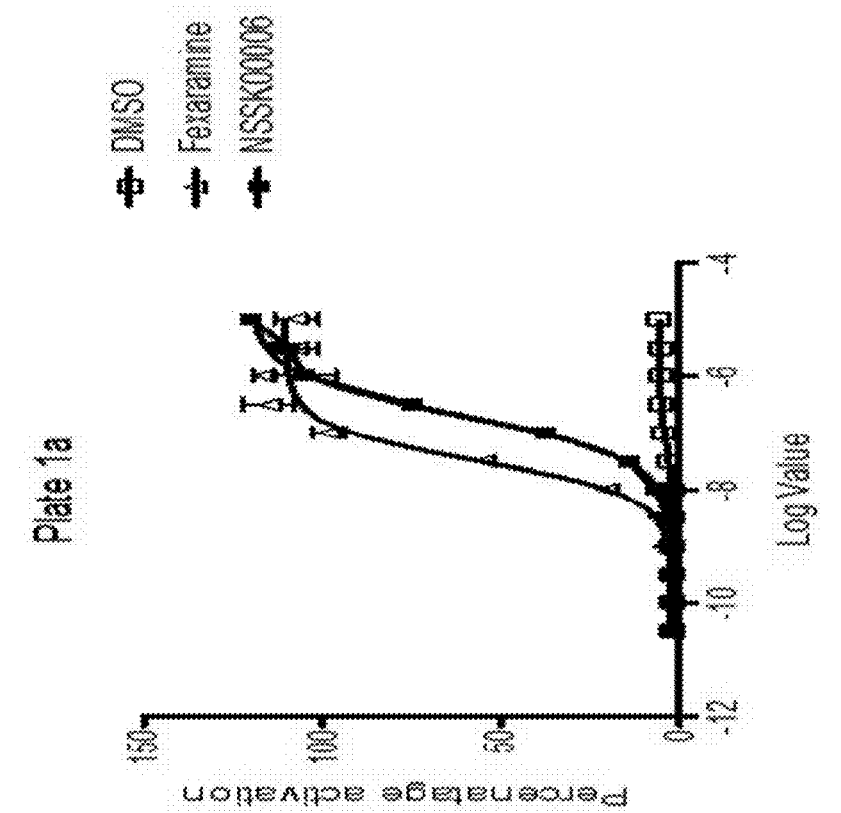

FIG. 22 is a graph of percentage activation of FXR versus the log value of concentration for NSSK00006, fexaramine and DMSO.

Figure 23:
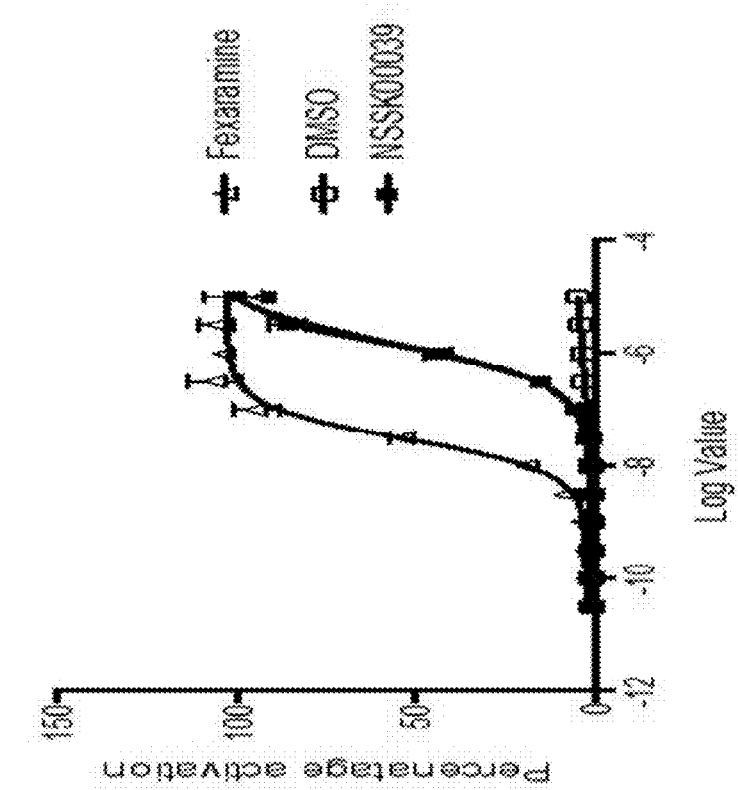

FIG. 23 is a graph of percentage activation of FXR versus the log value of concentration for NSSK00026, fexaramine and DMSO.

Figure 24:
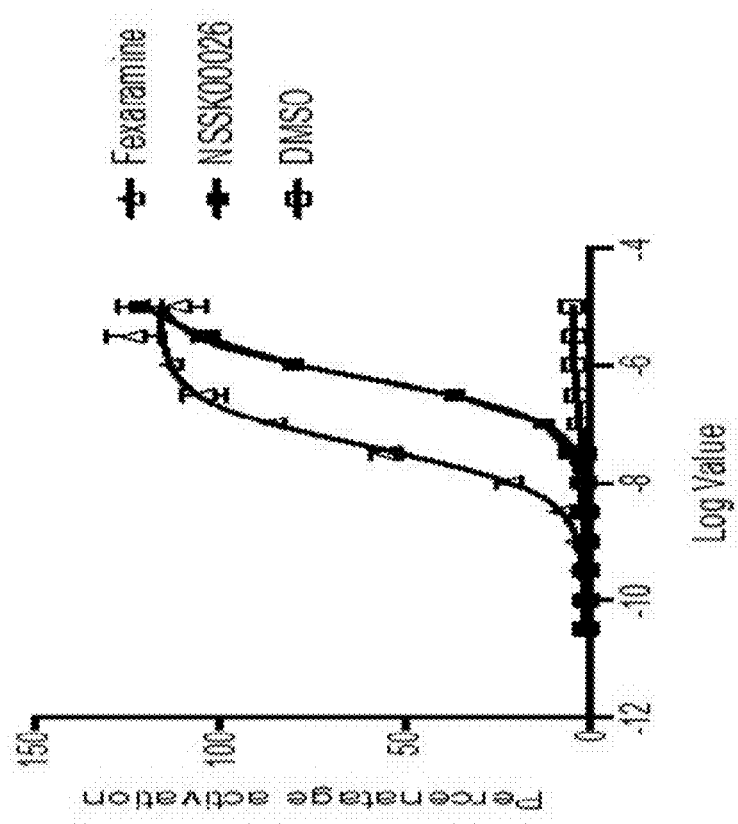

FIG. 24 is a graph of percentage activation of FXR versus the log value of concentration for NSSK00039, fexaramine and DMSO.

Figure 25:
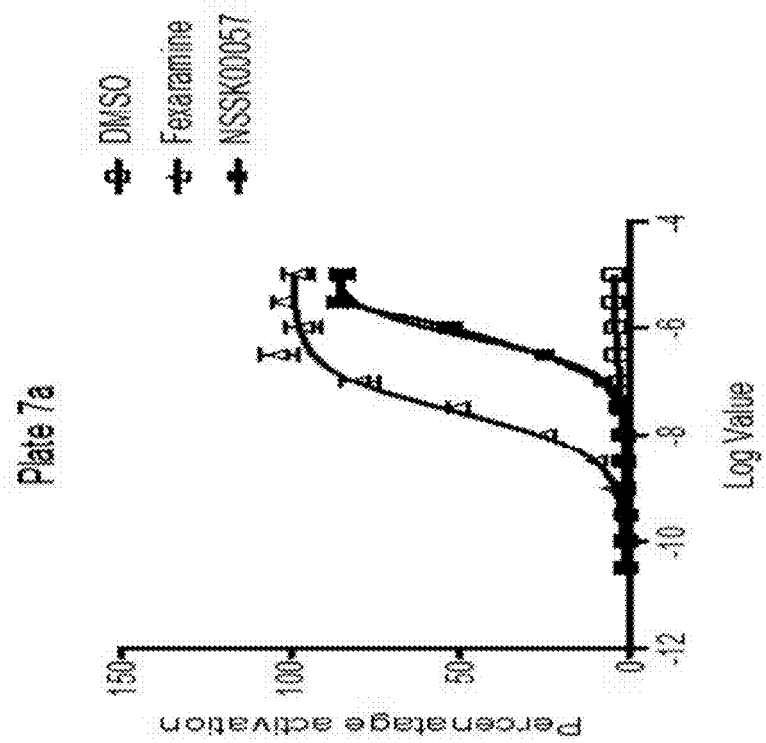

FIG. 25 is a graph of percentage activation of FXR versus the log value of concentration for NSSK00048, fexaramine and DMSO.

Figure 26:
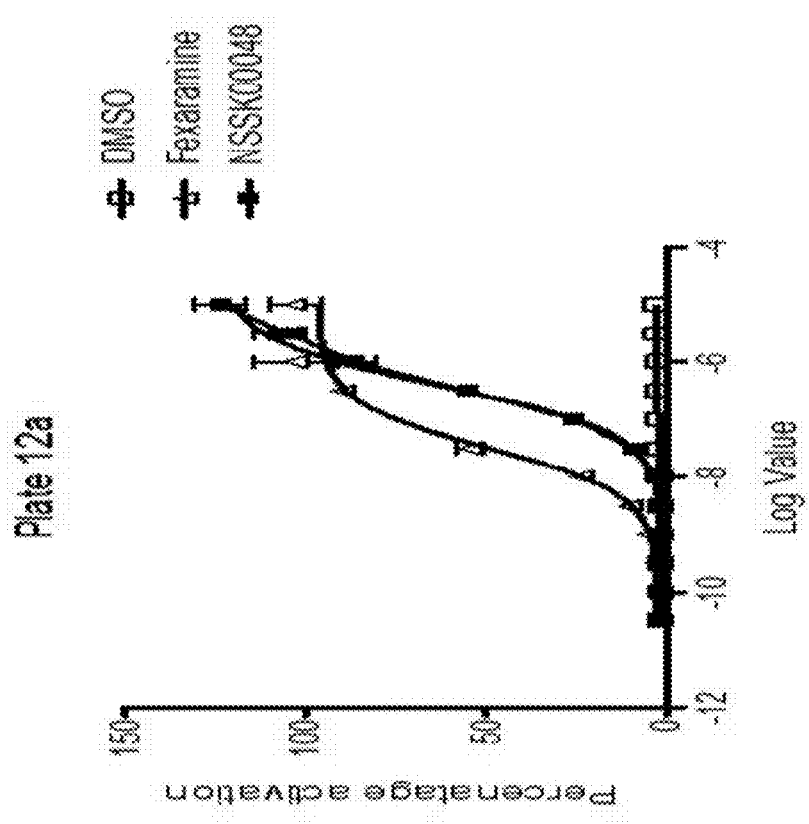

FIG. 26 is a graph of percentage activation of FXR versus the log value of concentration for NSSK00057, fexaramine and DMSO.

Figure 27:
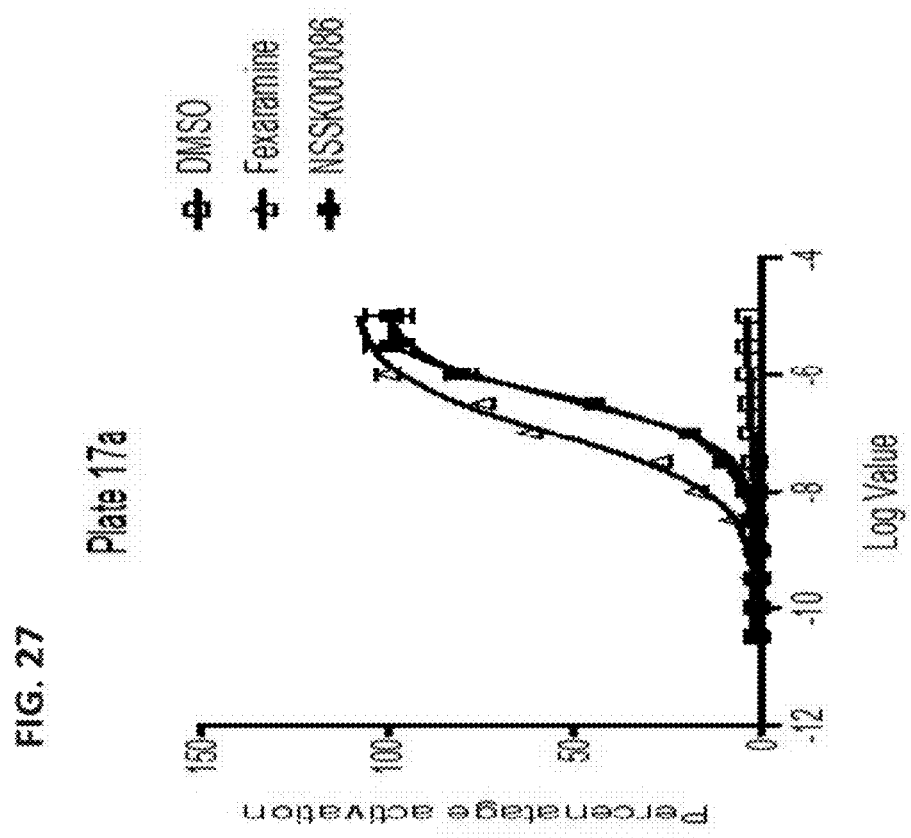

FIG. 27 is a graph of percentage activation of FXR versus the log value of concentration for NSSK00086, fexaramine and DMSO.

Figure 28B:
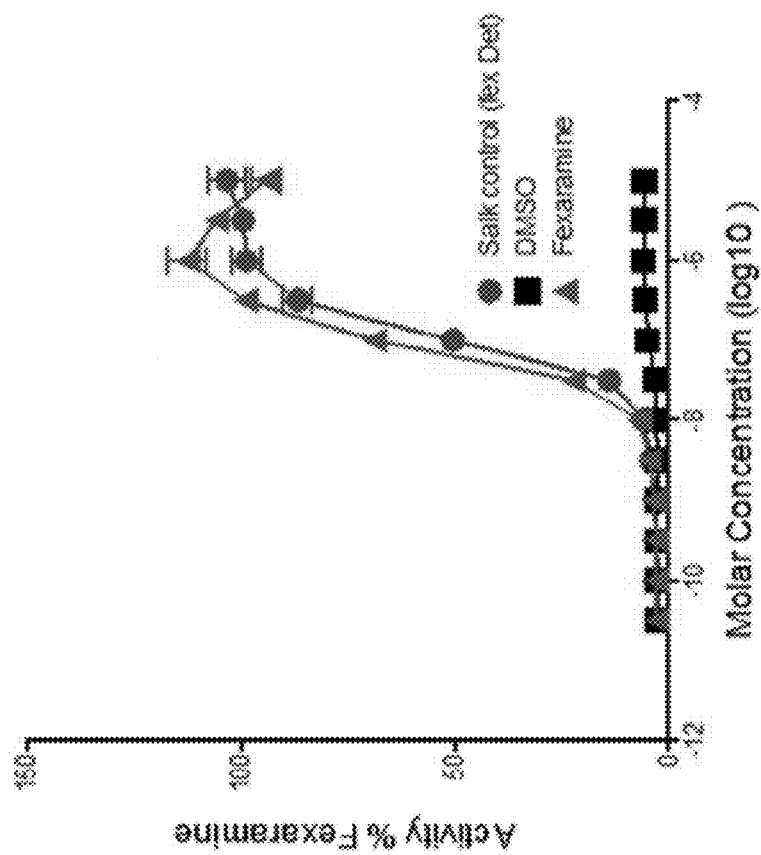
Figure 28A:
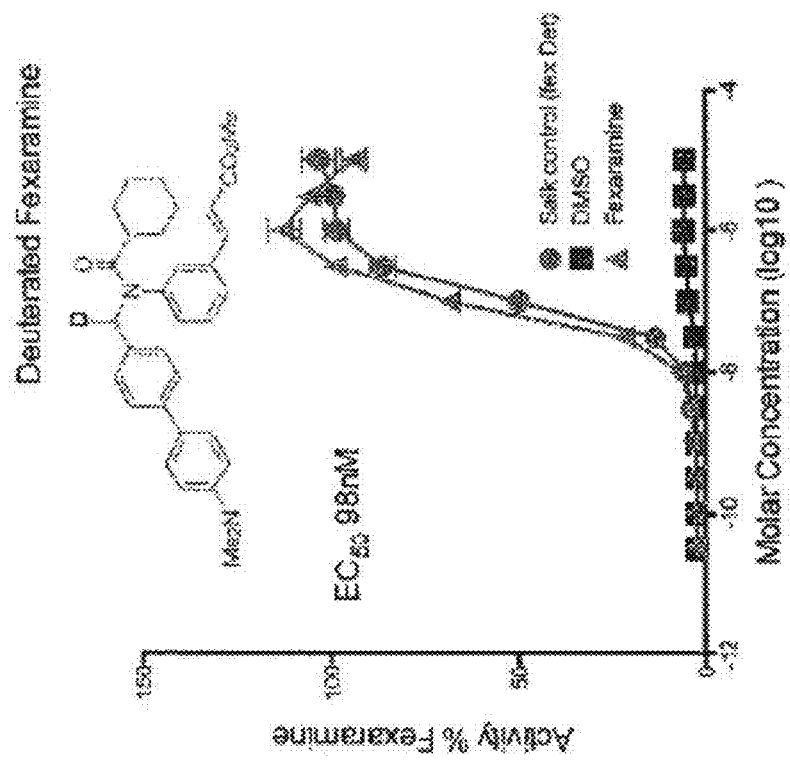

FIGS. 28A and 28B are graphs of percentage activity versus log value of the molar concentration for duplicate runs of deuterated fexaramine, fexaramine and DMSO.

FIGS. 29A-H show the effect of fexaramine and selectively-deuterated fexaramine analogs in vivo. (A) Structures of Fexaramine and analogs SALK24 (NSSK00024) and SALK110 (NSSK00110) indicating positions of selective deuteration. (B) Body weights of mice during course of drug treatment. (C) Core body temperature of mice before (Day 0) and after (day 14) treatment with the indicated FXR analogs. (D) Changes in the fasting glucose levels of ob/ob mice after treatment with the indicated Fex analogs for 1 and 2 weeks. (E) Glucose tolerance test (GTT) performed on ob/ob mice after 2 weeks treatment with the indicated analogs. (F) Fasting insulin levels in ob/ob mice after 2 weeks treatment with the indicated analogs. (G) Insulin secretion, measured during a GTT assay, in ob/ob mice after 2 weeks treatment with the indicated analogs. (H) Glucagon-like peptide-1 (GLP1) secretion, measured during a GTT assay, in ob/ob mice after 2 weeks treatment with the indicated analogs.

Figure 30:
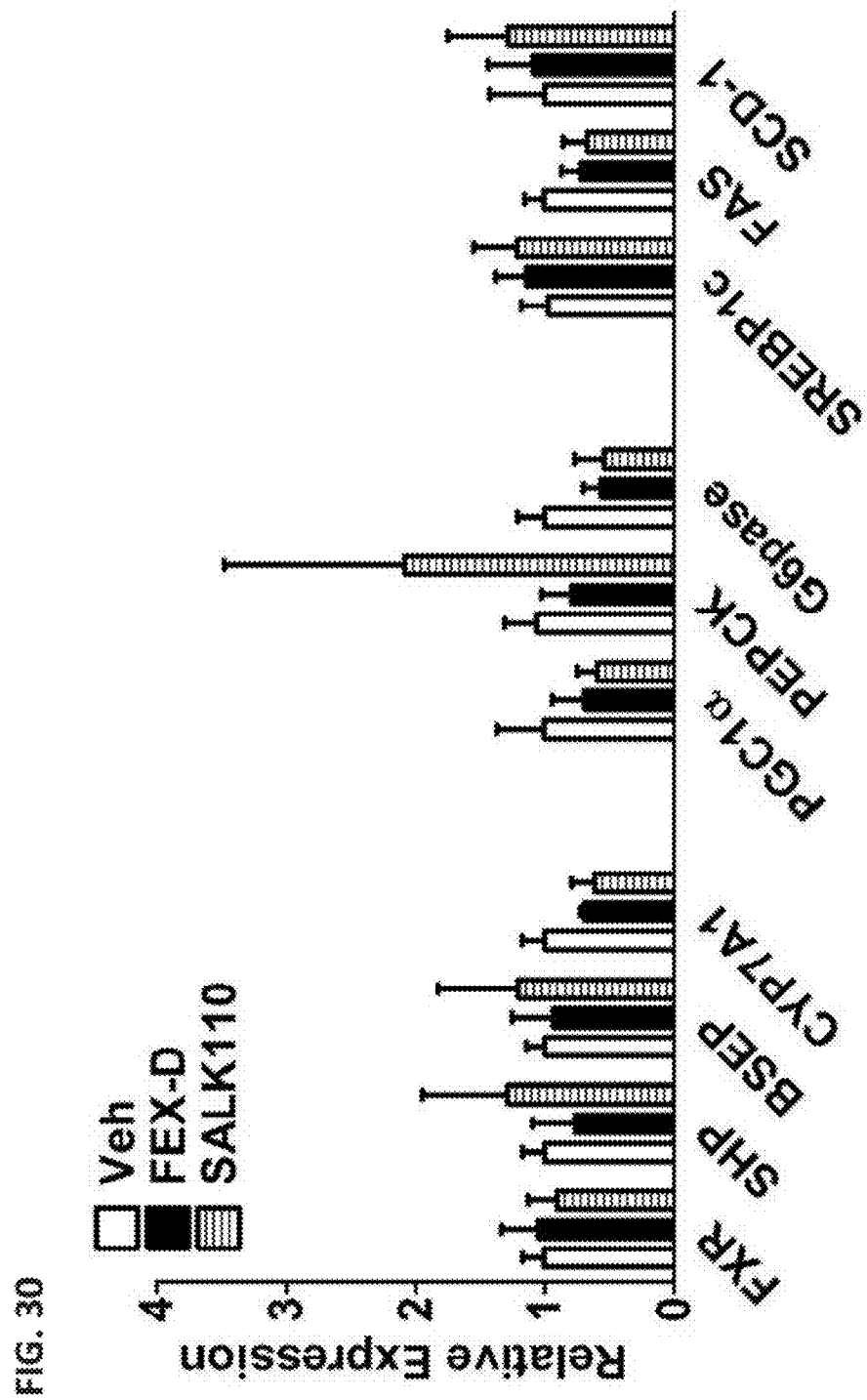

FIG. 30 is a bar graph showing expression of several genes in the liver after treatment with Fex-D or Salk110, as measured by QPCR. Data represent the mean±STD. Statistical analysis was performed with the Student's t test ($*p<0.05$, $**p<0.01$).

Figure 31:
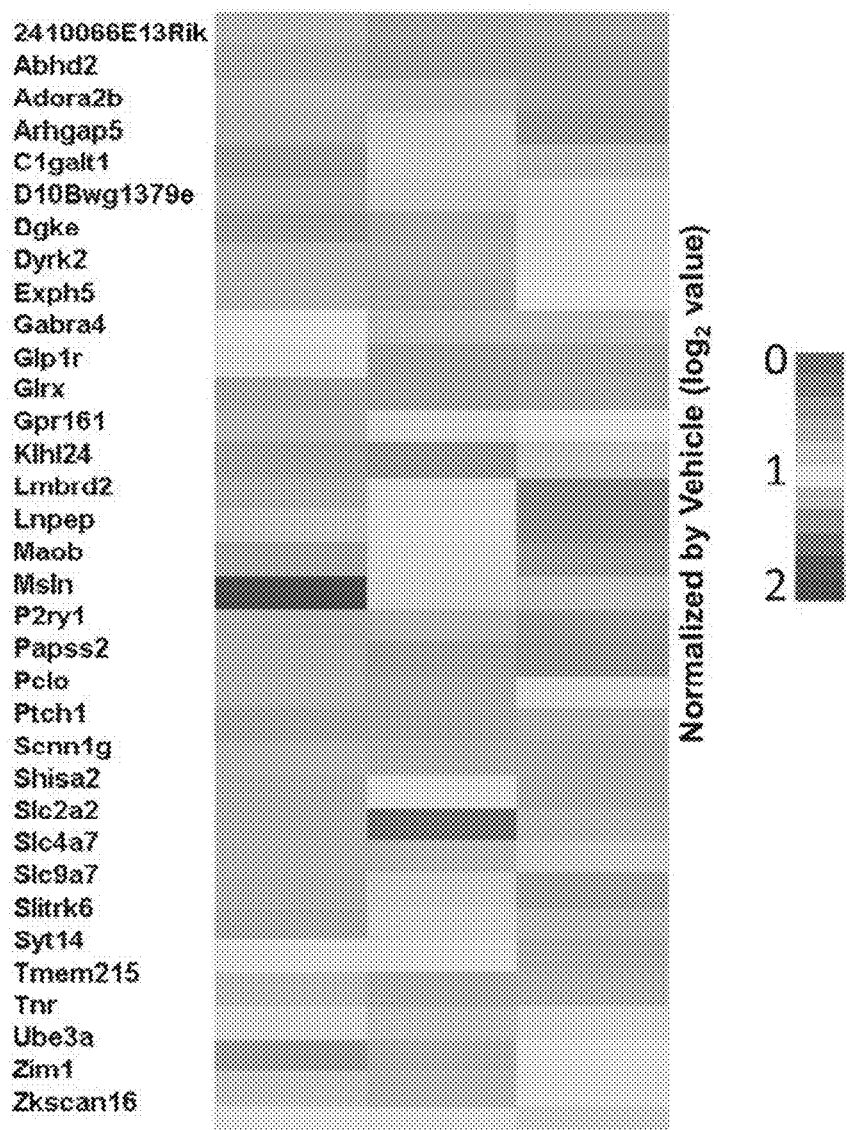

FIG. 31 is a heatmap comparing expression changes in selected genes induced by fexaramine analogs.

FIG. 32 is a table showing the relative transport rates of fexaramine and fexaramine analogs provided herein (NSSK00024, NSSK00027, NSSK00089, NSSK00096, and NSSK00110), as well as controls, in Caco2 cells.

Figure 33A:
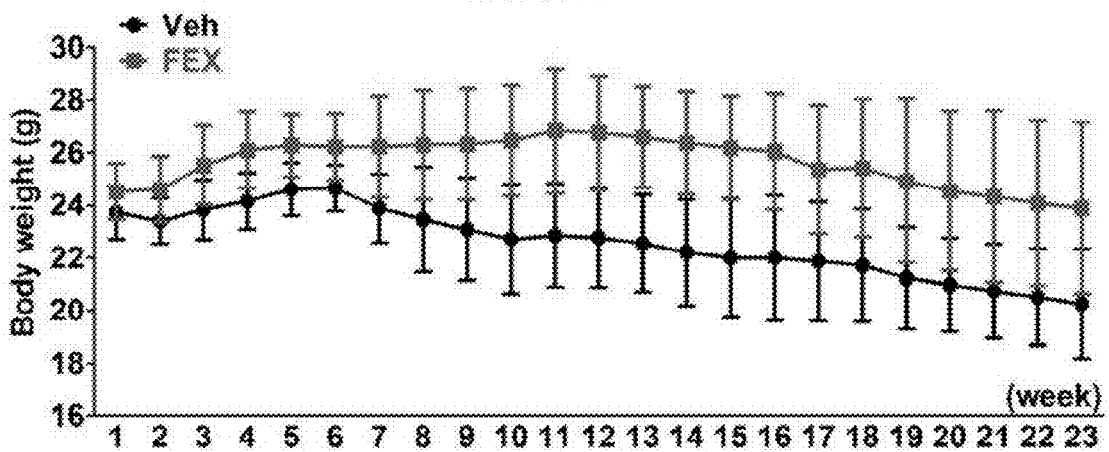
Figure 33B:
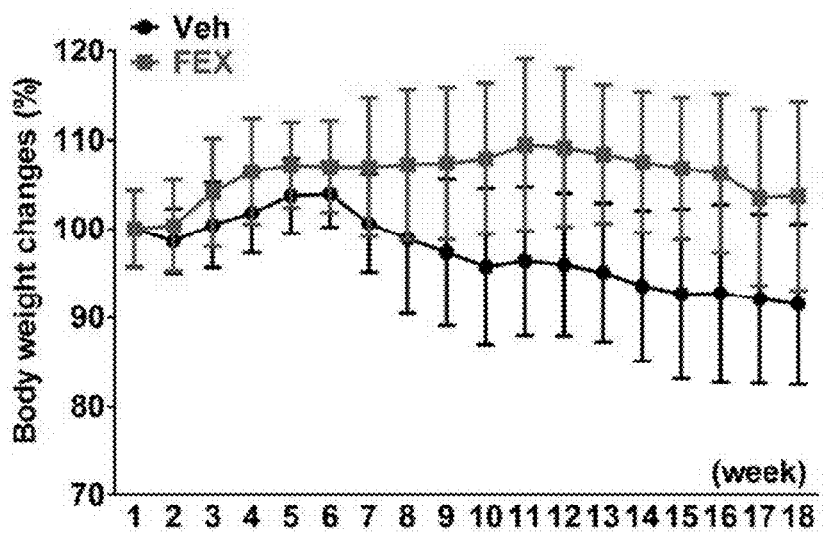
Figure 33C:
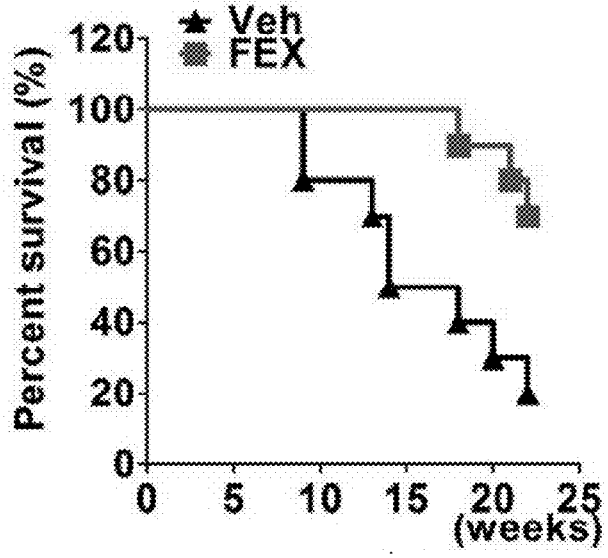

FIGS. 33A-33C show fexaramine-treated $APC^{min}$ mice are resistant to cachexia. (A) Body weight measurements of vehicle or Fex-treated $APC^{min}$ mice. (B) Normalized body weight changes of vehicle or Fex treated $APC^{min}$ mice. (C) Survival curves of vehicle and Fex-treated $APC^{min}$ mice.

FIGS. 34A-34D show fexaramine-treated $APC^{min}$ mice have reduced tumor burden. (A) Total tumor burden of vehicle or Fex treated $APC^{min}$ mice after 23 weeks. (B) Duodenal tumor burden of vehicle or Fex treated $APC^{min}$ mice after 23 weeks. (C) Jejunal tumor burden of vehicle or Fex treated $APC^{min}$ mice after 23 weeks. (D) Ileal tumor burden of vehicle or Fex treated $APC^{min}$ mice after 23 weeks.

FIGS. 35A-35D show fexaramine treatment of $APC^{min}$ mice reduces tumor size and distribution. (A) Tumor size distribution in the duodenum in vehicle and Fex treated $APC^{min}$ mice after 23 weeks. (B) Tumor size distribution in the jejunum in vehicle and Fex treated $APC^{min}$ mice after 23 weeks. (C) Tumor size distribution in the lieum in vehicle and Fex treated $APC^{min}$ mice after 23 weeks. (D) Tumor size distribution throughout the intestine in vehicle and Fex treated $APC^{min}$ mice after 23 weeks.

Figure 36:
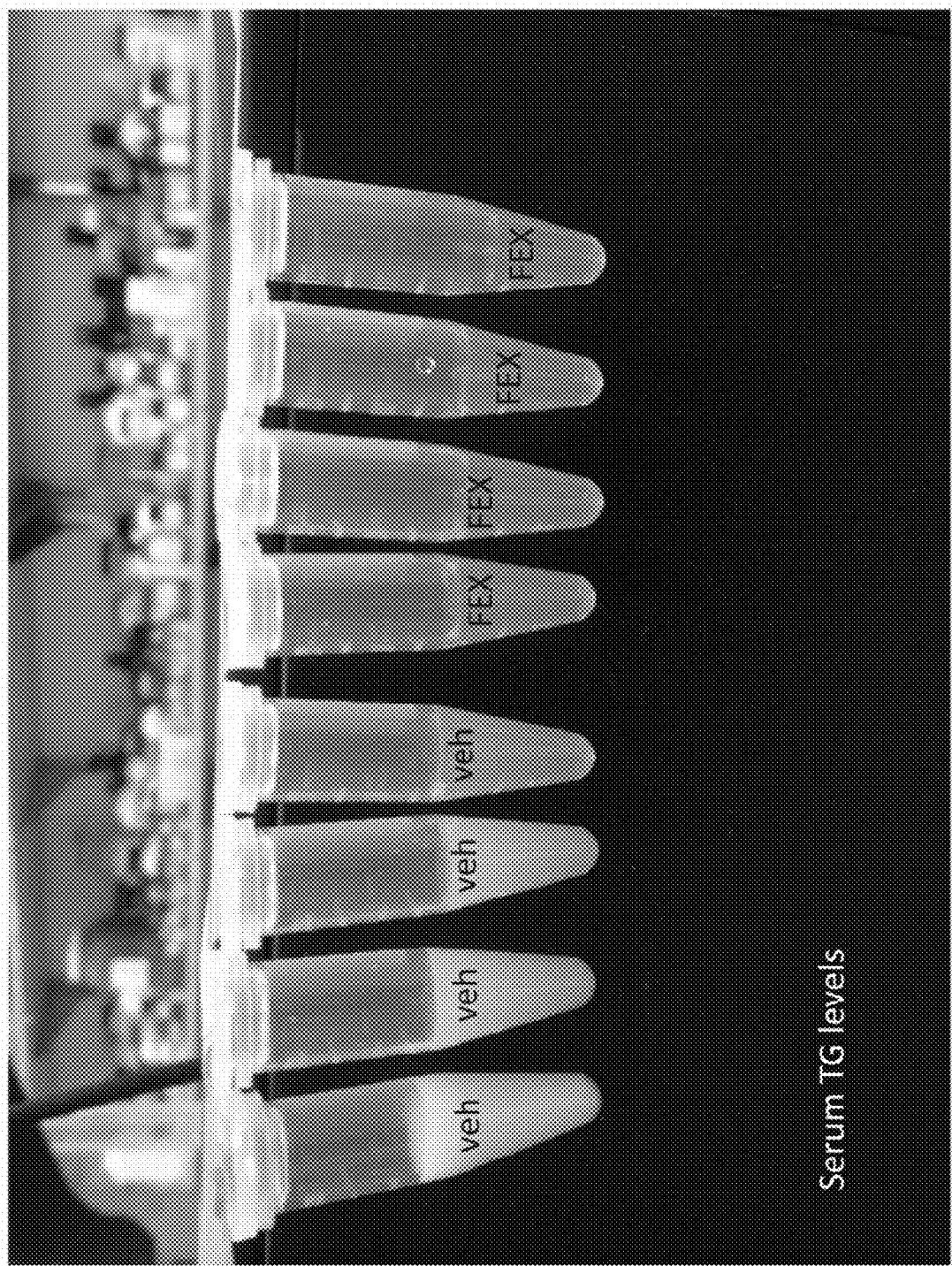

FIG. 36 is a digital image of serum from $APC^{min}$ mice, showing that fexaramine-treatment reduces circulating triglycerides.

Figure 37:
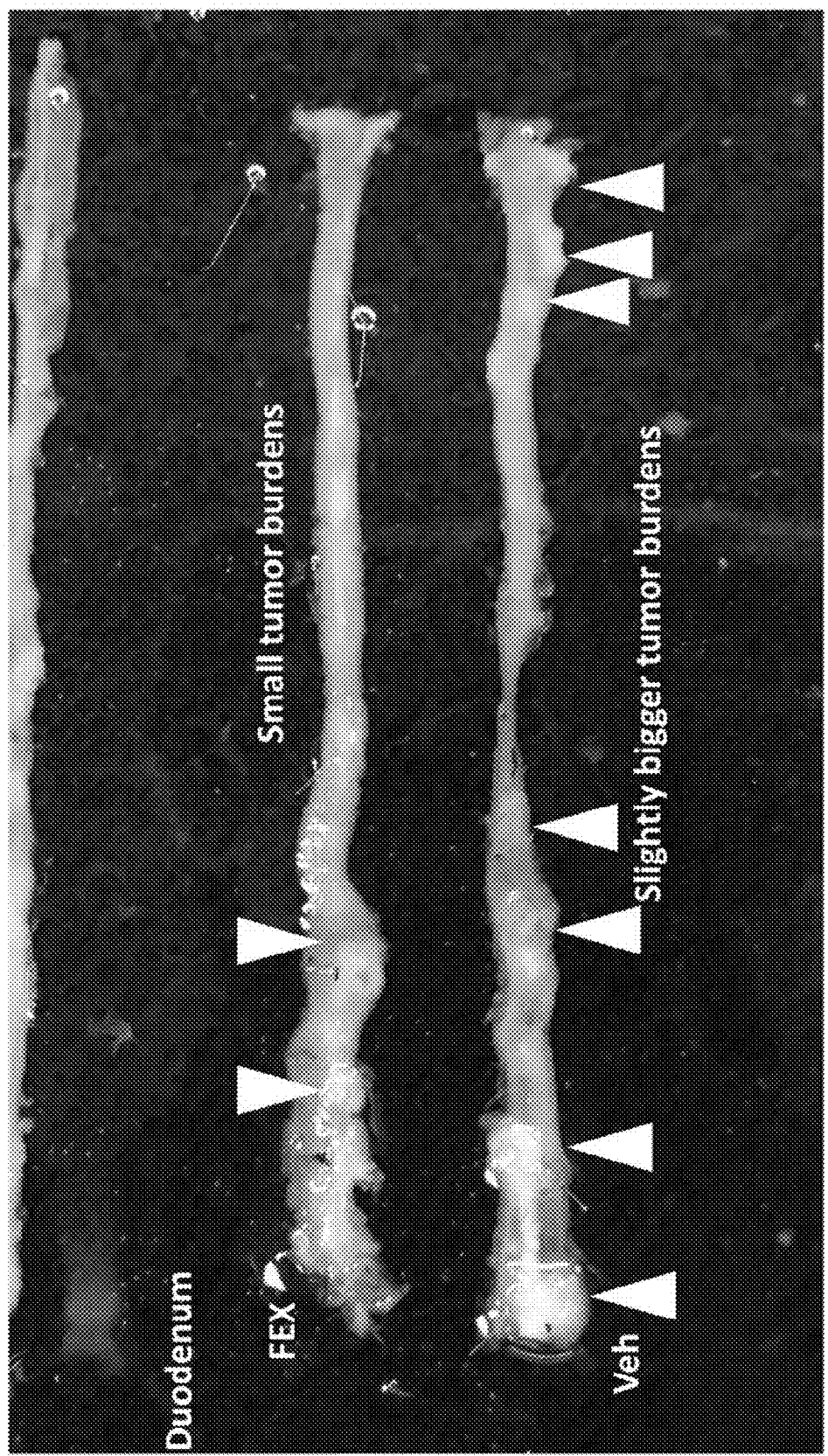

FIG. 37 is a digital image showing duodenum paraformaldehyde fixed intestinal sections of $APC^{min}$ mice with reduced tumor size Representative images of fixed duodenum tissue of vehicle or Fex treated $APC^{min}$ mice after 23 weeks treatment. White triangles point to identified tumors and showed a reduction in tumor size and number in Fex compared to Vehicle treated mice.

Figure 38:
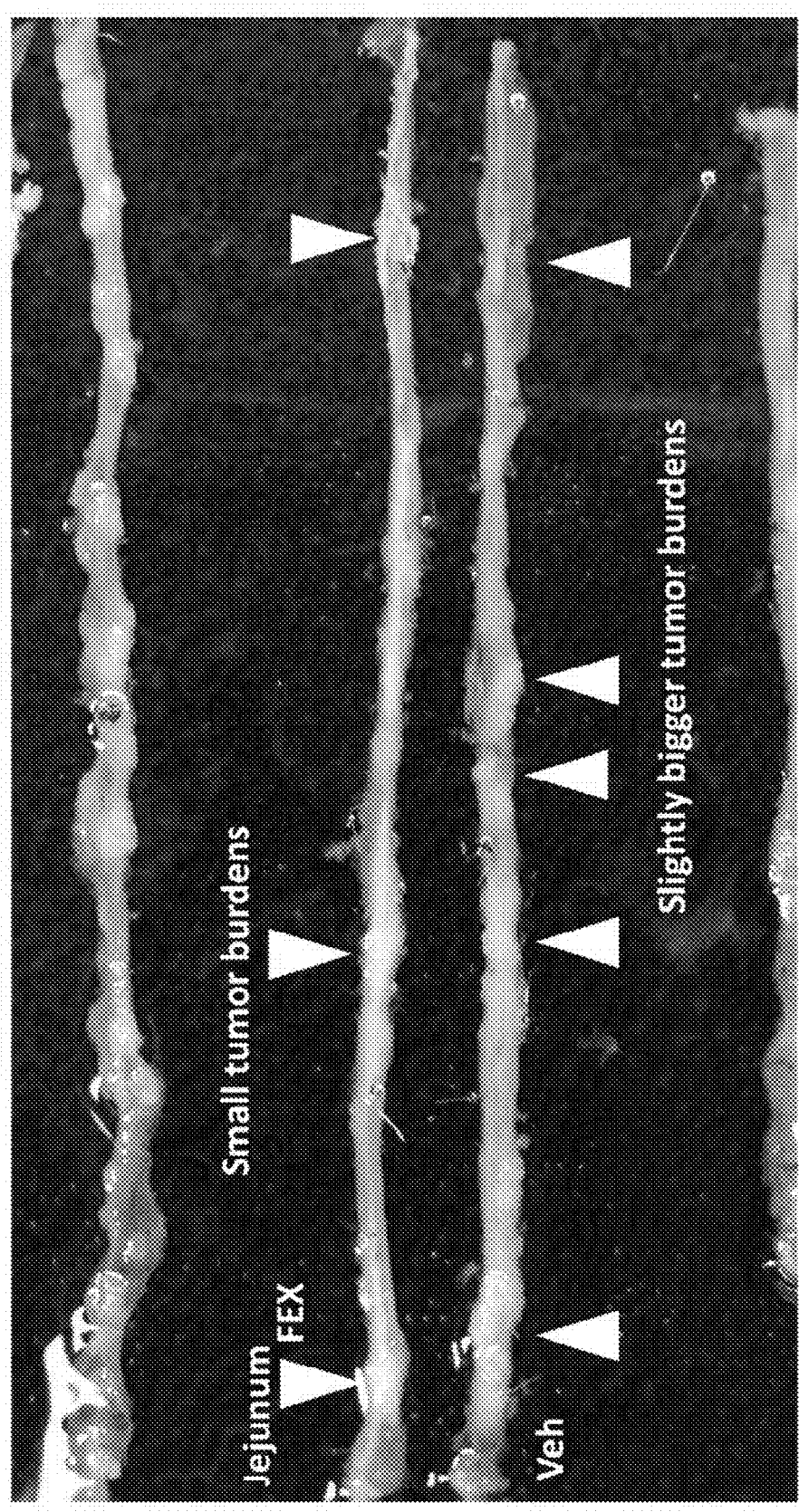

FIG. 38 is a digital image showing jejunum paraformaldehyde fixed intestinal sections of $APC^{min}$ mice showed reduced tumor size. Representative images of fixed jejunum tissue of vehicle or Fex treated $APC^{min}$ mice after 23 weeks treatment. White triangles point to identified tumors and showed reduction in tumor size and number in Fex compared to Vehicle treated mice.

Figure 39:
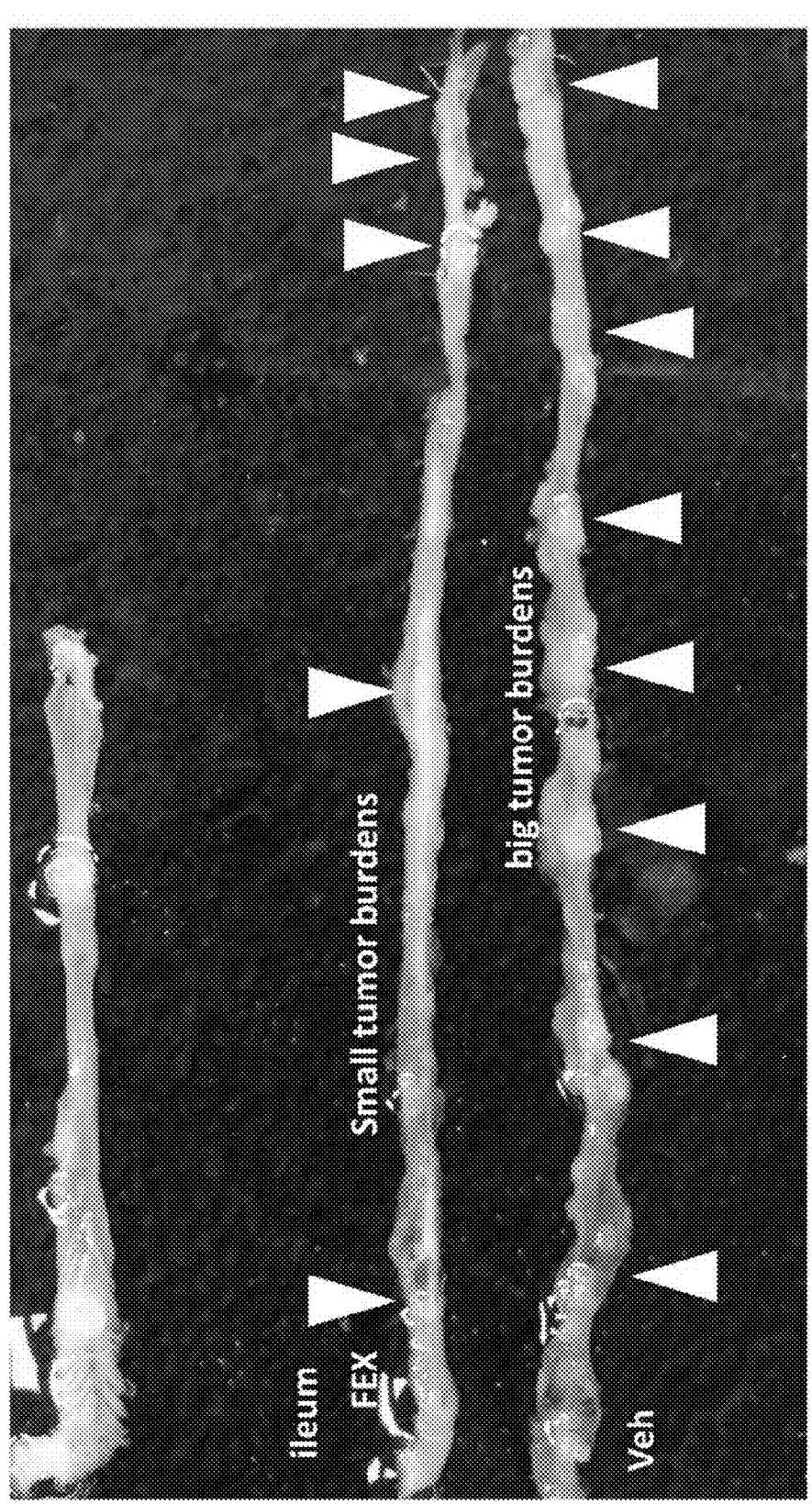

FIG. 39 is a digital image showing ileum paraformaldehyde fixed intestinal sections of $APC^{min}$ mice showed reduced tumor size. Representative images of fixed ileum tissue from vehicle or Fex treated $APC^{min}$ mice after 23 weeks treatment. White triangles point to identified tumors and showed reduction in tumor size and number in Fex compared to Vehicle treated mice.

Figure 40:

FIG. 40 is a digital image showing colon paraformaldehyde fixed intestinal sections of $APC^{min}$ mice showed reduced tumor size. Representative image of fixed colon tissue of vehicle or Fex treated $APC^{min}$ mice after 23 weeks treatment. White triangles point to identified tumors. No tumors were observed in Fex treated mice compared with vehicle treated which have tumors.

Figure 41:
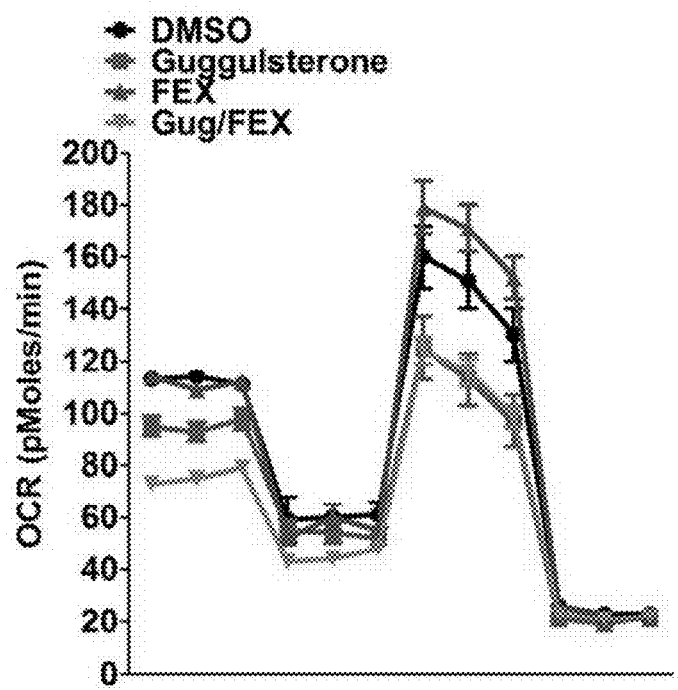

FIG. 41 is a graph showing the effects of modulating FXR activity on the oxidative metabolism of intestinal L cells. L cells were treated with the FXR agonist fexaramine, the FXR antagonist Guggulsterone, or a combination of both, prior to measurement of their oxygen consumption rate (OCR) in a Seahorse analyzer.

Figure 42A:
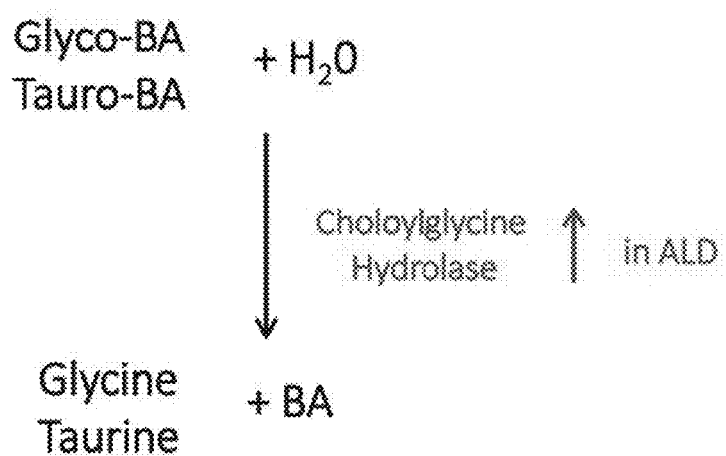
Figure 42B:
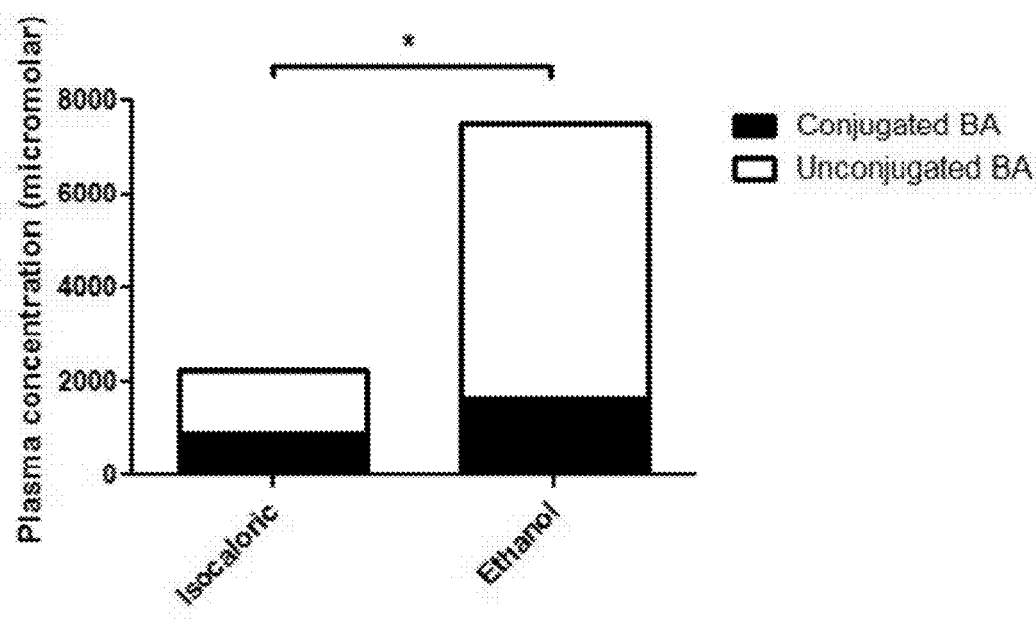
Figure 42C:
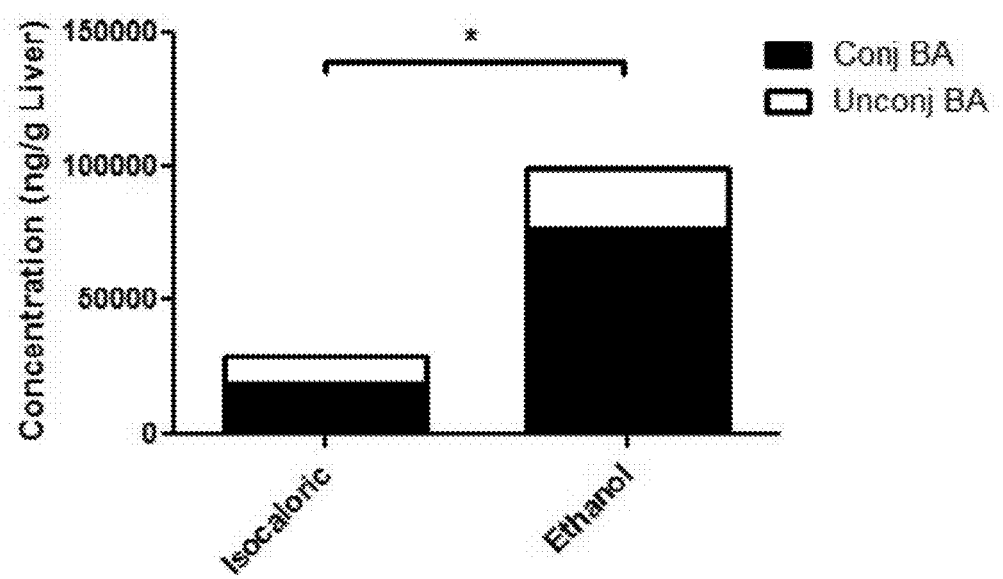

FIGS. 42A-42C demonstrate the metagenomics and metabolomics in alcoholic liver disease. (A) schematic drawing showing that the activity of the enzyme choloyl-glycine hydrolase, responsible for the deconjugation of bile acids, is increased in alcohol liver disease (ALD). (B) a bar graph showing the levels of conjugated and unconjugated bile acids in the plasma of C57BL/6J mice after intragastric feeding of an isocaloric diet or ethanol for 3 weeks and (C) a bar graph showing the levels of conjugated and unconjugated bile acids in the liver of mice after intragastric feeding of an isocaloric diet or ethanol for 3 weeks.

Figure 43A:
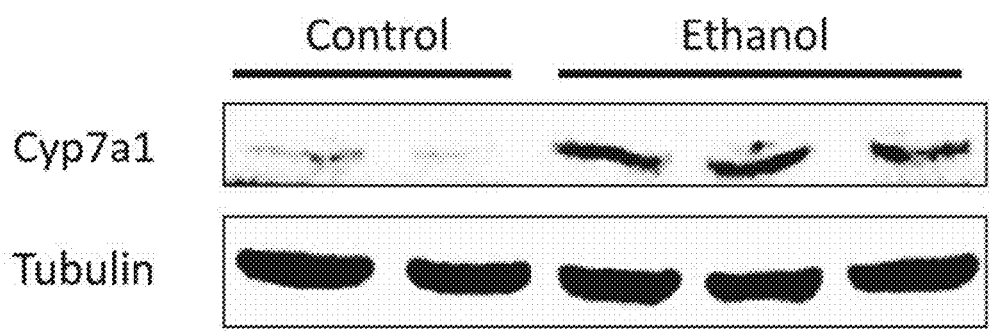
Figure 43B:
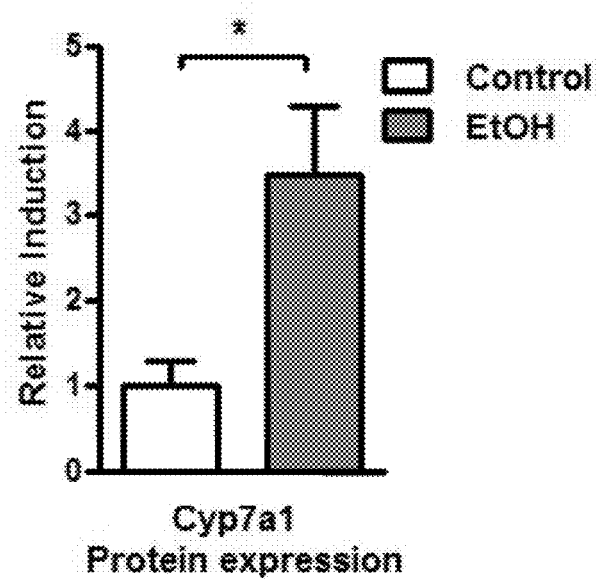

FIGS. 43A and 43B are a (A) digital image of a western blot of Cyp7a1 protein levels in the livers of mice following 3 weeks intragastric feeding of an isocaloric diet (control) or ethanol (tubulin is provided as a protein loading control) and (B) a bar graph quantifying Cyp7a1 protein levels, as measured by Western blot.

Figure 44A:
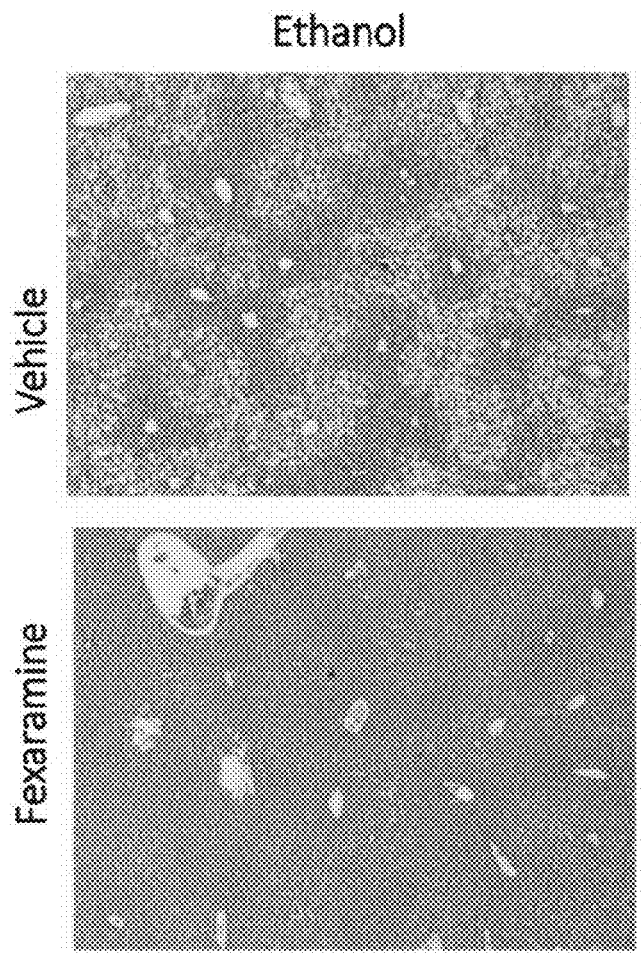
Figure 44B:
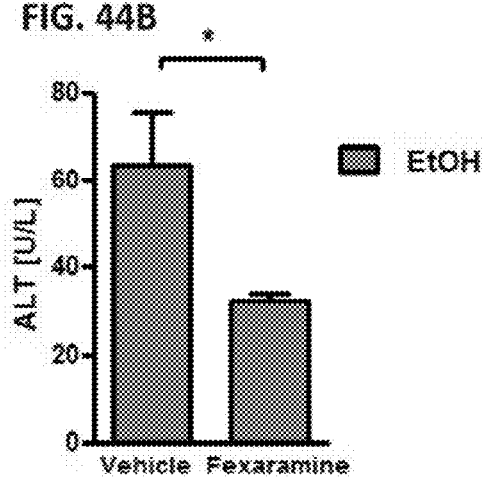
Figure 44C:
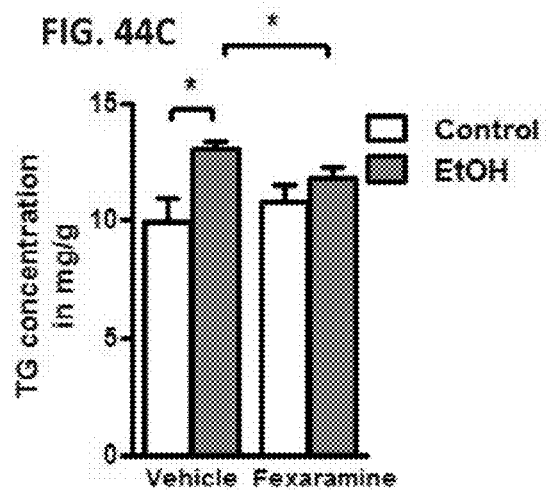

FIGS. 44A-44C are a (A) digital image of histology images of the liver and (B) and (C) bar graphs showing that administration of fexaramine can protect the liver from alcoholic liver disease, for example by decreasing fat in the liver, liver enzyme ALT and triglycerides (TG). C57BL/6J mice, fed an isocaloric diet or ethanol through continuous intragastric feeding for 3 weeks, were co-administered Fexaramine (100 mg/kg/day oral gavage) or vehicle. (A) Histological liver sections from ethanol fed mice after vehicle or fexaramine treatment. (B) Bar graph of serum alanine aminotransferase (ALT) levels in vehicle and fexaramine treated mice after 3 weeks of an ethanol diet (C) Liver triglyceride levels in vehicle and fexaramine treated mice after 3 weeks of an ethanol or isocaloric (control) diet.

Figure 45:
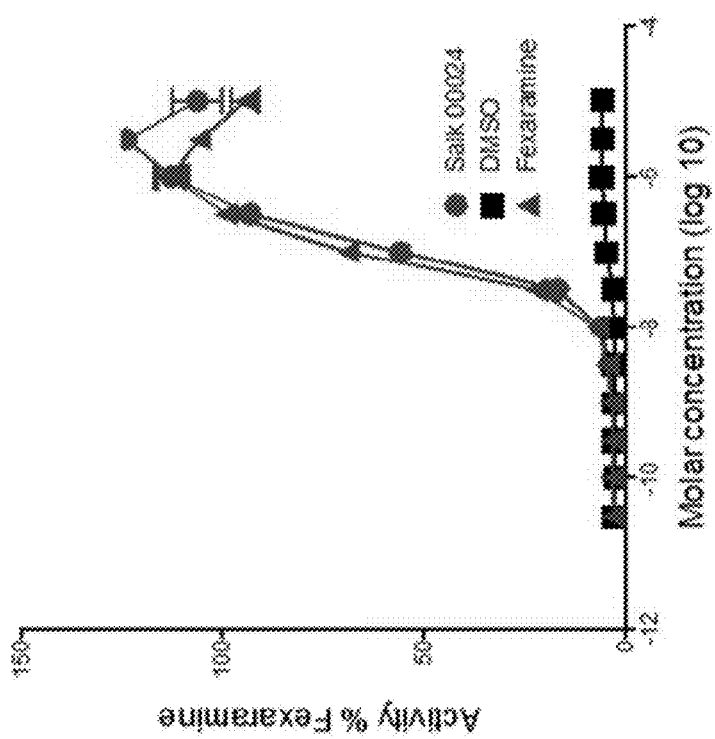

FIG. 45 is a graph of percentage activation of FXR versus the log value of concentration for a retest of NSSK00024, fexaramine and DMSO.

Figure 46:
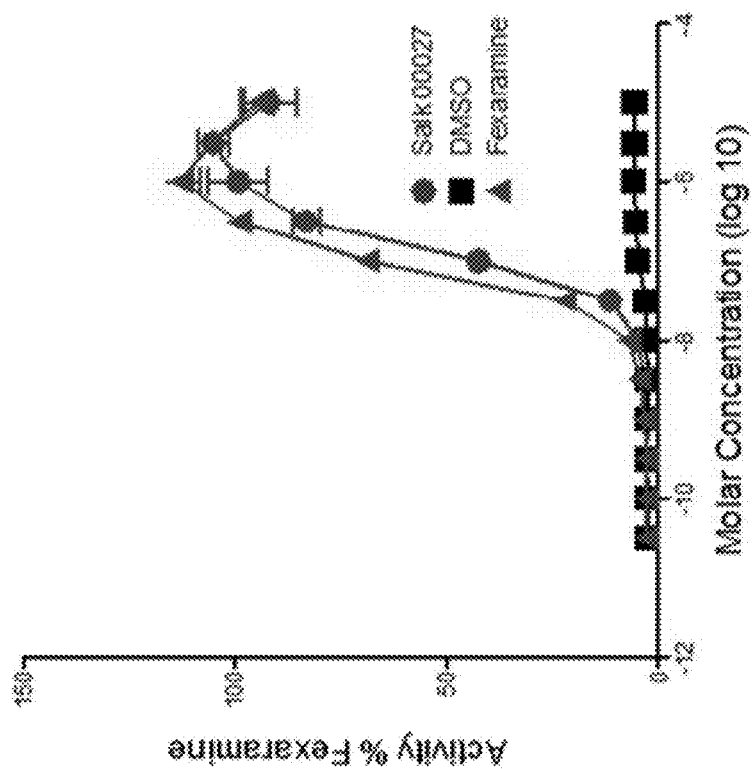

FIG. 46 is a graph of percentage activation of FXR versus the log value of concentration for a retest of NSSK00027, fexaramine and DMSO.

Figure 47:
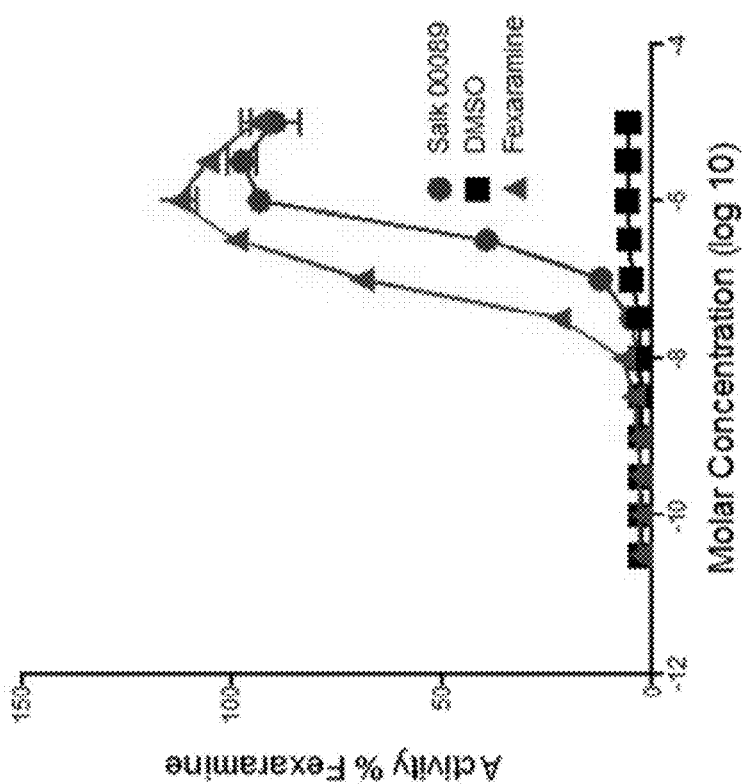

FIG. 47 is a graph of percentage activation of FXR versus the log value of concentration for a retest of NSSK00089, fexaramine and DMSO.

Figure 48:
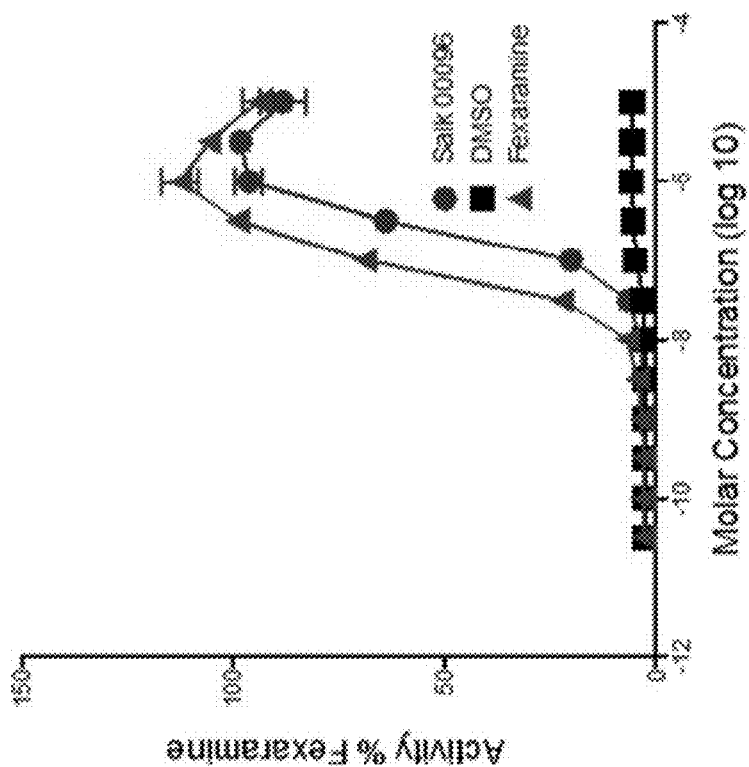

FIG. 48 is a graph of percentage activation of FXR versus the log value of concentration for a retest of NSSK00096, fexaramine and DMSO.

Figure 49:
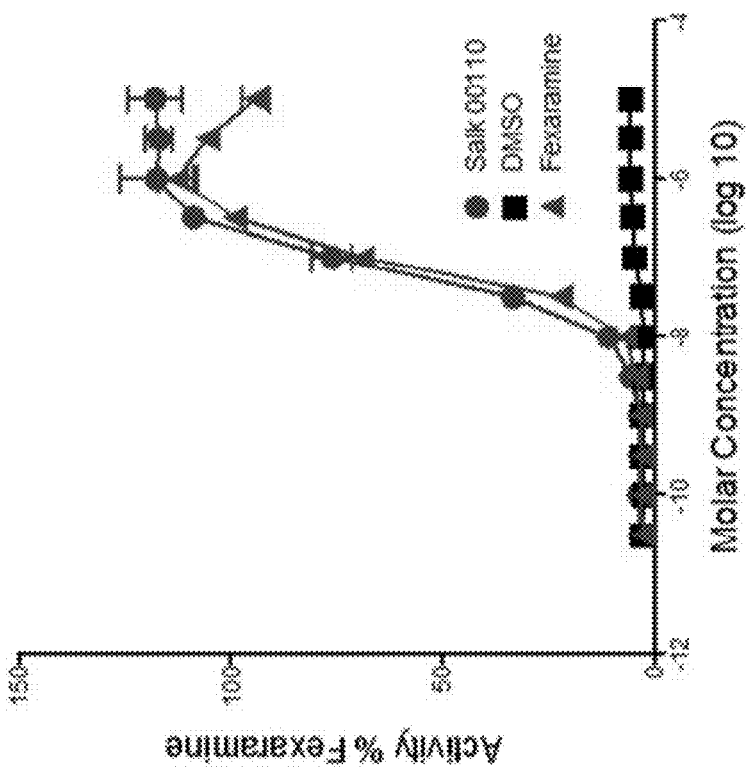

FIG. 49 is a graph of percentage activation of FXR versus the log value of concentration for a retest of NSSK00110, fexaramine and DMSO.

Figure 50:
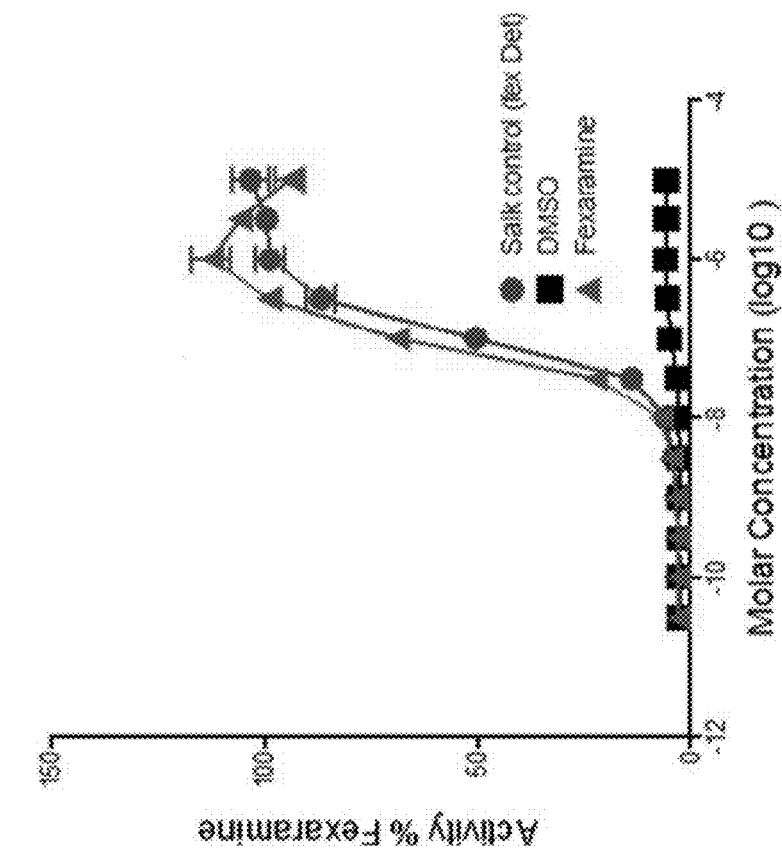

FIG. 50 is a graph of percentage activation of FXR versus the log value of concentration for a retest of deuterated feraramine, fexaramine and DMSO.

SEQUENCE LISTING

The amino acid sequences are shown using standard three letter code for amino acids, as defined in 37 C.F.R. 1.822.
SEQ ID NO. 1 is a protein sequence of GLP-1-(7-36).
SEQ ID NO. 2 is a protein sequence of GLP-2.

DETAILED DESCRIPTION

I. Terms

The following explanations of terms and methods are provided to better describe the present disclosure and to guide those of ordinary skill in the art in the practice of the present disclosure. The singular forms "a," "an," and "the" refer to one or more than one, unless the context clearly dictates otherwise. For example, the term "comprising a FXR agonist" includes single or plural FXR agonists and is considered equivalent to the phrase "comprising at least one FXR agonist." The term "or" refers to a single element of stated alternative elements or a combination of two or more elements, unless the context clearly indicates otherwise. As used herein, "comprises" means "includes." Thus, "comprising A or B," means "including A, B, or A and B," without excluding additional elements. Dates of GenBank® Accession Nos. referred to herein are the sequences available at least as early as Mar. 13, 2014. All references, including patents and patent applications, and GenBank® Accession numbers cited herein are incorporated by reference.

Unless explained otherwise, all technical and scientific terms used herein have the same meaning as commonly understood to one of ordinary skill in the art to which this disclosure belongs. Although methods and materials similar or equivalent to those described herein can be used in the practice or testing of the present disclosure, suitable methods and materials are described below. The materials, methods, and examples are illustrative only and not intended to be limiting.

All groups herein are understood to include substituted groups unless specifically stated otherwise, or context indicates otherwise. A substituted group means that one or more hydrogen atoms of the specified group or radical is each, independently of one another, replaced with the same or different non-hydrogen substituent. Exemplary substituent groups are identified below.

Substituent groups for substituting for one or more hydrogens (any two hydrogens on a single carbon can be replaced with $=O$, $=NR^{70}$, $=N-OR^{70}$, $=N_2$ or $=S$) on saturated carbon atoms in the specified group or radical are, unless otherwise specified, $-R^{60}$, halo, deuterium, $=O$, $-OR^{70}$, $-SR^{70}$, $-NR^{80}R^{80}$, trihalomethyl, $-CN$, $-OCN$, $-SCN$, $-NO$, $-NO_2$, $=N_2$, $-N_3$, $-SO_2R^{70}$, $-SO_2O^-M^+$, $-SO_2OR^{70}$, $-OSO_2R^{70}$, $-OSO_2O^-M^+$, $-OSO_2OR^{70}$, $-P(O)(O)2(M^+)_2$, $-P(O)(OR^{70})O^-M^+$, $-P(O)(OR^{70})_2$, $-C(O)R^{70}$, $-C(S)R^{70}$, $-C(NR^{70})R^{70}$, $-C(O)O^-M^+$, $-C(O)OR^{70}$, $-C(S)OR^{70}$, $-C(O)NR^{80}R^{80}$, $-C(NR^{70})NR^{80}R^{80}$, $-OC(O)R^{70}$, $-OC(O)O^-M^+$, $-OC(O)OR^{70}$, $-OC(S)OR^{70}$, $-NR^{70}C(O)R^{70}$, $-NR^{70}C(S)R^{70}$, $-NR^{70}CO_2^-M^+$, $-NR^{70}CO_2R^{70}$, $-NR^{70}C(S)OR^{70}$, $-NR^{70}C(O)NR^{80}R^{80}$, $-NR^{70}C(NR^{70})R^{70}$ or $-NR^{70}C(NR^{70})NR^{80}R^{80}$, where $R^{60}$ is selected from alkyl, alkenyl, cycloalkyl, heteroalkyl, heterocycloalkylalkyl, cycloalkylalkyl, aryl, arylalkyl, heteroaryl or heteroarylalkyl, each of which may be optionally further substituted; each $R^{70}$ is independently hydrogen or $R^{60}$; each $R^{80}$ is independently $R^{70}$ or alternatively, two $R^{80}$'s, taken together with the nitrogen atom to which they are bonded, form a 5-, 6- or 7-membered heterocycloalkyl which may optionally include from 1 to 4 of the same or different additional heteroatoms selected from O, N or S, of which N may have $-H$ or $C_1$-$C_3$ alkyl substitution; and each $M^+$ is a counter ion with a net single positive charge. Each $M^+$ may independently be, for example, an alkali ion, such as $K^+$, $Na^+$, $Li^+$; an ammonium ion, such as $^+N(R^{60})_4$; or an alkaline earth ion, such as $[Ca^{2+}]_{0.5}$, $[Mg^{2+}]_{0.5}$, or $[Ba^{2+}]_{0.5}$ ("subscript 0.5" means e.g. that one of the counter ions for such divalent alkali earth ions can be an ionized form of a compound of the invention and the other a typical counter ion such as chloride, or two ionized compounds of the invention can serve as counter ions for such divalent alkali earth ions, or a doubly ionized compound of the invention can serve as the counter ion for such divalent alkali earth ions). As specific examples, $-NR^{80}R^{80}$ is meant to include $-NH_2$, $-NH$-alkyl, N-pyrrolidinyl, N-piperazinyl, 4N-methyl-piperazin-1-yl, N-morpholinyl and $-N(alkyl)_2$ such as, for example, $-N(methyl)_2$ or $-N(methyl)(ethyl)$.

Substituent groups for hydrogens on unsaturated carbon atoms in "substituted" alkene, cycloalkene, alkyne, aryl and heteroaryl groups are, unless otherwise specified, $-R^{60}$, halo, deuterium, $-O^-M^+$, $-OR^{70}$, $-SR^{70}$, $-S^-M^+$, $-NR^{80}R^{80}$, trihalomethyl, $-CF_3$, $-CN$, $-OCN$, $-SCN$, $-NO$, $-NO_2$, $-N_3$, $-SO_2R^{70}$, $-SO_3^-M^+$, $-SO_3R^{70}$, $-OSO_2R^{70}$, $-OSO_3^-M^+$, $-OSO_3R^{70}$, $-PO_3^{-2}(M^+)_2$, $-P(O)(OR^{70})O^-M^+$, $-P(O)(OR^{70})_2$, $-C(O)R^{70}$, $-C(S)R^{70}$, $-C(NR^{70})R^{70}$, $-CO_2^-M^+$, $-CO_2R^{70}$, $-C(S)OR^{70}$, $-C(O)NR^{80}R^{80}$, $-C(NR^{70})NR^{80}R^{80}$, $-OC(O)R^{70}$, $-OC(S)R^{70}$, $-OCO_2^-M^+$, $-OCO_2R^{70}$, $-OC(S)OR^{70}$, $-NR^{70}C(O)R^{70}$, $-NR^{70}C(S)R^{70}$, $-NR^{70}CO_2^-M^+$, $-NR^{70}CO_2R^{70}$, $-NR^{70}C(S)OR^{70}$, $-NR^{70}C(O)NR^{80}R^{80}$, $-NR^{70}C(NR^{70})R^{70}$ or $-NR^{70}C(NR^{70})NR^{80}R^{80}$, where $R^{60}$, $R^{70}$, $R^{80}$ and $M^+$ are as previously defined, provided that in case of substituted alkene or alkyne, the substituents are not $-O^-M^+$, $-OR^{70}$, $-SR^{70}$, or $-S^-M^+$.

Substituent groups for replacing hydrogens on nitrogen atoms in "substituted" heterocyclic groups are, unless otherwise specified, $-R^{60}$, $-O^-M^+$, $-OR^{70}$, $-SR^{70}$, $-S^-M^+$, $-NR^{80}R^{80}$, trihalomethyl, $-CF_3$, $-CN$, $-NO$, $-NO_2$, $-S(O)_2R^{70}$, $-S(O)_2O^-M^+$, $-S(O)_2OR^{70}$, $-OS(O)_2R^{70}$, $-OS(O)_2O^-M^+$, $OS(O)_2OR^{70}$, $-P(O)(O^-)_2(M^+)_2$, $-P(O)(OR^{70})O^-M^+$, $-P(O)(OR^{70})(OR^{70})$, $-C(O)R^{70}$, $-C(S)R^{70}$, $-C(NR^{70})R^{70}$, $-C(O)OR^{70}$, $-C(S)OR^{70}$, $-C(O)NR^{80}R^{80}$, $-C(NR^{70})NR^{80}R^{80}$, $-OC(O)R^{70}$, $-OC(S)R^{70}$, $-OC(O)OR^{70}$, $-OC(S)OR^{70}$, $-NR^{70}C(O)R^{70}$, $-NR^{70}C(S)R^{70}$, $-NR^{70}C(O)OR^{70}$, $-NR^{70}C(S)OR^{70}$, $-NR^{70}C(O)NR^{80}R^{80}$, $-NR^{70}C(NR^{70})R^{70}$ or $-NR^{70}C(NR^{70})NR^{80}R^{80}$, where $R^{60}$, $R^{70}$, $R^{80}$ and $M^+$ are as previously defined.

In a preferred embodiment, a group that is substituted has 1 substituent, 1 or 2 substituents, 1, 2, or 3 substituents or 1, 2, 3 or 4 substituents.

Also, it is understood that the above definitions are not intended to include impermissible substitution patterns. Such impermissible substitution patterns are understood by a person having ordinary skill in the art.

Additionally, it is understood by a person of ordinary skill in the art that if an atom does not appear to have sufficient specific bonds to satisfy valence requirements, such as an apparent trivalent carbon, there are sufficient implicit hydrogens present to satisfy those valence requirements.

As used herein, the wavyline "〰" indicates the point of attachment for a group or radical.

"Alkyl" refers to a hydrocarbon group having a saturated carbon chain, which, unless otherwise specified, may optionally be substituted, particularly with substituents as described in the definition of "substituted." The chain may be cyclic, branched or unbranched. The term "lower alkyl" means that the alkyl chain includes 1-10 carbon atoms e.g. methyl, ethyl, n-propyl, isopropyl, n-butyl, iso-butyl, sec-butyl, tert-butyl, n-pentyl, tert-pentyl, neopentyl, isopentyl, sec-pentyl, 3-pentyl, hexyl, heptyl, octyl, nonyl or decyl. Also, by way of example, a methyl group, an ethyl group, an n-propyl and an isopropyl group are all represented by the term $C_{1-3}$ alkyl. Likewise terms indicating larger numerical ranges of carbon atoms are representative of any linear or branched hydrocarbyl falling within the numerical range. This inclusiveness applies to other hydrocarbyl terms bearing such numerical ranges. The terms alkenyl and alkynyl refer to hydrocarbon groups having carbon chains containing one or more double or triple bonds, respectively.

"Alkylene" refers to divalent saturated aliphatic hydrocarbyl groups preferably having from 1 to 10 carbon atoms, more preferably 1 to 4 carbon atoms, that are either straight-chained or branched, which may optionally be substituted, particularly with substituents as described herein, unless otherwise specified. This term is exemplified by groups such as methylene (—$CH_2$—), ethylene (—$CH_2CH_2$—), n-propylene (—$CH_2CH_2CH_2$), iso-propylene (—$CH_2CH(CH_3)$—) or (—$CH(CH_3)CH_2$—), and the like.

"Alkenylene" refers to divalent unsaturated aliphatic hydrocarbyl groups preferably having from 2 to 10 carbon atoms, more preferably 2 to 4 carbon atoms, that are either straight-chained or branched, and include at least one double bond. Unless otherwise specified, the group may be optionally be substituted, particularly with substituents as described herein. This term is exemplified by groups such as ethenylene (—CH=CH—) and propenylene (—CH=CHCH$_2$—) and the like.

"Alkynylene" refers to divalent unsaturated aliphatic hydrocarbyl groups preferably having from 2 to 10 carbon atoms, more preferably 2 to 4 carbon atoms, that are either straight-chained or branched and include at least one triple bond. Unless otherwise specified, the group may be optionally be substituted, particularly with substituents as described herein. This term is exemplified by groups such as ethynylene (—C≡C—) and n-propynylene (—C≡CCH$_2$—) and the like.

"Alkylthio" refers to the group —S-alkyl.

"Alkoxy" refers to the group —O-alkyl. Alkoxy includes, by way of example, methoxy, ethoxy, n-propoxy, iso-propoxy, n-butoxy, t-butoxy, sec-butoxy, n-pentoxy, and the like.

"Acyl" refers to the groups H—C(O)—, alkyl-C(O)—, alkenyl-C(O), alkynyl-C(O)—, cycloalkyl-C(O)—, cycloalkenyl-C(O)—, aryl-C(O)—, heteroaryl-C(O)—, or heterocyclic-C(O)—. By way of example, "acyl" includes the "acetyl" group $CH_3C(O)$—.

"Amino" refers to the group —$NR^{21}R^{22}$, wherein $R^{21}$ and $R^{22}$ independently are selected from hydrogen, alkyl, alkenyl, alkynyl, aryl, cycloalkyl, cycloalkenyl, heteroaryl, or heterocyclic, or where $R^{21}$ and $R^{22}$ are optionally joined together with the nitrogen bound thereto to form a heterocyclic group.

"Aminocarbonyl" refers to the group —$C(O)NR^{21}R^{22}$, wherein $R^{21}$ and $R^{22}$ independently are selected from hydrogen, alkyl, alkenyl, alkynyl, aryl, cycloalkyl, cycloalkenyl, heteroaryl, or heterocyclic, or where $R^{21}$ and $R^{22}$ are optionally joined together with the nitrogen bound thereto to form a heterocyclic group.

"Aminosulfonyl" refers to the group —$SO_2NR^{21}R^{22}$ where $R^{21}$ and $R^{22}$ are independently are selected from hydrogen, alkyl, alkenyl, alkynyl, aryl, cycloalkyl, cycloalkenyl, heteroaryl, or heterocyclic, or where $R^{21}$ and $R^{22}$ are optionally joined together with the nitrogen bound thereto to form a heterocyclic group.

"Aryl" or "Ar" refers to an aromatic moiety, such as a carbocyclic group of from 6 to 15 carbon atoms having a single ring (e.g., phenyl) or multiple condensed rings (e.g., naphthyl or anthryl) in which at least one of the condensed rings is aromatic (e.g., 2-benzoxazolinone, 2H-1,4-benzoxazin-3(4H)-one-7-yl, 9,10-dihydrophenanthrene, and the like), provided that the point of attachment is through an atom of the aromatic aryl group. Unless otherwise specified, the aryl group may be optionally be substituted, particularly with substituents as described herein. Preferred aryl groups include phenyl and naphthyl.

"Alkenyl" refers to straight chain or branched hydrocarbyl groups having from 2 to 6 carbon atoms and preferably 2 to 4 carbon atoms and having at least 1 double bond. Unless otherwise specified, the alkenyl group may be optionally substituted. Such groups are exemplified, for example, bi-vinyl, allyl, and but-3-en-1-yl. Included within this term are the cis and trans isomers or mixtures of these isomers, unless otherwise specified.

"Alkynyl" refers to straight chain or branched hydrocarbyl groups having from 2 to 6 carbon atoms, and preferably 2 to 4 carbon atoms, and having at least 1 site of triple bond unsaturation. Unless otherwise specified, the alkynyl group may be optionally substituted. Such groups are exemplified, for example, by ethynyl, 1-propynyl and 2-propynyl.

"Boronic acid" refers to the groups —$B(OR)_2$, where each R independently is selected from H, alkyl, cycloalkyl, aryl or where the R substituents form a ring, such as in a picolinate ester

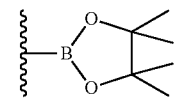

or a catechol ester

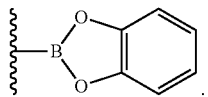.

"Cycloalkyl" refers to a cyclic alkyl group of from 3 to 10 carbon atoms having a single ring, which, unless otherwise specified, may be optionally substituted. Examples of suitable cycloalkyl groups include, for instance, cyclopropyl, cyclobutyl, cyclopentyl, cyclohexyl, cycloheptyl, cyclooctyl and the like.

"Cycloalkenyl" refers to a cyclic alkenyl group of from 3 to 10 carbon atoms having a single ring, which, unless otherwise specified, may be optionally substituted. Examples of suitable cycloalkenyl groups include, for instance, cyclohexenyl, cyclopentenyl, and cyclobutenyl.

"Halo", "halide" or "halogen" refers to fluoro, chloro, bromo, and iodo and is preferably fluoro or chloro.

"Hydroxy" or "hydroxyl" refers to the group —OH.

"Heteroaryl" refers to an aromatic group having from 1 to 10 carbon atoms and at least one, and more typically 1 to 4, heteroatoms selected from oxygen, nitrogen or sulfur within the ring. Unless otherwise specified, the heteroaryl group may be optionally substituted. Such heteroaryl groups can have a single ring (e.g., pyridinyl, imidazolyl or furyl) or multiple condensed rings (e.g., indolizinyl, quinolinyl, benzimidazolyl, benzopyrazolyl or benzothienyl), wherein at least one of the condensed rings is aromatic and may or may not contain a heteroatom, provided that the point of attachment is through an atom of an aromatic ring. In one embodiment, the nitrogen and/or sulfur ring atom(s) of the heteroaryl group are optionally oxidized to provide N-oxide (N→O), sulfinyl, or sulfonyl moieties. Preferred heteroaryls include pyridinyl, pyrrolyl, indolyl, thiophenyl, benzopyrazolyl and furanyl.

"Heterocycle," "heterocyclic," "heterocycloalkyl," and "heterocyclyl" refer to a saturated or unsaturated group having a single ring or multiple condensed rings, including fused, bridged and spiro ring systems, and having from 3 to 15 ring atoms, including at least one, and more typically 1 to 4, hetero atoms. The hetero atoms are selected from nitrogen, sulfur, or oxygen. Unless otherwise specified, the group may be optionally substituted. In fused ring systems, one or more of the rings can be cycloalkyl, aryl, or heteroaryl, provided that the point of attachment is through a non-aromatic ring. In one embodiment, the nitrogen and/or sulfur atom(s) of the heterocyclic group are optionally oxidized to provide for the N-oxide, —S(O)—, or —SO₂— moieties.

Examples of heterocycles and heteroaryls include, but are not limited to, azetidine, pyrrole, imidazole, pyrazole, pyridine, pyrazine, pyrimidine, pyridazine, indolizine, isoindole, indole, dihydroindole, indazole, purine, quinolizine, isoquinoline, quinoline, phthalazine, naphthylpyridine, quinoxaline, quinazoline, cinnoline, pteridine, carbazole, carboline, phenanthridine, acridine, phenanthroline, isothiazole, phenazine, isoxazole, phenoxazine, phenothiazine, imidazolidine, imidazoline, piperidine, piperazine, indoline, phthalimide, 1,2,3,4-tetrahydroisoquinoline, 4,5,6,7-tetrahydrobenzo[b]thiophene, thiazole, thiazolidine, thiophene, benzo[b]thiophene, morpholinyl, thiomorpholinyl (also referred to as thiamorpholinyl), 1,1-dioxothiomorpholinyl, piperidinyl, pyrrolidine, tetrahydrofuranyl, and the like.

"Nitro" refers to the group —NO₂.

"Polycyclic" refers to a saturated or unsaturated polycyclic ring system having from about 5 to about 25 carbon atoms and having two or more rings (e.g. 2, 3, 4, or 5 rings). The rings can be fused and/or bridged to form the polycyclic ring system, and unless otherwise specified, may be optionally substituted. For example, the term includes bicyclo [4,5], [5,5], [5,6] or [6,6] ring systems, as well as the following bridged ring systems:

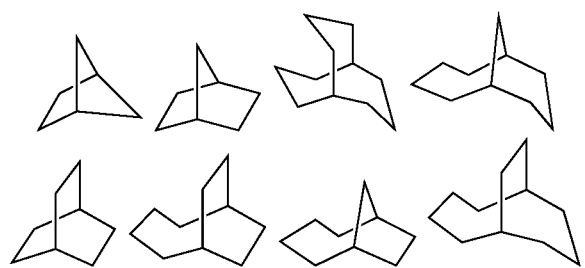
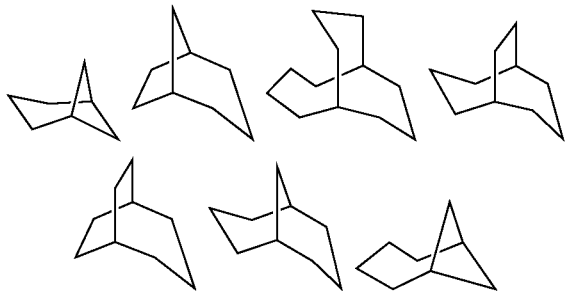

(i.e., [2.1.1], [2.2.1], [3.3.3], [4.3.1], [2.2.2], [4.2.2], [4.2.1], [4.3.2], [3.1.1], [3.2.1], [4.3.3], [3.3.2], [3.2.2], [3.3.1] and [4.1.1] polycyclic rings, respectively), and adamantyl. Polycyclic groups can be linked to the remainder of the compound through any synthetically feasible position. If a stereocenter is created then all possible stereocenters are contemplated. Like the other polycarbocycles, these representative bicyclo and fused ring systems can optionally comprise one or more double bonds in the ring system.

"Sulfonyl" refers to the group —SO₂—, and includes —SO₂-alkyl, —SO₂-alkenyl, —SO₂-cycloalkyl, —SO₂-cycloalkenyl, —SO₂-aryl, —SO₂-heteroaryl, or —SO₂-heterocyclic, wherein alkyl, alkenyl, cycloalkyl, cycloalkenyl, aryl, heteroaryl, and heterocyclic are as defined herein. Sulfonyl includes groups such as methyl-SO₂, phenyl-SO₂—, and 4-methylphenyl-SO₂—.

The terms "carboxyl bioisosteric," or "carboxyl bioisostere" refer to a group with similar physical or chemical properties to a carboxyl group that produce broadly similar biological properties, but which may reduce toxicity or modify the activity of the compound, and may alter the metabolism of the compound. Exemplary carboxyl bioisosteres include, but are not limited to,

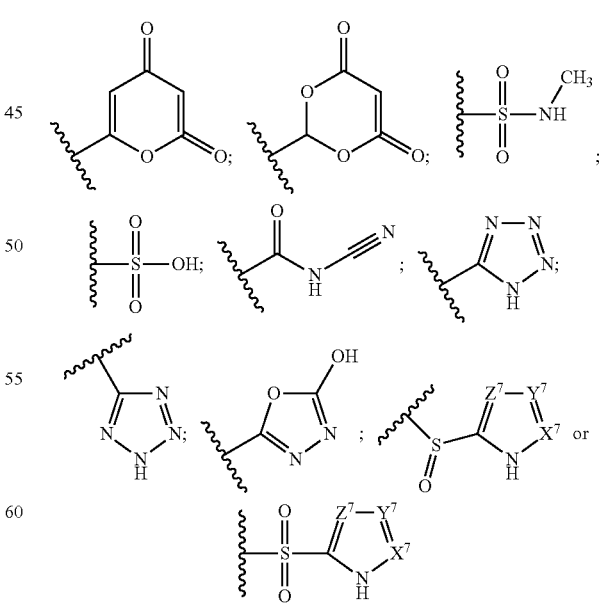

where X⁷, Y⁷, and Z⁷ are each independently selected from N, CH₂ or CO;

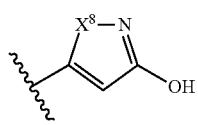

where $X^8$ is selected from O, S or NMe;

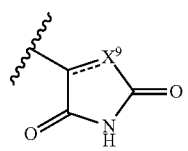

where $X^9$ is selected from O, N, S, CH or $CH_2$;

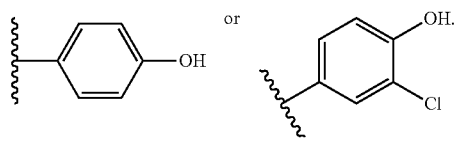 [SMILES: *c1ccc(O)cc1 ; *c1ccc(O)c(Cl)c1]

Additional carboxyl bioisosteric groups contemplated by the present disclosure include

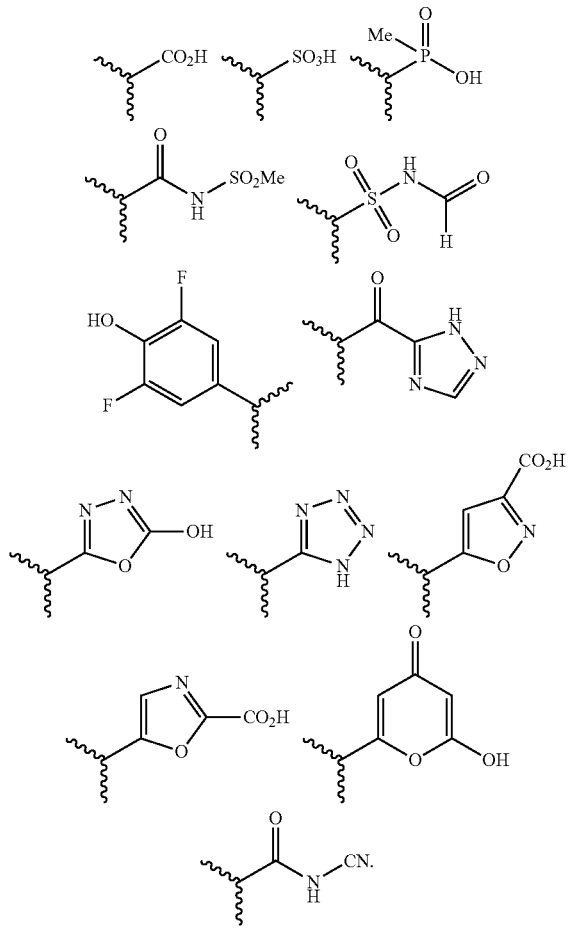

Particular examples of the presently disclosed compounds include one or more asymmetric centers; thus these compounds can exist in different stereoisomeric forms. Accordingly, compounds and compositions may be provided as individual pure enantiomers or as stereoisomeric mixtures, including racemic mixtures. In certain embodiments the compounds disclosed herein are synthesized in or are purified to be in substantially enantiopure form, such as in a 90% enantiomeric excess, a 95% enantiomeric excess, a 97% enantiomeric excess or even in greater than a 99% enantiomeric excess, such as in enantiopure form.

Prodrugs of the disclosed compounds also are contemplated herein. A prodrug is an active or inactive compound that is modified chemically through in vivo physiological action, such as hydrolysis, metabolism and the like, into an active compound following administration of the prodrug to a subject. The term "prodrug" as used throughout this text means the pharmacologically acceptable derivatives such as esters, amides and phosphates, such that the resulting in vivo biotransformation product of the derivative is the active drug as defined in the compounds described herein. Prodrugs preferably have excellent aqueous solubility, increased bioavailability and are readily metabolized into the active inhibitors in vivo. Prodrugs of a compounds described herein may be prepared by modifying functional groups present in the compound in such a way that the modifications are cleaved, either by routine manipulation or in vivo, to the parent compound. The suitability and techniques involved in making and using prodrugs are well known by those skilled in the art. For a general discussion of prodrugs involving esters see Svensson and Tunek, *Drug Metabolism Reviews* 165 (1988) and Bundgaard, *Design of Prodrugs*, Elsevier (1985).

The term "prodrug" also is intended to include any covalently bonded carriers that release an active parent drug of the present invention in vivo when the prodrug is administered to a subject. Since prodrugs often have enhanced properties relative to the active agent pharmaceutical, such as, solubility and bioavailability, the compounds disclosed herein can be delivered in prodrug form. Thus, also contemplated are prodrugs of the presently disclosed compounds, methods of delivering prodrugs and compositions containing such prodrugs. Prodrugs of the disclosed compounds typically are prepared by modifying one or more functional groups present in the compound in such a way that the modifications are cleaved, either in routine manipulation or in vivo, to yield the parent compound. Prodrugs include compounds having a phosphonate and/or amino group functionalized with any group that is cleaved in vivo to yield the corresponding amino and/or phosphonate group, respectively. Examples of prodrugs include, without limitation, compounds having an acylated amino group, an ascorbate moiety, an ortho ester, an imidate group and/or a phosphonate ester or phosphonate amide group.

"Pharmaceutically acceptable salt" refers to pharmaceutically acceptable salts of a compound, which salts are derived from a variety of organic and inorganic counter ions well known in the art and include, by way of example only, sodium, potassium, calcium, magnesium, ammonium, tetraalkylammonium, and the like. If the molecule contains a basic functionality, pharmaceutically acceptable salts include salts of organic or inorganic acids, such as hydrochloride, hydrobromide, tartrate, mesylate, acetate, maleate, oxalate, and the like.

"Pharmaceutically acceptable excipient" refers to a substantially physiologically inert substance that is used as an additive in a pharmaceutical composition. As used herein, an excipient may be incorporated within particles of a pharmaceutical composition, or it may be physically mixed with particles of a pharmaceutical composition. An excipient can be used, for example, as a carrier, flavoring, thickener, diluent, buffer, preservative, or surface active agent and/or to modify properties of a pharmaceutical composition. Examples of excipients include, but are not limited, to polyvinylpyrrolidone (PVP), tocopheryl polyethylene glycol 1000 succinate (also known as vitamin E TPGS, or TPGS), dipalmitoyl phosphatidyl choline (DPPC), trehalose, sodium bicarbonate, glycine, sodium citrate, and lactose.

"Enteric coating" refers to a coating such as may be applied to disclosed compounds or compositions comprising the compounds to help protect drugs from disintegration, digestion etc. in the stomach, such as by enzymes or the pH of the stomach. Typically, the coating helps prevent the drug from being digested in the stomach, and allows delivery of the medication to the intestine.

The terms "administer," "administering", "administration," and the like, as used herein, refer to methods that may be used to enable delivery of agents or compositions to the desired site of biological action. These methods include, but are not limited to oral routes, intraduodenal routes and rectal administration. Administration techniques that are optionally employed with the agents and methods described herein are found in sources e.g., Goodman and Gilman, The Pharmacological Basis of Therapeutics, current ed.; Pergamon; and Remington's, Pharmaceutical *Sciences* (current edition), Mack Publishing Co., Easton, Pa. In certain embodiments, the agents and compositions described herein are administered orally.

The term "calorie" refers to the amount of energy, e.g. heat, required to raise the temperature of 1 gram of water by 1° C. In various fields such as medicine, nutrition, and the exercise sciences, the term "calorie" is often used to describe a kilocalorie. A kilocalorie is the amount of energy needed to increase the temperature of 1 kilogram of water by 1° C. One kilocalorie equals 1000 calories. The kilocalorie is abbreviated as kc, kcal or Cal, whereas the calorie or gram calorie is abbreviated as cal. In some embodiments, food intake in the subject is measured in terms of overall calorie consumption. Likewise, in some embodiments, fat intake can be measured in terms of calories from fat.

As used herein, the terms "co-administration," "administered in combination with," and their grammatical equivalents, are meant to encompass administration of the selected therapeutic agents to a single patient, and are intended to include treatment regimens in which the agents are administered by the same or different route of administration or at the same or different times. In some embodiments the agents described herein will be co-administered with other agents. These terms encompass administration of two or more agents to the subject so that both agents and/or their metabolites are present in the subject at the same time. They include simultaneous administration in separate compositions, administration at different times in separate compositions, and/or administration in a composition in which both agents are present. Thus, in some embodiments, the agents described herein and the other agent(s) are administered in a single composition. In some embodiments, the agents described herein and the other agent(s) are admixed in the composition.

The terms "effective amount," "pharmaceutically effective amount" or "therapeutically effective amount" as used herein, refer to a sufficient amount of at least one agent being administered to achieve a desired result, e.g., to relieve to some extent one or more symptoms of a disease or condition being treated. In certain instances, the result is a reduction and/or alleviation of the signs, symptoms, or causes of a disease, or any other desired alteration of a biological system. In certain instances, an "effective amount" for therapeutic uses is the amount of the composition comprising an agent as set forth herein required to provide a clinically significant decrease in a disease. An appropriate "effective" amount in any individual case can be determined using any suitable technique, such as a dose escalation study.

"Enhancing enteroendocrine peptide secretion" refers to a sufficient increase in the level of the enteroendocrine peptide agent to, for example, decrease hunger in a subject, to curb appetite in a subject and/or decrease the food intake of a subject or individual and/or treat any disease or disorder described herein.

"FXR": farnesoid X receptor (also known as nuclear receptor subfamily 1, group H, member 4 (NR1H4)) (OMIM: 603826): This protein functions as a receptor for bile acids, and when bound to bile acids, regulates the expression of genes involved in bile acid synthesis and transport. FXR is expressed at high levels in the liver and intestine. Chenodeoxycholic acid and other bile acids are natural ligands for FXR. Similar to other nuclear receptors, when activated, FXR translocates to the cell nucleus, forms a dimer (in this case a heterodimer with RXR) and binds to hormone response elements on DNA, which up- or down-regulates the expression of certain genes. One of the primary functions of FXR activation is the suppression of cholesterol 7 alpha-hydroxylase (CYP7A1), the rate-limiting enzyme in bile acid synthesis from cholesterol. FXR does not directly bind to the CYP7A1 promoter. Rather, FXR induces expression of small heterodimer partner (SHP), which then functions to inhibit transcription of the CYP7A1 gene. In this way, a negative feedback pathway is established in which synthesis of bile acids is inhibited when cellular levels are already high. FXR sequences are publically available, for example from GenBank® sequence database (e.g., accession numbers NP_001193906 (human, protein) and NP_001156976 (mouse, protein), and NM_001206977 (human, nucleic acid) and NM_001163504 (mouse, nucleic acid)).

The term "metabolic disorder" refers to any disorder that involves an alteration in the normal metabolism of carbohydrates, lipids, proteins, nucleic acids or a combination thereof. A metabolic disorder is associated with either a deficiency or excess in a metabolic pathway resulting in an imbalance in metabolism of nucleic acids, proteins, lipids, and/or carbohydrates. Factors affecting metabolism include, but are not limited to, the endocrine (hormonal) control system (e.g., the insulin pathway, the enteroendocrine hormones including GLP-1, GLP-2, oxyntomodulin, PYY or the like), the neural control system (e.g., GLP-1 in the brain) or the like. Examples of metabolic disorders include and are not limited to diabetes, insulin resistance, dyslipidemia, metabolic syndrome, or the like.

The term "metabolic rate" refers to the rate at which the subject uses energy. This is also known as the rate of metabolism, or the rate of energy consumption, and reflects the overall activity of the individual's metabolism. The term basal metabolism refers to the minimum amount of energy required to maintain vital functions in an individual at complete rest, measured by the basal metabolic rate in a fasting individual who is awake and resting in a comfortably warm environment. The term "basal metabolic rate" refers to the rate at which energy is used by an individual at rest. Basal metabolic rate is measured in humans by the heat given off per unit time, and expressed as the calories released per kilogram of body weight or per square meter of body surface per hour. The heart beating, breathing, maintaining body temperature, and other basic bodily functions all contribute to basal metabolic rate. Basal metabolic rate can be determined to be the stable rate of energy metabolism measured in individuals under conditions of minimum environmental and physiological stress, or essentially at rest with no temperature change. The basal metabolic rate among individuals can vary widely. One example of an average value for basal metabolic rate is about 1 calorie per hour per kilogram of body weight.

The terms "non-systemic" or "minimally absorbed" as used herein refer to low systemic bioavailability and/or absorption of an administered compound. In some instances a non-systemic compound is a compound that is substantially not absorbed systemically. In some embodiments, FXR agonist compositions described herein deliver an FXR agonist to the distal ileum, colon, and/or rectum and not systemically (e.g., a substantial portion of the FXR agonist administered is not systemically absorbed). In some embodiments, the systemic absorption of a non-systemic compound is <0.1%, <0.3%, <0.5%, <0.6%, <0.7%, <0.8%, <0.9%, <1%, <1.5%, <2%, <3%, or <5% of the administered dose (wt. % or mol %). In some embodiments, the systemic absorption of a non-systemic compound is <15% of the administered dose. In some embodiments, the systemic absorption of a non-systemic compound is <25% of the administered dose. In an alternative approach, a non-systemic FXR agonist is a compound that has lower systemic bioavailability relative to the systemic bioavailability of a systemic FXR agonist. In some embodiments, the bioavailability of a non-systemic FXR agonist described herein is <30%, <40%, <50%, <60%, or <70% of the bioavailability of a systemic FXR agonist. In some embodiments, the serum concentration of the FXR agonist in the subject remains below the compound's $EC_{50}$ following administration.

The terms "prevent," "preventing" or "prevention," and other grammatical equivalents as used herein, include preventing additional symptoms, preventing the underlying metabolic causes of symptoms, inhibiting the disease or condition, e.g., arresting the development of the disease or condition and are intended to include prophylaxis. The terms further include achieving a prophylactic benefit. For prophylactic benefit, the compositions are optionally administered to a patient at risk of developing a particular disease, to a patient reporting one or more of the physiological symptoms of a disease, or to a patient at risk of reoccurrence of the disease.

The term "subject", "patient" or "individual" may be used interchangeably herein and refer to mammals and non-mammals, e.g., suffering from a disorder described herein. Examples of mammals include, but are not limited to, any member of the mammalian class: humans, non-human primates such as chimpanzees, and other apes and monkey species; farm animals such as cattle, horses, sheep, goats, swine; domestic animals such as rabbits, dogs, and cats; laboratory animals including rodents, such as rats, mice and guinea pigs, and the like. Examples of non-mammals include, but are not limited to, birds, fish, amphibians, and the like. In one embodiment of the methods and compositions provided herein, the mammal is a human.

The terms "treat," "treating" or "treatment," and other grammatical equivalents as used herein, include alleviating, inhibiting or reducing symptoms, reducing or inhibiting severity of, reducing incidence of, prophylactic treatment of, reducing or inhibiting recurrence of, preventing, delaying onset of, delaying recurrence of, abating or ameliorating a disease or condition symptoms, ameliorating the underlying metabolic causes of symptoms, inhibiting the disease or condition, e.g., arresting the development of the disease or condition, relieving the disease or condition, causing regression of the disease or condition, relieving a condition caused by the disease or condition, or stopping the symptoms of the disease or condition. The terms further include achieving a therapeutic benefit. Therapeutic benefit means eradication or amelioration of the underlying disorder being treated, and/or the eradication or amelioration of one or more of the physiological symptoms associated with the underlying disorder, such that an improvement is observed in the patient.

II. Overview

Disclosed herein are compounds that have activity as FXR agonists that are structurally distinct from bile acids, other synthetic FXR ligands, and other natural FXR ligands. Also disclosed herein are embodiments of a method for treating or preventing inflammation in the intestines and/or a metabolic disorder, such as diabetes or obesity, by administering a therapeutically effective amount of an FXR agonist to the GI tract of a subject, such as one of the novel FXR agonists disclosed herein. Also disclosed herein are methods for treating or preventing a cell proliferative disorder, such as cancer, for example in the intestine, by administering a therapeutically effective amount of an FXR agonist to the subject (e.g., to the GI tract), such as one of the novel FXR agonists disclosed herein. Also disclosed herein are methods for treating or preventing alcoholic liver disease (e.g., steatosis, cirrhosis, alcoholic hepatitis, elevated liver enzymes), such as in an alcoholic subject, by administering a therapeutically effective amount of an FXR agonist to the subject (e.g., to the GI tract), such as one of the novel FXR agonists disclosed herein.

The absorption of these FXR agonists is substantially restricted to the intestinal lumen when delivered orally. In various embodiments, administration of one or more of the disclosed FXR agonists results in activation of FXR transcriptional activity in the intestine, without substantially affecting other target tissues, such as liver or kidney. Surprisingly, despite this restricted activity, chronic administration with these agonists led to beneficial body-wide effects in obese subjects. The disclosed FXR agonists have potent anti-obesity and glucose lowering effects in vivo. These effects have not been observed with systemically-acting FXR ligands and include reductions in weight gain, hyperglycemia, and insulin resistance. In addition, administration of these FXR agonists produced a beneficial, anti-inflammatory effect in the intestines.

III. Compounds

Disclosed herein are embodiments of a compound having activity as an FXR agonist. Certain disclosed embodiments have formula 1

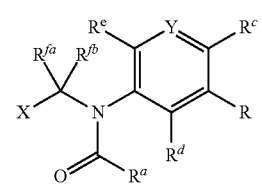

Formula 1 or a pharmaceutically acceptable salt thereof, wherein R is selected from

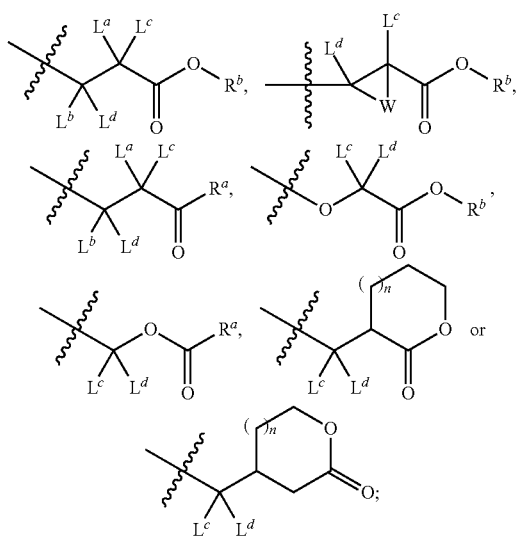

$R^a$ is selected from aryl, heteroaryl, alkyl, alkenyl, cycloalkyl, heterocyclic, or polycyclic; $R^b$ is selected from hydrogen, alkyl, alkenyl, or cycloalkyl; Y is $CR^g$, N or N—O (N-oxide); $R^c$, $R^d$, $R^e$ and $R^g$ are each independently selected from hydrogen, deuterium, halide, alkyl, alkenyl, alkoxy, alkylthio, amino, sulfonyl, aminosulfonyl, aminocarbonyl, acyl, hydroxyl or nitro; $R^{fa}$ and $R^{fb}$ are each independently selected from hydrogen, deuterium, halide or alkyl; $L^a$ and $L^b$ are each independently selected from hydrogen, deuterium, alkyl or cycloalkyl, or together form a pi-bond; $L^c$ and $L^d$ are each independently selected from hydrogen, deuterium, alkyl or cycloalkyl; W is selected from O or —$C(L^c)(L^d))_s$—; s is 1, 2, 3, 4, 5 or 6; n is 0 or 1; and X is aryl, heterocyclic or heteroaryl. In some embodiments when $R^b$ is hydrogen, the compounds have activity as FXR agonists. In other embodiments when $R^b$ is hydrogen, the compounds may have reduced or substantially no activity as FXR agonists.

Also with reference to formula 1, the following provisos apply:

if W is $CH_2$ and $L^c$ and $L^d$ are both H, then X is not a benzopyran;

if R is

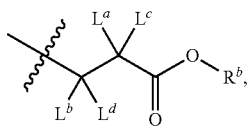

$L^c$ and $L^d$ are both H, and $L^a$ and $L^b$ are both H or together form a pi-bond, then X is not a benzopyran;

X is not substituted with —$R^x$-$L^x$-$R^{x2}$, where $R^x$ is selected from O, $NR^{x3}$, sulfonyl or S; $R^{x3}$ is selected from H, alkyl, alkenyl, alkynyl, cycloalkyl, cycloalkenyl, or aryl; $L^x$ is selected from a bond, alkylene, alkenylene, alkynylene, cycloalkyl, cycloalkenyl, heterocyclic, aryl, heteroaryl or $CR^{x4}R^{x5}$; $R^{x4}$ and $R^{x5}$ are each independently selected from H, D, halogen, alkyl, alkenyl, alkynyl, cycloalkyl, cycloalkenyl, —$C(O)OR^{x6}$, or —$C(O)NR^{x6}R^{x7}$; $R^{x6}$ and $R^{x7}$ are each independently selected from H, alkyl, alkenyl, alkynyl, cycloalkyl or cycloalkenyl; $R^{x2}$ is selected from —C(O)$L^{x2}R^{x8}$ or a carboxyl bioisostere; $L^{x2}$ is a bond or $NR^{x3}$; $R^{x8}$ is H, alkyl, alkenyl, alkynyl, cycloalkyl, cycloalkenyl, —$OR^{x9}$, $N(R^{x9})_2$, —$C(O)R^{x9}$, —$S(O)_2R^{x9}$, —$C(O)OR^{x9}$, —$S(O)_2N(R^{x9})_2$ or $C(O)N(R^{x9})_2$; and each $R^{x9}$ is independently selected from H, alkyl, alkenyl, alkynyl, cycloalkyl or cycloalkenyl; and when R is

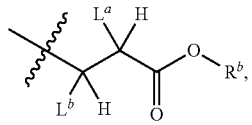

$R^c$, $R^d$, $R^e$ and $R^{fa}$ are all hydrogen, Y is CH and $L^a$ and $L^b$ are both H or together form a pi-bond, then if $R^a$ is cyclohexyl, $R^b$ is methyl, and $R^{fb}$ is H then X is not phenyl, 4-biphenyl, 4-bromophenyl, 3-bromophenyl, 2-bromophenyl, 4-tert-butylphenyl, 3-methoxyphenyl, 3,5-dimethoxyphenyl, 3-(trifluoromethyl)phenyl, 4-(3,4-difluorophenyl)phenyl, 4-(3-acetylphenyl)phenyl, 4-(4-methylthiophenyl)phenyl, 4-(4-methoxyphenyl)phenyl, 4-(3-methoxyphenyl)phenyl, 4-(2-methoxyphenyl)phenyl, 4-(3,5-dichlorophenyl)phenyl, 4-(4-tert-butylphenyl)phenyl, 4-(3-ethoxyphenyl)phenyl, 4-(3-chlorophenyl)phenyl, 4-(3-methylphenyl)phenyl, 4-(4-methylphenyl)phenyl, 4-(2-methoxy-5-chlorophenyl)phenyl, 4-(3-chloro-4-fluorophenyl)phenyl, 4-(4-trifluoromethoxyphenyl)phenyl, 4-(3-trifluoromethoxyphenyl)phenyl, 4-(2,6-dimethoxyphenyl)phenyl, 4-(4-dimethylaminophenyl)phenyl,

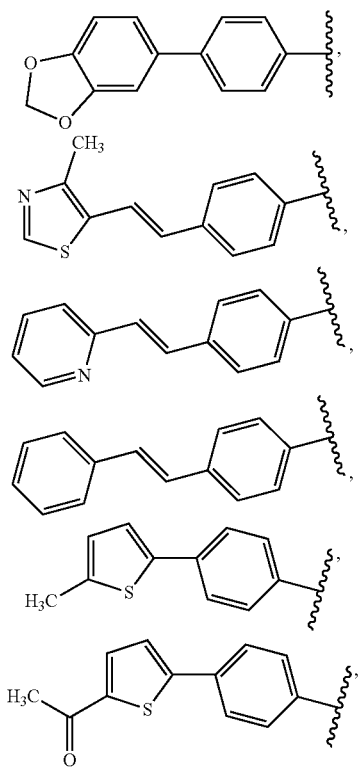

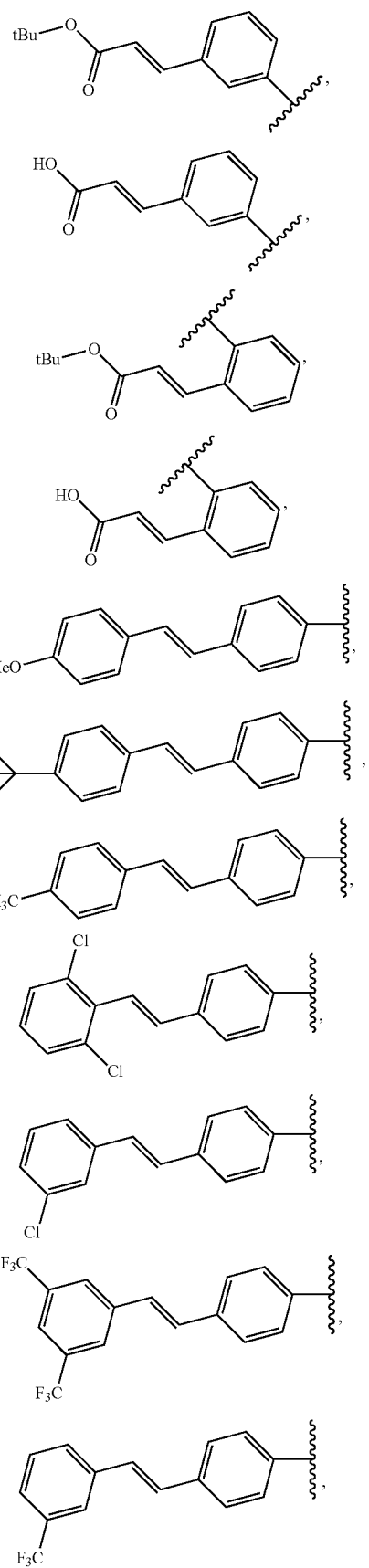
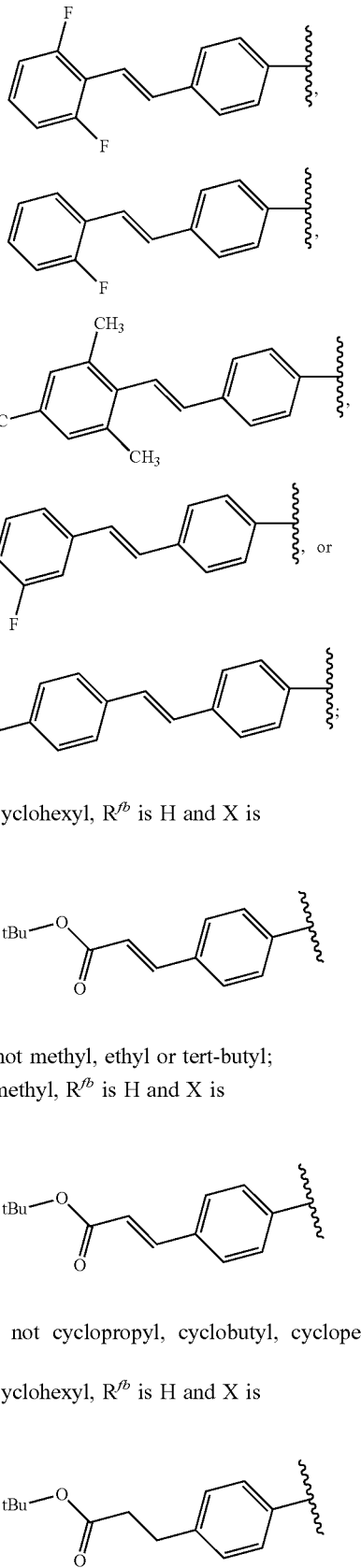
if $R^a$ is cyclohexyl, $R^{fb}$ is H and X is
then $R^b$ is not methyl, ethyl or tert-butyl;
if $R^b$ is methyl, $R^{fb}$ is H and X is
then $R^a$ is not cyclopropyl, cyclobutyl, cyclopentyl, or cyclohexyl;
if $R^a$ is cyclohexyl, $R^{fb}$ is H and X is
then $R^b$ is not methyl or tert-butyl;

if $R^a$ is cyclohexyl, $R^b$ is methyl, $R^{fb}$ is H and X is

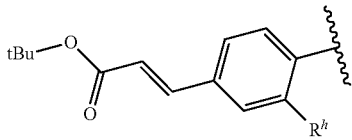

then $R^h$ is not hydroxyl, (trimethylsilyl)ethoxymethyl-O, methoxy, 0-benzyl, $OCH_2CO_2Et$, $OC(O)CH_3$, $OC(O)Ph$ or $OSO_2CH_3$;

if $R^a$ is cyclohexyl, $R^b$ is methyl, $R^{fb}$ is H and X is

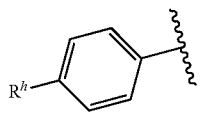

then $R^h$ is not —CH=CHC(O)OMe, —CH=CHC(O)OEt, —CH=CHC(O)NMe$_2$, —CH=CHC(O)NH$^t$Bu, —CH=CHC(O)O$^t$Bu, —CH=CHC(O)O$^i$Pr, —CH=CHC(O)OCH$_2$Ph, —CH=CHC(O)OH, —CH=CHCH$_2$OMe, —CH=CHCH$_2$OEt or —CH=CHCH$_2$OPh.

In some embodiments of formula 1, $R^b$ is substituted with substituents that improve the compounds water solubility. In certain embodiments, $R^b$ is selected from alkyl, alkenyl, or cycloalkyl, each substituted with one or more hydroxyl groups.

In some embodiments, $R^a$ is substituted with one or more hydroxyl groups, or a lower PEG group, such as PEG 2, PEG 3, PEG 4, PEG 5, PEG 6, PEG 8, PEG 10.

In some embodiments, X is not a benzopyran.

In particular embodiments, R is

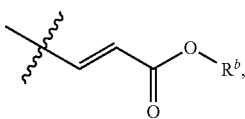

leading to compounds having formula 2

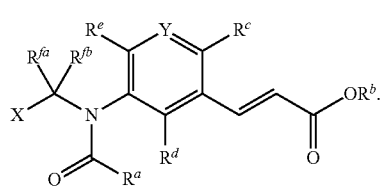

Formula 2

In some disclosed embodiments, the compounds having activity as FXR agonists have general formula 3

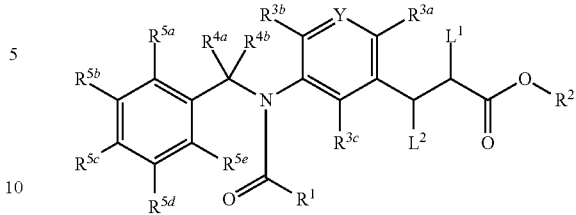

Formula 3 or a pharmaceutically acceptable salt thereof. With reference to formula 3, $R^1$ is selected from aryl, heteroaryl, heterocyclic, alkyl, alkenyl, cycloalkyl, cycloalkenyl or polycyclic; $R^2$ is selected from hydrogen, alkyl, alkenyl, or cycloalkyl; Y is selected from N, N—O (N-oxide) or C—$R^{3d}$; $R^{3a}$, $R^{3b}$, $R^{3c}$ and $R^{3d}$ are each independently selected from hydrogen, deuterium, halide, alkyl, alkenyl, alkoxy, alkylthio, amino, sulfonyl, aminosulfonyl, aminocarbonyl, acyl, hydroxyl or nitro; $R^{4a}$ and $R^{4b}$ are each independently selected from hydrogen (H), deuterium (D), halide or alkyl; $L^1$ and $L^2$ are independently selected from hydrogen, deuterium, alkyl, cycloalkyl, or together form a pi-bond; and $R^{5a}$, $R^{5b}$, $R^{5c}$, $R^{5d}$ and $R^{5e}$ are each independently selected from hydrogen, deuterium, halide, alkyl, alkenyl, alkoxy, alkylthio, amino, sulfonyl, aminosulfonyl, aminocarbonyl, acyl, aryl, heteroaryl, cycloalkyl, heterocyclyl, hydroxyl or nitro, or any two adjacent groups selected together form an aryl, heteroaryl, cycloalkyl or heterocyclic ring. In some embodiments when $R^2$ is hydrogen, the compounds have activity as FXR agonists. In other embodiments when $R^2$ is hydrogen, the compounds may have reduced or substantially no activity as FXR agonists.

Also with reference to formula II, none of $R^{5a}$, $R^{5b}$, $R^{5c}$, $R^{5d}$ or $R^{5e}$ is —$R^x$-$L^x$-$R^{x2}$, where $R^x$ is selected from O, $NR^{x3}$, sulfonyl or S; $R^{x3}$ is selected from H, alkyl, alkenyl, alkynyl, cycloalkyl, cycloalkenyl, or aryl; $L^x$ is selected from a bond, alkylene, alkenylene, alkynylene, cycloalkyl, cycloalkenyl, heterocyclic, aryl, heteroaryl or $CR^{x4}R^{x5}$; $R^{x4}$ and $R^{x5}$ are each independently selected from H, D, halogen, alkyl, alkenyl, alkynyl, cycloalkyl, cycloalkenyl, —C(O)OR$^{x6}$, or —C(O)NR$^{x6}$R$^{x7}$; $R^{x6}$ and $R^{x7}$ are each independently selected from H, alkyl, alkenyl, alkynyl, cycloalkyl or cycloalkenyl; $R^{x2}$ is selected from —C(O)L$^{x2}$R$^{x8}$ or a carboxyl bioisostere; $L^{x2}$ is a bond or NR$^{x3}$; $R^{x8}$ is H, alkyl, alkenyl, alkynyl, cycloalkyl, cycloalkenyl, —OR$^{x9}$, N(R$^{x9}$)$_2$, —C(O)R$^{x9}$, —S(O)$_2$R$^{x9}$, —C(O)OR$^{x9}$, —S(O)$_2$N(R$^{x9}$)$_2$ or —C(O)N(R$^{x9}$)$_2$; and each $R^{x9}$ is independently selected from H, alkyl, alkenyl, alkynyl, cycloalkyl or cycloalkenyl; and if $L^1$ and $L^2$ are both hydrogen or together form a pi-bond then at least one of the following conditions applies: Y is N or C-halogen; or $R^1$ is polycyclic; or $R^{4a}$ is D; or $R^{5a}$ is F, Cl, I; or $R^{5d}$ and $R^{5e}$ together form an aryl, heteroaryl, cycloalkyl or heterocyclic ring; or $R^{5b}$ and $R^{5c}$ together form an aryl, cycloalkyl, nitrogen-containing heterocyclic or nitrogen-containing heteroaryl ring, or any combination thereof.

In some embodiments, $R^2$ is substituted with one or more groups that improve the compounds water solubility. In certain embodiments, $R^2$ is substituted with one or more hydroxyl groups.

In some embodiments, one or more of $R^{5a}$, $R^{5b}$, $R^{5c}$, $R^{5d}$ or $R^{5e}$ is selected from

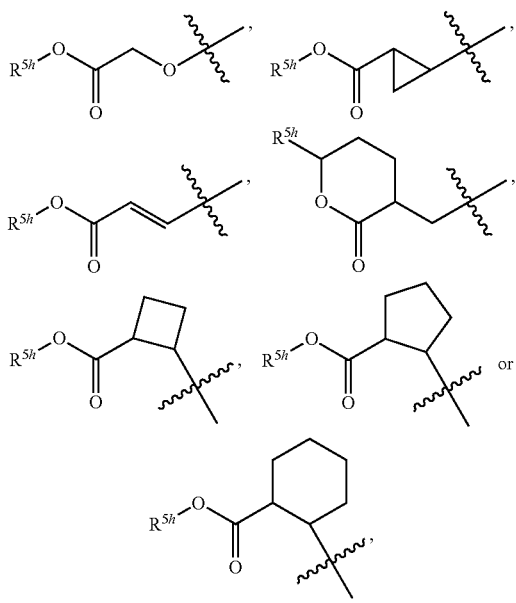

where $R^{5h}$ is alkyl, alkenyl, hydrogen, cycloalkyl, or heterocyclic.

In particular embodiments, $L^1$ and $L^2$ together form a pi-bond, leading to compounds having a formula 4

Formula 4

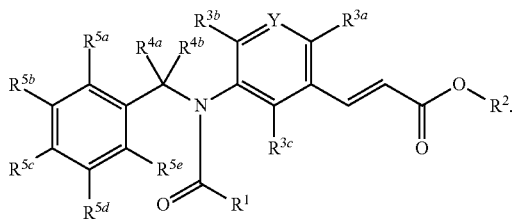

In some embodiments of general formula 4, Y is $CR^{3d}$, leading to compounds having general formula 5

Formula 5

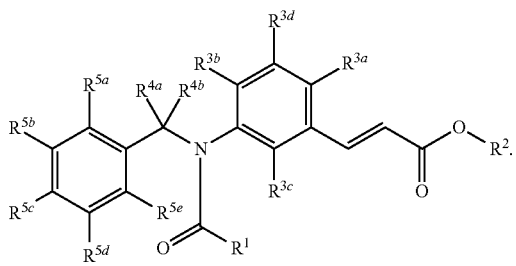

With reference to formula 5, $R^{3d}$ or $R^{5a}$ or both are halogen, such as F, Cl, Br or I, and $R^1$, $R^2$, $R^{3a}$, $R^{3b}$, $R^{3c}$, $R^{4a}$, $R^{4b}$, $R^{5b}$, $R^{5c}$, $R^{5d}$ and $R^{5e}$ are defined as for formula 3, above. In some working embodiments, $R^{3d}$ or $R^{5a}$ or both are F.

In other embodiments of formula 4, Y is N, resulting in compounds having general formula 6

Formula 6

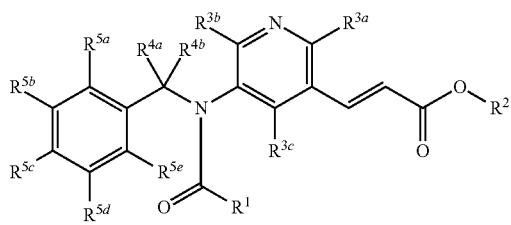

where $R^1$, $R^2$, $R^{3a}$, $R^{3b}$, $R^{3c}$, $R^{4a}$, $R^{4b}$, $R^{5a}$, $R^{5b}$, $R^{5c}$, $R^{5d}$ and $R^{5e}$ are defined as for formula 3.

In certain embodiments of formula 4, $R^1$ is polycyclic. This leads to compounds having general formula 7

Formula 7

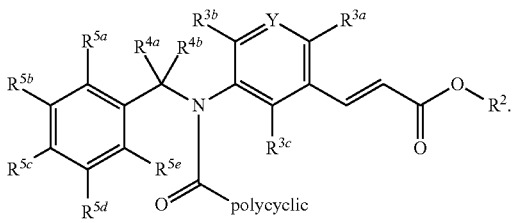

With reference to formula 7, $R^2$, $R^{3a}$, $R^{3b}$, $R^{3c}$, $R^{4a}$, $R^{4b}$, $R^{5a}$, $R^{5b}$, $R^{5c}$, $R^{5d}$, $R^{5e}$ and Y are defined as for formula 3, above. In some examples, the polycyclic is selected from

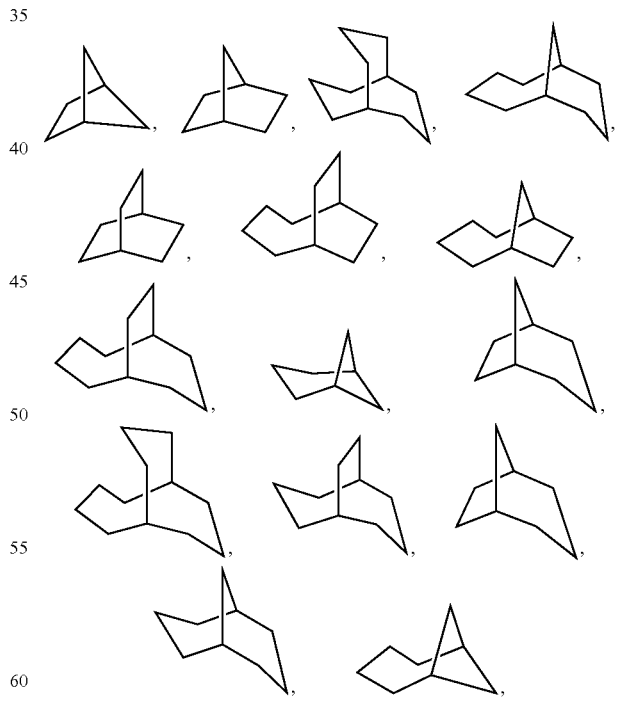

or adamantyl. In other examples, the polycyclic is selected from [2.1.1], [2.2.1], [3.3.3], [4.3.1], [2.2.2], [4.2.2], [4.2.1], [4.3.2], [3.1.1], [3.2.1], [4.3.3], [3.3.2], [3.2.2], [3.3.1], [4.1.1], or adamantyl. In certain working embodiments the polycyclic is

In certain embodiments of general formula 3, $R^{5c}$ is a nitrogen-containing heteroaryl ring. Exemplary nitrogen-containing heteroaryl rings include, but are not limited to, pyridine, pyrazole, pyrrole, imidazole, oxazole, isoxazole, thiazole, isothiazole, triazole, pyrimidine, pyrazine, triazine, benzopyrazole, benzimidazole, indole, quinoline, indazole, purine, quinoxaline, and acridine. In particular embodiments, the compounds have general formula 8

Formula 8

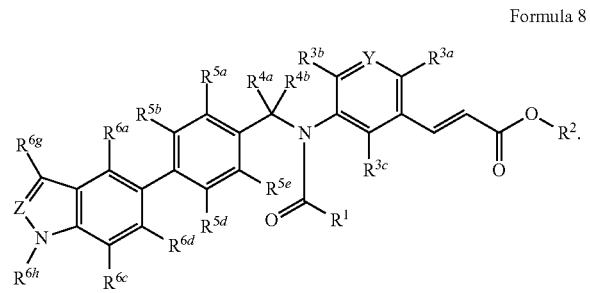

With reference to formula 8, $R^1$, $R^2$, $R^{3a}$, $R^{3b}$, $R^{3c}$, $R^{4a}$, $R^{4b}$, $R^{5a}$, $R^{5b}$, $R^{5e}$ and Y are defined as for formula 3, $R^{6a}$, $R^{6c}$, $R^{6d}$ and $R^{6g}$ are each independently selected from H, D, halogen or alkyl, $R^{6h}$ is selected from H, D, alkyl, cycloalkyl, aryl or heteroaryl, and Z is selected from N, CH or C-alkyl. In certain working embodiments, Z is N and/or $R^{6h}$ is methyl. In some examples $R^{6a}$, $R^{6c}$, $R^{6d}$ and $R^{6g}$ are all hydrogen. In particular examples, Y is C—$R^{3d}$ and at least one of $R^{3d}$ and $R^{5a}$ is F.

In certain embodiments of general formula 5, $R^{5c}$ is a 4-aminophenyl, leading to compounds having general formula 9

Formula 9

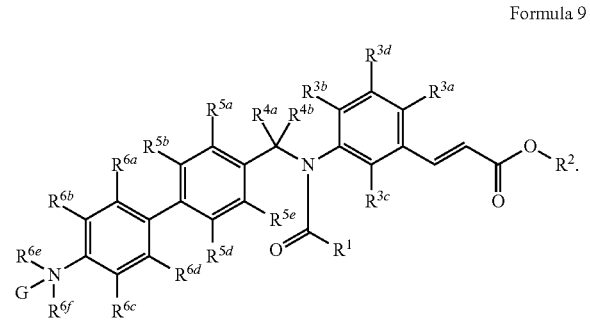

With reference to formula 9, $R^1$, $R^2$, $R^{3a}$, $R^{3b}$, $R^{3c}$, $R^{3d}$, $R^4$, $R^{5a}$, $R^{5b}$, $R^{5d}$ and $R^{5e}$ are defined as for formula 5, $R^{6a}$, $R^{6b}$, $R^{6c}$ and $R^{6d}$ are each independently selected from H, D, halogen or alkyl, G is a lone pair of electrons or an oxygen, and $R^{6e}$ and $R^{6f}$ are each independently selected from alkyl, H or cycloalkyl, with the provisos that $R^{3d}$ or $R^{5a}$ or both are halogen, or $R^4$ is D, or $R^1$ is polycyclic, or any combination thereof. In working embodiments, $R^{6e}$ and $R^{6f}$ are both methyl.

In certain embodiments, compounds having formula 9 are N-oxides, leading to compounds having formula 10

Formula 10

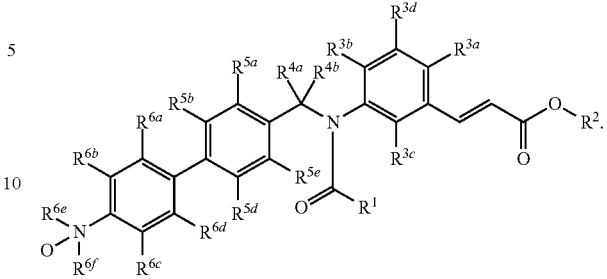

In particular examples of any of the above embodiments $R^{4a}$ is D, $R^{4b}$ is H, and/or $R^2$ is methyl. In other examples, both $R^{4a}$ and $R^{4b}$ are D. And in particular embodiments of formulas 3, 4, 5, 6, 7, 9 or 10, $R^1$ is cyclohexyl.

In some disclosed embodiments, the compounds having activity as FXR agonists have general formula 11

Formula 11

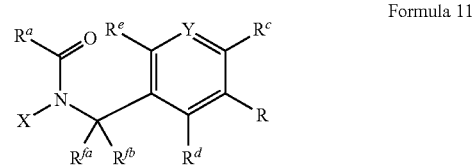

or a pharmaceutically acceptable salt thereof, wherein $R^a$ is selected from aryl, heteroaryl, alkyl, alkenyl, cycloalkyl, heterocyclic, or polycyclic; $R^b$ is selected from alkyl, alkenyl, or cycloalkyl; Y is $CR^g$, N or N—O (N-oxide); $R^c$, $R^d$, $R^e$ and $R^g$ are each independently selected from hydrogen, deuterium, halide, alkyl, alkenyl, alkoxy, alkylthio, amino, sulfonyl, aminosulfonyl, aminocarbonyl, cycloalkyl, heterocyclic, acyl, hydroxyl or nitro; $R^{fa}$ and $R^{fb}$ are each independently selected from hydrogen, deuterium, halide or alkyl; X is aryl, heterocyclic or heteroaryl; R is selected from

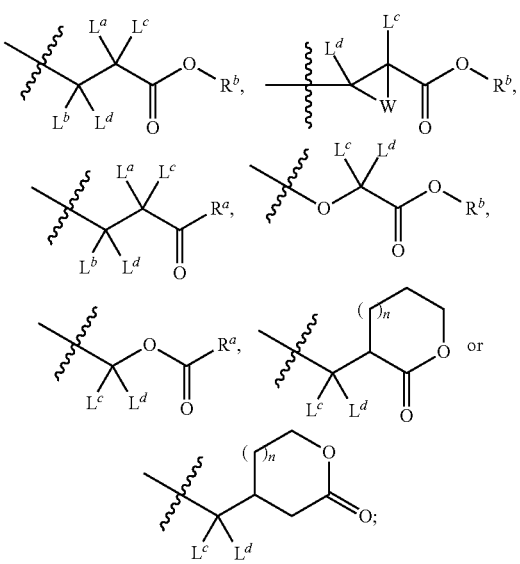

$L^a$ and $L^b$ are each independently selected from hydrogen, deuterium, alkyl or cycloalkyl, or together form a pi-bond;

$L^c$ and $L^d$ are each independently selected from hydrogen, deuterium, alkyl or cycloalkyl; W is selected from O or $-(C(L^c)(L^d))_s-$; s is 1, 2, 3, 4, 5 or 6; n is 0 or 1; and X is not substituted with $-R^x-L^x-R^{x2}$, where $R^x$ is selected from O, $NR^{x3}$, sulfonyl or S; $R^{x3}$ is selected from H, alkyl, alkenyl, alkynyl, cycloalkyl, cycloalkenyl, or aryl; $L^x$ is selected from a bond, alkylene, alkenylene, alkynylene, cycloalkyl, cycloalkenyl, heterocyclic, aryl, heteroaryl or $CR^{x4}R^{x5}$; $R^{x4}$ and $R^{x5}$ are each independently selected from H, D, halogen, alkyl, alkenyl, alkynyl, cycloalkyl, cycloalkenyl, $-C(O)OR^{x6}$, or $-C(O)NR^{x6}R^{x7}$; $R^{x6}$ and $R^{x7}$ are each independently selected from H, alkyl, alkenyl, alkynyl, cycloalkyl or cycloalkenyl; $R^{x2}$ is selected from $-C(O)L^{x2}R^{x8}$ or a carboxyl bioisostere; $L^{x2}$ is a bond or $NR^{x3}$; $R^{x8}$ is H, alkyl, alkenyl, alkynyl, cycloalkyl, cycloalkenyl, $-OR^{x9}$, $N(R^{x9})_2$, $-C(O)R^{x9}$, $-S(O)_2R^{x9}$, $-C(O)OR^{x9}$, $-S(O)_2N(R^{x9})_2$ or $-C(O)N(R^{x9})_2$; and each $R^{x9}$ is independently selected from H, alkyl, alkenyl, alkynyl, cycloalkyl or cycloalkenyl.

In some disclosed embodiments, the compounds having activity as FXR agonists have general formula 12

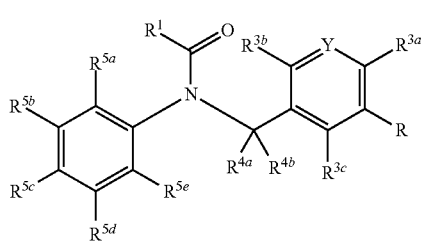

Formula 12 or a pharmaceutically acceptable salt thereof. With reference to formula 12, R is selected from

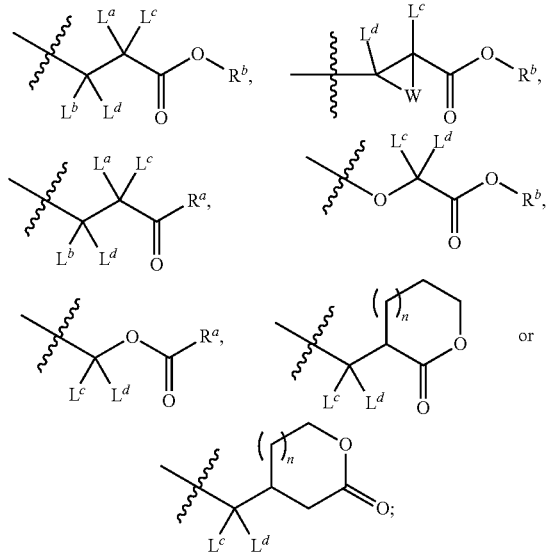

$L^a$ and $L^b$ are each independently selected from hydrogen, deuterium, alkyl or cycloalkyl, or together form a pi-bond; $L^c$ and $L^d$ are each independently selected from hydrogen, deuterium, alkyl or cycloalkyl; W is selected from O or $-(C(L^c)(L^d))_s-$; s is 1, 2, 3, 4, 5 or 6; n is 0 or 1; $R^1$ is selected from aryl, heteroaryl, heterocyclic, alkyl, alkenyl, cycloalkyl, cycloalkenyl or polycyclic; $R^2$ is selected from alkyl, alkenyl, or cycloalkyl; Y is selected from N, N—O (N-oxide) or $C-R^{3d}$; $R^{3a}$, $R^{3b}$, $R^{3c}$ and $R^{3d}$ are each independently selected from hydrogen, deuterium, halide, alkyl, alkenyl, alkoxy, alkylthio, amino, sulfonyl, aminosulfonyl, aminocarbonyl, acyl, hydroxyl or nitro; $R^{4a}$ and $R^{4b}$ are each independently selected from hydrogen, deuterium, halide or alkyl; $R^{5a}$, $R^{5b}$, $R^{5c}$, $R^{5d}$ and $R^{5e}$ are each independently selected from hydrogen, deuterium, halide, alkyl, alkenyl, alkoxy, alkylthio, amino, sulfonyl, aminosulfonyl, aminocarbonyl, acyl, aryl, heteroaryl, cycloalkyl, heterocyclyl, hydroxyl or nitro, or any two adjacent groups selected together form an aryl, heteroaryl, cycloalkyl or heterocyclic ring; and none of $R^{5a}$, $R^{5b}$, $R^{5c}$, $R^{5d}$ or $R^{5e}$ is $-R^x-L^x-R^{2x}$, where $R^x$ is selected from O, $NR^{x3}$, sulfonyl or S; $R^{x3}$ is selected from H, alkyl, alkenyl, alkynyl, cycloalkyl, cycloalkenyl, or aryl; $L^x$ is selected from a bond, alkylene, alkenylene, alkynylene, cycloalkyl, cycloalkenyl, heterocyclic, aryl, heteroaryl or $CR^{x4}R^{x5}$; $R^{x4}$ and $R^{x5}$ are each independently selected from H, D, halogen, alkyl, alkenyl, alkynyl, cycloalkyl, cycloalkenyl, $-C(O)OR^{x6}$, or $C(O)NR^{x6}R^{x7}$; $R^{x6}$ and $R^{x7}$ are each independently selected from H, alkyl, alkenyl, alkynyl, cycloalkyl or cycloalkenyl; $R^{x2}$ is selected from $-C(O)L^{x2}R^{x8}$ or a carboxyl bioisostere; $L^{x2}$ is a bond or $NR^{x3}$; $R^{x8}$ is H, alkyl, alkenyl, alkynyl, cycloalkyl, cycloalkenyl, $-OR^{x9}$, $N(R^{x9})_2$, $-C(O)R^{x9}$, $-S(O)_2R^{x9}$, $-C(O)OR^{x9}$, $-S(O)_2N(R^{x9})_2$ or $-C(O)N(R^{x9})_2$; and each $R^{x9}$ is independently selected from H, alkyl, alkenyl, alkynyl, cycloalkyl or cycloalkenyl.

In some other embodiments, the compounds having activity as FXR agonists have general formula 13

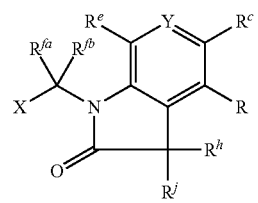

Formula 13 or a pharmaceutically acceptable salt thereof, wherein R is selected from

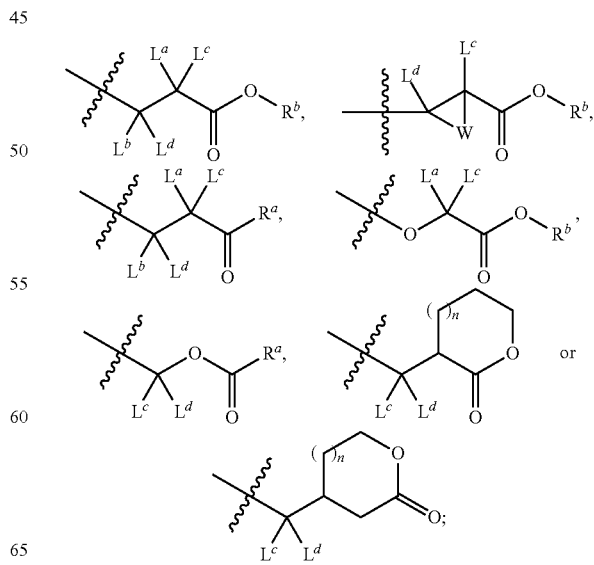

and $L^b$ are each independently selected from hydrogen, deuterium, alkyl or cycloalkyl, or together form a pi-bond; $L^c$ and $L^d$ are each independently selected from hydrogen, deuterium, alkyl or cycloalkyl; W is selected from O or —(C($L^c$)($L^d$))$_s$-; s is 1, 2, 3, 4, 5 or 6; n is 0 or 1; $R^b$ is selected from alkyl, alkenyl, or cycloalkyl; Y is $CR^g$, N or N—O (N-oxide); $R^c$, $R^e$ and $R^g$ are each independently selected from hydrogen, deuterium, halide, alkyl, alkenyl, alkoxy, alkylthio, amino, sulfonyl, aminosulfonyl, aminocarbonyl, cycloalkyl, heterocyclic, acyl, hydroxyl or nitro; $R^{fa}$ and $R^{fb}$ are each independently selected from hydrogen, deuterium, halide or alkyl; $R^h$ and $R^j$ are each independently selected from hydrogen, deuterium, halide, alkyl, cycloalkyl, heterocycloalkyl, alkenyl, aryl or heteroaryl; X is aryl, heterocyclic or heteroaryl; and X is not substituted with —$R^x$-$L^x$-$R^{x2}$, where $R^x$ is selected from O, $NR^{x3}$, sulfonyl or S; $R^{x3}$ is selected from H, alkyl, alkenyl, alkynyl, cycloalkyl, cycloalkenyl, or aryl; $L^x$ is selected from a bond, alkylene, alkenylene, alkynylene, cycloalkyl, cycloalkenyl, heterocyclic, aryl, heteroaryl or $CR^{x4}R^{x5}$; $R^{x4}$ and $R^{x5}$ are each independently selected from H, D, halogen, alkyl, alkenyl, alkynyl, cycloalkyl, cycloalkenyl, —C(O)$OR^{x6}$, or C(O)$NR^{x6}R^{x7}$; $R^{x6}$ and $R^{x7}$ are each independently selected from H, alkyl, alkenyl, alkynyl, cycloalkyl or cycloalkenyl; $R^{x2}$ is selected from —C(O)$L^{x2}R^{x8}$ or a carboxyl bioisostere; $L^{x2}$ is a bond or $NR^{x3}$; $R^{x8}$ is H, alkyl, alkenyl, alkynyl, cycloalkyl, cycloalkenyl, —$OR^{x9}$, $N(R^{x9})_2$, —C(O)$R^{x9}$, —S(O)$_2R^{x9}$, —C(O)$OR^{x9}$, —S(O)$_2N(R^{x9})_2$ or —C(O)N($R^{x9}$)$_2$; and each $R^{x9}$ is independently selected from H, alkyl, alkenyl, alkynyl, cycloalkyl or cycloalkenyl.

In some embodiments, prodrugs of compounds having activity as FXR agonists have general formula 14

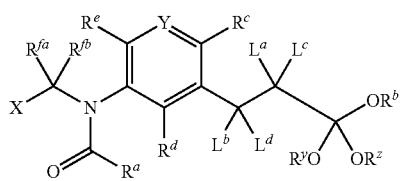

Formula 14 or a pharmaceutically acceptable salt thereof, wherein $R^a$ is selected from aryl, heteroaryl, alkyl, alkenyl, cycloalkyl, heterocyclic, or polycyclic; $R^b$ is selected from alkyl, alkenyl, or cycloalkyl; Y is $CR^g$, N or N—O (N-oxide); $R^c$, $R^d$, $R^e$ and $R^g$ are each independently selected from hydrogen, deuterium, halide, alkyl, alkenyl, alkoxy, alkylthio, amino, sulfonyl, aminosulfonyl, aminocarbonyl, acyl, hydroxyl or nitro; $R^{fa}$ and $R^{fb}$ are each independently selected from hydrogen, deuterium, halide or alkyl; X is aryl, heterocyclic or heteroaryl; $R^y$ and $R^z$ are selected from alkyl, cycloalkyl, heterocyclic alkyl, aryl, or heteroaryl, or $R^y$ and $R^z$ may together form a cycloheteroalkyl ring; $L^a$ and $L^b$ are independently H, D or alkyl or together form a π-bond, a cyclopropyl or an epoxide ring; $L^c$ and $L^d$ are independently H, D or alkyl; and X is not substituted with —$R^x$-$L^x$-$R^{x2}$, where $R^x$ is selected from O, $NR^{x3}$, sulfonyl or S; $R^{x3}$ is selected from H, alkyl, alkenyl, alkynyl, cycloalkyl, cycloalkenyl, or aryl; $L^x$ is selected from a bond, alkylene, alkenylene, alkynylene, cycloalkyl, cycloalkenyl, heterocyclic, aryl, heteroaryl or $CR^{x4}R^{x5}$; $R^{x4}$ and $R^{x5}$ are each independently selected from H, D, halogen, alkyl, alkenyl, alkynyl, cycloalkyl, cycloalkenyl, —C(O)$OR^{x6}$, —C(O)$NR^{x6}R^{x7}$; $R^{x6}$ and $R^{x7}$ are each independently selected from H, alkyl, alkenyl, alkynyl, cycloalkyl or cycloalkenyl; $R^{x2}$ is selected from —C(O)$L^{x2}R^{x8}$ or a carboxyl bioisostere; $L^{x2}$ is a bond or $NR^{x3}$; $R^{x8}$ is H, alkyl, alkenyl, alkynyl, cycloalkyl, cycloalkenyl, —$OR^{x9}$, $N(R^{x9})_2$, —C(O)$R^{x9}$, —S(O)$_2R^{x9}$, —C(O)$OR^{x9}$, —S(O)$_2N(R^{x9})_2$ or C(O)$N(R^{x9})_2$; and each $R^{x9}$ is independently selected from H, alkyl, alkenyl, alkynyl, cycloalkyl or cycloalkenyl.

In particular embodiments of formula 14, $R^y$ and $R^z$ together form a 5-membered heteroalkyl ring substituted with an ascorbate moiety, leading to compounds having formula 15

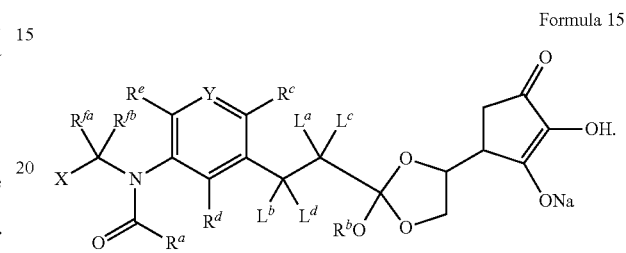

Formula 15

In other embodiments, prodrugs of compounds having activity as FXR agonists have general formula 16

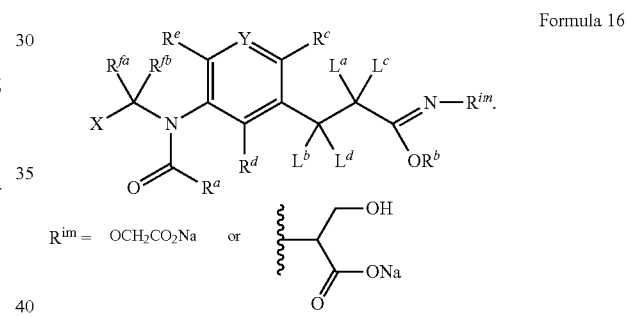

Formula 16

($R^{x9}$)$_2$ or —C(O)N($R^{x9}$)$_2$; and each $R^{x9}$ is independently selected from H, alkyl, alkenyl, alkynyl, cycloalkyl or cycloalkenyl.

In still further embodiments, prodrugs of compounds having activity as FXR agonists have general formula 17

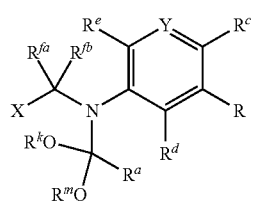

Formula 17 or a pharmaceutically acceptable salt thereof, wherein R is selected from

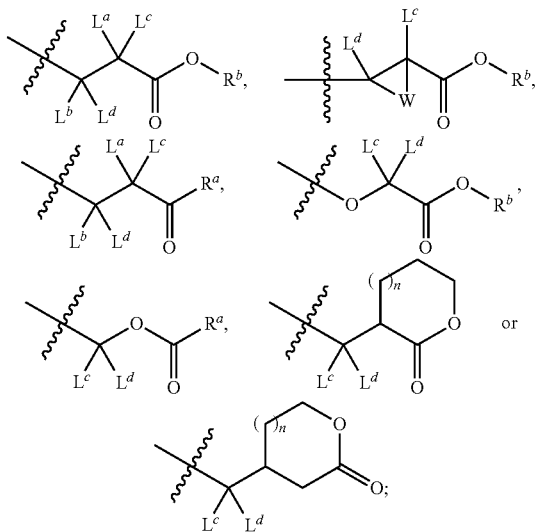

$L^a$ and $L^b$ are each independently selected from hydrogen, deuterium, alkyl or cycloalkyl, or together form a pi-bond; $L^c$ and $L^d$ are each independently selected from hydrogen, deuterium, alkyl or cycloalkyl; W is selected from O or —(C($L^c$)($L^d$))$_s$—; s is 1, 2, 3, 4, 5 or 6; n is 0 or 1; $R^a$ is selected from aryl, heteroaryl, alkyl, alkenyl, cycloalkyl, heterocyclic, or polycyclic; $R^b$ is selected from alkyl, alkenyl, or cycloalkyl; Y is $CR^g$, N or N—O (N-oxide); $R^c$, $R^d$, $R^e$ and $R^g$ are each independently selected from hydrogen, deuterium, halide, alkyl, alkenyl, alkoxy, alkylthio, amino, sulfonyl, aminosulfonyl, aminocarbonyl, cycloalkyl, heterocyclic, acyl, hydroxyl or nitro; $R^{fa}$ and $R^{fb}$ are each independently selected from hydrogen, deuterium, halide or alkyl; $R^k$ and $R^m$ are independently selected from H, alkyl, aryl, cycloalkyl, heterocycloalkyl, heteroaryl, or together $R^k$ and $R^m$ form a cycloalkyl or heterocycloalkyl ring; X is aryl, heterocyclic or heteroaryl; and X is not substituted with —$R^x$-$L^x$-$R^{x2}$, where $R^x$ is selected from O, $NR^{x3}$, sulfonyl or S; $R^{x3}$ is selected from H, alkyl, alkenyl, alkynyl, cycloalkyl, cycloalkenyl, or aryl; $L^x$ is selected from a bond, alkylene, alkenylene, alkynylene, cycloalkyl, cycloalkenyl, heterocyclic, aryl, heteroaryl or $CR^{x4}R^{x5}$; $R^{x4}$ and $R^{x5}$ are each independently selected from H, D, halogen, alkyl, alkenyl, alkynyl, cycloalkyl, cycloalkenyl, —C(O)O$R^{x6}$, or —C(O)N$R^{x6}R^{x7}$; $R^{x6}$ and $R^{x7}$ are each independently selected from H, alkyl, alkenyl, alkynyl, cycloalkyl or cycloalkenyl; $R^{x2}$ is selected from —C(O)$L^{x2}R^{x8}$ or a carboxyl bioisostere; $L^{x2}$ is a bond or $NR^{x3}$; $R^{x8}$ is H, alkyl, alkenyl, alkynyl, cycloalkyl, cycloalkenyl, —O$R^{x9}$, N($R^{x9}$)$_2$, —C(O)$R^{x9}$, —S(O)$_2R^{x9}$, —C(O)O$R^{x9}$, —S(O)$_2$N($R^{x9}$)$_2$ or —C(O)N($R^{x9}$)$_2$; and each $R^{x9}$ is independently selected from H, alkyl, alkenyl, alkynyl, cycloalkyl or cycloalkenyl.

In some embodiments of formula 17 $R^k$ and $R^m$ together form a 5-membered ring, leading to compounds having a formula 18

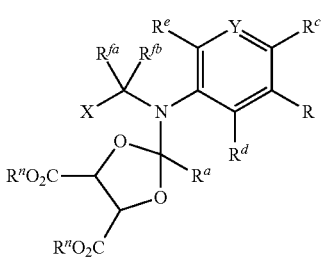

Formula 18 or pharmaceutically acceptable salt thereof, wherein each $R^n$ is independently selected from H, alkyl, or a metal salt such as Na, K, or Li.

In any of the above embodiments of formulas 1, 9 or 13-18, X is heteroaryl or heterocyclic, and in particular embodiments, X is pyridine or piperidine.

In other embodiments of formulas 1, 10, 11, or 13-18, X is a phenyl substituted with an aryl or heteroaryl group. In certain embodiments, X is a phenyl substituted with the aryl or heteroaryl group selected from benzoxazine, dihydrobenzoxazine, quinoxaline, tetrahydroquinoxaline, benzodioxane, benzothiazine, dihydrobenzothiazine, dihydrobenzothiazine-1,1-dioxide, benzodithiine, benzodithiine-1,1,4,4-tetraoxide, benzofuran, benzothiophene, indole, benzisoxazole, indazole, benzotriazole, benzimidazole, benzoxazole, benzthiazole or benzisothiazole. In particular embodiments, X is selected from

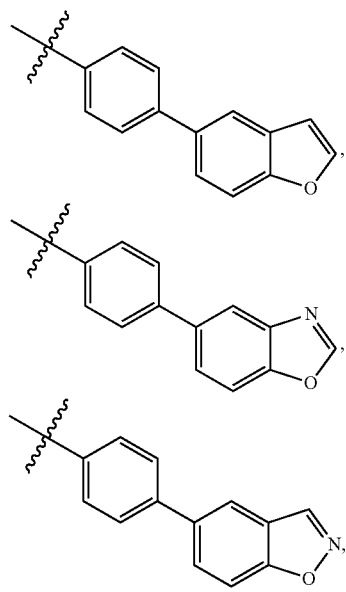

-continued
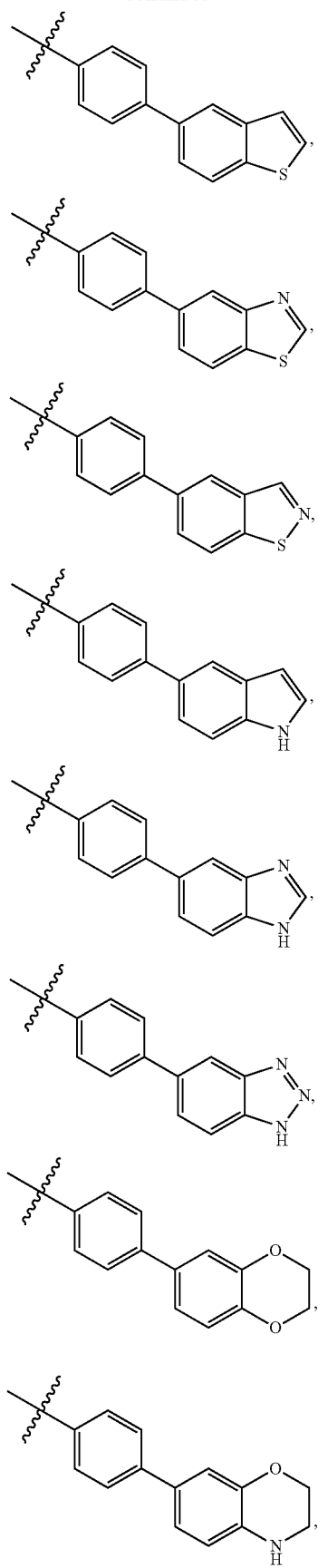
-continued
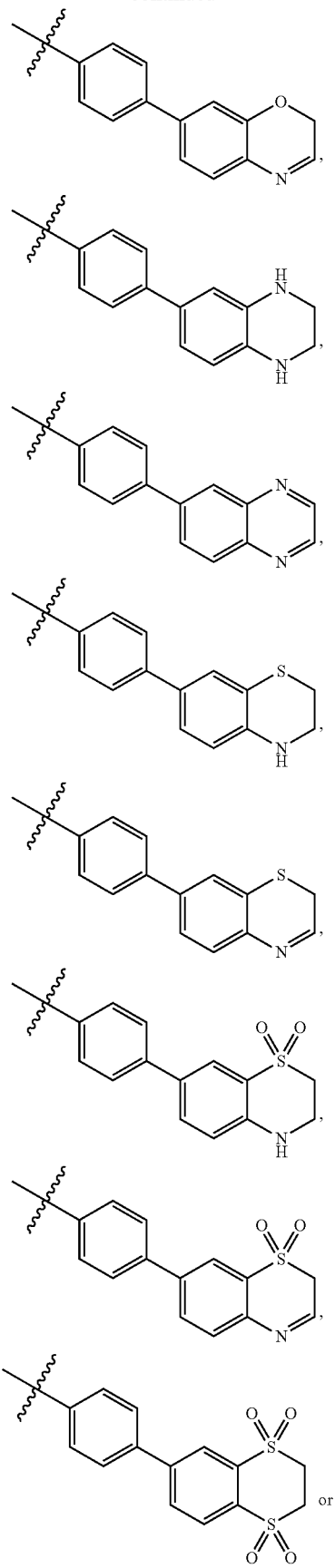
or

-continued

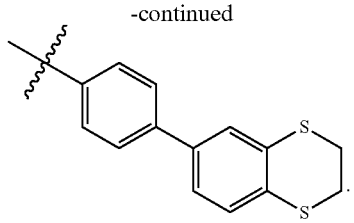

A person of ordinary skill in the art will appreciate that compounds of any of the above embodiments may have one or more stereocenter, and that each stereocenter independently may have an R or S configuration.

A person of ordinary skill in the art will appreciate that prodrug compounds satisfying one of formulas 14-18 may also have intrinsic activity as FXR agonists, as well as acting as a prodrug for a compound having FXR activity.

Exemplary working embodiments of compounds having activity as FXR agonists and satisfying one or more of the general formulas 1-18 are provided below.

NSSK0004

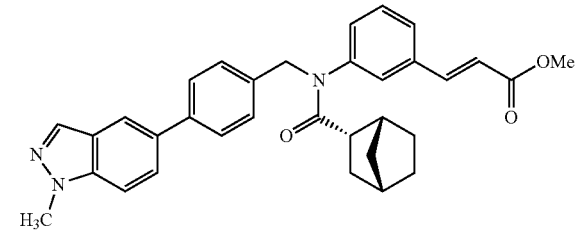

NSSK00017

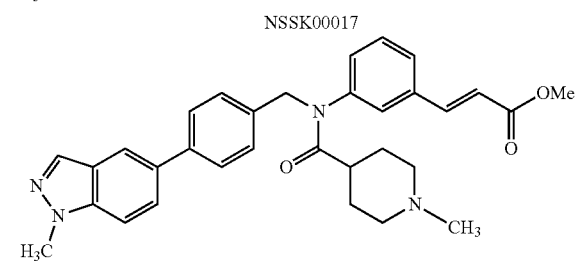

NSSK00035

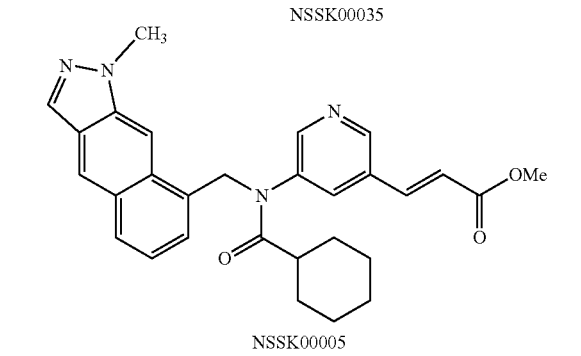

NSSK00005

-continued

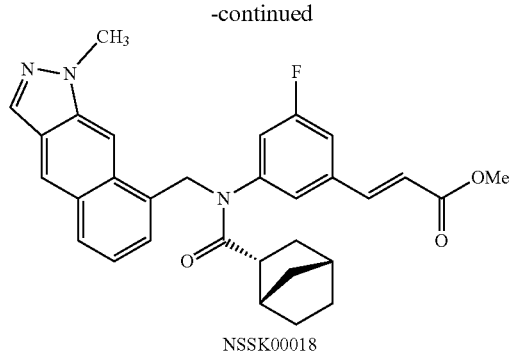

NSSK00018

NSSK00006

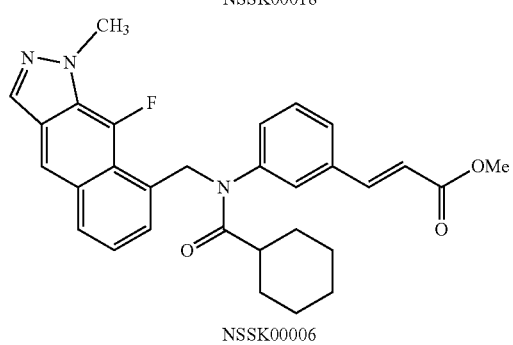

NSSK00019

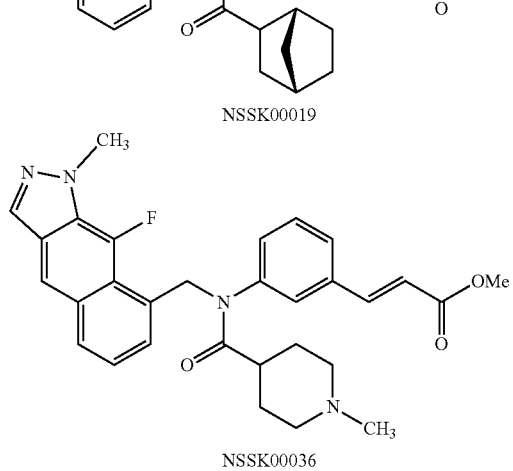

NSSK00036

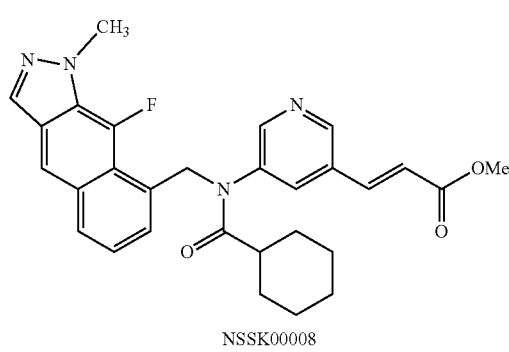

NSSK00008

-continued
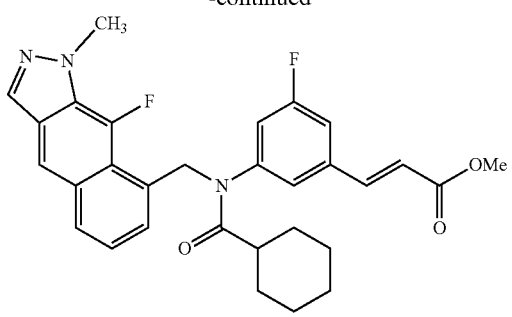
NSSK00007
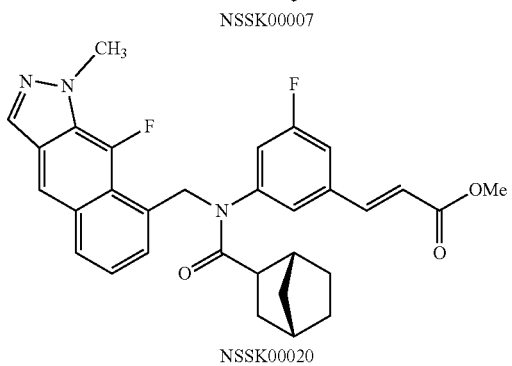
NSSK00020
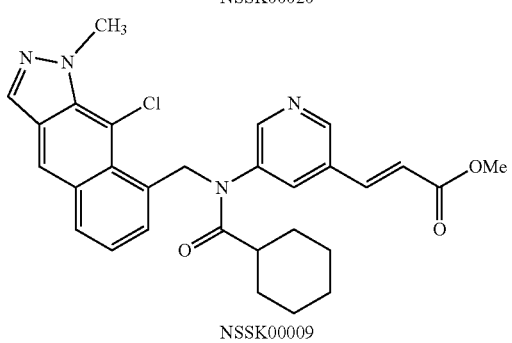
NSSK00009
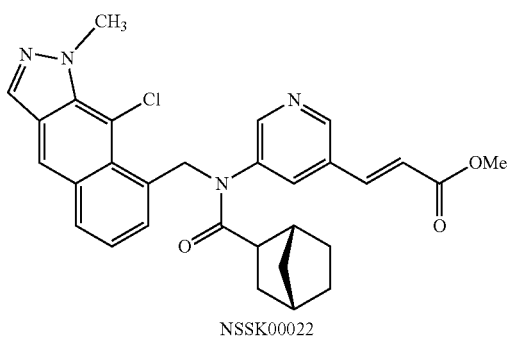
NSSK00022
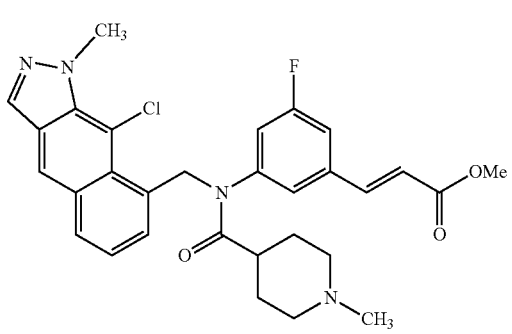
NSSK00037
-continued
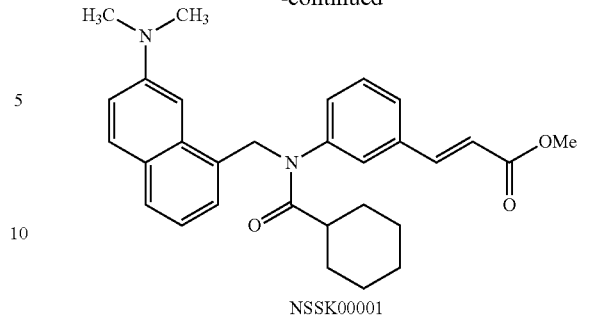
NSSK00001
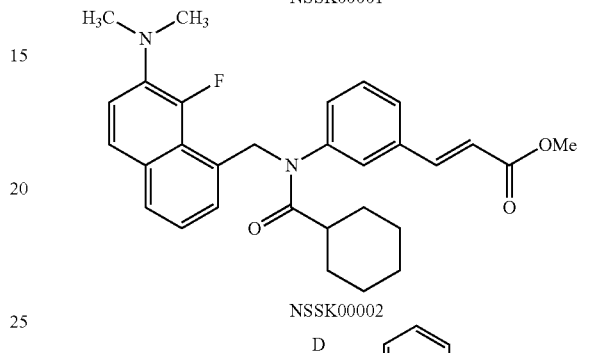
NSSK00002
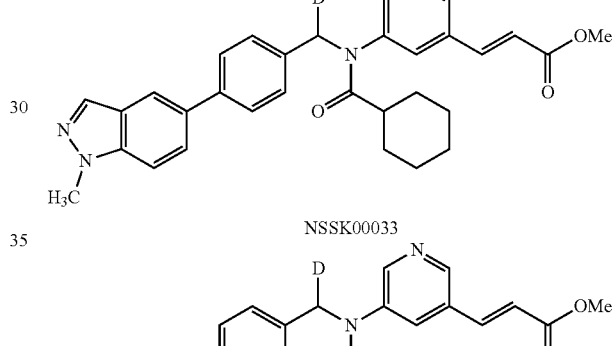
NSSK00033
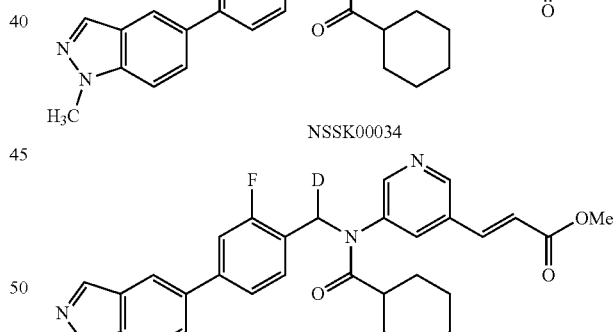
NSSK00034
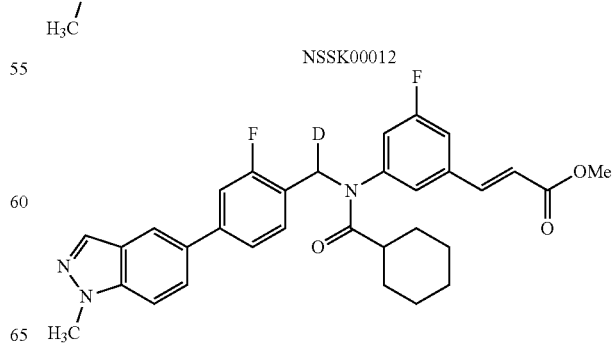
NSSK00012
NSSK00011

-continued
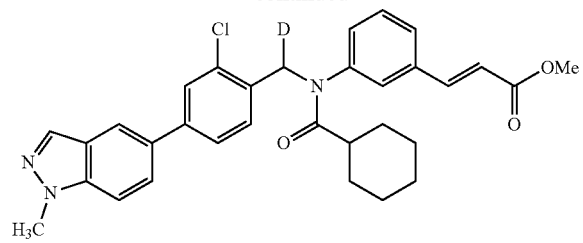
NSSK00014
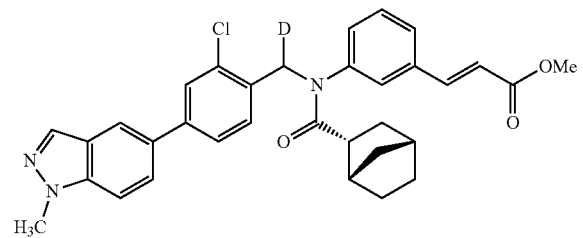
NSSK00013
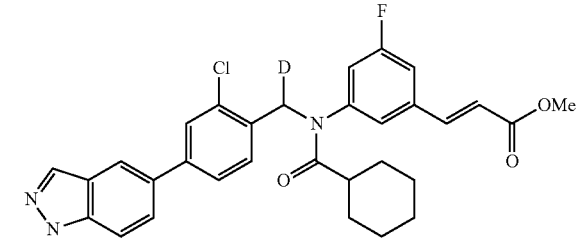
NSSK00016
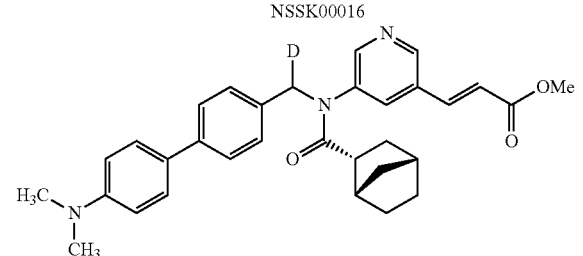
NSSK00026
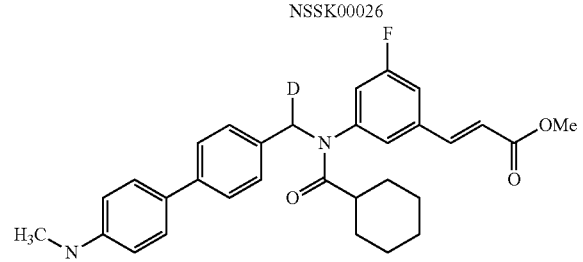
NSSK00025
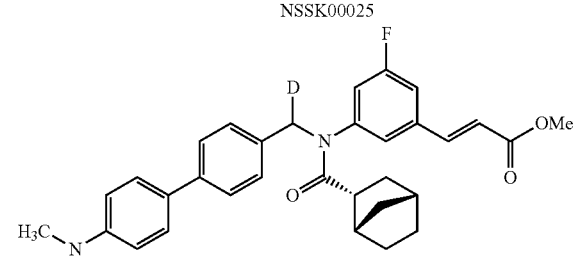
NSSK00024
-continued
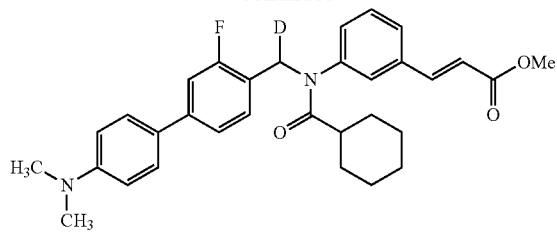
NSSK00027
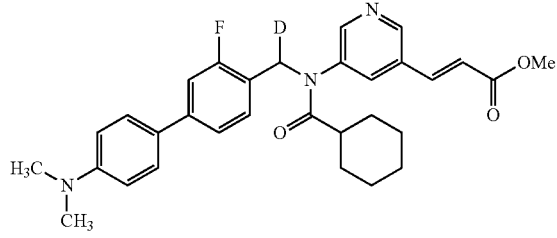
NSSK00030
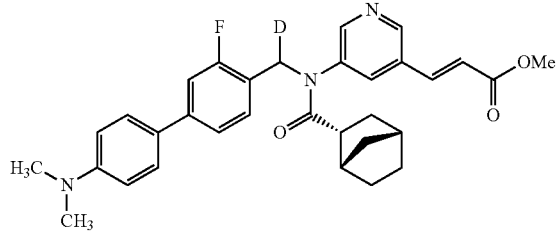
NSSK00029
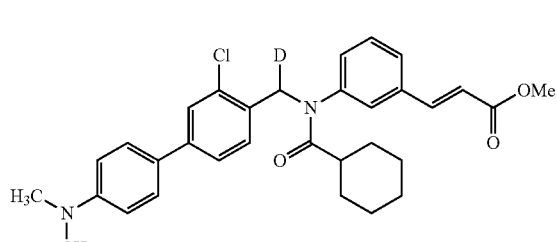
NSSK00031
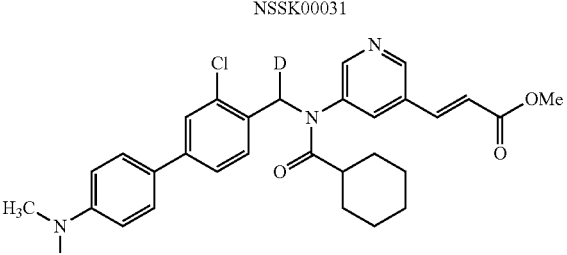
NSSK00032
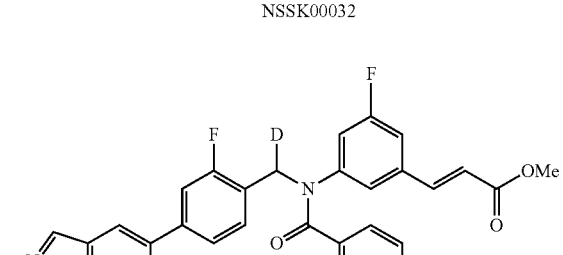
NSSK00039

-continued
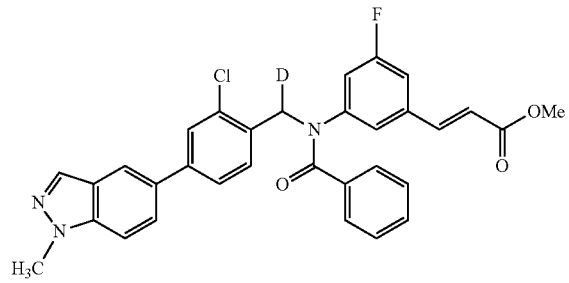
NSSK00041
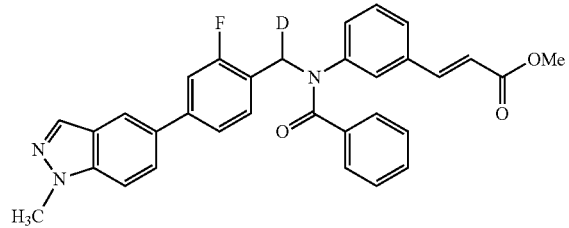
NSSK00038
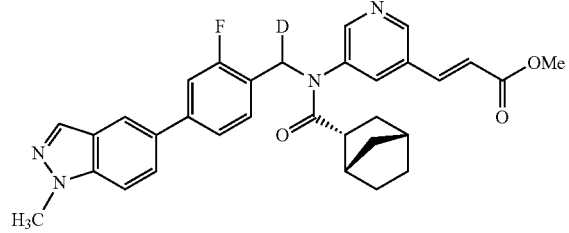
NSSK00066
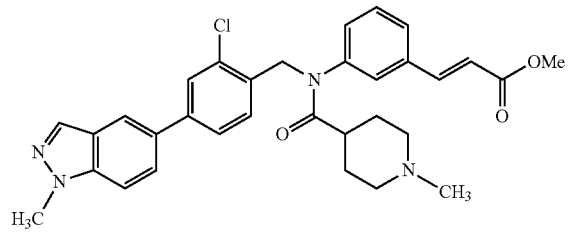
NSSK00075
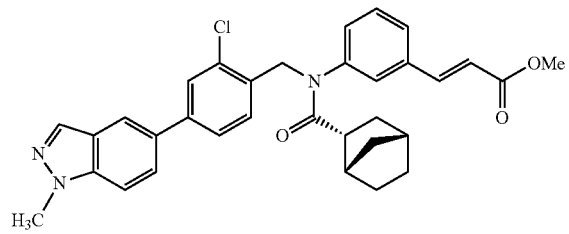
NSSK00046
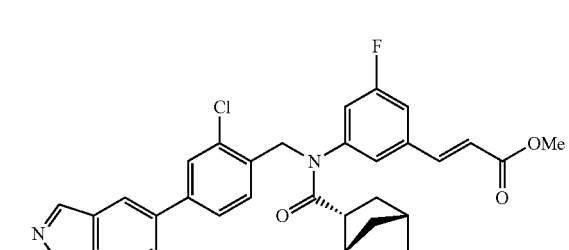
NSSK00047
-continued
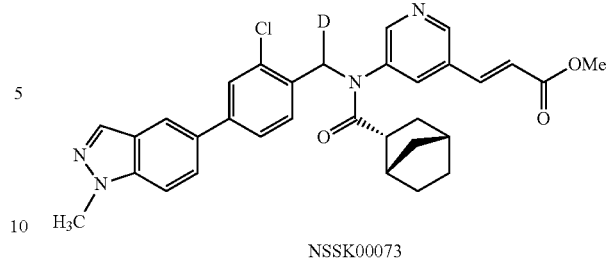
NSSK00073
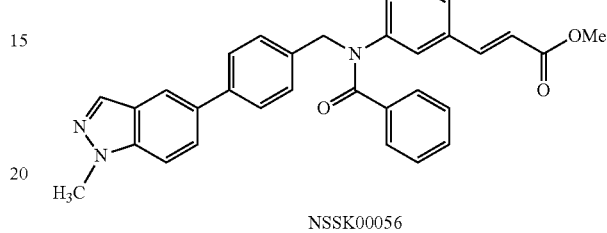
NSSK00056
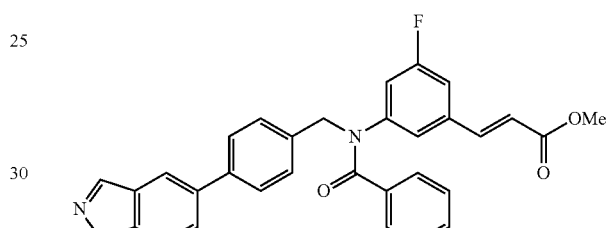
NSSK00058
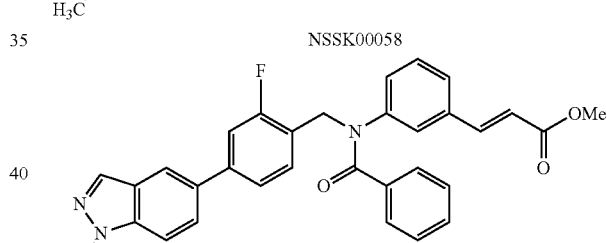
NSSK00057
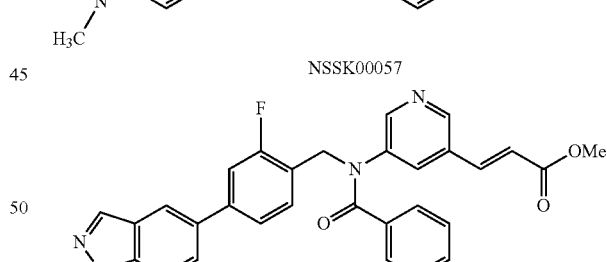
NSSK00061
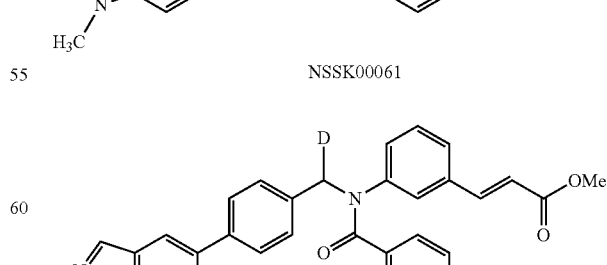
NSSK00049

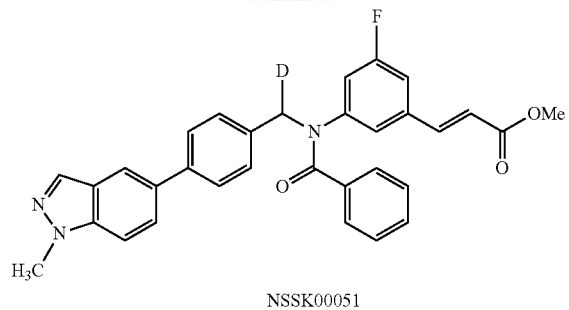
NSSK00051
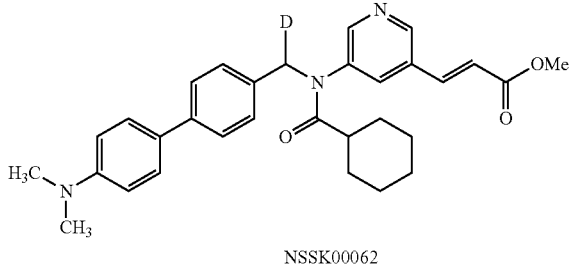
NSSK00062
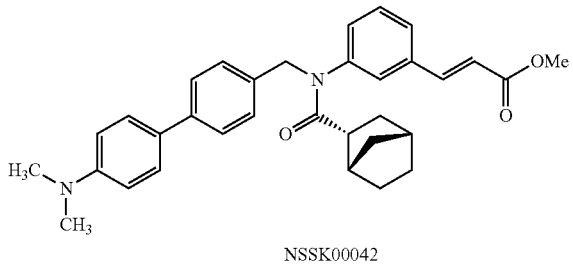
NSSK00042
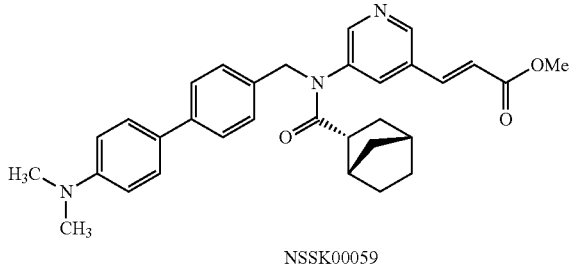
NSSK00059
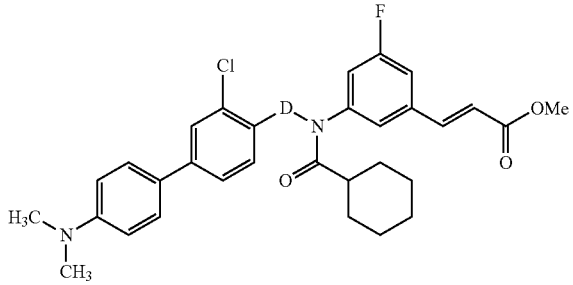
NSSK00072
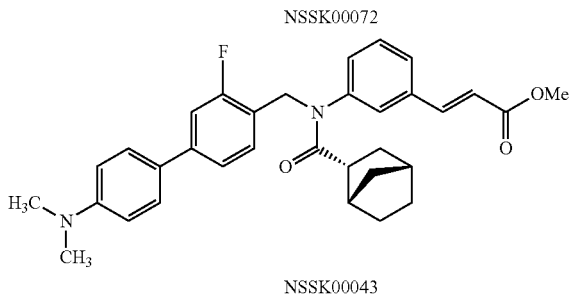
NSSK00043
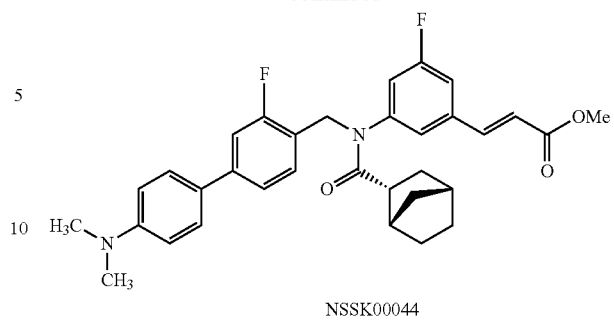
NSSK00044
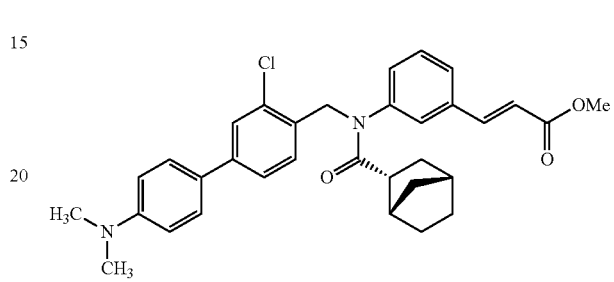
NSSK00052
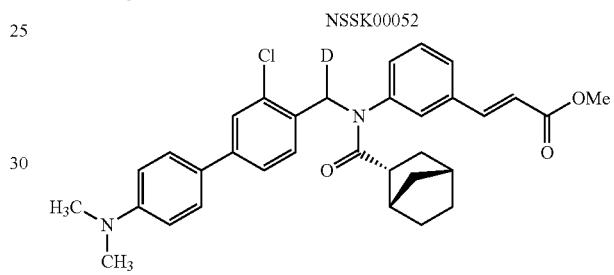
NSSK00045
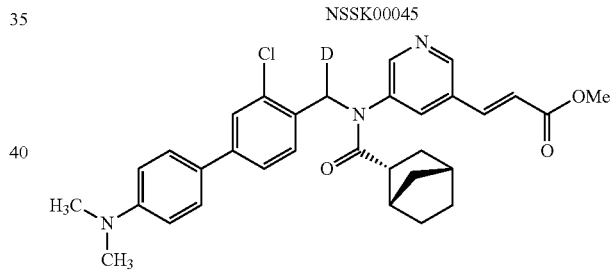
NSSK00064
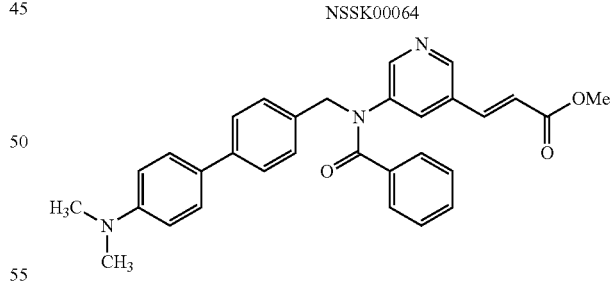
NSSK00060
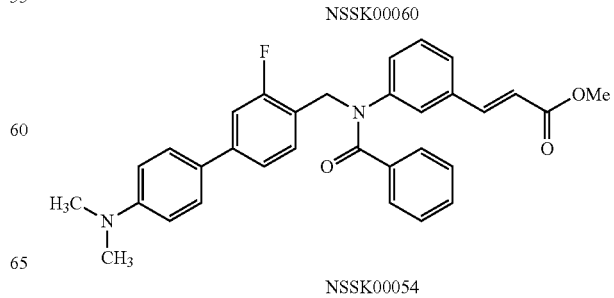
NSSK00054

-continued
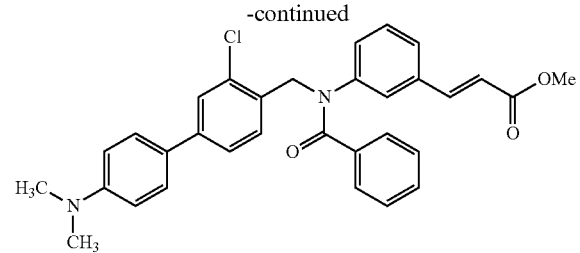
NSSK00055
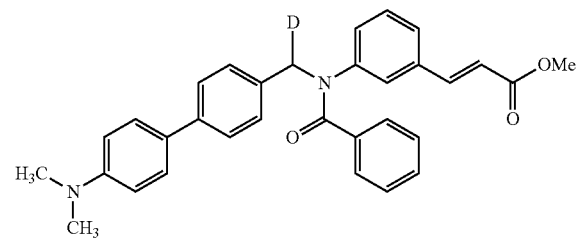
NSSK00048
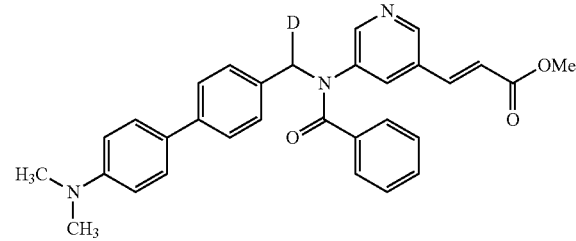
NSSK00050
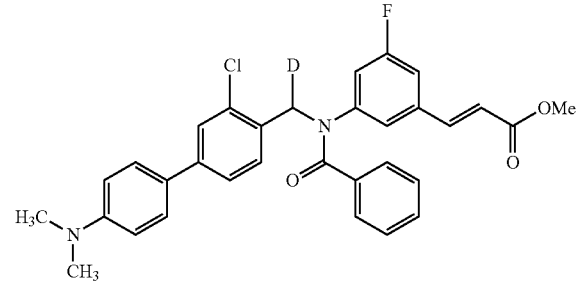
NSSK00096
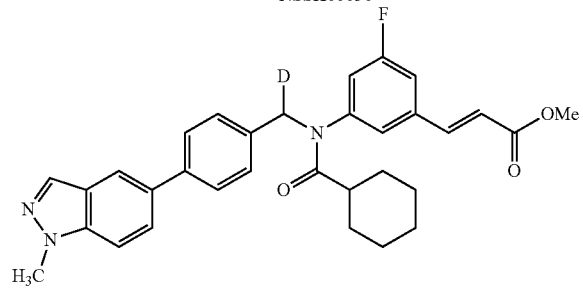
NSSK00084
-continued
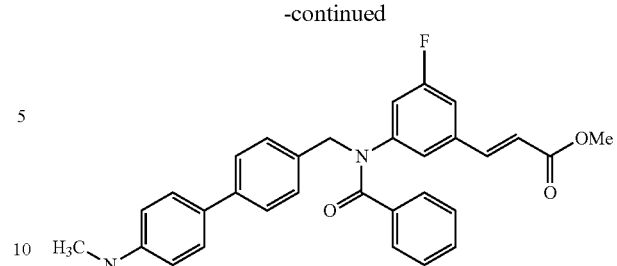
NSSK00068
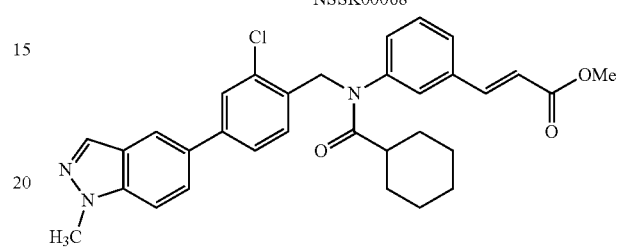
NSSK00091
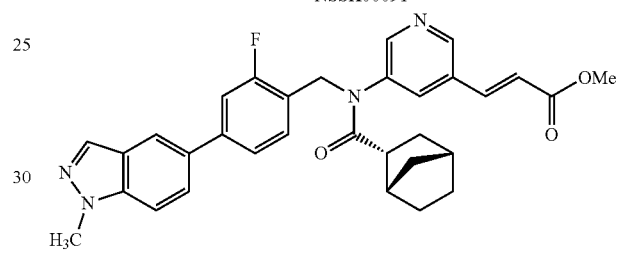
NSSK00088
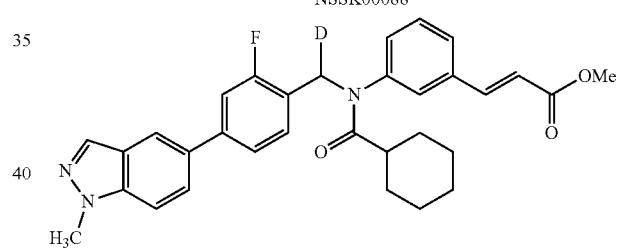
NSSK00089
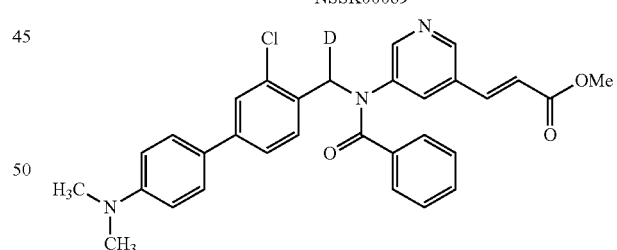
NSSK00065
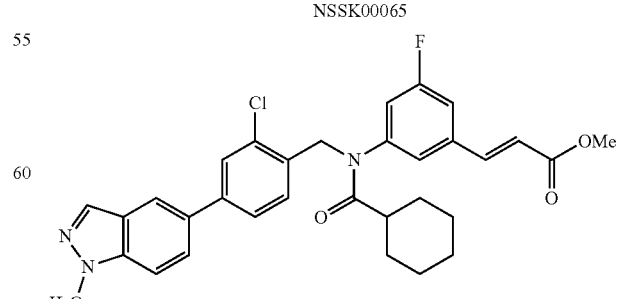
NSSK00097

-continued
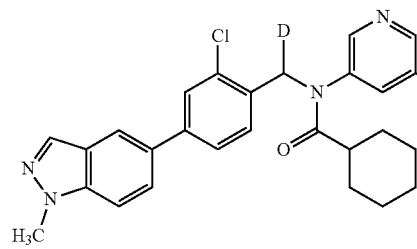
NSSK00095
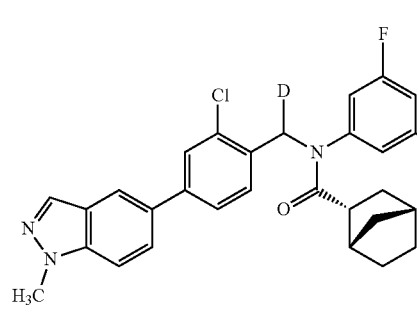
NSSK00094
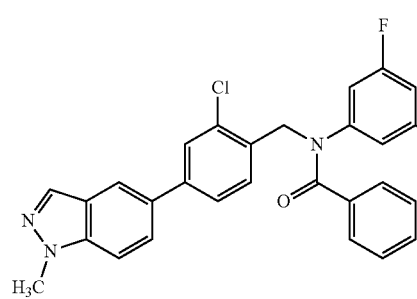
NSSK00100
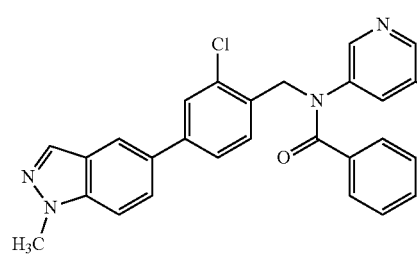
NSSK00092
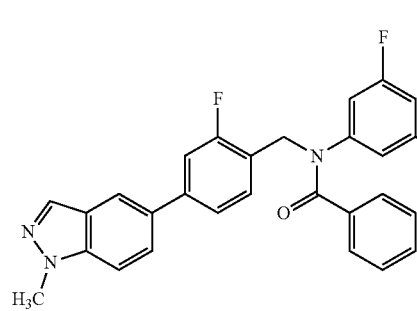
NSSK00099
-continued
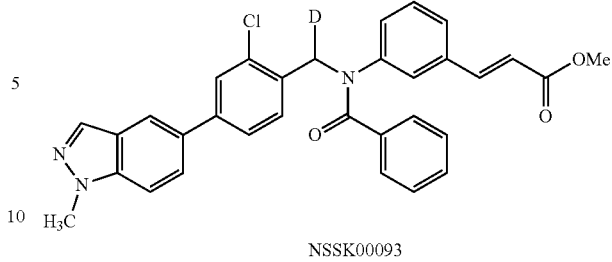
NSSK00093
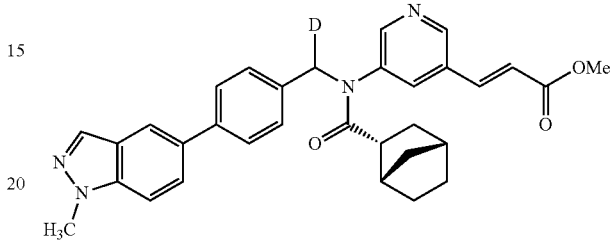
NSSK00087
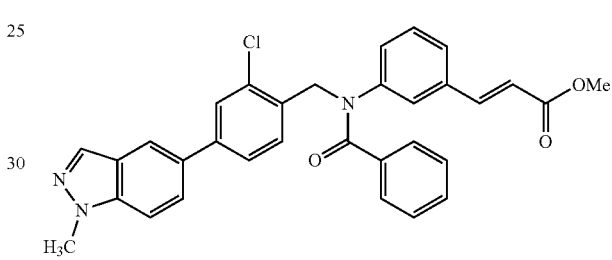
NSSK00098
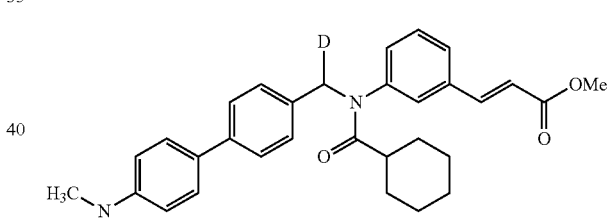
NSSK00077
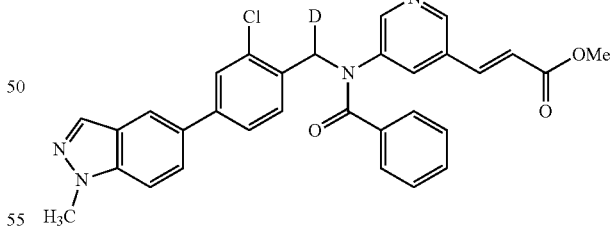
NSSK00101
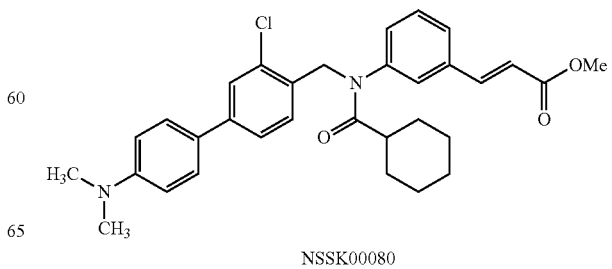
NSSK00080

-continued
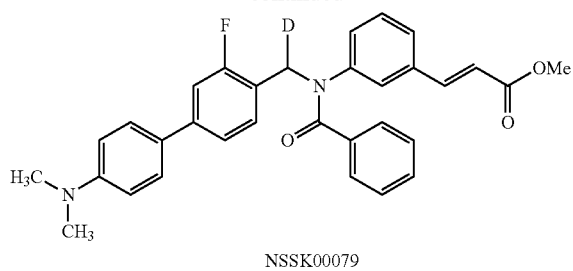
NSSK00079
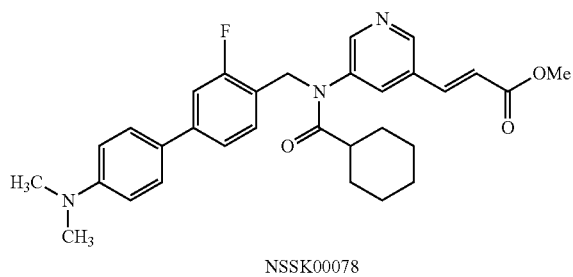
NSSK00078
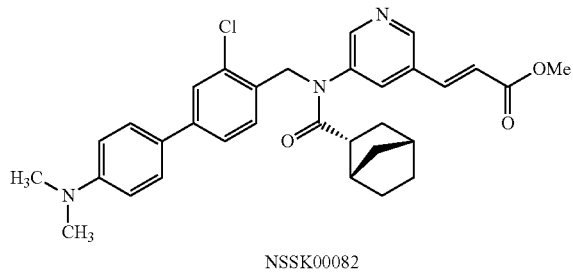
NSSK00082
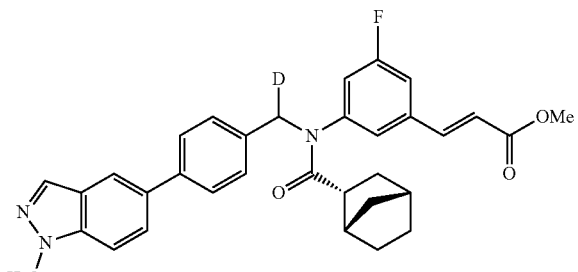
NSSK00113
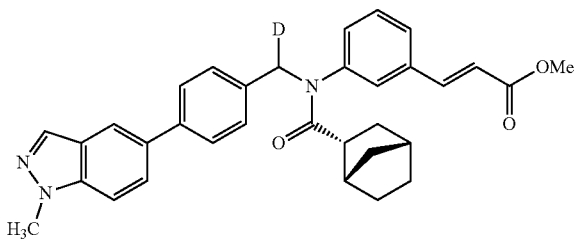
NSSK00086
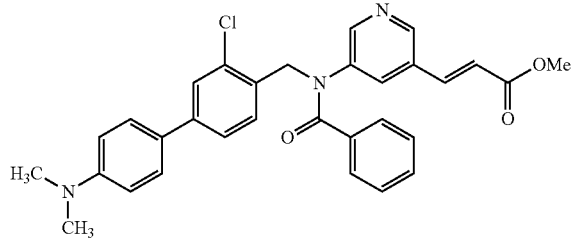
NSSK00081
-continued
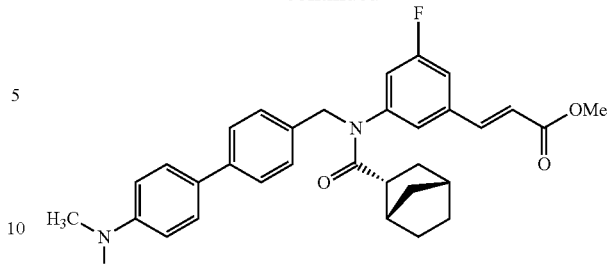
NSSK00102
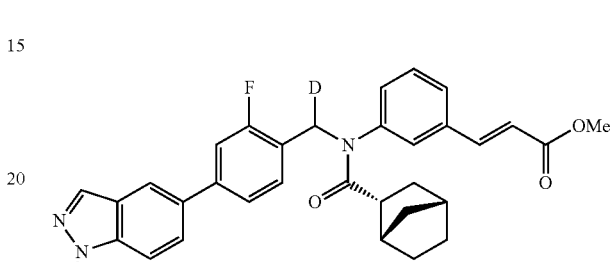
NSSK00070
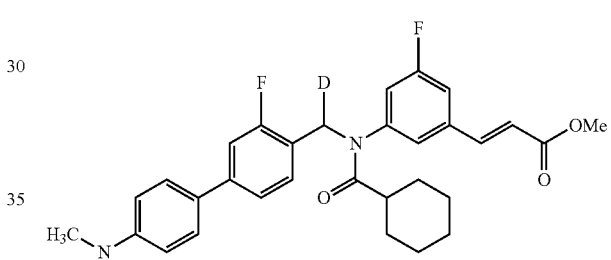
NSSK00109
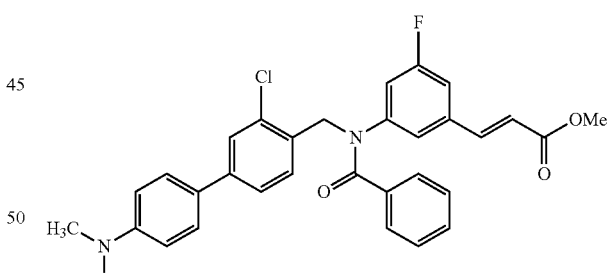
NSSK00103
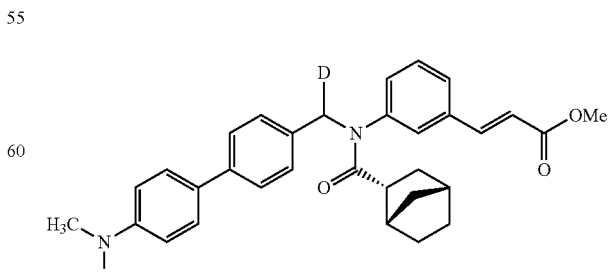
NSSK00107

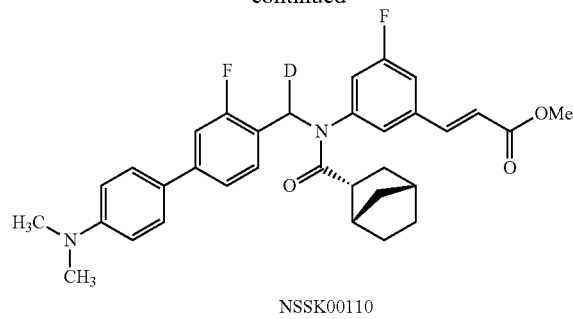
NSSK00110
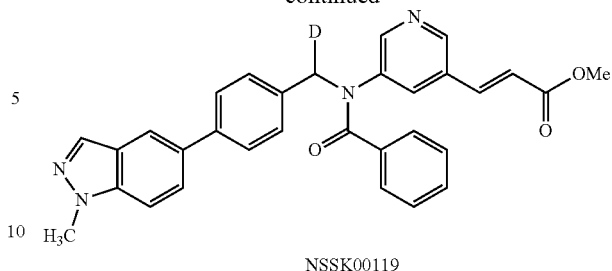
NSSK00119
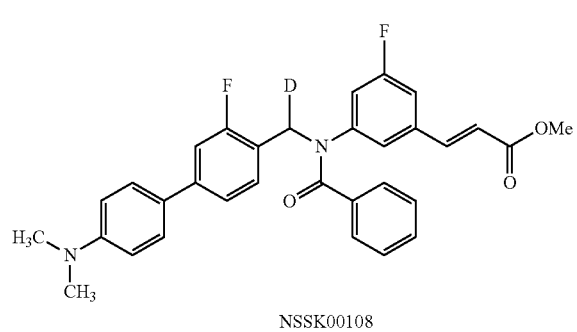
NSSK00108
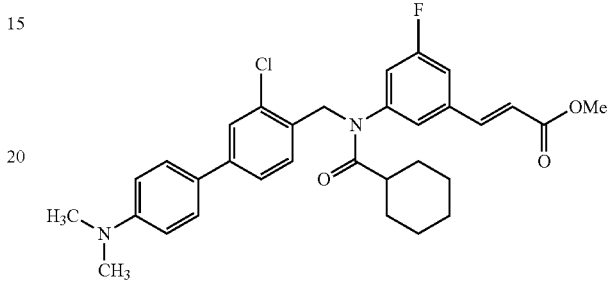
NSSK00117
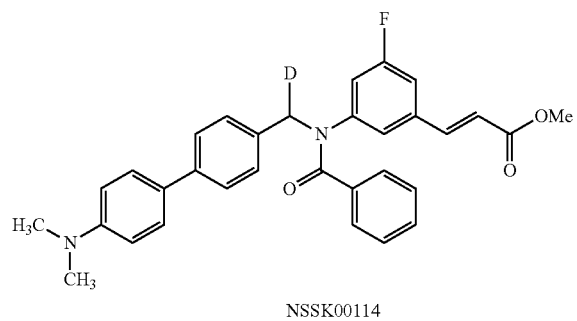
NSSK00114
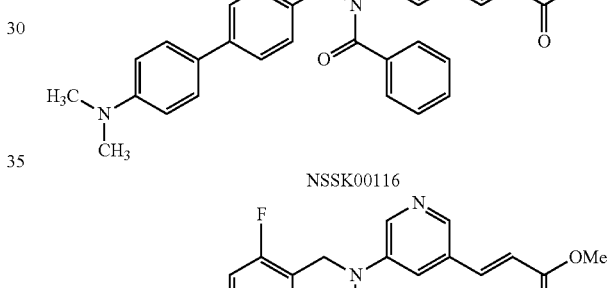
NSSK00116
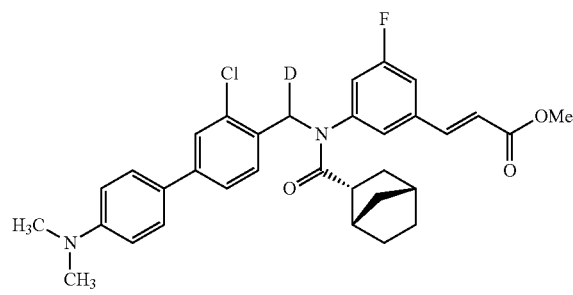
NSSK00104
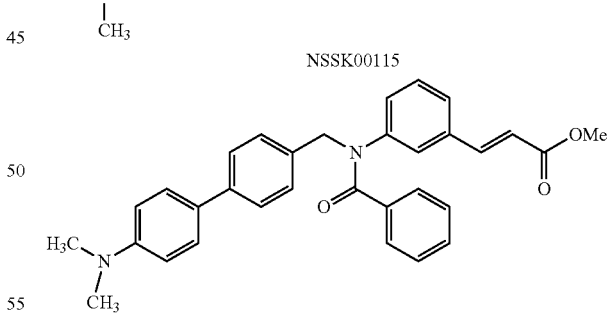
NSSK00115
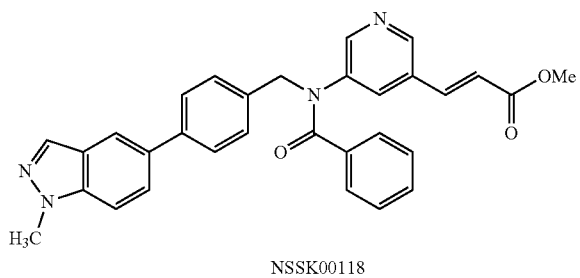
NSSK00118
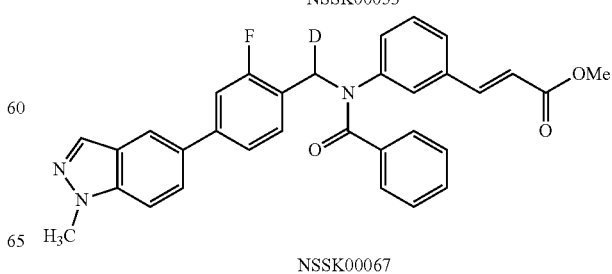
NSSK00053
NSSK00067

-continued
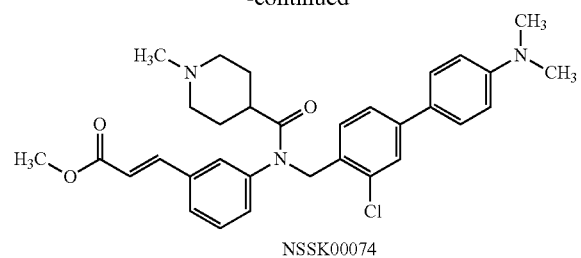
NSSK00074
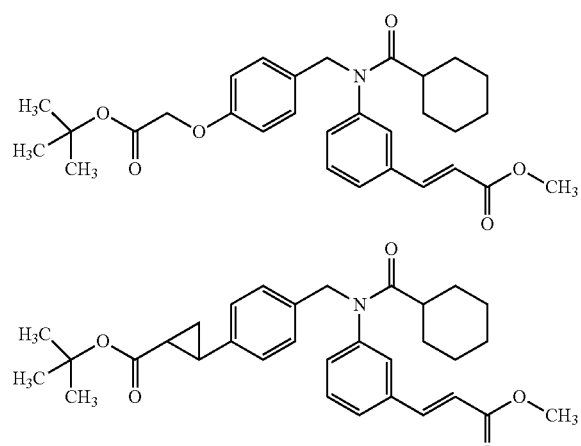
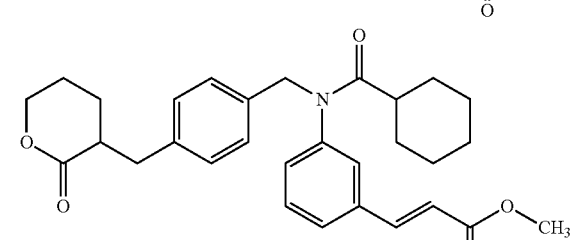
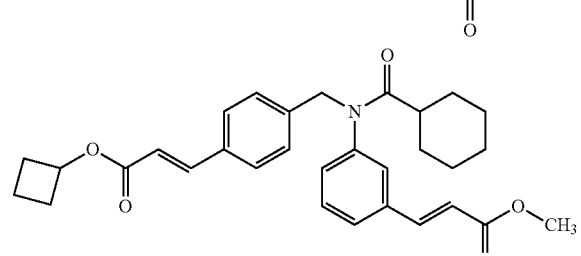
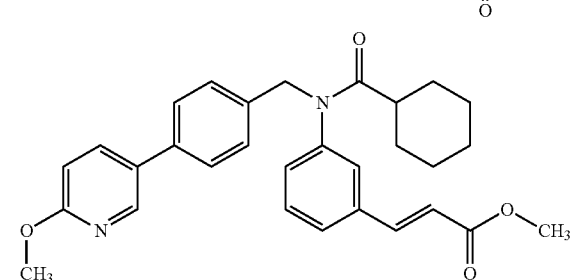
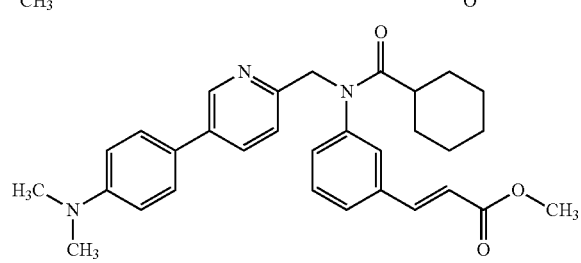
-continued
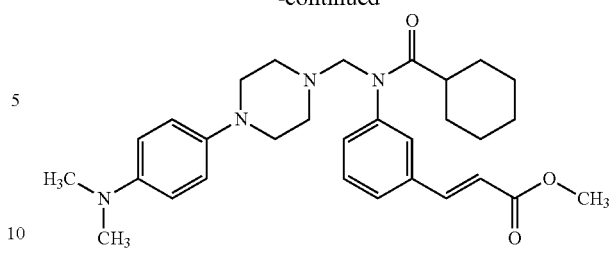
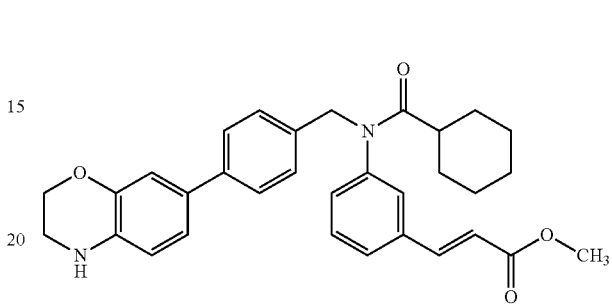
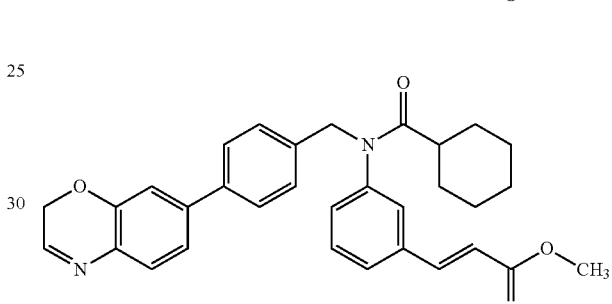
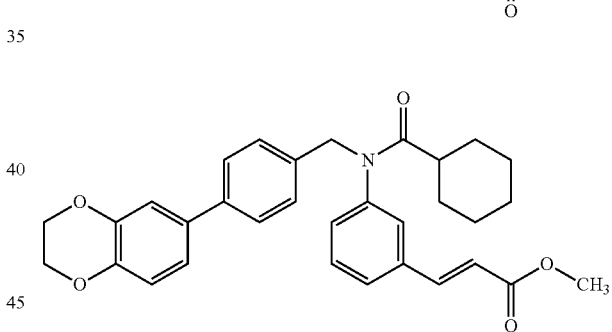
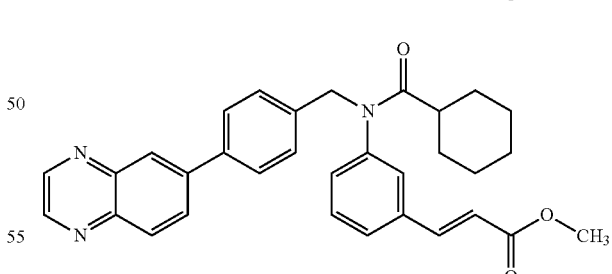
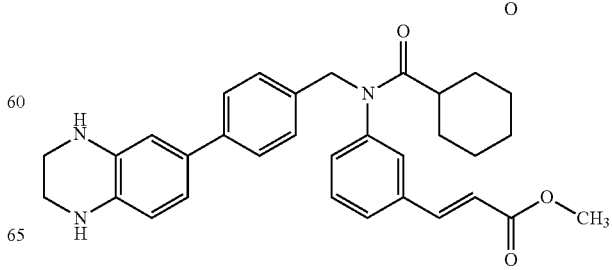

73
-continued
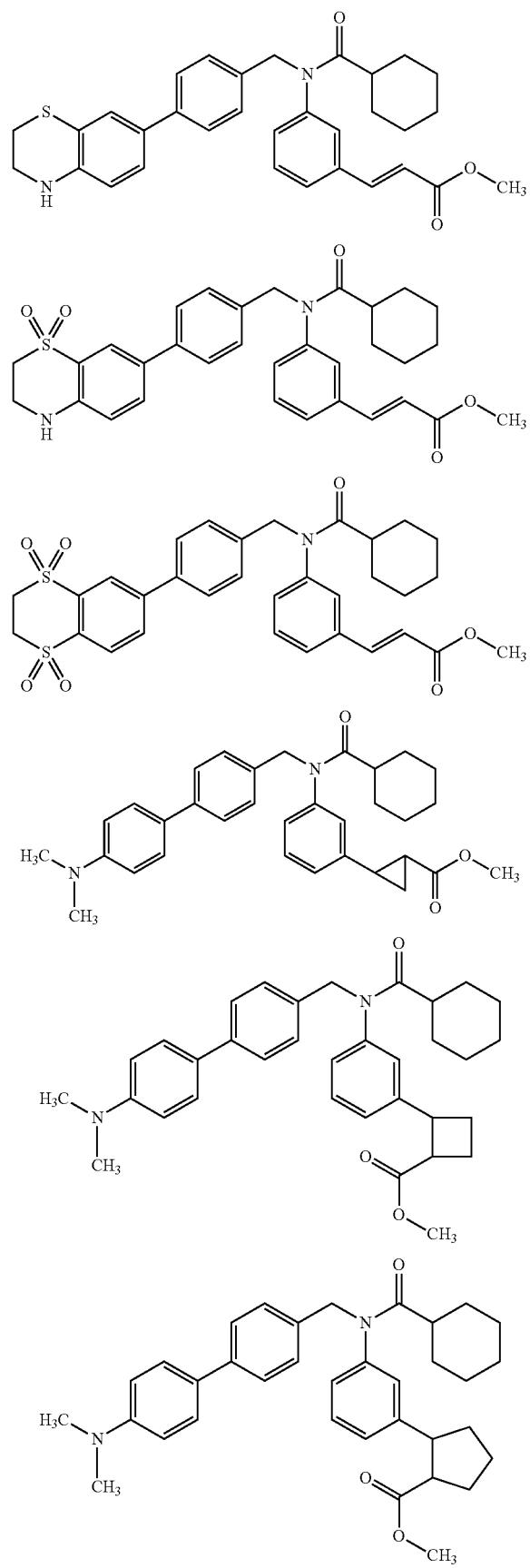
74
-continued
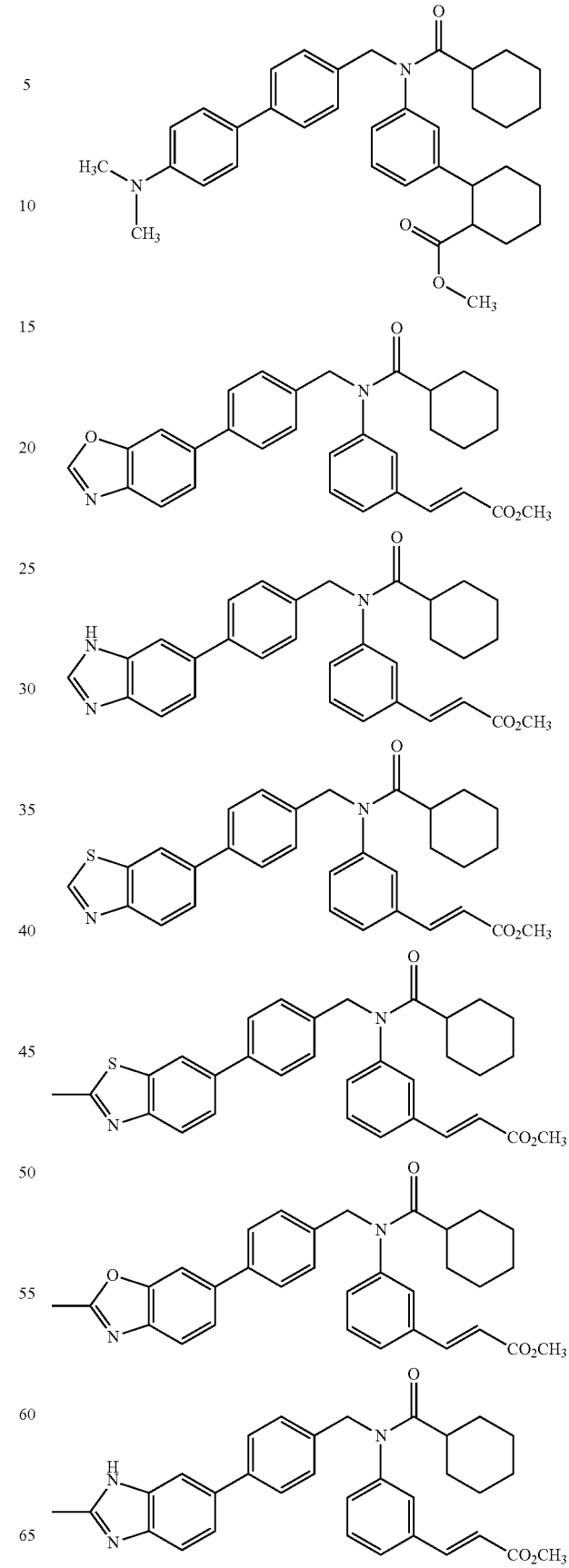

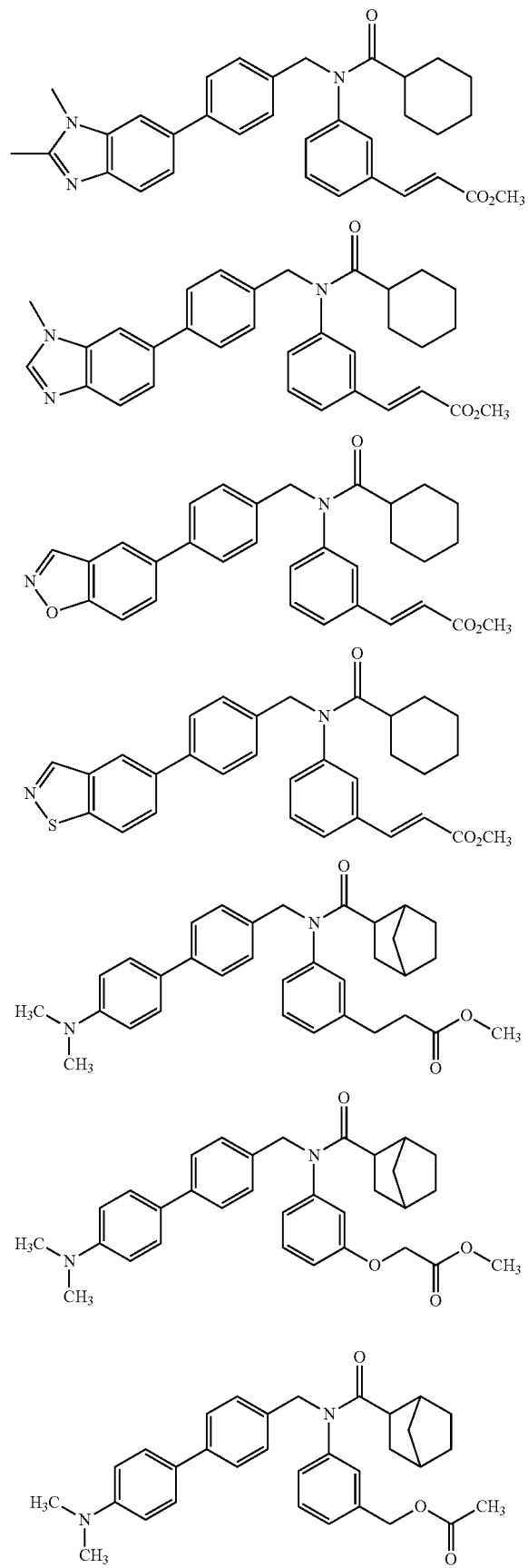
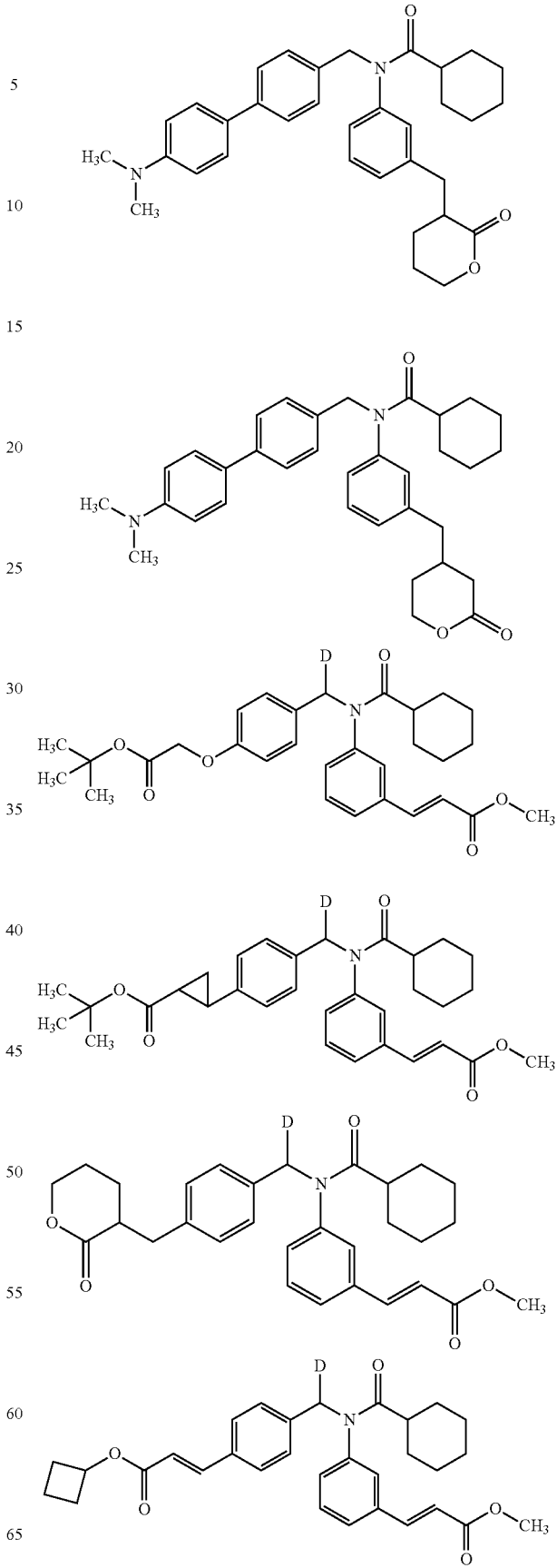

77
-continued
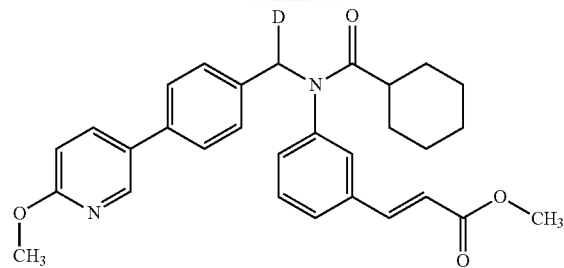
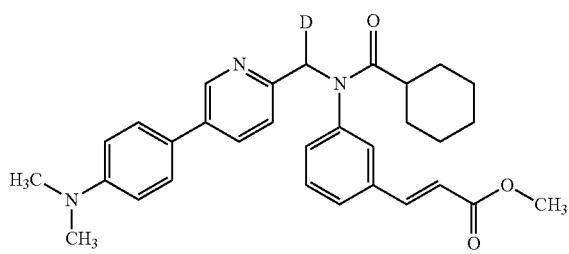
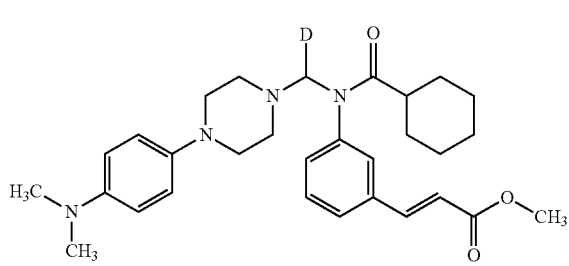
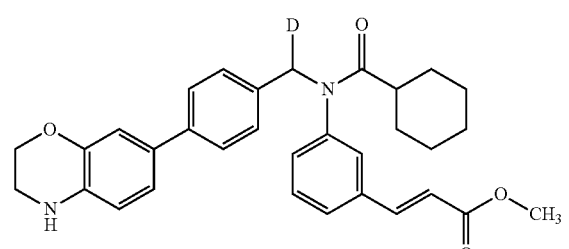
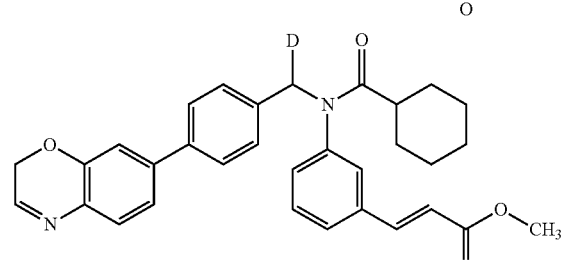
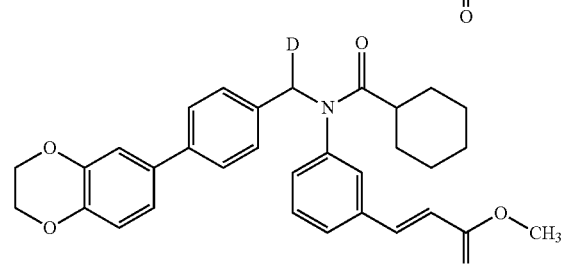
78
-continued
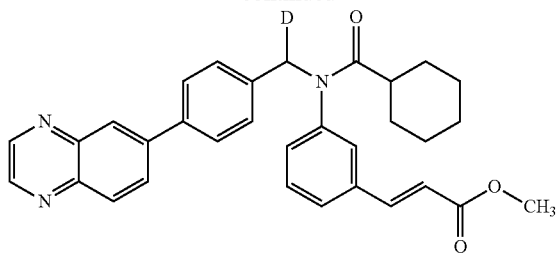
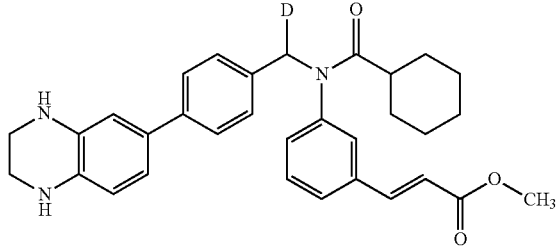
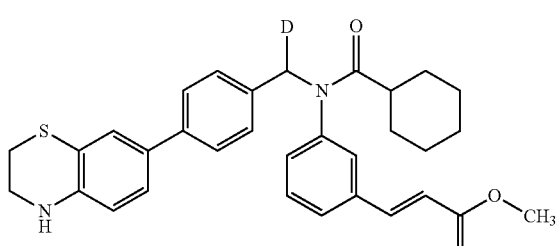
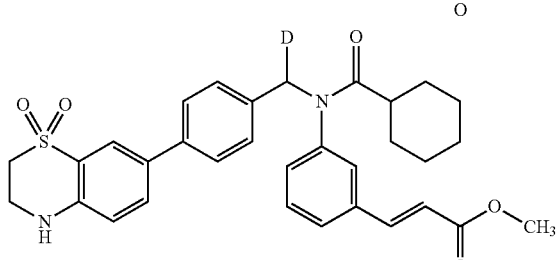
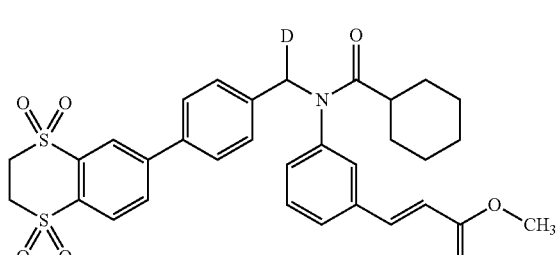
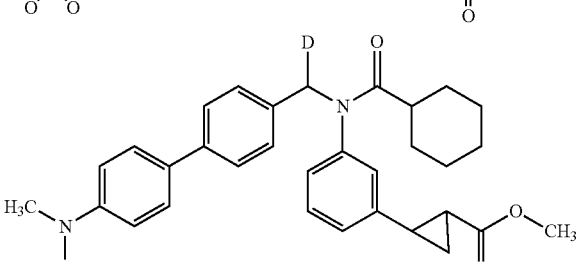

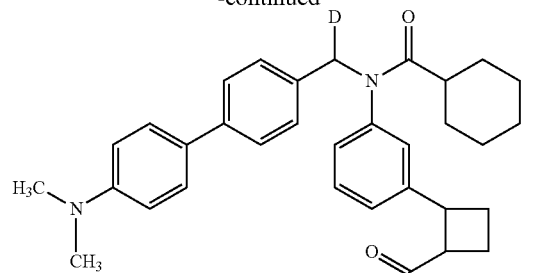
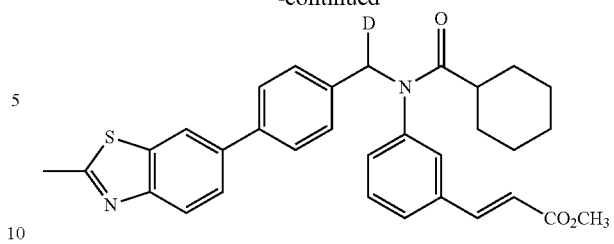

81
-continued
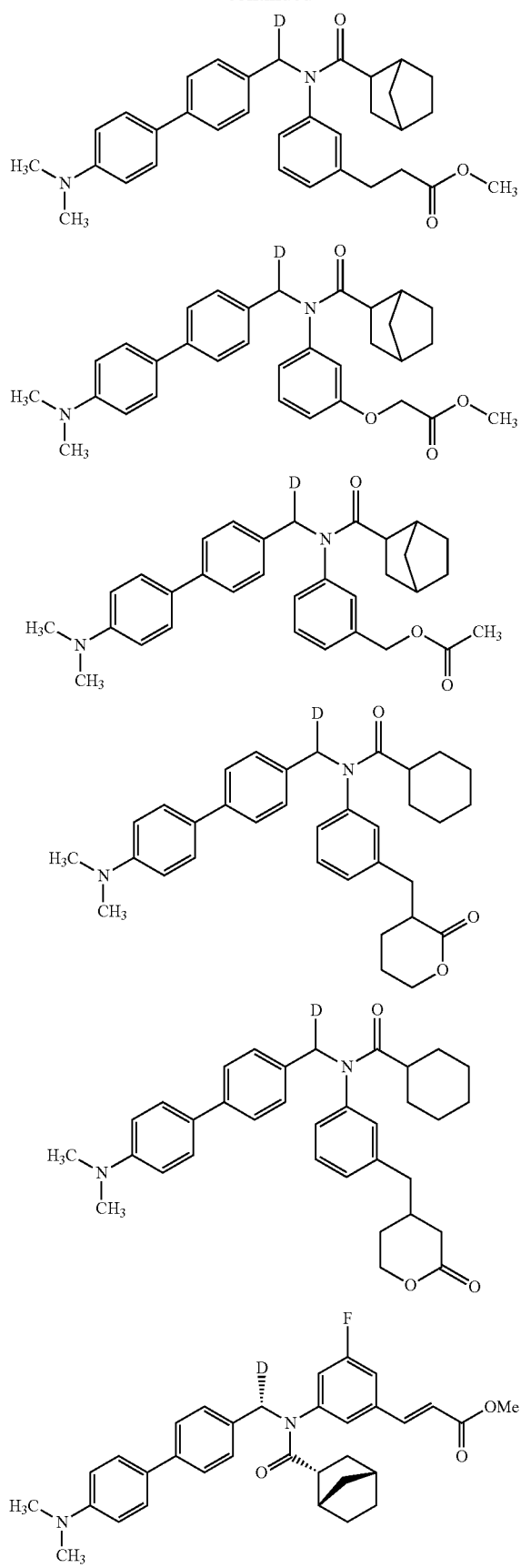
82
-continued
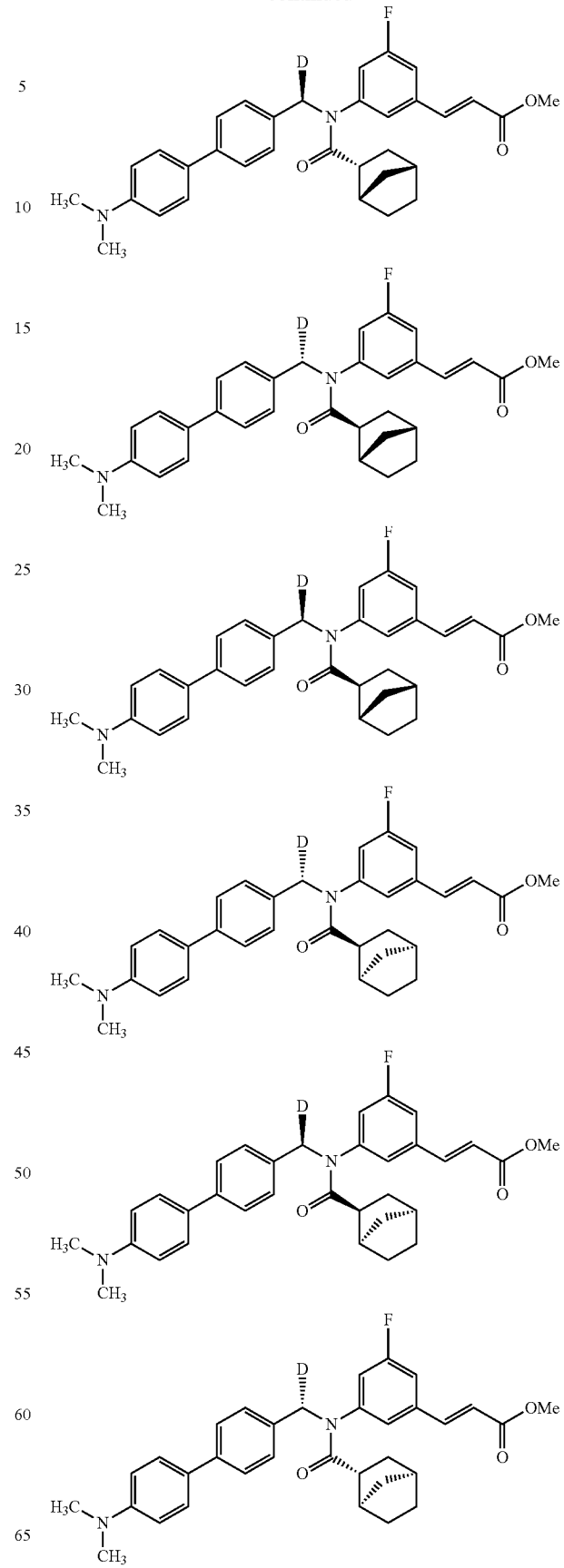

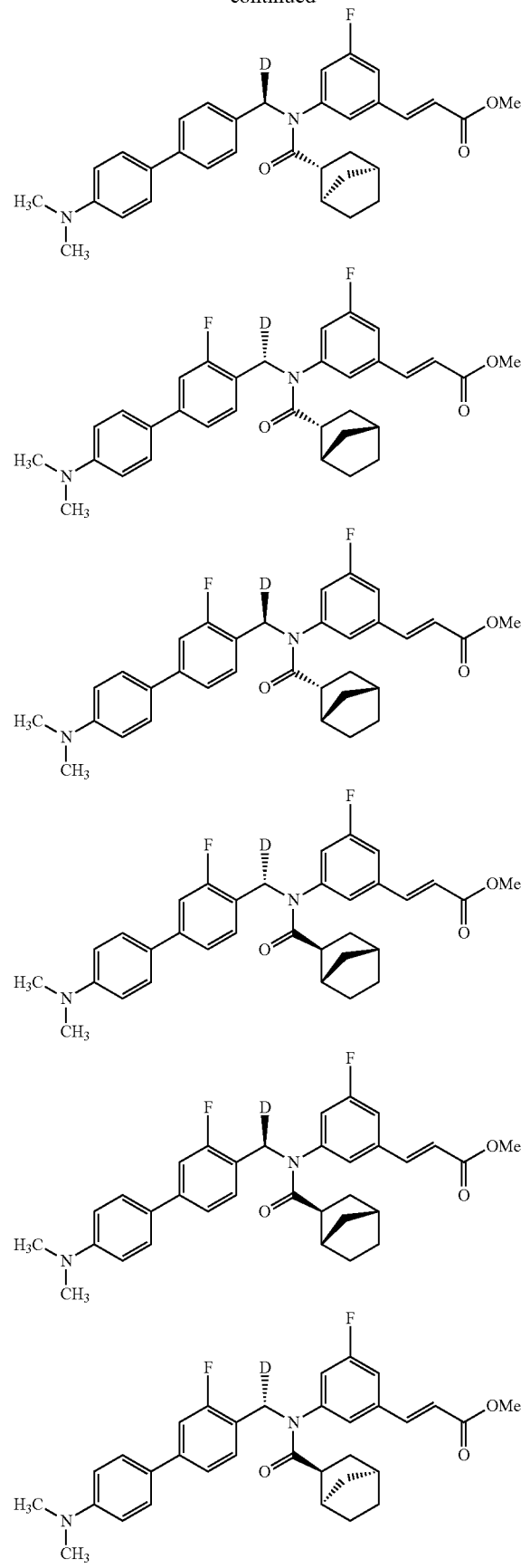
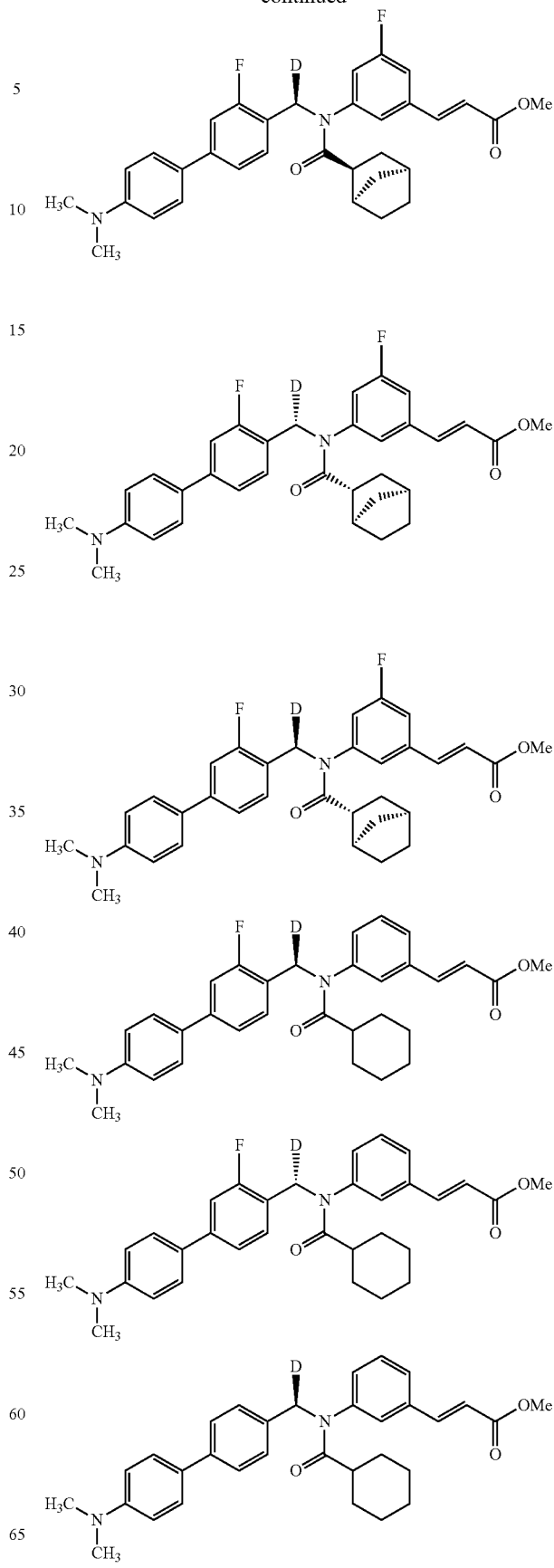

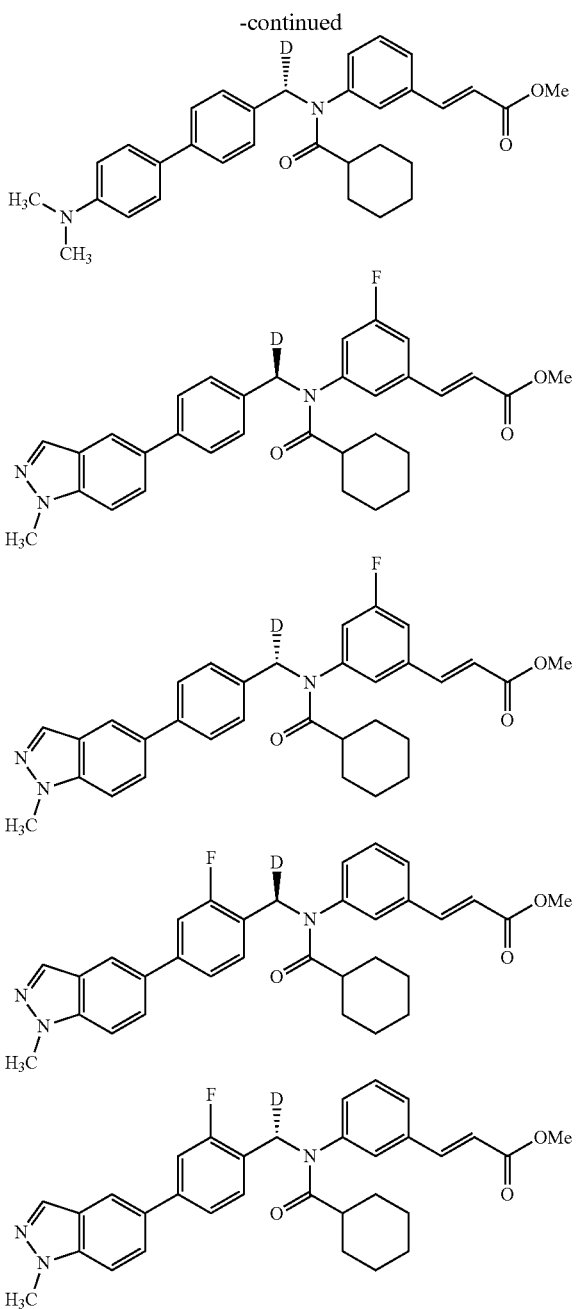

Other exemplary working embodiments include:
methyl (E)-3-(3-(N-(4-(1-methyl-1H-indazol-5-yl)benzyl)cyclohexanecarboxamido)phenyl)acrylate,
methyl (E)-3-(3-((1R,2S,4S)—N-(4-(1-methyl-1H-indazol-5-yl)benzyl)bicyclo[2.2.1]heptane-2-carboxamido)phenyl)acrylate,
methyl (E)-3-(3-(1-methyl-N-(4-(1-methyl-1H-indazol-5-yl)benzyl)piperidine-4-carboxamido)phenyl)acrylate,
methyl (E)-3-(5-(N-((1-methyl-1H-benzo[f]indazol-8-yl)methyl)cyclohexanecarboxamido)pyridin-3-yl)acrylate,
methyl (E)-3-(3-fluoro-5-((1S,2R,4R)—N-((1-methyl-1H-benzo[f]indazol-8-yl)methyl)bicyclo[2.2.1]heptane-2-carboxamido)phenyl)acrylate,
methyl (E)-3-(3-(N-((9-fluoro-1-methyl-1H-benzo[f]indazol-8-yl)methyl)cyclohexanecarboxamido)phenyl)acrylate,
methyl (E)-3-(3-((1R,4S)—N-((9-fluoro-1-methyl-1H-benzo[f]indazol-8-yl)methyl)bicyclo[2.2.1]heptane-2-carboxamido)phenyl)acrylate,
methyl (E)-3-(3-(N-((9-fluoro-1-methyl-1H-benzo[f]indazol-8-yl)methyl)-1-methylpiperidine-4-carboxamido)phenyl)acrylate,
methyl (E)-3-(5-(N-((9-fluoro-1-methyl-1H-benzo[f]indazol-8-yl)methyl)cyclohexanecarboxamido)pyridin-3-yl)acrylate,
methyl (E)-3-(3-fluoro-5-(N-((9-fluoro-1-methyl-1H-benzo[f]indazol-8-yl)methyl)cyclohexanecarboxamido)phenyl)acrylate,
methyl (E)-3-(3-fluoro-5-((1R,4S)—N-((9-fluoro-1-methyl-1H-benzo[f]indazol-8-yl)methyl)bicyclo[2.2.1]heptane-2-carboxamido)phenyl)acrylate,
methyl (E)-3-(5-(N-((9-chloro-1-methyl-1H-benzo[f]indazol-8-yl)methyl)cyclohexanecarboxamido)pyridin-3-yl)acrylate,
methyl (E)-3-(5-((1R,4S)—N-((9-chloro-1-methyl-1H-benzo[f]indazol-8-yl)methyl)bicyclo[2.2.1]heptane-2-carboxamido)pyridin-3-yl)acrylate,
methyl (E)-3-(3-(N-((9-chloro-1-methyl-1H-benzo[f]indazol-8-yl)methyl)-1-methylpiperidine-4-carboxamido)-5-fluorophenyl)acrylate,
methyl (E)-3-(3-(N-((7-(dimethylamino)naphthalen-1-yl)methyl)cyclohexanecarboxamido)phenyl)acrylate,
methyl (E)-3-(3-(N-((7-(dimethylamino)-8-fluoronaphthalen-1-yl)methyl)cyclohexanecarboxamido)phenyl)acrylate,
methyl (E)-3-(3-(N-((4-(1-methyl-1H-indazol-5-yl)phenyl)methyl-d)cyclohexanecarboxamido)phenyl)acrylate,
methyl (E)-3-(5-(N-((4-(1-methyl-1H-indazol-5-yl)phenyl)methyl-d)cyclohexanecarboxamido)pyridin-3-yl)acrylate,
methyl (E)-3-(5-(N-((2-fluoro-4-(1-methyl-1H-indazol-5-yl)phenyl)methyl-d)cyclohexanecarboxamido)pyridin-3-yl)acrylate,
methyl (E)-3-(3-fluoro-5-(N-((2-fluoro-4-(1-methyl-1H-indazol-5-yl)phenyl)methyl-d)cyclohexanecarboxamido)phenyl)acrylate,
methyl (E)-3-(3-(N-((2-chloro-4-(1-methyl-1H-indazol-5-yl)phenyl)methyl-d)cyclohexanecarboxamido)phenyl)acrylate,
methyl (E)-3-(3-((1S,2R,4R)—N-((2-chloro-4-(1-methyl-1H-indazol-5-yl)phenyl)methyl-d)bicyclo[2.2.1]heptane-2-carboxamido)phenyl)acrylate,
methyl (E)-3-(3-(N-((2-chloro-4-(1-methyl-1H-indazol-5-yl)phenyl)methyl-d)cyclohexanecarboxamido)-5-fluorophenyl)acrylate,
methyl (E)-3-(5-((1S,2R,4R)—N-((4'-(dimethylamino)-[1,1'-biphenyl]-4-yl)methyl-d)bicyclo[2.2.1]heptane-2-carboxamido)pyridin-3-yl)acrylate,
methyl (E)-3-(3-(N-((4'-(dimethylamino)-[1,1'-biphenyl]-4-yl)methyl-d)cyclohexanecarboxamido)-5-fluorophenyl)acrylate,
methyl (E)-3-(3-((1S,2R,4R)—N-((4'-(dimethylamino)-[1,1'-biphenyl]-4-yl)methyl-d)bicyclo[2.2.1]heptane-2-carboxamido)-5-fluorophenyl)acrylate,
methyl (E)-3-(3-(N-((4'-(dimethylamino)-3-fluoro-[1,1'-biphenyl]-4-yl)methyl-d)cyclohexanecarboxamido)phenyl)acrylate,
methyl (E)-3-(5-(N-((4'-(dimethylamino)-3-fluoro-[1,1'-biphenyl]-4-yl)methyl-d)cyclohexanecarboxamido)pyridin-3-yl)acrylate,
methyl (E)-3-(5-((1S,2R,4R)—N-((4'-(dimethylamino)-3-fluoro-[1,1'-biphenyl]-4-yl)methyl-d)bicyclo[2.2.1]heptane-2-carboxamido)pyridin-3-yl)acrylate, methyl (E)-3-(3-(N-((3-chloro-4'-(dimethylamino)-[1,1'-biphenyl]-4-yl)methyl-d)cyclohexanecarboxamido)phenyl)acrylate, methyl (E)-3-(5-(N-((3-chloro-4'-(dimethylamino)-[1,1'-biphenyl]-4-yl)methyl-d)cyclohexanecarboxamido)pyridin-3-yl)acrylate, methyl (E)-3-(3-fluoro-5-(N-((2-fluoro-4-(1-methyl-1H-indazol-5-yl)phenyl)methyl-d)benzamido)phenyl)acrylate, methyl (E)-3-(3-(N-((2-chloro-4-(1-methyl-1H-indazol-5-yl)phenyl)methyl-d)benzamido)-5-fluorophenyl)acrylate, methyl (E)-3-(3-(N-((2-fluoro-4-(1-methyl-1H-indazol-5-yl)phenyl)methyl-d)benzamido)phenyl)acrylate, methyl (E)-3-(5-((1S,2R,4R)—N-((2-fluoro-4-(1-methyl-1H-indazol-5-yl)phenyl)methyl-d)bicyclo[2.2.1]heptane-2-carboxamido)pyridin-3-yl)acrylate, methyl (E)-3-(3-(N-(2-chloro-4-(1-methyl-1H-indazol-5-yl)benzyl)-1-methylpiperidine-4-carboxamido)phenyl)acrylate, methyl (E)-3-(3-((1S,2R,4R)—N-(2-chloro-4-(1-methyl-1H-indazol-5-yl)benzyl)bicyclo[2.2.1]heptane-2-carboxamido)phenyl)acrylate, methyl (E)-3-(3-((1S,2R,4R)—N-(2-chloro-4-(1-methyl-1H-indazol-5-yl)benzyl)bicyclo[2.2.1]heptane-2-carboxamido)-5-fluorophenyl)acrylate, methyl (E)-3-(5-((1S,2R,4R)—N-((2-chloro-4-(1-methyl-1H-indazol-5-yl)phenyl)methyl-d)bicyclo[2.2.1]heptane-2-carboxamido)pyridin-3-yl)acrylate, methyl (E)-3-(3-(N-(4-(1-methyl-1H-indazol-5-yl)benzyl)benzamido)phenyl)acrylate, methyl (E)-3-(3-fluoro-5-(N-(4-(1-methyl-1H-indazol-5-yl)benzyl)benzamido)phenyl)acrylate, methyl (E)-3-(3-(N-(2-fluoro-4-(1-methyl-1H-indazol-5-yl)benzyl)benzamido)phenyl)acrylate, methyl (E)-3-(5-(N-(2-fluoro-4-(1-methyl-1H-indazol-5-yl)benzyl)benzamido)pyridin-3-yl)acrylate, methyl (E)-3-(3-(N-((4-(1-methyl-1H-indazol-5-yl)phenyl)methyl-d)benzamido)phenyl)acrylate, methyl (E)-3-(3-fluoro-5-(N-((4-(1-methyl-1H-indazol-5-yl)phenyl)methyl-d)benzamido)phenyl)acrylate, methyl (E)-3-(5-(N-((4'-(dimethylamino)-[1,1'-biphenyl]-4-yl)methyl-d)cyclohexanecarboxamido)pyridin-3-yl)acrylate, methyl (E)-3-(3-((1S,2R,4R)—N-((4'-(dimethylamino)-[1,1'-biphenyl]-4-yl)methyl)bicyclo[2.2.1]heptane-2-carboxamido)phenyl)acrylate, methyl (E)-3-(5-((1S,2R,4R)—N-((4'-(dimethylamino)-[1,1'-biphenyl]-4-yl)methyl)bicyclo[2.2.1]heptane-2-carboxamido)pyridin-3-yl)acrylate, methyl (E)-3-(3-(N-((3-chloro-4'-(dimethylamino)-[1,1'-biphenyl]-4-yl)methyl-d)cyclohexanecarboxamido)-5-fluorophenyl)acrylate, methyl (E)-3-(3-((1S,2R,4R)—N-((4'-(dimethylamino)-3-fluoro-[1,1'-biphenyl]-4-yl)methyl)bicyclo[2.2.1]heptane-2-carboxamido)phenyl)acrylate, methyl (E)-3-(3-((1S,2R,4R)—N-((4'-(dimethylamino)-3-fluoro-[1,1'-biphenyl]-4-yl)methyl)bicyclo[2.2.1]heptane-2-carboxamido)-5-fluorophenyl)acrylate, methyl (E)-3-(3-((1S,2R,4R)—N-((3-chloro-4'-(dimethylamino)-[1,1'-biphenyl]-4-yl)methyl)bicyclo[2.2.1]heptane-2-carboxamido)phenyl)acrylate, methyl (E)-3-(3-((1S,2R,4R)—N-((3-chloro-4'-(dimethylamino)-[1,1'-biphenyl]-4-yl)methyl-d)bicyclo[2.2.1]heptane-2-carboxamido)phenyl)acrylate, methyl (E)-3-(5-((1S,2R,4R)—N-((3-chloro-4'-(dimethylamino)-[1,1'-biphenyl]-4-yl)methyl-d)bicyclo[2.2.1]heptane-2-carboxamido)pyridin-3-yl)acrylate, methyl (E)-3-(5-(N-((4'-(dimethylamino)-[1,1'-biphenyl]-4-yl)methyl)benzamido)pyridin-3-yl)acrylate, methyl (E)-3-(3-(N-((4'-(dimethylamino)-3-fluoro-[1,1'-biphenyl]-4-yl)methyl)benzamido)phenyl)acrylate, methyl (E)-3-(3-(N-((3-chloro-4'-(dimethylamino)-[1,1'-biphenyl]-4-yl)methyl-d)benzamido)phenyl)acrylate, methyl (E)-3-(3-(N-((4'-(dimethylamino)-[1,1'-biphenyl]-4-yl)methyl-d)benzamido)phenyl)acrylate, methyl (E)-3-(5-(N-((4'-(dimethylamino)-[1,1'-biphenyl]-4-yl)methyl-d)benzamido)pyridin-3-yl)acrylate, methyl (E)-3-(3-(N-((3-chloro-4'-(dimethylamino)-[1,1'-biphenyl]-4-yl)methyl-d)benzamido)-5-fluorophenyl)acrylate, methyl (E)-3-(3-fluoro-5-(N-((4-(1-methyl-1H-indazol-5-yl)phenyl)methyl-d)cyclohexanecarboxamido)phenyl)acrylate, methyl (E)-3-(3-fluoro-5-(N-(4-(1-methyl-1H-indazol-5-yl)benzyl)cyclohexanecarboxamido)phenyl)acrylate, methyl (E)-3-(3-(N-((4'-(dimethylamino)-[1,1'-biphenyl]-4-yl)methyl)benzamido)-5-fluorophenyl)acrylate, methyl (E)-3-(3-(N-(2-chloro-4-(1-methyl-1H-indazol-5-yl)benzyl)cyclohexanecarboxamido)phenyl)acrylate, methyl (E)-3-(5-((1S,2R,4R)—N-((2-fluoro-4-(1-methyl-1H-indazol-5-yl)benzyl)bicyclo[2.2.1]heptane-2-carboxamido)pyridin-3-yl)acrylate, methyl (E)-3-(3-(N-((2-fluoro-4-(1-methyl-1H-indazol-5-yl)phenyl)methyl-d)cyclohexanecarboxamido)phenyl)acrylate, methyl (E)-3-(5-(N-((3-chloro-4'-(dimethylamino)-[1,1'-biphenyl]-4-yl)methyl-d)benzamido)pyridin-3-yl)acrylate, methyl (E)-3-(3-(N-(2-chloro-4-(1-methyl-1H-indazol-5-yl)benzyl)cyclohexanecarboxamido)-5-fluorophenyl)acrylate, methyl (E)-3-(5-(N-((2-chloro-4-(1-methyl-1H-indazol-5-yl)phenyl)methyl-d)cyclohexanecarboxamido)pyridin-3-yl) acrylate, methyl (E)-3-(3-((1S,2R,4R)—N-((2-chloro-4-(1-methyl-1H-indazol-5-yl)phenyl)methyl-d)bicyclo[2.2.1]heptane-2-carboxamido)-5-fluorophenyl)acrylate, methyl (E)-3-(3-(N-(2-chloro-4-(1-methyl-1H-indazol-5-yl)benzyl)benzamido)-5-fluorophenyl)acrylate, methyl (E)-3-(5-(N-(2-chloro-4-(1-methyl-1H-indazol-5-yl)benzyl)benzamido)pyridin-3-yl)acrylate, methyl (E)-3-(3-fluoro-5-(N-(2-fluoro-4-(1-methyl-1H-indazol-5-yl)benzyl)benzamido)phenyl)acrylate, methyl (E)-3-(3-(N-((2-chloro-4-(1-methyl-1H-indazol-5-yl)phenyl)methyl-d)benzamido)phenyl)acrylate, methyl (E)-3-(5-((1S,2R,4R)—N-((4-(1-methyl-1H-indazol-5-yl)phenyl)methyl-d)bicyclo[2.2.1]heptane-2-carboxamido)pyridin-3-yl)acrylate, methyl (E)-3-(3-(N-(2-chloro-4-(1-methyl-1H-indazol-5-yl)benzyl)benzamido)phenyl)acrylate, methyl (E)-3-(3-(N-((4'-(dimethylamino)-[1,1'-biphenyl]-4-yl)methyl-d)cyclohexanecarboxamido)phenyl)acrylate, methyl (E)-3-(5-(N-((2-chloro-4-(1-methyl-1H-indazol-5-yl)phenyl)methyl-d)benzamido)pyridin-3-yl)acrylate, methyl (E)-3-(3-(N-((3-chloro-4'-(dimethylamino)-[1,1'-biphenyl]-4-yl)methyl)cyclohexanecarboxamido)phenyl)acrylate, methyl (E)-3-(3-(N-((4'-(dimethylamino)-3-fluoro-[1,1'-biphenyl]-4-yl)methyl-d)benzamido)phenyl)acrylate, methyl (E)-3-(5-(N-((4'-(dimethylamino)-3-fluoro-[1,1'-biphenyl]-4-yl)methyl)cyclohexanecarboxamido)pyridin-3-yl) acrylate, methyl (E)-3-(5-((1S,2R,4R)—N-((3-chloro-4'-(dimethylamino)-[1,1'-biphenyl]-4-yl)methyl-d)bicyclo[2.2.1]heptane-2-carboxamido)pyridin-3-yl)acrylate, methyl (E)-3-(3-fluoro-5-((1S,2R,4R)—N-((4-(1-methyl-1H-indazol-5-yl)phenyl)methyl-d)bicyclo[2.2.1]heptane-2-carboxamido)phenyl)acrylate, methyl (E)-3-(3-((1S,2R,4R)—N-((4-(1-methyl-1H-indazol-5-yl)phenyl)methyl-)bicyclo[2.2.1]heptane-2-carboxamido)phenyl)acrylate, methyl (E)-3-(5-(N-((3-chloro-4'-(dimethylamino)-[1,1'-biphenyl]-4-yl)methyl)benzamido)pyridin-3-yl)acrylate, methyl (E)-3-(3-((1S,2R,4R)—N-((4'-(dimethylamino)-[1,1'-biphenyl]-4-yl)methyl)bicyclo[2.2.1]heptane-2-carboxamido)-5-fluorophenyl)acrylate, methyl (E)-3-(3-((1S,2R,4R)—N-((2-fluoro-4-(1-methyl-1H-indazol-5-yl)phenyl)methyl-d)bicyclo[2.2.1]heptane-2-carboxamido)phenyl)acrylate, methyl (E)-3-(3-(N-((4'-(dimethylamino)-3-fluoro-[1,1'-biphenyl]-4-yl)methyl-d)cyclohexanecarboxamido)-5-fluorophenyl)acrylate, methyl (E)-3-(3-(N-((3-chloro-4'-(dimethylamino)-[1,1'-biphenyl]-4-yl)methyl)benzamido)-5-fluorophenyl)acrylate, methyl (E)-3-(3-((1S,2R,4R)—N-((4'-(dimethylamino)-[1,1'-biphenyl]-4-yl)methyl-d)bicyclo[2.2.1]heptane-2-carboxamido)phenyl)acrylate, methyl (E)-3-(3-((1S,2R,4R)—N-((4'-(dimethylamino)-3-fluoro-[1,1'-biphenyl]-4-yl)methyl-d)bicyclo[2.2.1]heptane-2-carboxamido)-5-fluorophenyl)acrylate, methyl (E)-3-(3-(N-((4'-(dimethylamino)-3-fluoro-[1,1'-biphenyl]-4-yl)methyl-d)benzamido)-5-fluorophenyl)acrylate, methyl (E)-3-(3-(N-((4'-(dimethylamino)-[1,1'-biphenyl]-4-yl)methyl-d)benzamido)-5-fluorophenyl)acrylate, methyl (E)-3-(3-((1S,2R,4R)—N-((3-chloro-4'-(dimethylamino)-[1,1'-biphenyl]-4-yl)methyl-d)bicyclo[2.2.1]heptane-2-carboxamido)-5-fluorophenyl)acrylate, methyl (E)-3-(5-(N-(4-(1-methyl-1H-indazol-5-yl)benzyl)benzamido)pyridin-3-yl)acrylate, methyl (E)-3-(5-(N-((4-(1-methyl-1H-indazol-5-yl)phenyl)methyl-d)benzamido)pyridin-3-yl)acrylate, methyl (E)-3-(3-(N-((3-chloro-4'-(dimethylamino)-[1,1'-biphenyl]-4-yl)methyl)cyclohexanecarboxamido)-5-fluorophenyl)acrylate, methyl (E)-3-(5-(N-((4'-(dimethylamino)-3-fluoro-[1,1'-biphenyl]-4-yl)methyl-d)benzamido)pyridin-3-yl)acrylate, methyl (E)-3-(5-((1S,2R,4R)—N-((4'-(dimethylamino)-3-fluoro-[1,1'-biphenyl]-4-yl)methyl)bicyclo[2.2.1]heptane-2-carboxamido)pyridin-3-yl)acrylate, methyl (E)-3-(3-(N-(4-(2-(tert-butoxy)-2-oxoethoxy)benzyl)cyclohexanecarboxamido)phenyl)acrylate, tert-butyl (E)-2-(4-((N-(3-(3-methoxy-3-oxoprop-1-en-1-yl)phenyl)cyclohexanecarboxamido)methyl)phenyl)cyclopropane-1-carboxylate, methyl (E)-3-(3-(N-(4-((2-oxotetrahydro-2H-pyran-3-yl)methyl)benzyl)cyclohexanecarboxamido)phenyl)acrylate, cyclobutyl (E)-3-(4-((N-(3-((E)-3-methoxy-3-oxoprop-1-en-1-yl)phenyl)cyclohexanecarboxamido)methyl)phenyl)acrylate, methyl (E)-3-(3-(N-(4-(6-methoxypyridin-3-yl)benzyl)cyclohexanecarboxamido)phenyl)acrylate, methyl (E)-3-(3-(N-((5-(4-(dimethylamino)phenyl)pyridin-2-yl)methyl)cyclohexanecarboxamido)phenyl)acrylate, methyl (E)-3-(3-(N-((4-(4-(dimethylamino)phenyl)piperazin-1-yl)methyl)cyclohexanecarboxamido)phenyl)acrylate, methyl (E)-3-(3-(N-(4-(3,4-dihydro-2H-benzo[b][1,4]oxazin-7-yl)benzyl)cyclohexanecarboxamido)phenyl)acrylate, methyl (E)-3-(3-(N-(4-(2H-benzo[b][1,4]oxazin-7-yl)benzyl)cyclohexanecarboxamido)phenyl)acrylate, methyl (E)-3-(3-(N-(4-(2,3-dihydrobenzo[b][1,4]dioxin-6-yl)benzyl)cyclohexanecarboxamido)phenyl)acrylate, methyl (E)-3-(3-(N-(4-(quinoxalin-6-yl)benzyl)cyclohexanecarboxamido)phenyl)acrylate, methyl (E)-3-(3-(N-(4-(1,2,3,4-tetrahydroquinoxalin-6-yl)benzyl)cyclohexanecarboxamido)phenyl)acrylate, methyl (E)-3-(3-(N-(4-(3,4-dihydro-2H-benzo[b][1,4]thiazin-7-yl)benzyl)cyclohexanecarboxamido)phenyl)acrylate, methyl (E)-3-(3-(N-(4-(1,1-dioxido-3,4-dihydro-2H-benzo[b][1,4]thiazin-7-yl)benzyl)cyclohexanecarboxamido)phenyl)acrylate, methyl (E)-3-(3-(N-(4-(1,1,4,4-tetraoxido-2,3-dihydrobenzo[b][1,4]dithiin-6-yl)benzyl)cyclohexanecarboxamido)phenyl)acrylate, methyl 2-(3-(N-((4'-(dimethylamino)-[1,1'-biphenyl]-4-yl)methyl)cyclohexanecarboxamido)phenyl)cyclopropane-1-carboxylate, methyl 2-(3-(N-((4'-(dimethylamino)-[1,1'-biphenyl]-4-yl)methyl)cyclohexanecarboxamido)phenyl)cyclobutane-1-carboxylate, methyl 2-(3-(N-((4'-(dimethylamino)-[1,1'-biphenyl]-4-yl)methyl)cyclohexanecarboxamido)phenyl)cyclopentane-1-carboxylate, methyl 2-(3-(N-((4'-(dimethylamino)-[1,1'-biphenyl]-4-yl)methyl)cyclohexanecarboxamido)phenyl)cyclohexane-1-carboxylate, methyl (E)-3-(3-(N-(4-(benzo[d]oxazol-6-yl)benzyl)cyclohexanecarboxamido)phenyl)acrylate, methyl (E)-3-(3-(N-(4-(1H-benzo[d]imidazol-6-yl)benzyl)cyclohexanecarboxamido)phenyl)acrylate, methyl (E)-3-(3-(N-(4-(benzo[d]thiazol-6-yl)benzyl)cyclohexanecarboxamido)phenyl)acrylate, methyl (E)-3-(3-(N-(4-(2-methylbenzo[d]thiazol-6-yl)benzyl)cyclohexanecarboxamido)phenyl)acrylate, methyl (E)-3-(3-(N-(4-(2-methylbenzo[d]oxazol-6-yl)benzyl)cyclohexanecarboxamido)phenyl)acrylate, methyl (E)-3-(3-(N-(4-(2-methyl-1H-benzo[d]imidazol-6-yl)benzyl)cyclohexanecarboxamido)phenyl)acrylate, methyl (E)-3-(3-(N-(4-(1,2-dimethyl-1H-benzo[d]imidazol-6-yl)benzyl)cyclohexanecarboxamido)phenyl)acrylate, methyl (E)-3-(3-(N-(4-(1-methyl-1H-benzo[d]imidazol-6-yl)benzyl)cyclohexanecarboxamido)phenyl)acrylate, methyl (E)-3-(3-(N-(4-(benzo[d]isoxazol-5-yl)benzyl)cyclohexanecarboxamido)phenyl)acrylate, methyl (E)-3-(3-(N-(4-(benzo[d]isothiazol-5-yl)benzyl)cyclohexanecarboxamido)phenyl)acrylate, methyl 3-(3-(N-((4'-(dimethylamino)-[1,1'-biphenyl]-4-yl)methyl)bicyclo[2.2.1]heptane-2-carboxamido)phenyl)propanoate, methyl 2-(3-(N-((4'-(dimethylamino)-[1,1'-biphenyl]-4-yl)methyl)bicyclo[2.2.1]heptane-2-carboxamido)phenoxy)acetate, 3-(N-((4'-(dimethylamino)-[1,1'-biphenyl]-4-yl)methyl)bicyclo[2.2.1]heptane-2-carboxamido)benzyl acetate, N-((4'-(dimethylamino)-[1,1'-biphenyl]-4-yl)methyl)-N-(3-((2-oxotetrahydro-2H-pyran-3-yl)methyl)phenyl)cyclohexanecarboxamide, N-((4'-(dimethylamino)-[1,1'-biphenyl]-4-yl)methyl)-N-(3-((2-oxotetrahydro-2H-pyran-4-yl)methyl)phenyl)cyclohexanecarboxamide, methyl (E)-3-(3-(N-((4-(2-(tert-butoxy)-2-oxoethoxy)phenyl)methyl-d)cyclohexanecarboxamido)phenyl)acrylate, tert-butyl (E)-2-(4-((N-(3-(3-methoxy-3-oxoprop-1-en-1-yl)phenyl)cyclohexanecarboxamido)methyl-d)phenyl)cyclopropane-1-carboxylate, methyl (E)-3-(3-(N-((4-((2-oxotetrahydro-2H-pyran-3-yl)methyl)phenyl)methyl-d)cyclohexanecarboxamido)phenyl)acrylate, cyclobutyl (E)-3-(4-((N-(3-((E)-3-methoxy-3-oxoprop-1-en-1-yl)phenyl)cyclohexanecarboxamido)methyl-d)phenyl)acrylate, methyl (E)-3-(3-(N-((4-(6-methoxypyridin-3-yl)phenyl)methyl-d)cyclohexanecarboxamido)phenyl)acrylate, methyl (E)-3-(3-(N-((5-(4-(dimethylamino)phenyl)pyridin-2-yl)methyl-d)cyclohexanecarboxamido)phenyl)acrylate, methyl (E)-3-(3-(N-((4-(4-(dimethylamino)phenyl)piperazin-1-yl)methyl-d)cyclohexanecarboxamido)phenyl)acrylate, methyl (E)-3-(3-(N-((4-(3,4-dihydro-2H-benzo[b][1,4]oxazin-7-yl)phenyl)methyl-d)cyclohexanecarboxamido)phenyl)acrylate, methyl (E)-3-(3-(N-((4-(2H-benzo[b][1,4]oxazin-7-yl)phenyl)methyl-d)cyclohexanecarboxamido)phenyl)acrylate, methyl (E)-3-(3-(N-((4-(2,3-dihydrobenzo[b][1,4]dioxin-6-yl)phenyl)methyl-d)cyclohexanecarboxamido)phenyl)acrylate, methyl (E)-3-(3-(N-((4-(quinoxalin-6-yl)phenyl)methyl-d)cyclohexanecarboxamido)phenyl)acrylate, methyl (E)-3-(3-(N-((4-(1,2,3,4-tetrahydroquinoxalin-6-yl)phenyl)methyl-d)cyclohexanecarboxamido)phenyl)acrylate, methyl (E)-3-(3-(N-((4-(3,4-dihydro-2H-benzo[b][1,4]thiazin-7-yl)phenyl)methyl-d)cyclohexanecarboxamido)phenyl)acrylate, methyl (E)-3-(3-(N-((4-(1,1-dioxido-3,4-dihydro-2H-benzo[b][1,4]thiazin-7-yl)phenyl)methyl-d)cyclohexanecarboxamido)phenyl)acrylate, methyl (E)-3-(3-(N-((4-(1,1,4,4-tetraoxido-2,3-dihydrobenzo[b][1,4]dithiin-6-yl)phenyl)methyl-d)cyclohexanecarboxamido)phenyl)acrylate, methyl 2-(3-(N-((4'-(dimethylamino)-[1,1'-biphenyl]-4-yl)methyl-d)cyclohexanecarboxamido)phenyl)cyclopropane-1-carboxylate, methyl 2-(3-(N-((4'-(dimethylamino)-[1,1'-biphenyl]-4-yl)methyl-d)cyclohexanecarboxamido)phenyl)cyclobutane-1-carboxylate, methyl 2-(3-(N-((4'-(dimethylamino)-[1,1'-biphenyl]-4-yl)methyl-d)cyclohexanecarboxamido)phenyl)cyclopentane-1-carboxylate, methyl 2-(3-(N-((4'-(dimethylamino)-[1,1'-biphenyl]-4-yl)methyl-d)cyclohexanecarboxamido)phenyl)cyclohexane-1-carboxylate, methyl (E)-3-(3-(N-((4-(benzo[d]oxazol-6-yl)phenyl)methyl-d)cyclohexanecarboxamido)phenyl)acrylate, methyl (E)-3-(3-(N-((4-(1H-benzo[d]imidazol-6-yl)phenyl)methyl-d)cyclohexanecarboxamido)phenyl)acrylate, methyl (E)-3-(3-(N-((4-(benzo[d]thiazol-6-yl)phenyl)methyl-d)cyclohexanecarboxamido)phenyl)acrylate, methyl (E)-3-(3-(N-((4-(2-methylbenzo[d]thiazol-6-yl)phenyl)methyl-d)cyclohexanecarboxamido)phenyl)acrylate, methyl (E)-3-(3-(N-((4-(2-methylbenzo[d]oxazol-6-yl)phenyl)methyl-d)cyclohexanecarboxamido)phenyl)acrylate, methyl (E)-3-(3-(N-((4-(2-methyl-1H-benzo[d]imidazol-6-yl)phenyl)methyl-d)cyclohexanecarboxamido)phenyl)acrylate, methyl (E)-3-(3-(N-((4-(1,2-dimethyl-1H-benzo[d]imidazol-6-yl)phenyl)methyl-d)cyclohexanecarboxamido)phenyl)acrylate, methyl (E)-3-(3-(N-((4-(1-methyl-1H-benzo[d]imidazol-6-yl)phenyl)methyl-d)cyclohexanecarboxamido)phenyl)acrylate, methyl (E)-3-(3-(N-((4-(benzo[d]isoxazol-5-yl)phenyl)methyl-d)cyclohexanecarboxamido)phenyl)acrylate, methyl (E)-3-(3-(N-((4-(benzo[d]isothiazol-5-yl)phenyl)methyl-d)cyclohexanecarboxamido)phenyl)acrylate, methyl 3-(3-(N-((4'-(dimethylamino)-[1,1'-biphenyl]-4-yl)methyl-d)bicyclo[2.2.1]heptane-2-carboxamido)phenyl)propanoate, methyl 2-(3-(N-((4'-(dimethylamino)-[1,1'-biphenyl]-4-yl)methyl-d)bicyclo[2.2.1]heptane-2-carboxamido)phenoxy)acetate, 3-(N-((4'-(dimethylamino)-[1,1'-biphenyl]-4-yl)methyl-d)bicyclo[2.2.1]heptane-2-carboxamido)benzyl acetate, N-((4'-(dimethylamino)-[1,1'-biphenyl]-4-yl)methyl-d)-N-(3-((2-oxotetrahydro-2H-pyran-3-yl)methyl)phenyl)cyclohexanecarboxamide, N-((4'-(dimethylamino)-[1,1'-biphenyl]-4-yl)methyl-d)-N-(3-((2-oxotetrahydro-2H-pyran-4-yl)methyl)phenyl)cyclohexanecarboxamide, methyl (E)-3-(3-((1S,2R,4R)—N—((S)-(4'-(dimethylamino)-[1,1'-biphenyl]-4-yl)methyl-d)bicyclo[2.2.1]heptane-2-carboxamido)-5-fluorophenyl)acrylate, methyl (E)-3-(3-((1S,2R,4R)—N—((R)-(4'-(dimethylamino)-[1,1'-biphenyl]-4-yl)methyl-d)bicyclo[2.2.1]heptane-2-carboxamido)-5-fluorophenyl)acrylate, methyl (E)-3-(3-((1S,2S,4R)—N—((S)-(4'-(dimethylamino)-[1,1'-biphenyl]-4-yl)methyl-d)bicyclo[2.2.1]heptane-2-carboxamido)-5-fluorophenyl)acrylate, methyl (E)-3-(3-((1S,2S,4R)—N—((R)-(4'-(dimethylamino)-[1,1'-biphenyl]-4-yl)methyl-d)bicyclo[2.2.1]heptane-2-carboxamido)-5-fluorophenyl)acrylate, methyl (E)-3-(3-((1R,2S,4S)—N—((S)-(4'-(dimethylamino)-[1,1'-biphenyl]-4-yl)methyl-d)bicyclo[2.2.1]heptane-2-carboxamido)-5-fluorophenyl)acrylate, methyl (E)-3-(3-((1R,2S,4S)—N—((R)-(4'-(dimethylamino)-[1,1'-biphenyl]-4-yl)methyl-d)bicyclo[2.2.1]heptane-2-carboxamido)-5-fluorophenyl)acrylate, methyl (E)-3-(3-((1R,2R,4S)—N—((5)-(4'-(dimethylamino)-[1,1'-biphenyl]-4-yl)methyl-d)bicyclo[2.2.1]heptane-2-carboxamido)-5-fluorophenyl)acrylate, methyl (E)-3-(3-((1R,2R,4S)—N—((R)-(4'-(dimethylamino)-[1,1'-biphenyl]-4-yl)methyl-d)bicyclo[2.2.1]heptane-2-carboxamido)-5-fluorophenyl)acrylate, methyl (E)-3-(3-((1S,2R,4R)—N—((5)-(4'-(dimethylamino)-3-fluoro-[1,1'-biphenyl]-4-yl)methyl-d)bicyclo[2.2.1]heptane-2-carboxamido)-5-fluorophenyl)acrylate, methyl (E)-3-(3-((1S,2R,4R)—N—((R)-(4'-(dimethylamino)-3-fluoro-[1,1'-biphenyl]-4-yl)methyl-d)bicyclo[2.2.1]heptane-2-carboxamido)-5-fluorophenyl)acrylate, methyl (E)-3-(3-((1S,2S,4R)—N—((S)-(4'-(dimethylamino)-3-fluoro-[1,1'-biphenyl]-4-yl)methyl-d)bicyclo[2.2.1]heptane-2-carboxamido)-5-fluorophenyl)acrylate, methyl (E)-3-(3-((1S,2S,4R)—N—((R)-(4'-(dimethylamino)-3-fluoro-[1,1'-biphenyl]-4-yl)methyl-d)bicyclo[2.2.1]heptane-2-carboxamido)-5-fluorophenyl)acrylate, methyl (E)-3-(3-((1R,2S,4S)—N—((S)-(4'-(dimethylamino)-3-fluoro-[1,1'-biphenyl]-4-yl)methyl-d)bicyclo[2.2.1]heptane-2-carboxamido)-5-fluorophenyl)acrylate, methyl (E)-3-(3-((1R,2S,4S)—N—((R)-(4'-(dimethylamino)-3-fluoro-[1,1'-biphenyl]-4-yl)methyl-d)bicyclo[2.2.1]heptane-2-carboxamido)-5-fluorophenyl)acrylate, methyl (E)-3-(3-((1R,2R,4S)—N—((S)-(4'-(dimethylamino)-3-fluoro-[1,1'-biphenyl]-4-yl)methyl-d)bicyclo[2.2.1]heptane-2-carboxamido)-5-fluorophenyl)acrylate, methyl (E)-3-(3-((1R,2R,4S)—N—((R)-(4'-(dimethylamino)-3-fluoro-[1,1'-biphenyl]-4-yl)methyl-d)bicyclo[2.2.1]heptane-2-carboxamido)-5-fluorophenyl)acrylate, methyl (R,E)-3-(3-(N-((4'-(dimethylamino)-3-fluoro-[1,1'-biphenyl]-4-yl)methyl-d)cyclohexanecarboxamido)phenyl)acrylate, methyl (S,E)-3-(3-(N-((4'-(dimethylamino)-3-fluoro-[1,1'-biphenyl]-4-yl)methyl-d)cyclohexanecarboxamido)phenyl)acrylate, methyl (R,E)-3-(3-(N-((4'-(dimethylamino)-[1,1'-biphenyl]-4-yl)methyl-d)cyclohexanecarboxamido)phenyl)acrylate, methyl (S,E)-3-(3-(N-((4'-(dimethylamino)-[1,1'-biphenyl]-4-yl)methyl-d)cyclohexanecarboxamido)phenyl)acrylate, methyl (R,E)-3-(3-fluoro-5-(N-((4-(1-methyl-1H-indazol-5-yl)phenyl)methyl-d)cyclohexanecarboxamido)phenyl)acrylate, methyl (S,E)-3-(3-fluoro-5-(N-((4-(1-methyl-1H-indazol-5-yl)phenyl)methyl-d)cyclohexanecarboxamido)phenyl)acrylate, methyl (R,E)-3-(3-(N-((2-fluoro-4-(1-methyl-1H-indazol-5-yl)phenyl)methyl-d)cyclohexanecarboxamido)phenyl)acrylate, or methyl (S,E)-3-(3-(N-((2-fluoro-4-(1-methyl-1H-indazol-5-yl)phenyl)methyl-d)cyclohexanecarboxamido)phenyl)acrylate.

In particular working embodiments, the compound is selected from

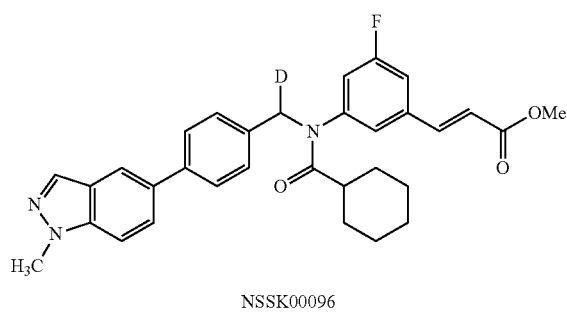

NSSK00096 methyl (E)-3-(3-fluoro-5-(N-((4-(1-methyl-1H-indazol-5-yl)phenyl)methyl-d)cyclohexanecarboxamido)phenyl)acrylate,

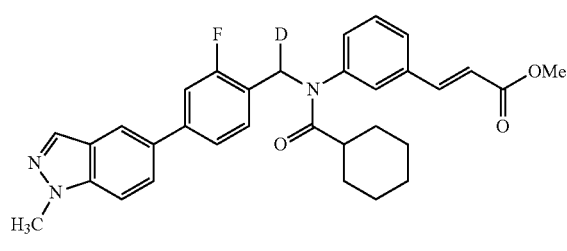

NSSK00089 methyl (E)-3-(3-(N-((2-fluoro-4-(1-methyl-1H-indazol-5-yl)phenyl)methyl-d)cyclohexanecarboxamido)phenyl)acrylate,

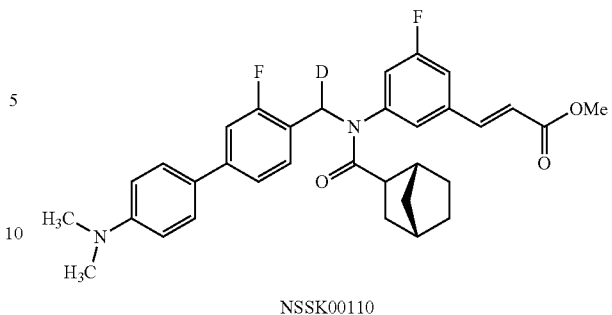

NSSK00110 methyl (E)-3-(3-((1R,4S)—N-((4'-(dimethylamino)-3-fluoro-[1,1'-biphenyl]-4-yl)methyl-d)bicyclo[2.2.1]heptane-2-carboxamido)-5-fluorophenyl)acrylate,

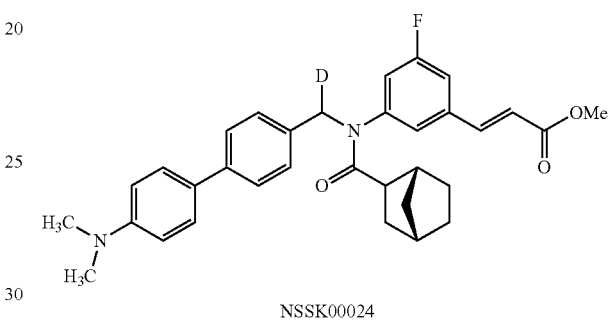

NSSK00024 methyl (E)-3-(3-((1R,4S)—N-((4'-(dimethylamino)-[1,1'-biphenyl]-4-yl)methyl-d)bicyclo[2.2.1]heptane-2-carboxamido)-5-fluorophenyl)acrylate, and

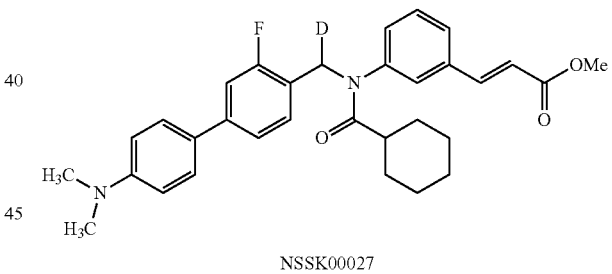

NSSK00027 methyl (E)-3-(3-(N-((4'-(dimethylamino)-3-fluoro-[1,1'-biphenyl]-4-yl)methyl-d)cyclohexanecarboxamido)phenyl)acrylate.

In other particular embodiments, the compound is methyl (E)-3-(3-((1S,2R,4R)—N—((S)-(4'-(dimethylamino)-[1,1'-biphenyl]-4-yl)methyl-d)bicyclo[2.2.1]heptane-2-carboxamido)-5-fluorophenyl)acrylate, methyl (E)-3-(3-((1S,2R,4R)—N—((R)-(4'-(dimethylamino)-[1,1'-biphenyl]-4-yl)methyl-d)bicyclo[2.2.1]heptane-2-carboxamido)-5-fluorophenyl)acrylate, methyl (E)-3-(3-((1S,2S,4R)—N—((S)-(4'-(dimethylamino)-[1,1'-biphenyl]-4-yl)methyl-d)bicyclo[2.2.1]heptane-2-carboxamido)-5-fluorophenyl)acrylate, methyl (E)-3-(3-((1S,2S,4R)—N—((R)-(4'-(dimethylamino)-[1,1'-biphenyl]-4-yl)methyl-d)bicyclo[2.2.1]heptane-2-carboxamido)-5-fluorophenyl)acrylate, methyl (E)-3-(3-((1R,2S,4S)—N—((S)-(4'-(dimethylamino)-[1,1'-biphenyl]-4-yl)methyl-d)bicyclo[2.2.1]heptane-2-carboxamido)-5-fluorophenyl)acrylate, methyl (E)-3-(3-((1R,2S,4S)—N—((R)-(4'-(dimethylamino)-[1,1'-biphenyl]-4-yl)methyl-d)bicyclo[2.2.1]heptane-2-carboxamido)-5-fluorophenyl)acrylate,
methyl (E)-3-(3-((1R,2R,4S)—N—((S)-(4'-(dimethylamino)-[1,1'-biphenyl]-4-yl)methyl-d)bicyclo[2.2.1]heptane-2-carboxamido)-5-fluorophenyl)acrylate,
methyl (E)-3-(3-((1R,2R,4S)—N—((R)-(4'-(dimethylamino)-[1,1'-biphenyl]-4-yl)methyl-d)bicyclo[2.2.1]heptane-2-carboxamido)-5-fluorophenyl)acrylate,
methyl (E)-3-(3-((1S,2R,4R)—N—((S)-(4'-(dimethylamino)-3-fluoro-[1,1'-biphenyl]-4-yl)methyl-d)bicyclo[2.2.1]heptane-2-carboxamido)-5-fluorophenyl)acrylate,
methyl (E)-3-(3-((1S,2R,4R)—N—((R)-(4'-(dimethylamino)-3-fluoro-[1,1'-biphenyl]-4-yl)methyl-d)bicyclo[2.2.1]heptane-2-carboxamido)-5-fluorophenyl)acrylate,
methyl (E)-3-(3-((1S,2S,4R)—N—((S)-(4'-(dimethylamino)-3-fluoro-[1,1'-biphenyl]-4-yl)methyl-d)bicyclo[2.2.1]heptane-2-carboxamido)-5-fluorophenyl)acrylate,
methyl (E)-3-(3-((1S,2S,4R)—N—((R)-(4'-(dimethylamino)-3-fluoro-[1,1'-biphenyl]-4-yl)methyl-d)bicyclo[2.2.1]heptane-2-carboxamido)-5-fluorophenyl)acrylate,
methyl (E)-3-(3-((1R,2S,4S)—N—((S)-(4'-(dimethylamino)-3-fluoro-[1,1'-biphenyl]-4-yl)methyl-d)bicyclo[2.2.1]heptane-2-carboxamido)-5-fluorophenyl)acrylate,
methyl (E)-3-(3-((1R,2S,4S)—N—((R)-(4'-(dimethylamino)-3-fluoro-[1,1'-biphenyl]-4-yl)methyl-d)bicyclo[2.2.1]heptane-2-carboxamido)-5-fluorophenyl)acrylate,
methyl (E)-3-(3-((1R,2R,4S)—N—((S)-(4'-(dimethylamino)-3-fluoro-[1,1'-biphenyl]-4-yl)methyl-d)bicyclo[2.2.1]heptane-2-carboxamido)-5-fluorophenyl)acrylate,
methyl (E)-3-(3-((1R,2R,4S)—N—((R)-(4'-(dimethylamino)-3-fluoro-[1,1'-biphenyl]-4-yl)methyl-d)bicyclo[2.2.1]heptane-2-carboxamido)-5-fluorophenyl)acrylate,
methyl (R,E)-3-(3-(N-((4'-(dimethylamino)-3-fluoro-[1,1'-biphenyl]-4-yl)methyl-d)cyclohexanecarboxamido)phenyl)acrylate,
methyl (S,E)-3-(3-(N-((4'-(dimethylamino)-3-fluoro-[1,1'-biphenyl]-4-yl)methyl-d)cyclohexanecarboxamido)phenyl)acrylate,
methyl (R,E)-3-(3-(N-((4'-(dimethylamino)-[1,1'-biphenyl]-4-yl)methyl-d)cyclohexanecarboxamido)phenyl)acrylate,
methyl (S,E)-3-(3-(N-((4'-(dimethylamino)-[1,1'-biphenyl]-4-yl)methyl-d)cyclohexanecarboxamido)phenyl)acrylate,
methyl (R,E)-3-(3-fluoro-5-(N-((4-(1-methyl-1H-indazol-5-yl)phenyl)methyl-d)cyclohexanecarboxamido)phenyl)acrylate,
methyl (S,E)-3-(3-fluoro-5-(N-((4-(1-methyl-1H-indazol-5-yl)phenyl)methyl-d)cyclohexanecarboxamido)phenyl)acrylate,
methyl (R,E)-3-(3-(N-((2-fluoro-4-(1-methyl-1H-indazol-5-yl)phenyl)methyl-d)cyclohexanecarboxamido)phenyl)acrylate, or
methyl (S,E)-3-(3-(N-((2-fluoro-4-(1-methyl-1H-indazol-5-yl)phenyl)methyl-d)cyclohexanecarboxamido)phenyl)acrylate.

Also provided herein are kits that include any FXR agonist (or composition containing such an agonist) described herein and a device for localized delivery within a region of the intestines, such as the ileum or colon. In certain embodiments, the device is a syringe, bag, or a pressurized container.

IV. Compositions

Also disclosed herein are pharmaceutical compositions comprising at least one compound having formulas 1-18. Remington's Pharmaceutical Sciences, by E. W. Martin, Mack Publishing Co., Easton, Pa., 15th Edition, 1975, incorporated herein by reference, describes exemplary formulations (and components thereof) suitable for pharmaceutical delivery of the disclosed compounds. Pharmaceutical compositions comprising at least one of the disclosed compounds can be formulated for use in human or veterinary medicine. Particular formulations of a disclosed pharmaceutical composition may depend, for example, on the mode of administration (e.g., oral). In some embodiments, disclosed pharmaceutical compositions include a pharmaceutically acceptable carrier in addition to at least one or two or more active ingredients, such as a compound or compounds disclosed herein. In other embodiments, other medicinal or pharmaceutical agents, for example, with similar, related or complementary effects on the affliction being treated (such as obesity, dyslipidemia, or diabetes), can also be included as active ingredients in a pharmaceutical composition. For example, one or more of the disclosed compounds can be formulated with one or more of (such as 1, 2, 3, 4, or 5 of) an antibiotic (e.g., metronidazole, vancomycin, and/or fidaxomicin), statin, alpha-glucosidase inhibitor, amylin agonist, dipeptidyl-peptidase 4 (DPP-4) inhibitor (such as sitagliptin, vildagliptin, saxagliptin, linagliptin, anaglptin, teneligliptin, alogliptin, gemiglptin, or dutoglpitin), meglitinide, sulfonylurea, peroxisome proliferator-activated receptor (PPAR)-gamma agonist (e.g., a thiazolidinedione (TZD) [such as ioglitazone, rosiglitazone, rivoglitazone, or troglitazone], aleglitazar, farglitazar, muraglitazar, or tesaglitazar), anti-inflammatory agent (e.g., oral corticosteroid), chemotherapeutic, biologic, radiotherapeutic, nicotinamide ribonucleoside, analogs of nicotinamide ribonucleoside that promotes NAD+ production of which is a substrate for many enzymatic reactions such as p450s which are a target of FXR (e.g., see Yang et al., *J. Med. Chem.* 50:6458-61, 2007), and the like.

Pharmaceutically acceptable carriers useful for the disclosed method and composition will depend on the particular mode of administration being employed. For example, for solid compositions (e.g., powder, pill, tablet, or capsule forms), conventional non-toxic solid carriers can include, without limitation, pharmaceutical grades of sugars, such as mannitol or lactose, polysaccharides, such as starch, or salts of organic acids, such as magnesium stearate. In addition to biologically neutral carriers, pharmaceutical compositions can optionally contain minor amounts of auxiliary substances (e.g., excipients), such as wetting or emulsifying agents, preservatives, and pH buffering agents and the like; for example, sodium acetate or sorbitan monolaurate. Other non-limiting excipients include nonionic solubilizers, such as cremophor, or proteins, such as human serum albumin or plasma preparations. In some embodiments, the pharmaceutical composition comprises a sufficient amount of a disclosed compound to have a desired therapeutic effect. Typically, the disclosed compound constitutes greater than 0% to less than 100% of the pharmaceutical composition, such as 10% or less, 20% or less, 30% or less, 40% or less, 50% or less, 60% or less, 70% or less, 80% or less, 90% or less, or 90% to less than 100% of the pharmaceutical composition.

The disclosed pharmaceutical compositions may be formulated as a pharmaceutically acceptable salt, solvate, hydrate, N-oxide or combination thereof, of a disclosed compound. Additionally, the pharmaceutical composition may comprise one or more polymorph of the disclosed compound. Pharmaceutically acceptable salts are salts of a free base form of a compound that possesses the desired pharmacological activity of the free base. These salts may be derived from inorganic or organic acids. Non-limiting examples of suitable inorganic acids include hydrochloric acid, nitric acid, hydrobromic acid, sulfuric acid, hydriodic acid, and phosphoric acid. Non-limiting examples of suitable organic acids include acetic acid, propionic acid, glycolic acid, lactic acid, pyruvic acid, malonic acid, succinic acid, malic acid, maleic acid, fumaric acid, tartaric acid, citric acid, benzoic acid, cinnamic acid, mandelic acid, methanesulfonic acid, ethanesulfonic acid, p-toluenesulfonic acid, methyl sulfonic acid, salicylic acid, formic acid, trichloroacetic acid, trifluoroacetic acid, gluconic acid, asparagic acid, aspartic acid, benzenesulfonic acid, p-toluenesulfonic acid, naphthalenesulfonic acid, and the like. Examples of other suitable pharmaceutically acceptable salts are found in Remington's Pharmaceutical Sciences, 17th Edition, Mack Publishing Company, Easton, Pa., 1985.

In some embodiments, the compounds disclosed herein may be formulated to have a suitable particle size. A suitable particle size may be one which reduces or substantially precludes separation of the components of the composition, e.g., no separation between the drug and any other components of the composition, such as a second drug, a pharmaceutically acceptable excipient, a corticosteroid, an antibiotic or any combination thereof. Additionally, the particle size may be selected to ensure the composition is suitable for delivery, such as oral delivery.

In certain embodiments, the composition further includes an enteric coating. Typically, an enteric coating is a polymer barrier applied to an oral medication to help protect the drug from the acidity and/or enzymes of the stomach, esophagus and/or mouth. In some embodiments, this coating can reduce or substantially prevent systemic delivery of the disclosed compound, thereby allowing substantially selective delivery to the intestines. In some embodiments, the enteric coating will not dissolve in the acid environment of the stomach, which has an acidic, pH of about 3, but will dissolve in the alkaline environments of the small intestine, with, for example, a pH of about 7 to 9. Materials used for enteric coating include, but are not limited to, fatty acids, waxes, shellac, plastics and plant fibers. In some embodiments, the coating may comprise methyl acrylate-methacrylic acid copolymers, cellulose acetate succinate, hydroxy propyl methyl cellulose phthalate, hydroxy propyl methyl cellulose acetate succinate (hypromellose acetate succinate), polyvinyl acetate phthalate (PVAP), methyl methacrylate-methacrylic acid copolymers, shellac, cellulose acetate trimellitate, sodium alginate, or any combination thereof.

V. Methods of Making the Compounds

Embodiments of a method of making compounds that have formulas 1-18 are also disclosed herein. A general method of making the compounds comprises reacting an aldehyde with a first amine to form an imine, reacting the imine with a reducing agent to form a second amine, and reacting the second amine with an activated carboxylic acid derivative or a carboxylic acid to form an amide.

Other embodiments further comprise contacting the aldehyde with a boronic acid, contacting the amide with a vinyl ester, contacting the first amine with a vinyl ester, contacting the amide with a boronic acid, or any combination thereof. In certain embodiments the reducing agent is a deuterated reducing agent, and the compound comprises deuterium.

One exemplary embodiment of the general method is shown in Scheme 1.

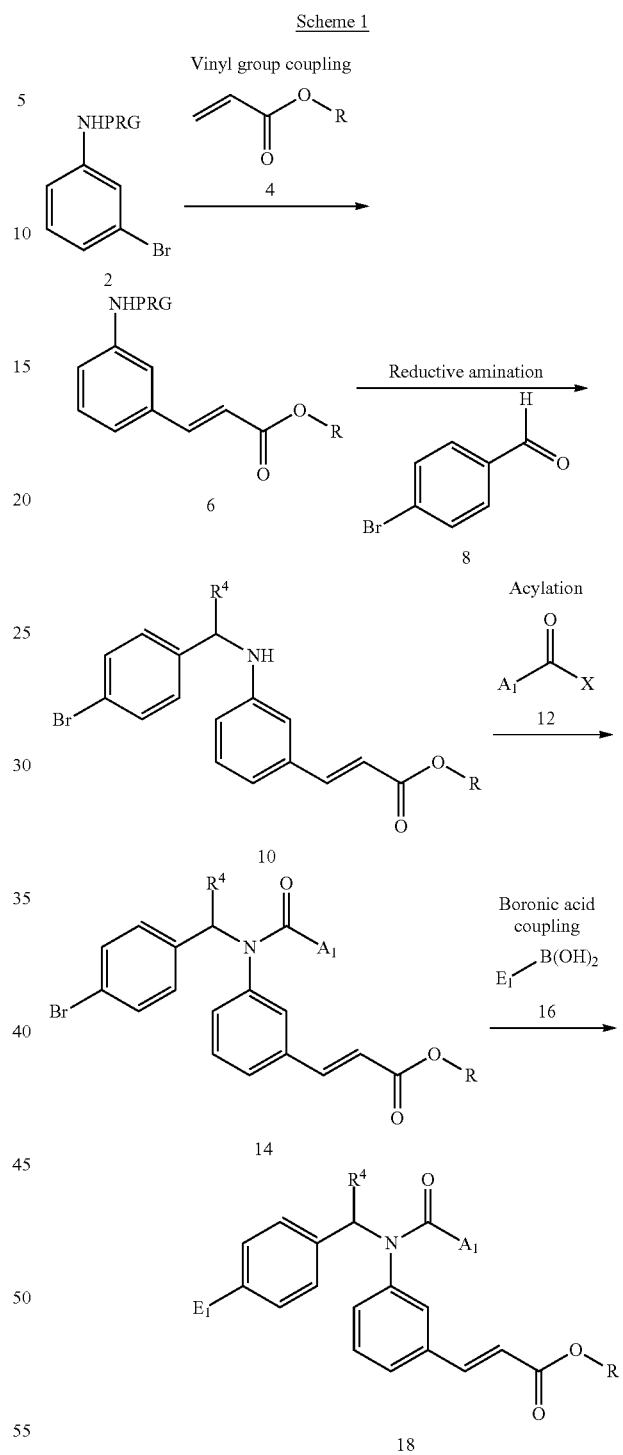

where PRG = Nitrogen protecting group such as Bn, Bz, Boc, Cbz, etc.

A. Vinyl Group Coupling

With reference to scheme 1, a protected aromatic amine 2 was coupled to a vinyl ester 4 by a suitable coupling technique to form compound 6. The amine of the aromatic amine 2 was protected by a suitable protecting group, as will be understood by a person of ordinary skill in the art. Additional information concerning protecting groups is provided by Greene and Wuts, *Protective Groups in Organic*

*Synthesis;* 3rd Ed.; John Wiley & Sons, New York, 1999, which is incorporated herein by reference. Exemplary amine protecting groups include, but are not limited to, tert-butyloxycarbonyl (Boc), benzyl, benzoyl, or benzoyloxycarbonyl (Cbz). In some embodiments the technique is a Stille coupling. In certain working embodiments, coupling comprised treating the protected aromatic amine with a vinyl group in the presence of a suitable catalyst, such as a palladium catalyst, and optionally, a suitable phosphine compound. Suitable palladium catalysts include, but are not limited to, Bis(dibenzylideneacetone)palladium ($Pd_2(dba)_3$) or palladium acetate ($Pd(OAc)_3$). In certain working examples $Pd_2(dba)_3$ was used as a catalyst with tri(o-tolyl) phosphine ($P(o-tol)_3$) as the phosphine. The coupling reaction is conducted in any suitable solvent, such as dimethylformamide, at a temperature effective to facilitate a reaction. In some embodiments the effective temperature is from greater than 0° C. to at least 130° C., such as from about 20° C. to about 110° C., from about 80° C. to about 100° C. In certain working embodiments the temperature was about 95° C.

B. Reductive Amination

The amine protecting group of compound 6 was removed by treatment with a suitable reagent. Suitable de-protection reagents and conditions for a specific protecting group can be selected by a person of ordinary skill in the art, and is further disclosed by consulting Greene and Wuts. In certain working embodiments, trifluoroacetic acid (TFA) was used to remove a Boc protecting group. In certain disclosed embodiments, the de-protected amine (not shown) was then treated with an aldehyde, such as aldehyde 8, in the presence of a reducing agent. In other embodiments, the amine was treated with an aldehyde, and subsequently treated by a reducing agent. The reducing agent is selected to place a desired $R^4$ group into the molecule. In some embodiments $R^4$ is hydrogen; in others it is deuterium. Suitable reducing agents include, but are not limited to, sodium triacetoxyborohydride, sodium triacetoxyborodeuteride, sodium cyanoborohydride, sodium cyanoborodeuteride, sodium borohydride, lithium borohydride, sodium borodeuteride or lithium borodeuteride. Suitable solvents for the reduction include, but are not limited to, toluene, halogenated solvents, THF, hexanes, cyclohexane, acetic acid, deuterated acetic acid, alcohols such as methanol, ethanol propanol, isopropanol, or deuterated alcohols such as methanol-$d_4$. Typically, the reducing agent was $NaBH(OAc)_3$, $NaBD(OAc)_3$, $NaBD_3CN$, $NaBH_4$ or $NaBD_4$ and the solvent was THF, $CD_3OD$, acetic acid or deuterated acetic acid.

C. Acylation

Subsequent to the reductive amination, compound 10 was acylated with acylating agent 12 under suitable conditions, such as by treatment with a carboxylic acid or an activated carboxylic acid derivative, such as an acid chloride, an acid bromide, or an anhydride. A person of ordinary skill in the art will understand which activated carboxylic acid derivatives are suitable for a particular carboxylic acid. Alternatively, a carboxylic acid may be coupled to the amine using a suitable coupling reagent known to a person of ordinary skill in the art. Exemplary coupling reagents include, but are not limited to, HATU, dicyclohexylcarbodiimide (DCCI, DCC) or 1-ethyl-3-(3-dimethylaminopropyl)carbodiimide (EDC, EDCI, EDAC). In working embodiments the carboxylic acid was activated by forming an acid chloride. The acylation reactions proceed in a suitable solvent, typically an aprotic solvent, such as pyridine, dichloromethane, chloroform, dioxane, toluene, DMF, THF or acetonitrile. Optionally, the reaction with a carboxylic acid or a carboxylic acid derivative may proceed in the presence of one or more additional compounds, such as potassium carbonate, triethylamine, diisopropylethylamine, sodium carbonate, 4-(dimethylamino)pyridine (DMAP) or pyridine. The reactions are performed at a temperature effective to facilitate the reaction, such as from greater than about −10° C. to greater than about 120° C., typically from about 5° C. to about 90° C., more typically from about 25° C. to about 65° C.

D. Boronic Acid Coupling

After the acylation reaction, compound 14 was treated with a boronic acid 16, in a Suzuki-type coupling. In some embodiments, the coupling was performed in the presence of a catalyst effective to facilitate the coupling reaction, and optionally in the presence of one or more additional compounds. Typical catalysts for a Suzuki coupling are palladium or nickel catalysts, including but not limited to, $NiCl_2(dppf)$, $NiCl_2(dppp)$, $Pd(PPh_3)_4$, $Pd(OAC)_2$ or $PdCl_2(PPh_3)_4$. In working embodiments the catalyst was $Pd(PPh_3)_4$. Typical additional compounds include, but are not limited to, triphenylphosphine ($PPh_3$), and/or bases such as potassium carbonate, sodium carbonate, cesium carbonate, sodium hydroxide, potassium hydroxide, triethylamine, sodium ethoxide, sodium methoxide, tripotassium phosphate or any combination thereof. In certain working embodiments, the additional compound was sodium carbonate. The coupling reaction is performed in any suitable solvent, such as DMF, ethanol, methanol, isopropanol, propanol, benzene, toluene, THF, dioxane, water or any combination thereof. In certain working embodiments, DMF-ethanol-water was used as the solvent.

A person of ordinary skill in the art will recognize that the various steps described above with reference to Scheme 1 do not necessarily have to be performed in the particular order depicted. The reactions can be performed in any order suitable to result in making the desired compound 18. For example, in certain embodiments, the sequence of reactions followed the order described in Scheme 2.

Scheme 2

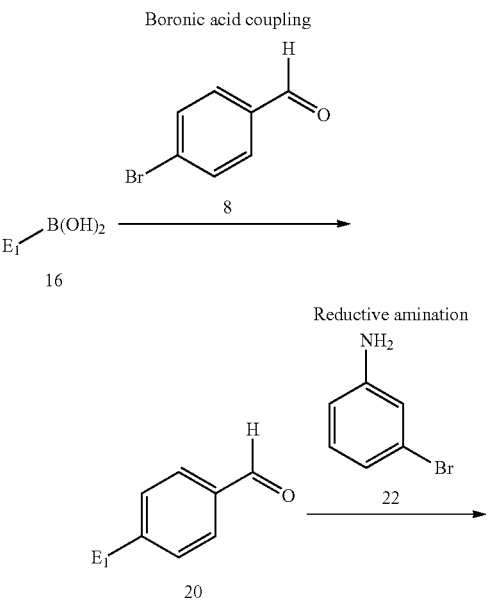

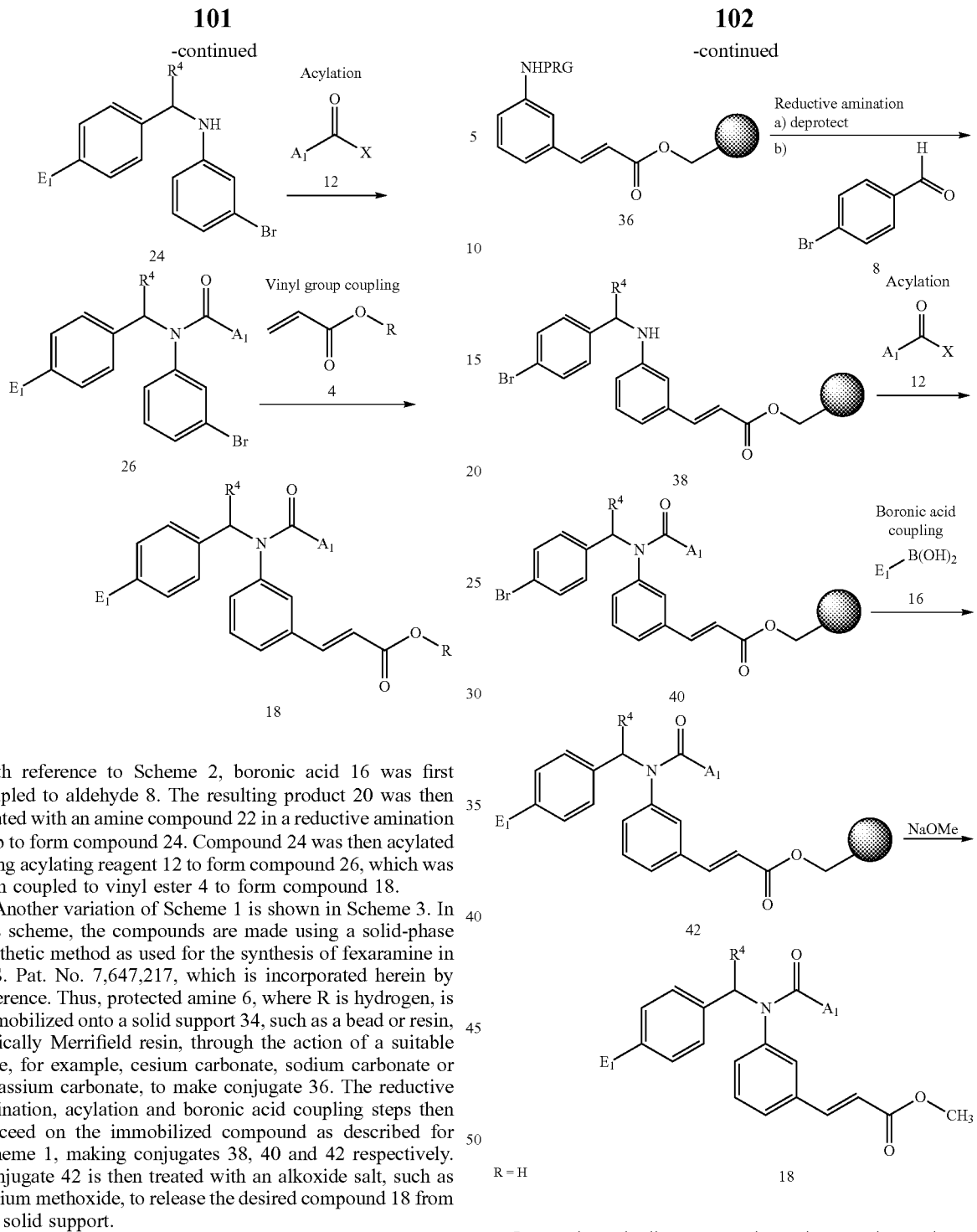

With reference to Scheme 2, boronic acid 16 was first coupled to aldehyde 8. The resulting product 20 was then treated with an amine compound 22 in a reductive amination step to form compound 24. Compound 24 was then acylated using acylating reagent 12 to form compound 26, which was then coupled to vinyl ester 4 to form compound 18.

Another variation of Scheme 1 is shown in Scheme 3. In this scheme, the compounds are made using a solid-phase synthetic method as used for the synthesis of fexaramine in U.S. Pat. No. 7,647,217, which is incorporated herein by reference. Thus, protected amine 6, where R is hydrogen, is immobilized onto a solid support 34, such as a bead or resin, typically Merrifield resin, through the action of a suitable base, for example, cesium carbonate, sodium carbonate or potassium carbonate, to make conjugate 36. The reductive amination, acylation and boronic acid coupling steps then proceed on the immobilized compound as described for Scheme 1, making conjugates 38, 40 and 42 respectively. Conjugate 42 is then treated with an alkoxide salt, such as sodium methoxide, to release the desired compound 18 from the solid support.

In certain embodiments, an alternative reaction pathway was followed. Scheme 4 outlines an exemplary alternative route. First, a halogenated nitrobenzene 28 was coupled to vinyl ester 4 in the presence of a suitable catalyst and an additional compound (not shown) to form compound 30. In working embodiments the catalyst was $Pd(OAc)_2$, and the additional compound was sodium acetate. The nitro group of compound 30 was then reduced to an amine by a suitable reagent to form amine 32. Suitable reagents include, but are not limited to, tin chloride, iron powder in an acid medium, zinc powder or catalytic hydrogenation using a transition metal catalyst comprising palladium, platinum, nickel, rhodium or ruthenium. In working embodiments tin chloride ($SnCl_2$) was used as the reducing agent.

Scheme 4

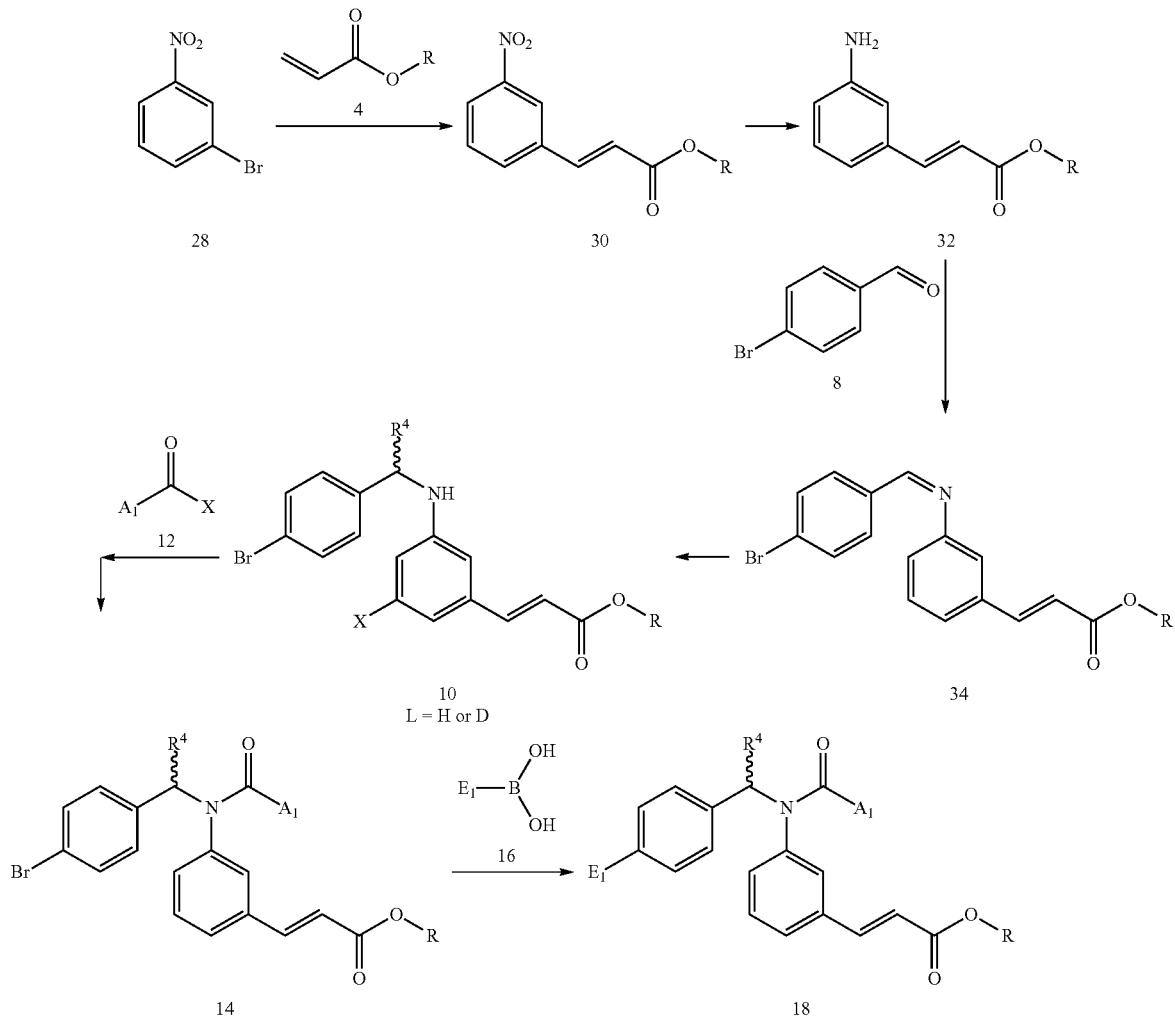

Amine 32 was then treated with an aldehyde 8 in a de-hydration reaction. Suitable dehydrating agents include, but are not limited to, an acid catalyst such as para-toluene sulfonic acid, a base such as triethylamine, malononitrile, molecular sieve, magnesium sulfate, sodium sulfate, or any combination thereof. Suitable solvents for the de-hydration reaction include toluene, xylenes, DMSO, DMF, THF, alcohols such as methanol or any combination thereof. Resulting imine compound 34 was then treated with a suitable reducing agent to form amine 10. In working embodiments, a deuterated reducing agent was used. In some embodiments sodium cyanodeuteroborohydride was used, and in others sodium deuteroborohydride was used. Any suitable, non-protonated solvent can be used, and in some working embodiments the solvent was methanol-$d_4$ and in others it was THF.

Amine 10 was then treated with acylating reagent 12, as described above with reference to Scheme 1, to form compound 14. In working embodiments the amine was treated with carboxylic acids in the presence of HATU and diisopropylethylamine in DMF. In other working embodiments the amine was treated with carboxylic acid chlorides in dichloromethane in the presence of triethylamine.

Compound 14 was then treated with boronic acid 16 as described above with reference to Scheme 1. In certain working embodiments, compound 14 was treated with boronic acid 16 in a DME-ethanol-water solvent system, in the presence of Pd(PPh$_3$)$_4$ and sodium carbonate. In other working embodiments dioxane-water was used as the solvent, Pd(dppf)Cl$_2$ was the catalyst and potassium carbonate was used as a base.

One exemplary method of making compounds having formula 13 is shown in Scheme 5. This method is a modification of the method of Lee and Hartwig, *J. Org. Chem.* 2001, 66, 3402-3415.

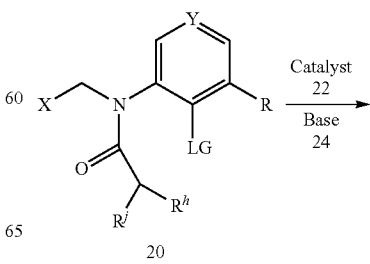

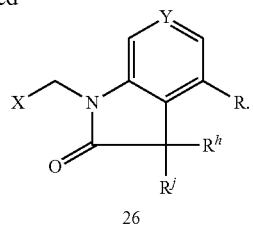

26

With reference to Scheme 5, compound 20 is reacted with a catalyst 22 and a base 24 in a suitable solvent, to form compound 26. Leaving group LG on compound 20 is any suitable leaving group, such as a halide, mesylate, tosylate or trifluoromethylsulfonate. Catalyst 22 is any catalyst that facilitates the formation of compound 26. Suitable catalysts include, but are not limited to, palladium catalysts such as Pd(OAc)$_2$, and may also comprise one or more ligands, such as PCy$_3$, or sterically hindered N-heterocyclic carbine ligands. The amount of the catalyst used is any suitable amount to catalyze the reaction at a suitable rate, such as from about 1 mol % to greater than about 20 mol %, preferably from about 5 mol % to about 10 mol %. Base 24 is any suitable base that facilitates the reaction. In some embodiments an excess of the base is used, such as from greater than 1 equivalent to greater than about 5 equivalents, preferably from about 1.1 equivalents to about 2 equivalents. Suitable bases include, but are not limited to, tert-butoxide salts, such as sodium, lithium or potassium tert-butoxide. The solvent can be any solvent suitable to facilitate a reaction. In some embodiments the solvent is 1,4-dioxane.

Embodiments of a method of making prodrugs of compounds having formulas 1-13 are also disclosed herein. One general method of making prodrugs is disclosed by Poon, et al. *Bioorg. med. Chem. Lett.* 2005, 15: 2259-2263, and is shown in Scheme 6. Briefly, the method comprises making the thioester of the compound, and forming the ortho ester or imidate.

Scheme 6

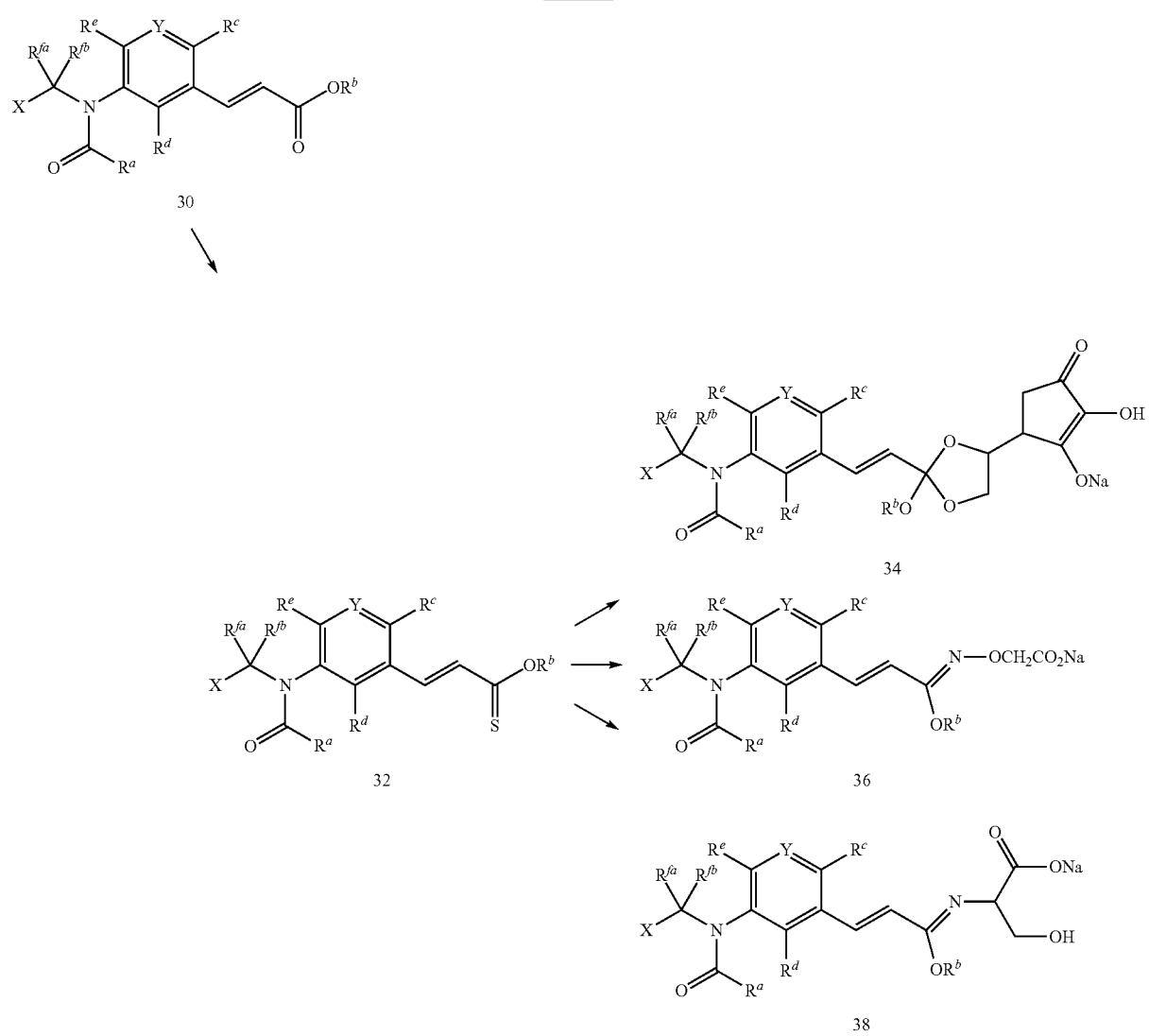

With reference to Scheme 6, ester compound 30 is reacted with reagent suitable to form thioester compound 32. Suitable reagents include, but are not limited to, Lawesson's reagent or P$_2$S$_5$. The reaction is performed in a suitable solvent, usually an aprotic solvent such as toluene, acetonitrile, cyclohexane, dichloromethane, or chloroform. The reaction may also be heated, such as to reflux.

The thioester compound 32 is then reacted with reagents suitable to form the desired prodrug, in the presence of a metal salt and a base. The metal salt is any metal salt suitable to mediate the desulfurization-condensation reaction between the thioester compound 32 and the alcohol or amine. Suitable metal salts include, but are not limited to, silver salts such as AgOTf. Suitable bases include, but are not limited to organic bases such as triethylamine or diisopropylethylamine. The reactions are performed in solvent suitable to facilitate the reaction, such as an aprotic solvent. Suitable solvents include, but are not limited to, acetonitrile, DMF, dimethylacetyl, N-methyl-2-pyrrolidone.

To form compound 34, thioester 32 is reacted with dibenzylascorbate, AgOTf and triethylamine in acetonitrile. An intermediate compound is formed initially (not shown) which is then reacted with hydrogen in the presence of a palladium catalyst in alcohol to form compound 34. Compound 36 is formed by reacting compound 32 with hydroxylamine, in the presence of AgOTf and triethylamine in acetonitrile. The intermediate compound (not shown) is then reacted with 2-bromoacetic acid and sodium hydroxide, to form compound 36. Compound 38 is made by reacting compound 32 with serine-OMe in the presence of AgOTf and triethylamine, in acetonitrile. The intermediate compound formed (not shown) is then reacted with Sodium trimethylsilanolate (NaOTMS) in THF to form compound 38.

A method of making compounds having formula 17 and 18 is shown in Scheme 7, and is a modification of a method disclosed by Ates and Curran, *J. Am. Chem. Soc.* 2001, 123: 5130-5131.

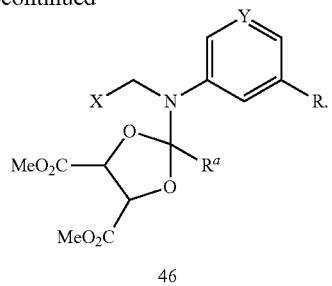

With reference to Scheme 7, compound 40 is reacted with a methylating agent, such as methyl trifluoromethanesulfonate, in a suitable solvent to make compound 42. Suitable solvents include, but are not limited to, halogenated solvents such as dichloromethane and chloroform. Compound 42 is reacted with a metal alkoxide solution, such as sodium methoxide in methanol, to form compound 44, an exemplary compound satisfying formula 17. Compound 44 is further reacted with dimethyl tartrate in a vacuum to form compound 46, an exemplary compound satisfying formula 18.

VI. Methods of Using the Compounds/Compositions

Orally delivered fexaramine (Fex) (Downes et al., *Mol Cell* 11:1079-1092, 2003) is poorly absorbed, resulting in intestinally-restricted FXR activation. It is shown herein that despite this restricted activation, Fex treatment of diet-induced obesity (DIO) mice produces a novel metabolic profile that includes reduced weight gain, decreased inflammation, browning of white adipose tissue and increased insulin sensitization. The beneficial systemic efficacy achieved with Fex suggests intestinal FXR therapy as a potentially safer approach in the treatment of insulin resistance and metabolic syndrome.

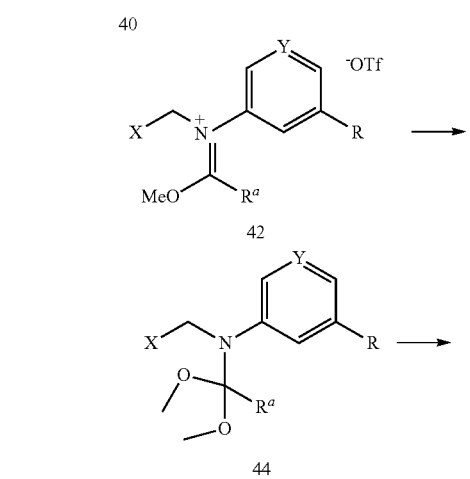

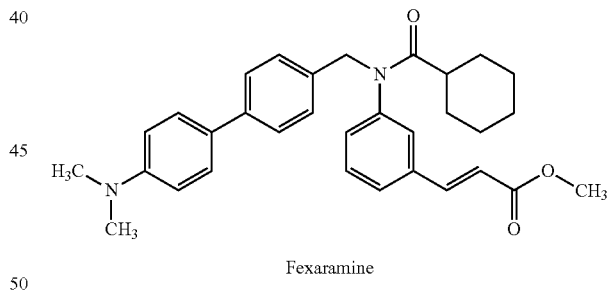

Fexaramine

It is shown herein that the gut-biased FXR agonist fexaramine has profound metabolic benefits in a mouse model of obesity. Fex protects against diet-induced weight gain by promoting the expression of genes involved in thermogenesis, mitochondrial biogenesis, and fatty acid oxidation. Linked to the unexpected browning of white adipose, Fex lowers inflammatory cytokine levels while up-regulating β-adrenergic signaling. These changes appear to be mediated in part by a change in bile acid levels and composition. In addition, intestinal-specific FXR activation corrected numerous obesity-related defects, enhanced glucose tolerance, and lowered hepatic glucose production. Notably, these physiologic changes are dependent on FXR expression and result in hepatic insulin sensitization and BAT activation, properties not formerly associated with this class of drug.

The initial event triggering systemic metabolic activation is likely coordinated by FGF15, a key regulator of energy expenditure reported to increase metabolic rate, and improve glucose and lipid homeostasis without significant changes in food intake (Fu et al., *Endocrinology* 145:2594-2603, 2004; Bhatnagar et al., *J Biol Chem* 284:10023-10033, 2009). The absence of a change in food intake is significant as failure of appetite control is a major reason for weight gain (Foster-Schubert & Cummings, *Endocr Rev* 27:779-793, 2006). Thus, systemic increases in energy expenditure, as seen in Fex-treated mice, may offer a viable alternative for obesity treatments. However, this explanation alone is not sufficient as systemic FXR agonists, while robustly inducing FGF15, do not display many of the benefits of gut-biased FXR activation.

One major difference between gut-biased and systemic FXR activation is the impact on serum bile acids, which for Fex includes a marked change in the relative composition of circulating BAs. A reduction in hepatic CYP7A1 accompanied by an increase in CYP7B1 expression shifts BA synthesis away from cholic acid towards chenodeoxycholic acid derivatives, most notably lithocholic acid. While the absolute amount of lithocholic acid did not change following Fex the relative amount increased dramatically. Lithocholic acid is a hydrophobic secondary bile acid and the most potent endogenous ligand for the G protein-coupled bile acid receptor TGR5 (Ullmer et al., *Br. J. Pharmacol.* 169:671-684, 2013). Interestingly, Fex treatment induces metabolic changes similar to those observed with systemic administration of a synthetic TGR5 agonist (Ullmer et al., *Br. J. Pharmacol.* 169:671-684, 2013). Also, induction of DIO2, a downstream target of TGR5 (Watanabe et al., *Nature* 439: 484-489, 2006), in BAT with oral Fex implicates this pathway in the observed increased energy expenditure. Indeed, the metabolic improvements attributed to Fex treatment were tempered in TGR$^{-/-}$ mice, indicating that TGR5 activation is important in mediating some of the actions of Fex. Furthermore, the coordinate "browning" of the WAT depot provides an independent yet complementary contribution to increased thermogenic capacity.

These results uncover a new therapeutic avenue to manipulate energy expenditure without appetite changes through intestinally-biased activation of the nuclear receptor FXR. While contrary indications have been recently reported, the integral role of FXR in gut homeostasis confounds these studies (Kim et al., *J Lipid Res* 48:2664-2672, 2007; Li, et al., *Nat Commun* 4:2384, 2013). Gut-restricted drugs such as Fex inherently offer improved safety profiles, achieving systemic efficacy while avoiding systemic toxicity. In support of the remarkable metabolic improvements achieved via oral Fex treatment, intestinal FXR has been recently identified as a molecular target of vertical sleeve gastrectomy (Ryan et al., *Nature* 509:183-188, 2014), indicating that Fex may offer a non-surgical alternative for the control of metabolic disease.

A. Treatment or Prevention of Metabolic Disorders

Treatment of subjects, including diet-induced obesity (DIO) subjects, with one or more of the disclosed FXR agonists (such as two or more, three or more, four or more, or five or more of the disclosed FXR agonists, such as 2, 3, 4, or 5 of the disclosed FXR agonists) produces beneficial body-wide metabolic effects such as reduced weight gain, decreased inflammation, browning of white adipose tissue, activation of BAT, improved insulin sensitization, or combinations thereof. Thus, intestinally-restricted FXR administration is superior to systemic FXR therapy for body-wide metabolic disorders including obesity and metabolic syndrome. One or more of the FXR agonists disclosed herein can be administered to a gastrointestinal (GI) tract of the subject to activate FXR receptors in the intestines, and thereby treat or prevent a metabolic disorder in the subject. Thus, the FXR agonist(s) can be administered to, without limitation, the mouth (such as by injection or by ingestion by the subject), the esophagus, the stomach or the intestines themselves.

Orally delivered, these agonists can in some examples be ineffectively absorbed, resulting in intestinally-restricted FXR activation. In some embodiments, FXR activation is completely limited to the intestine. In some embodiments, administration of one or more of the disclosed agonists does not result in significant activation in the liver or kidney. In other embodiments, some measurable extra-intestinal FXR activation occurs, however the FXR activation is considerably greater in the intestines than in other locations in the body, such as in the liver or kidney. In some embodiments, the FXR agonist is minimally absorbed. In some embodiments, the FXR agonist is directly administered to the intestines (such as to the distal ileum) of an individual in need thereof. In some embodiments, the FXR agonist is directly administered to the colon or the rectum of an individual in need thereof. In some embodiments, the FXR agonist is administered orally, and less than 50%, less than 40%, less than 30%, less than 20%, less than 10%, less than 9%, less than 8%, less than 7%, less than 6%, less than 5%, less than 4%, less than 3%, less than 2%, or less than 1% of the FXR agonist is systemically absorbed.

In some examples, the subject to be treated is one who is diabetic (for example has type II diabetes), is hyperglycemic, and/or is insulin resistant. In some examples, the subject is obese, for example has a body mass index (BMI) of 25 of higher, 30 or greater, 35 or greater, 40 or greater, such as a BMI of 25 to 29, 30 to 34, or 35 to 40.

In some examples, the disclosed methods reduce weight gain in a subject (such as a human), such as diet-induced weight gain. In some examples, such methods reduce weight gain in the subject by at least 5%, at least 10%, at least 15%, at least 20%, at least 30% or even at least 50% (such as 5% to 50%, 5% to 25%, 10% to 20%, or 10% to 30%), for example relative to a subject not treated with the disclosed therapies. Similarly, in some examples, the disclosed methods reduce the BMI of a subject (such as a human). In some examples, such methods reduce the BMI of a subject by at least 5%, at least 10%, at least 15%, at least 20%, or at least 30% (such as 5% to 30%, 5% to 25%, 10% to 20%, or 10% to 30%), for example relative to a subject not treated with the disclosed therapies.

In some examples, the disclosed methods increase browning of white adipose tissue in a subject (such as a human). In some examples, such methods increase browning of white adipose tissue in the subject by at least 5%, at least 10%, at least 15%, at least 20%, at least 30% or even at least 50% (such as 5% to 50%, 5% to 25%, 10% to 20%, or 10% to 30%), for example relative to a subject not treated with the disclosed therapies.

In some embodiments, the method reduces or prevents diet-induced weight gain, for example in a mammalian subject, such as a human. In some embodiments, the one or more FXR agonists are administered to an obese subject whose obesity is diet-related (i.e., diet-induced obesity). In other embodiments, the one or more FXR agonists can be administered to an obese subject whose obesity is not diet-related (such as an individual with familial/genetic obesity or obesity resulting from medication use). In other embodiments, the one or more FXR agonists can be administered to a subject who is overweight (but not obese) or a subject that is neither overweight nor obese. Thus, in some embodiments, the one or more FXR agonists can be used to prevent obesity from developing. In some embodiments, the targeting of the therapy to the intestines reduces the chance of side effects which can result from systemic action, thus improving the safety profile of the therapy.

In some embodiments, the one or more FXR agonists are administered to an obese or non-obese subject for a metabolic disorder or condition other than obesity or weight gain. In certain embodiments, the metabolic disorder is insulin resistance, including non-insulin-dependent diabetes mellitus (NIDDM) (i.e., type II diabetes). The administration of the one or more FXR agonists can result in increased insulin sensitivity to insulin in the liver, leading to increased uptake of glucose into hepatic cells. In certain embodiments, the metabolic disorder is dyslipidemia, including hyperlipidemia (elevated LDL, VLDL or triglycerides) or low HDL levels. Thus, in certain embodiments, administration of one or more FXR agonists can result in improved glucose and/or lipid homeostasis in the subject. In some embodiments, administration of the one or more FXR agonists results in a decrease in the amount of hepatic triglycerides, serum lipids and/or triglycerides in the subject. Thus, in some examples, the disclosed methods decrease the amount of serum lipids and/or triglycerides in a subject (such as a human). In some examples, such methods decrease serum lipids and/or triglycerides in the subject by at least 5%, at least 10%, at least 15%, at least 20%, at least 30%, at least 50% or even at least 75% (such as 5% to 50%, 5% to 25%, 10% to 20%, 10% to 70%, or 10% to 30%), for example relative to levels observed in a subject not treated with the disclosed therapies. In some examples, such methods decrease hepatic triglycerides in the subject by at least 5%, at least 10%, at least 15%, at least 20%, at least 30%, at least 50% or even at least 75% (such as 5% to 50%, 5% to 25%, 10% to 20%, 10% to 70%, or 10% to 30%), for example relative to levels observed in a subject not treated with the disclosed therapies. In some examples, the disclosed methods increase insulin sensitivity to insulin in the liver of a subject (such as a human). In some examples, such methods increase insulin sensitivity to insulin in the liver of the subject by at least 5%, at least 10%, at least 15%, at least 20%, at least 30% or even at least 50% (such as 5% to 50%, 5% to 25%, 10% to 20%, or 10% to 30%), for example relative to a subject not treated with the disclosed therapies.

In some embodiments, administration of the one or more FXR agonists results in no substantial change in food intake and/or fat consumption in the subject. In other embodiments, food intake and/or fat consumption is reduced minimally, such as by less than 15%, less than 10%, or less than 5%. In some embodiments, no substantial change in appetite in the subject results. In other embodiments, reduction in appetite is minimal as reported by the subject.

In some embodiments, administration of the one or more FXR agonists results in an increase in the metabolic rate in the subject. Thus, in some examples, the disclosed methods increase the metabolic rate in a subject (such as a human). In some examples, such methods increase the metabolic rate in the subject by at least 5%, at least 10%, at least 15%, at least 20%, at least 30%, at least 50% or even at least 75% (such as 5% to 50%, 5% to 25%, 10% to 20%, 10% to 70%, or 10% to 30%), for example relative to a subject not treated with the disclosed therapies.

In some embodiments, this increase in metabolism results from enhanced oxidative phosphorylation in the subject, which in turn can lead to increased energy expenditure in tissues (such as BAT). Thus, in some examples, the disclosed methods increase BAT activity in a subject (such as a human). In some examples, such methods increase BAT activity in a subject by at least 5%, at least 10%, at least 15%, at least 20%, at least 30%, at least 50% or even at least 75% (such as 5% to 50%, 5% to 25%, 10% to 20%, 10% to 70%, or 10% to 30%), for example relative to a subject not treated with the disclosed therapies.

In some embodiments, administration of the one or more FXR agonists results in a decrease in the amount of serum insulin in the subject. Thus, in some examples, the disclosed methods decrease the amount of serum insulin in a subject (such as a human). In some examples, such methods decrease serum insulin in the subject by at least 5%, at least 10%, at least 15%, at least 20%, at least 30%, at least 50% or even at least 75% (such as 5% to 50%, 5% to 25%, 10% to 20%, 10% to 70%, or 10% to 30%), for example relative to levels observed in a subject not treated with the disclosed therapies.

In some embodiments, administration of the one or more FXR agonists results in a decrease in the amount of serum glucose in the subject. Thus, in some examples, the disclosed methods decrease the amount of serum glucose in a subject (such as a human). In some examples, such methods decrease serum glucose in the subject by at least 5%, at least 10%, at least 15%, at least 20%, at least 30%, at least 50% or even at least 75% (such as 5% to 50%, 5% to 25%, 10% to 20%, 10% to 70%, or 10% to 30%), for example relative to levels observed in a subject not treated with the disclosed therapies. Embodiments of a method are provided for lowering elevations in blood glucose resulting from food intake in a subject. Thus, in some examples, such methods decrease blood glucose in a subject by at least 5%, at least 10%, at least 15%, at least 20%, at least 30%, at least 50% or even at least 75% (such as 5% to 50%, 5% to 25%, 10% to 20%, 10% to 70%, or 10% to 30%), for example relative to a subject not treated with the disclosed therapies. Such methods can include orally administering to the subject a therapeutically effective amount of one of the disclosed minimally absorbed FXR agonists. In some embodiments, a method for lowering elevated body weight in a subject is provided, wherein the method includes orally administering to said subject a therapeutically effective amount of one of the disclosed minimally absorbed FXR agonists. Thus, in some examples, such methods decrease the body weight of a subject by at least 5%, at least 10%, at least 15%, at least 20%, at least 30%, or at least 50% (such as 5% to 50%, 5% to 25%, 5% to 20%, 10% to 20%, 10% to 70%, or 10% to 30%), for example relative to a subject not treated with the disclosed therapies. In some embodiments, the elevated body weight and/or elevated glucose levels resulted from a particular pattern of food intake, such as a high fat diet and/or a high calorie diet.

In some embodiments, the one or more FXR agonists are co-administered with one or more additional compounds or therapies, for treatment or prevention of a metabolic disorder. For example, the one or more FXR agonists can be administered with an insulin sensitizing drug, an insulin secretagogue, an alpha-glucosidase inhibitor, a GLP agonist, a DPP-4 inhibitor (such as sitagliptin, vildagliptin, saxagliptin, linagliptin, anagliptin, teneligliptin, alogliptin, gemigliptin, or dutoglpitin), a catecholamine (such as epinephrine, norepinephrine, or dopamine), peroxisome proliferator-activated receptor (PPAR)-gamma agonist (e.g., a thiazolidinedione (TZD) [such as ioglitazone, rosiglitazone, rivoglitazone, or troglitazone], aleglitazar, farglitazar, muraglitazar, or tesaglitazar), or a combination thereof. Likewise, the one or more FXR agonists can be administered with a statin, HMG-CoA reductase inhibitor, fish oil, fibrate, niacin or other treatment for dyslipidemia. In some embodiments, provided herein is a method for treating a metabolic disorder in a subject, such as lowering elevated body weight and/or lowering elevated blood glucose from food intake, comprising orally co-administering to said subject a therapeutically effective amount of a disclosed minimally absorbed FXR agonist and retinoic acid. 9 cis-retinoic acid is the ligand for retinoic acid receptor (RXR), the heterodimeric partner of FXR. In one example, nicotinamide ribonucleoside and/or analogs of nicotinamide ribonucleoside that promotes NAD+ production of which is a substrate for many enzymatic reactions such as p450s which are a target of FXR (e.g., see Yang et al., *J. Med. Chem.* 50:6458-61, 2007), are also administered.

Glucagon-like peptide-1 (GLP-1) is an incretin derived from the transcription product of the proglucagon gene. The major source of GLP-1 in the body is the intestinal L cell that secretes GLP-1 as a gut hormone. The biologically active forms of GLP-1 include GLP-1-(7-37) and GLP-1-(7-36) NH$_2$ (HAEGTFTSDVSSYLEGQAAKEFIAWLVKGR; SEQ ID NO: 1), which result from selective cleavage of the proglucagon molecule. GLP-2 is a 33 amino acid peptide (HADGSFSDEMNTILDNLAARDFINWLIQTKITD; SEQ ID NO: 2) in humans. GLP-2 is created by specific post-translational proteolytic cleavage of proglucagon in a process that also liberates GLP-1. GLP agonists are a class of drugs ("incretin mimetics") that can be used to treat type 2 diabetes. Examples include, but are not limited to: exenatide (Byetta/Bydureon), liraglutide (Victoza), lixisenatide (Lyxumia), and albiglutide (Tanzeum). In certain embodiments, the FXR agonist enhances the secretion of glucagon-like peptide-1 (GLP-1) and/or glucagon-like peptide-2 (GLP-2). In some embodiments, the FXR agonist enhances the secretion of a pancreatic polypeptide-fold such as peptide YY (PYY). In certain embodiments, the FXR agonist enhances the activity of FGF15 or FGF19. In certain embodiments, the FXR agonist enhances secretion of an enteroendocrine peptide and/or is administered in combination with an agent that enhances secretion or activity of an enteroendocrine peptide. Thus, in some examples, the disclosed methods increase the secretion of one or more of GLP-1, GLP-2, and PYY in a subject (such as a human). In some examples, such methods increase the secretion of one or more of GLP-1, GLP-2, and PYY in the subject by at least 5%, at least 10%, at least 15%, at least 20%, at least 30%, at least 50% or even at least 75% (such as 5% to 50%, 5% to 25%, 10% to 20%, 10% to 70%, or 10% to 30%), for example relative to a subject not treated with the disclosed therapies. Furthermore, in some examples, the disclosed methods increase the secretion of one or more of GLP-1, GLP-2, and PYY in a subject (such as a human). In some examples, such methods increase the activity of one or more of FGF15 and FGF19 in the subject by at least 5%, at least 10%, at least 15%, at least 20%, at least 30%, at least 50% or even at least 75% (such as 5% to 50%, 5% to 25%, 10% to 20%, 10% to 70%, or 10% to 30%), for example relative to a subject not treated with the disclosed therapies.

The gut-biased FXR agonists disclosed herein can have profound metabolic benefits with respect to obesity. The gut-biased FXR agonists can protect against diet-induced weight gain by, for example, promoting the expression of genes involved in thermogenesis, mitochondrial biogenesis, and/or fatty acid oxidation. In some embodiments, linked to the unexpected browning of white adipose, the disclosed gut-biased FXR agonists can lower inflammatory cytokine levels while up-regulating β-adrenergic signaling. These changes can be mediated, at least in part, by a change in bile acid levels and composition. In various embodiments, a prandial activation of intestinal FXR is triggered by administering to a subject one of the FXR agonists disclosed herein, such as synthetic FXR agonist fexaramine (Fex). The intestinal-specific FXR activation disclosed herein can be utilized to enhance glucose tolerance and lower hepatic glucose production. Thus, in some examples, such methods decrease hepatic glucose production in a subject by at least 5%, at least 10%, at least 15%, at least 20%, at least 30%, at least 50% or even at least 75% (such as 5% to 50%, 5% to 25%, 10% to 20%, 10% to 70%, or 10% to 30%), for example relative to a subject not treated with the disclosed therapies. These physiologic changes can result in hepatic insulin sensitization and/or BAT activation—properties not previously associated with FXR agonists.

In contrast to the effects of system-wide drugs (including systemic FXR agonists), selective activation of intestinal FXR as disclosed herein can mimic the restricted bile acid response linked to feeding. The gut-specific FXR agonists disclosed herein robustly induce enteral FGF15, leading to alterations in bile acid composition without activating hepatic FXR target genes. Unlike systemic drugs, these FXR agonists can protect against diet-induced weight gain, reduce body-wide inflammation, enhance thermogenesis, promote browning of white adipose tissue, promote activation of BAT, and suppress hepatic glucose production.

In some embodiments, the initial event triggering systemic metabolic activation is coordinated by FGF15 (the mouse equivalent of human FGF19) or FGF19. In an embodiment, administration of the FXR agonist results in activation of FGF15 or FGF19 (such as an increase in FGF15 or FGF19 activity of at least 25%, at least 50%, at least 75%, at least 90%, or at least 95%, relative to no treatment with an FXR agonist disclosed herein), which in turn can regulate energy expenditure, such as by increasing metabolic rate, improving glucose homeostasis (such as by improving insulin sensitivity), and/or improving lipid homeostasis without requiring significant changes in food intake. The absence of a required or resulting change in food intake can be expected to increase effectiveness, as failure of appetite control is a major reason for weight gain and difficulty in losing weight. Thus, systemic increases in energy expenditure, as seen in Fex-treated mice, can form the basis for an obesity treatment.

In some embodiments, treatment with one or more of the disclosed FXR agonists can produce a change in the bile acid pool, such as a dramatic increase in the level of deoxycholic acid (such as an increase of at least 25%, at least 50%, at least 75%, at least 90%, or at least 100%, relative to no treatment with an FXR agonist disclosed herein), a potent ligand for the G protein-coupled bile acid receptor TGR5. Fex treatment was observed to induce DIO2, a downstream target of TGR5, in brown adipose tissue (BAT), thus implicating this additional pathway in the observed increase in energy expenditure. Furthermore, the coordinate "browning" of white adipose tissue provides an independent yet complementary contribution to increased thermogenic capacity.

Thus, a new therapeutic avenue exists to manipulate energy expenditure without appetite changes through intestinally-biased activation of the nuclear receptor FXR. Furthermore, gut-restricted FXR agonists such as Fex can offer improved safety profiles with limited circulation in the serum, thus reducing the risks of off-target effects and toxicity. The remarkable metabolic improvements achieved with Fex treatment provide a new role for intestinal targeting in the control of metabolic disease.

B. Treatment or Prevention of Inflammation

Also provided herein are embodiments of a method for treating or preventing an inflammatory intestinal condition. Certain disclosed embodiments can include administering a therapeutically effective amount of one or more FXR agonists to an individual in need thereof, such as one or more of the novel FXR agonists disclosed herein (such as 1, 2, 3, 4 or 5 such agonists).

Thus, in some examples, the disclosed embodiments reduce inflammation in a subject (such as a human), such as inflammation in the intestine. In some examples, disclosed embodiments reduce inflammation (such as intestinal inflammation) in the subject by at least 5%, at least 10%, at least 15%, at least 20%, at least 30% or even at least 50% (such as 5% to 50%, 5% to 25%, 10% to 20%, or 10% to 30%), for example relative to a subject not treated with the disclosed therapies.

In various embodiments, the inflammatory condition can be necrotizing enterocolitis (NEC), gastritis, ulcerative colitis, inflammatory bowel disease, irritable bowel syndrome, pseudomembranous colitis, gastroenteritis, radiation induced enteritis, chemotherapy induced enteritis, gastroesophageal reflux disease (GERD), peptic ulcer, non-ulcer dyspepsia (NUD), celiac disease, intestinal celiac disease, gastrointestinal complications following bariatric surgery, gastric carcinogenesis, or gastric carcinogenesis following gastric or bowel resection. In some embodiments, the inflammatory condition is NEC and the subject is a newborn or prematurely born infant. In some embodiments, the subject is enterally-fed infant or formula-fed infant.

In some embodiments, the one or more FXR agonists are co-administered with one or more additional compounds or therapies, for treatment or prevention of an inflammatory intestinal condition. In some embodiments, the one or more FXR agonists are co-administered with an oral corticosteroid and/or other anti-inflammatory or immuno-modulatory therapy. In some embodiments, the FXR agonist can be administered to the subject in conjunction with one or more antibiotics (e.g., metronidazole, vancomycin, and/or fidaxomicin) to treat or prevent the inflammatory condition. In some embodiments, the FXR agonist can be administered to the subject in conjunction with or following antibiotic therapy to treat or prevent pseudomembranous colitis associated with bacterial overgrowth (such as *C. dificile* overgrowth) in the subject. In some embodiments, the FXR agonist can be administered to the subject in conjunction with metronidazole or other indicated therapy to treat inflammation associated with bacterial overgrowth in an intestinal area. In some embodiments, the FXR agonist can be administered to the subject in conjunction with the ingestion of foods or other substances predicted to induce inflammation in the gastro-intestinal system of the subject (such as in a subject with celiac disease). In one example, nicotinamide ribonucleoside and/or analogs of nicotinamide ribonucleoside that promotes NAD+ production of which is a substrate for many enzymatic reactions such as p450s which are a target of FXR (e.g., see Yang et al., *J. Med. Chem.* 50:6458-61, 2007), are also administered.

C. Prevention and/or Treatment of Cell Proliferation Diseases

Disclosed herein are embodiments of a method for preventing and/or treating cell proliferation diseases, such as certain types of cancer. Certain disclosed embodiments can include administering a therapeutically effective amount of one or more FXR agonists to an individual in need thereof, such as one or more of the novel FXR agonists disclosed herein (such as 1, 2, 3, 4 or 5 such agonists).

In some embodiments, the compounds disclosed herein may be used in the prevention or treatment of adenocarcinomas, i.e. carcinoma derived from glandular tissue or in which the tumor cells form recognizable glandular structures. Adenocarcinomas can be classified according to the predominant pattern of cell arrangement, as papillary, alveolar, etc., or according to a particular product of the cells, as mucinous adenocarcinoma. Adenocarcinomas arise in several tissues, including the colon, kidney, breast, cervix, esophagus, gastric, pancreas, prostate and lung.

In certain embodiments, the compounds disclosed herein may be used in the prevention or treatment of a cancer of the intestine, such as colon cancer, i.e. cancer that forms in the tissues of the colon (the longest part of the large intestine), or a cancer of another part of the intestine, such as the jejunum, and/or ileum. Colon cancer is also referred to as "colorectal cancer." Most colon cancers are adenocarcinomas (cancers that begin in cells that may line internal organs and have gland-like properties). Cancer progression is characterized by stages, or the extent of cancer in the body. Staging is usually based on the size of the tumor, whether lymph nodes contain cancer, and whether the cancer has spread from the original site to other parts of the body. Stages of colon cancer include stage I, stage II, stage III and stage IV. In some embodiments herein, the colon adenocarcinoma is from any stage. In other embodiments, the colon adenocarcinoma is a stage I cancer, a stage II cancer or a stage III cancer.

Thus, in some examples, the disclosed embodiments reduce tumor burden in a subject (such as a human). In some examples, disclosed embodiments reduce tumor burden (such as colon tumor burden) in the subject by at least 5%, at least 10%, at least 15%, at least 20%, at least 30% or even at least 50% (such as 5% to 50%, 5% to 25%, 10% to 20%, or 10% to 30%), for example relative to a subject not treated with the disclosed therapies.

Thus, in some examples, the disclosed embodiments reduce tumor size and/or volume in a subject (such as a human). In some examples, disclosed embodiments reduce tumor size and/or volume (such as a colon tumor) in the subject by at least 5%, at least 10%, at least 15%, at least 20%, at least 30% or even at least 50% (such as 5% to 50%, 5% to 25%, 10% to 20%, or 10% to 30%), for example relative to a subject not treated with the disclosed therapies.

Thus, in some examples, the disclosed embodiments reduce effects of cachexia due to a tumor in a subject (such as a human). In some examples, disclosed embodiments reduce effects of cachexia (such as due to a colon tumor) in the subject by at least 5%, at least 10%, at least 15%, at least 20%, at least 30% or even at least 50% (such as 5% to 50%, 5% to 25%, 10% to 20%, or 10% to 30%), for example relative to a subject not treated with the disclosed therapies.

Thus, in some examples, the disclosed embodiments increase survival rates of a subject (such as a human) with a tumor. In some examples, disclosed embodiments increase survival rates of a subject (such as a human) with a tumor (such as a colon cancer) in the subject by at least 5%, at least 10%, at least 15%, at least 20%, at least 30% or even at least 50% (such as 5% to 50%, 5% to 25%, 10% to 20%, or 10% to 30%), for example relative to a subject not treated with the disclosed therapies.

In some embodiments, the compounds disclosed herein may be administered in combination with one or more additional anticancer therapies (such as a biologic [e.g., antibody, for example bevacizumab, cetuximab, or panitumumab], chemotherapeutic, or radiologic, for example FOLFOX, FOLFIRI, CapeOX, 5-FU, leucovorin, regorafenib, irinotecan, and oxaliplatin), to prevent or treat a cell proliferation disease. In one example, nicotinamide ribonucleoside and/or analogs of nicotinamide ribonucleoside that promotes NAD+ production of which is a substrate for many enzymatic reactions such as p450s which are a target of FXR (e.g., see Yang et al., *J. Med. Chem.* 50:6458-61, 2007), are also administered.

D. Prevention and/or Treatment of Alcoholic and Non-Alcoholic Liver Disease

Disclosed herein are embodiments of a method for preventing and/or treating alcoholic or non-alcoholic liver diseases, such as steatosis, cirrhosis, alcoholic hepatitis, NASH and NAFLD. In some embodiments, the compounds disclosed herein may be used in the prevention or treatment of alcoholic liver diseases. Certain disclosed embodiments can include administering a therapeutically effective amount of one or more FXR agonists to an individual in need thereof, such as one or more of the novel FXR agonists disclosed herein (such as 1, 2, 3, 4 or 5 such agonists).

Thus, in some examples, the disclosed embodiments reduce fatty liver (steatosis) in a subject (such as a human). In some examples, disclosed embodiments reduce steatosis in the subject (such as in an alcoholic) by at least 5%, at least 10%, at least 15%, at least 20%, at least 30% or even at least 50% (such as 5% to 50%, 5% to 25%, 10% to 20%, or 10% to 30%), for example relative to a subject not treated with the disclosed therapies.

Thus, in some examples, the disclosed embodiments reduce cirrhosis in a subject (such as a human). In some examples, disclosed embodiments reduce cirrhosis in the subject (such as in an alcoholic) by at least 5%, at least 10%, at least 15%, at least 20%, at least 30% or even at least 50% (such as 5% to 50%, 5% to 25%, 10% to 20%, or 10% to 30%), for example relative to a subject not treated with the disclosed therapies. Thus the disclosed embodiments can reduce liver inflammation and/or fibrosis, for example by at least 5%, at least 10%, at least 15%, at least 20%, at least 30% or even at least 50% (such as 5% to 50%, 5% to 25%, 10% to 20%, or 10% to 30%), for example relative to a subject not treated with the disclosed therapies.

Thus, in some examples, the disclosed embodiments reduce alcoholic hepatitis in a subject (such as a human). In some examples, disclosed embodiments reduce alcoholic hepatitis in the subject (such as in an alcoholic) by at least 5%, at least 10%, at least 15%, at least 20%, at least 30% or even at least 50% (such as 5% to 50%, 5% to 25%, 10% to 20%, or 10% to 30%), for example relative to a subject not treated with the disclosed therapies. Thus the disclosed embodiments can reduce inflammation of hepatocytes, for example by at least 5%, at least 10%, at least 15%, at least 20%, at least 30% or even at least 50% (such as 5% to 50%, 5% to 25%, 10% to 20%, or 10% to 30%), for example relative to a subject not treated with the disclosed therapies.

Thus, in some examples, the disclosed embodiments reduce liver enzymes in a subject (such as a human). In some examples, disclosed embodiments reduce liver enzymes (e.g., serum ALT and/or AST levels) in the subject (such as in an alcoholic) by at least 5%, at least 10%, at least 15%, at least 20%, at least 30% or even at least 50% (such as 5% to 50%, 5% to 25%, 10% to 20%, or 10% to 30%), for example relative to a subject not treated with the disclosed therapies.

Thus, in some examples, the disclosed embodiments reduce liver triglycerides in a subject (such as a human). In some examples, disclosed embodiments reduce liver triglycerides in the subject (such as in an alcoholic) by at least 5%, at least 10%, at least 15%, at least 20%, at least 30% or even at least 50% (such as 5% to 50%, 5% to 25%, 10% to 20%, or 10% to 30%), for example relative to a subject not treated with the disclosed therapies.

In some embodiments, the compounds disclosed herein may be administered in combination with one or more additional therapies for treating alcoholic or non-alcoholic liver disease (such as antioxidants, corticosteroids, and/or anti-TNF), to prevent or treat alcoholic or non-alcoholic liver disease. In one example, nicotinamide ribonucleoside and/or analogs of nicotinamide ribonucleoside that promotes NAD+ production of which is a substrate for many enzymatic reactions such as p450s which are a target of FXR (e.g., see Yang et al., *J. Med. Chem.* 50:6458-61, 2007), are also administered.

E. Prevention and/or Treatment of Other Diseases

Disclosed herein are embodiments of a method for preventing and/or treating cholestatic disorders, such primary biliary cirrhosis (PBC), primary sclerosing cholangitis (PSC), overlap syndrome (PBC plus autoimmune hepatitis), cholestasis resulting from a drug (e.g., one or more of androgen, birth control pills, gold salts, nitrofurantoin, anabolic steroids, chlorpromazine, prochlorperazine, sulindac, cimetidine, estrogen, statins, and antibiotics such as TMP/SMX, flucoxacillin and erythromycin), drug-induced cholestatic hepatitis, total parenteral nutrition (TPN)-induced cholestasis, ICU/sepsis-related cholestasis, obstetric cholestasis, graft vs. host disease, prolonged cholestasis due to hepatitis A, B or C infection, cholestasis due to cystic fibrosis, alcoholic hepatitis, progressive familial intrahepatic cholestasis (PFIC) syndromes, Alagille syndrome, biliary atresia, or any combination thereof. Certain disclosed embodiments can include administering a therapeutically effective amount of one or more FXR agonists to an individual in need thereof, such as one or more of the novel FXR agonists disclosed herein (such as 1, 2, 3, 4 or 5 such agonists). Thus, in some examples, the disclosed embodiments increase bile flow in a subject (such as a human) by at least 5%, at least 10%, at least 15%, at least 20%, at least 30%, at least 40%, at last 50%, at least 60%, at least 70%, at least 80%, at least 90%, at least 100%, or even at least 200% (such as 5% to 50%, 5% to 25%, 50% to 75%, or 75% to 200%), for example relative to a subject not treated with the disclosed therapies.

Disclosed herein are embodiments of a method for preventing and/or treating an intestinal permeability condition, such as Crohn's disease, ulcerative colitis, infectious colitis, celiac disease, type 1 diabetes, inflammatory bowel disease, irritable bowel syndrome, or any combination thereof. Certain disclosed embodiments can include administering a therapeutically effective amount of one or more FXR agonists to an individual in need thereof, such as one or more of the novel FXR agonists disclosed herein (such as 1, 2, 3, 4 or 5 such agonists). In some examples, disclosed embodiments reduce undesired intestinal permeability in the subject by at least 5%, at least 10%, at least 15%, at least 20%, at least 30% or even at least 50% (such as 5% to 50%, 5% to 25%, 10% to 20%, or 10% to 30%), for example relative to a subject not treated with the disclosed therapies.

Disclosed herein are embodiments of a method for preventing and/or treating a disorder that causes or results from an altered intestinal microbiome, such as celiac disease, the intestinal permeability conditions described herein, the intestinal inflammation disorders described herein, alcoholic hepatitis, necrotizing enterocolitis, Crohn's disease, ulcerative colitis, intestinal lesions (such as those in a cystic fibrosis patient), cirrhosis, or any combination thereof. Certain disclosed embodiments can include administering a therapeutically effective amount of one or more FXR agonists to an individual in need thereof, such as one or more of the novel FXR agonists disclosed herein (such as 1, 2, 3, 4 or 5 such agonists). In some examples, disclosed embodiments bring the intestinal microbiome closer to normal levels in the subject, for example within 20%, with in 10% or within 5% of normal for example relative to a subject not treated with the disclosed therapies.

Disclosed herein are embodiments of a method for treating an inborn error of metabolism, such as cerebrotendinous xanthomatosis. Certain disclosed embodiments can include administering a therapeutically effective amount of one or more FXR agonists to an individual in need thereof, such as one or more of the novel FXR agonists disclosed herein (such as 1, 2, 3, 4 or 5 such agonists). In some examples, disclosed embodiments reduce plasma cholesterol levels in the subject by at least 5%, at least 10%, at least 15%, at least 20%, at least 30% or even at least 50% (such as 5% to 50%, 5% to 25%, 10% to 20%, or 10% to 30%), for example relative to a subject not treated with the disclosed therapies.

Disclosed herein are embodiments of a method for treating a bile disorder, such as benign biliary stricture, malignant biliary obstruction, bile acid diarrhea, or any combination thereof. Certain disclosed embodiments can include administering a therapeutically effective amount of one or more FXR agonists to an individual in need thereof, such as one or more of the novel FXR agonists disclosed herein (such as 1, 2, 3, 4 or 5 such agonists). In some examples, disclosed embodiments reduce production of bile acids in the subject by at least 5%, at least 10%, at least 15%, at least 20%, at least 30% or even at least 50% (such as 5% to 50%, 5% to 25%, 10% to 20%, or 10% to 30%), for example relative to a subject not treated with the disclosed therapies. In some examples, disclosed embodiments increase intestinal absorption of bile acids in the subject by at least 5%, at least 10%, at least 10%, at least 15%, at least 20%, at least 30%, at least 40%, at last 50%, at least 60%, at least 70%, at least 80%, at least 90%, at least 100%, or even at least 200% (such as 5% to 50%, 5% to 25%, 50% to 75%, or 75% to 200%), for example relative to a subject not treated with the disclosed therapies.

Disclosed herein are embodiments of a method for treating or preventing a malabsorption disorder (e.g., intestinal malabsorption), such as short bowel syndrome (or symptoms arising from such, such as diarrhea, steatorhea, malnutrition, fatigue, vitamin deficiency), environmental enteropathy, or tropical sprue. Certain disclosed embodiments can include administering a therapeutically effective amount of one or more FXR agonists to an individual in need thereof, such as one or more of the novel FXR agonists disclosed herein (such as 1, 2, 3, 4 or 5 such agonists). In some examples, disclosed embodiments increase bowel absorption in the subject by at least 5%, at least 10%, at least 10%, at least 15%, at least 20%, at least 30%, at least 40%, at last 50%, at least 60%, at least 70%, at least 80%, at least 90%, at least 100%, or even at least 200% (such as 5% to 50%, 5% to 25%, 50% to 75%, or 75% to 200%), for example relative to a subject not treated with the disclosed therapies.

F. Administration

The particular mode of administration and the dosage regimen will be selected by the attending clinician, taking into account the particulars of the case (e.g. the subject, the disease, the disease state involved, the particular treatment, and whether the treatment is prophylactic). Treatment can involve daily or multi-daily or less than daily (such as weekly or monthly etc.) doses over a period of a few days to months, or even years. For example, a therapeutically effective amount of one or more compounds disclosed herein can be administered in a single dose, twice daily, weekly, or in several doses, for example daily, or during a course of treatment. In a particular non-limiting example, treatment involves once daily dose or twice daily dose.

In some embodiments, the FXR agonist(s) is administered orally. In some embodiments, the FXR agonist is administered as an ileal-pH sensitive release formulation that delivers the FXR agonist to the intestines, such as to the ileum of an individual. In some embodiments, the FXR agonist is administered as an enterically coated formulation. In some embodiments, oral delivery of an FXR agonist provided herein can include formulations, as are well known in the art, to provide prolonged or sustained delivery of the drug to the gastrointestinal tract by any number of mechanisms. These include, but are not limited to, pH sensitive release from the dosage form based on the changing pH of the small intestine, slow erosion of a tablet or capsule, retention in the stomach based on the physical properties of the formulation, bioadhesion of the dosage form to the mucosal lining of the intestinal tract, or enzymatic release of the active drug from the dosage form. The intended effect is to extend the time period over which the active drug molecule is delivered to the site of action (e.g., the intestines) by manipulation of the dosage form. Thus, enteric-coated and enteric-coated controlled release formulations are within the scope of the present disclosure. Suitable enteric coatings include cellulose acetate phthalate, polyvinylacetate phthalate, hydroxypropylmethylcellulose phthalate and anionic polymers of methacrylic acid and methacrylic acid methyl ester.

In some embodiments, the FXR agonist is administered before ingestion of food, such as at least 10 minutes, at least 15 minutes, at least 20 minutes, or at least 30 minutes before ingestion of food (such as 10-60 minutes or 10-30 minutes before ingesting food). In some embodiments of the methods described herein, the FXR agonist is administered less than about 60 minutes before ingestion of food. In some embodiments of the methods described above, the FXR agonist is administered less than about 30 minutes before ingestion of food. In some embodiments of the methods described herein, the FXR agonist is administered after ingestion of food. In some embodiments, the methods further comprise administration of a DPP-IV inhibitor, a TGR5 agonist, a biguanide, an incretin mimetic, or GLP-1 or an analog thereof. In some embodiments, the methods further comprise administration of a steroid or other anti-inflammatory compound which may have an effect in the gut. In some embodiments, the methods further include co-administration of an antibiotic therapy, and the FXR agonist treats or prevents inflammation, such as inflammation associated with antibiotic-induced colitis.

The composition administered can include at least one of a spreading agent or a wetting agent. In some embodiments, the absorption inhibitor is a mucoadhesive agent (e.g., a mucoadhesive polymer). In some embodiments, the mucoadhesive agent is selected from methyl cellulose, polycarbophil, polyvinylpyrrolidone, sodium carboxymethyl cellulose, and a combination thereof. In some embodiments, a pharmaceutical composition administered further includes an enteroendocrine peptide and/or an agent that enhances secretion or activity of an enteroendocrine peptide.

The pharmaceutical compositions that comprise one or more compounds disclosed herein can be formulated in unit dosage form, suitable for individual administration of precise dosages. In one non-limiting example, a unit dosage contains from about 1 mg to about 50 g of one or more compounds disclosed herein, such as about 10 mg to about 10 g, about 100 mg to about 10 g, about 100 mg to about 1 g, about 500 mg to about 5 g, or about 500 mg to about 1 g. In other examples, a therapeutically effective amount of one or more compounds disclosed herein is from about 0.01 mg/kg to about 500 mg/kg, for example, about 0.5 mg/kg to about 500 mg/kg, about 5 mg/kg to about 250 mg/kg, or about 50 mg/kg to about 100 mg/kg. In other examples, a therapeutically effective amount of one or more compounds disclosed herein is from about 50 mg/kg to about 250 mg/kg, for example about 100 mg/kg.

VII. Working Examples

Example 1

Activity of Orally-Administered Fexaramine is Restricted to the Intestine

Figure 1A:
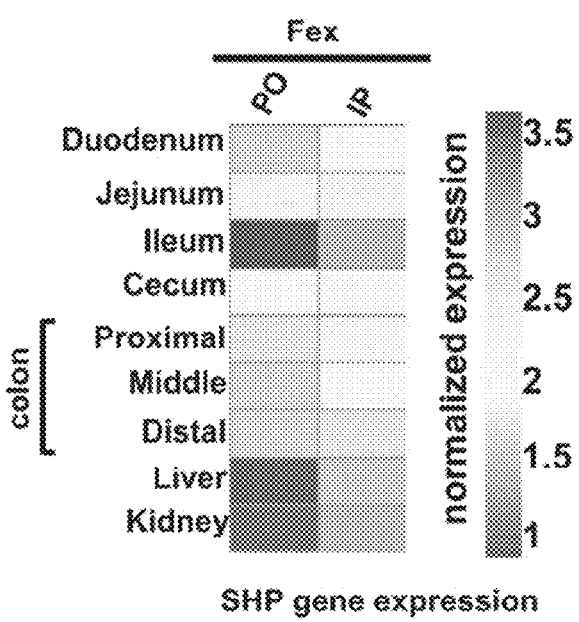
FIGS. 1A-1C are a comparative expression chart and two bar charts, respectively, illustrating increased levels of FXR target gene expression in the intestine relative to expression in the liver and kidney. 8 week-old C57BL/6J mice were treated with vehicle or fexaramine (100 mg/kg) via oral (PO) or intraperitoneal (IP) injection for three days (FIGS. 1A-1B) or five days (FIG. 1C).
Figure 1B:
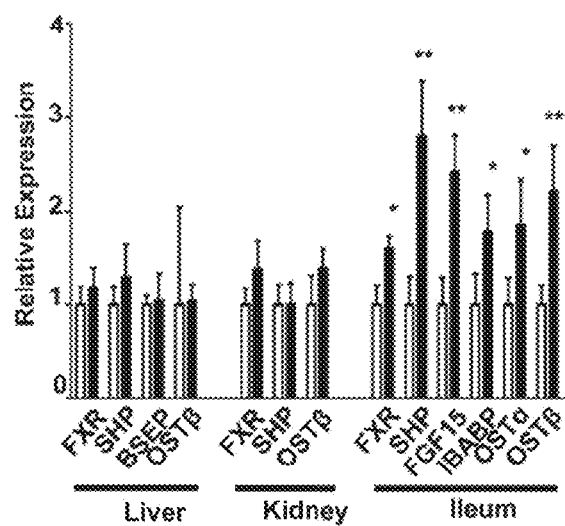
Figure 1C:
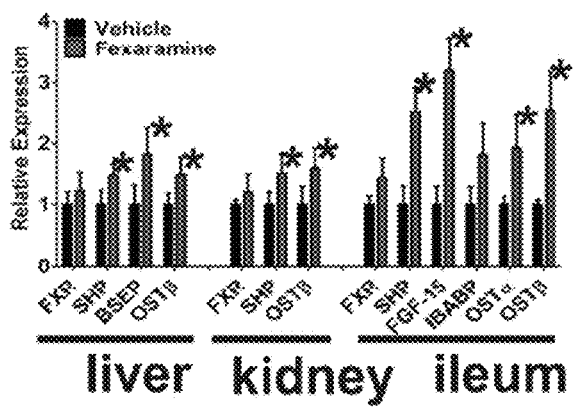
Figure 1D:
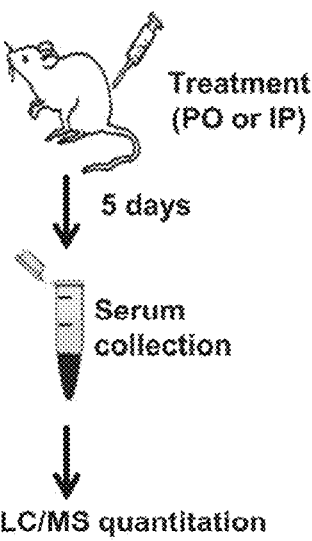
FIG. 1D is a schematic diagram illustrating an experimental procedure used to evaluate fexaramine, where mice were treated with vehicle or fexaramine (100 mg/kg) via PO or IP injection, and LC/MS quantification of serum fexaramine was conducted five days later.
Figure 1E:
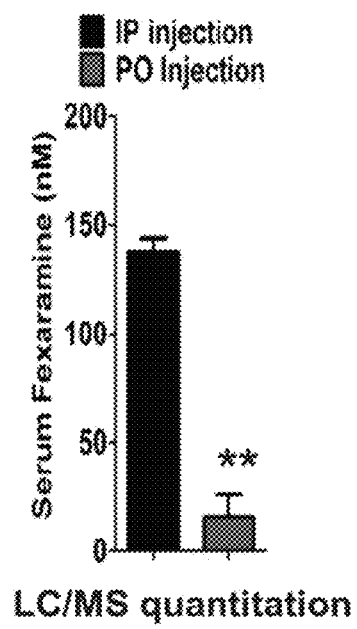
FIG. 1E is a bar chart illustrating serum fexaramine concentrations after administration as described in FIG. 1D. Data represent mean values±STD. Statistical analysis was performed with the Student's t test ($*p<0.05$, $**p<0.01$).
Figure 1F:
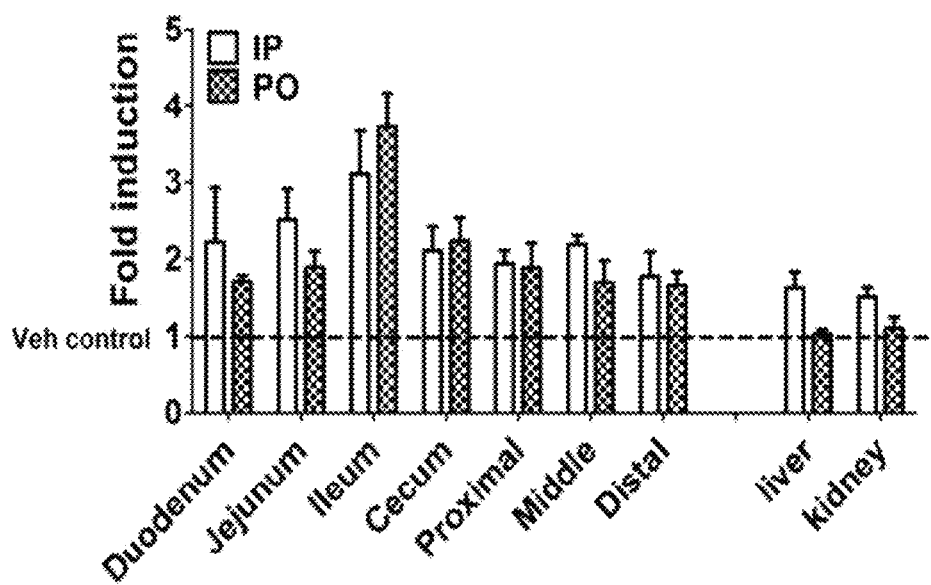
FIG. 1F is a bar chart illustrating that orally delivered fexaramine is intestinally-restricted. Mice received vehicle or Fexaramine (100 mg/kg) via per os (PO) or intraperitoneal (IP) injection for 5 days. Expression of the FXR target gene SHP after PO or IP injection in selected tissues is shown.

Upon exploration of the in vivo effects of fexaramine (Fex) administration, it was discovered that due to ineffectual absorption, oral (PO) and intraperitoneal (IP) drug delivery produced very different effects (FIGS. 1D and 1E). While robust induction of the FXR target gene SHP was seen throughout the intestine with both acute PO and IP Fex treatment (100 mg/kg for five days), induction of SHP was only seen in liver and kidney after IP treatment (FIG. 1A). Consistent with this notion, PO Fex treatment induced multiple FXR target genes in the intestine including IBABP, OSTα and FGF15, but failed to affect the expression of these genes in liver or kidney (FIGS. 1B, 1C and 1F). Quantification of serum Fex levels revealed an order of magnitude lower drug levels after acute PO—compared to IP-treatment (~10% of IP levels) (FIGS. 1D and 1E). Notably, the serum levels of Fex after PO administration were below the 25 nM $EC_{50}$ of Fex, consistent with the lack of target gene activation in the kidney and liver.

Example 2

Fexaramine Prevents Diet-Induced Obesity Weight Gain

To investigate the physiological effects of intestinal FXR activation by fexaramine, mice were subjected to chronic fexaramine (100 mg/kg Fex) PO treatment for 5 weeks. Chronically treated chow-fed mice were indistinguishable from vehicle-treated mice in terms of weight gain, basal metabolic activity and glucose tolerance (FIGS. 3A-3D).

Figure 2E:
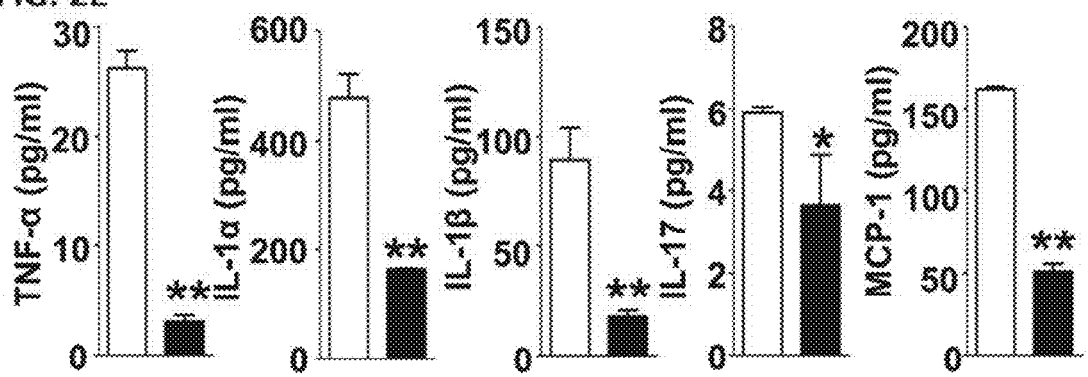
Figure 4A:
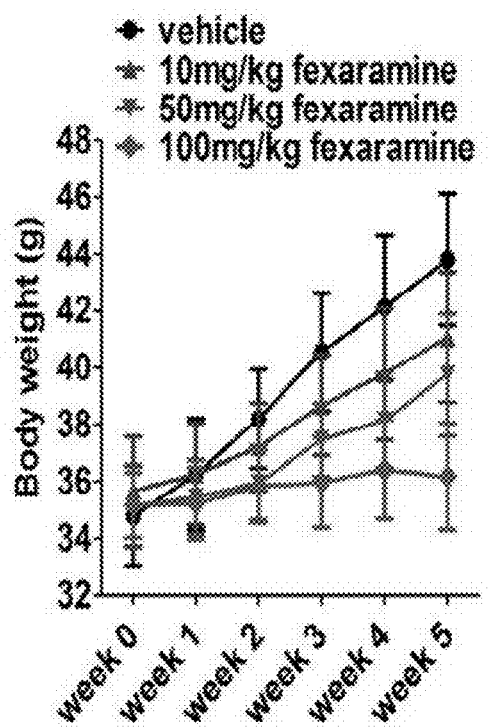
FIG. 4A is a line graph showing the effects of fexaramine at various dosage levels on the body weight of mice fed a HFD for 14 weeks and then administered daily oral injections of vehicle or fexaramine (10, 50 or 100 mg/kg) for 5 weeks with HFD. Data represent the mean±STD. Statistical analysis was performed with the Student's t test ($*p<0.05$, $**p<0.01$).
Figure 4B:
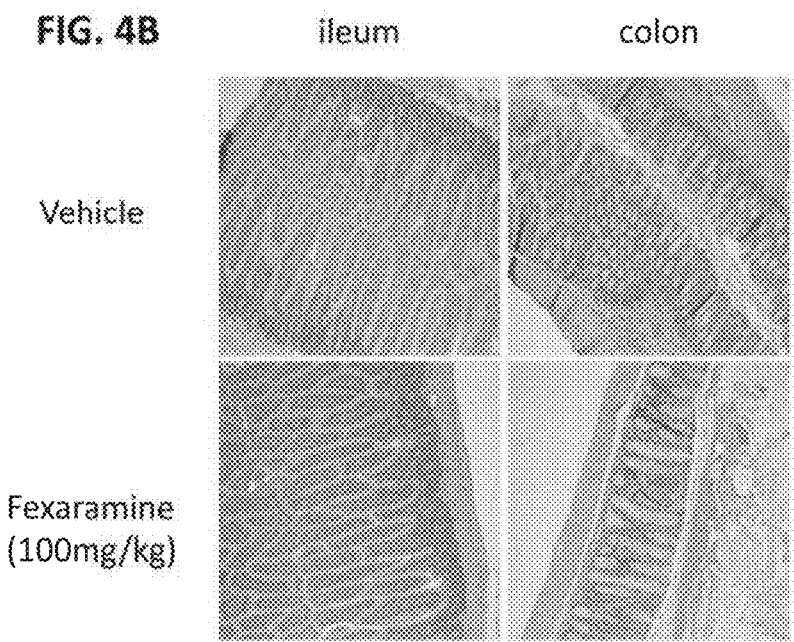
FIG. 4B is a set of digital images showing histological analysis of the ileum and colon following treatment with fexaramine or vehicle. Mice were fed on HFD for 14 weeks, and then administered daily oral injections of vehicle or fexaramine (100 mg/kg) for 5 weeks with HFD.
Figure 4C:
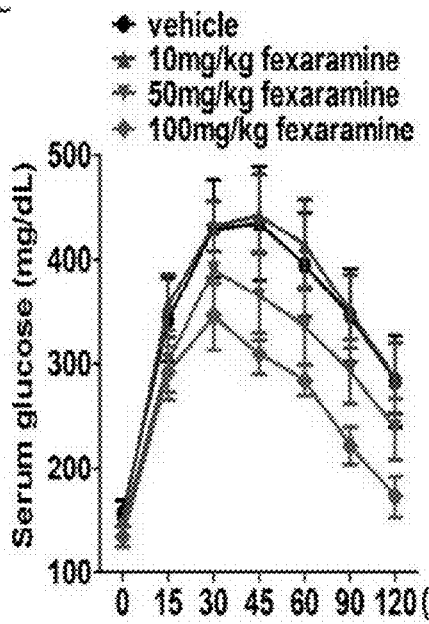
FIG. 4C is a line graph showing n glucose tolerance tests in mice fed a HFD for 14 weeks and then administered daily oral injections of vehicle or fexaramine (10, 50 or 100 mg/kg) for 5 weeks with HFD. Data represent the mean±STD. Statistical analysis was performed with the Student's t test ($*p<0.05$, $**p<0.01$).
Figure 4D:
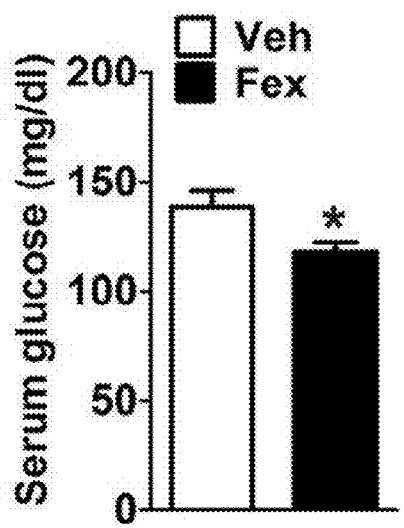
FIG. 4D is a line graph showing fasting glucose levels in 14 week HFD-fed mice treated with vehicle or fexaramine (100 mg/kg/day os for 5 week). Data represent the mean±STD. Statistical analysis was performed with the Student's t test ($*p<0.05$, $**p<0.01$).
Figure 5A:
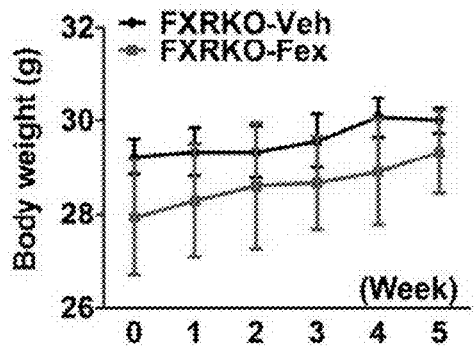
Figure 5B:
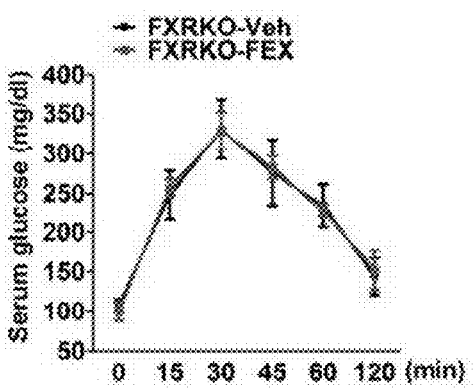
Figure 5C:
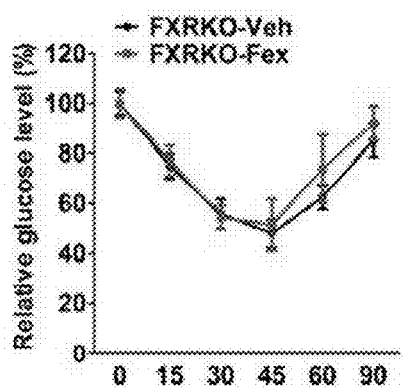
Figure 5D:
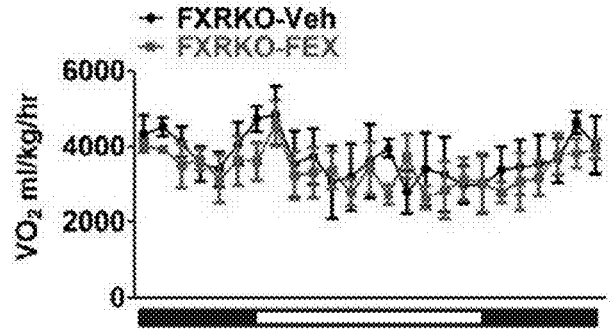

The physiological effects of fexaramine in established obesity (diet-induced obesity, DIO) models were evaluated. C57BL/6J mice were fed a diet of 60% fat for 14 weeks and then treated PO with vehicle or fexaramine (100 mg/kg) for 5 weeks. Surprisingly, chronic fexaramine oral administration prevented weight gain in DIO mice (FIG. 2A). Prevention of weight gain by fexaramine occurred in a dose-dependent manner (FIG. 4A) with no signs of intestinal toxicity (FIG. 4B). At the highest dose weight gain was almost completely abrogated. The reduction in weight gain of Fex-treated mice was largely attributed to reduced overall fat mass (as analyzed by MRI), with significant reductions in wet weights of both subcutaneous (inguinal) and visceral (gonadal and mesenteric) adipose depots (FIGS. 2B and 2C). Consistent with reduced adiposity, Fex-treated mice showed significant improvements in their endocrine and metabolic profiles including reduced glucose, insulin, leptin, cholesterol, and resistin levels (FIGS. 2D and 4D).

Obesity and its metabolic complications are associated with chronic low-grade inflammation, reflected by elevated serum levels of inflammatory cytokines. Serum levels of inflammatory cytokines TNFα, IL-1α, IL-1β, IL-17 and MCP-1 were markedly decreased by fexaramine (FIG. 2E) (such as reductions of at least 50%, at least 75%, at least 80%, or even at least 90%), indicating that fexaramine-induced weight gain resistance reduced systemic inflammation.

Figure 2F:
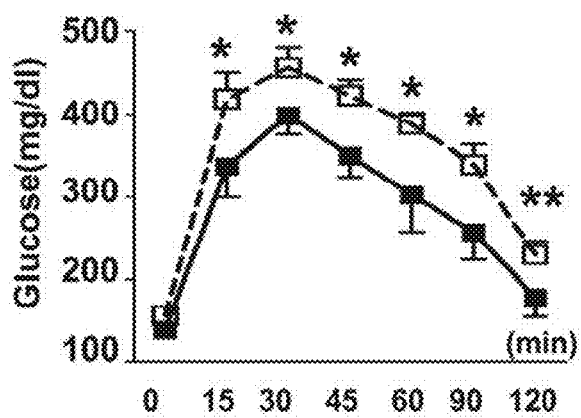
Figure 2G:
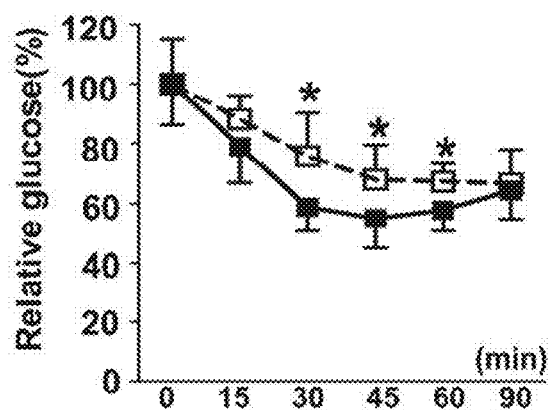
Figure 3A:
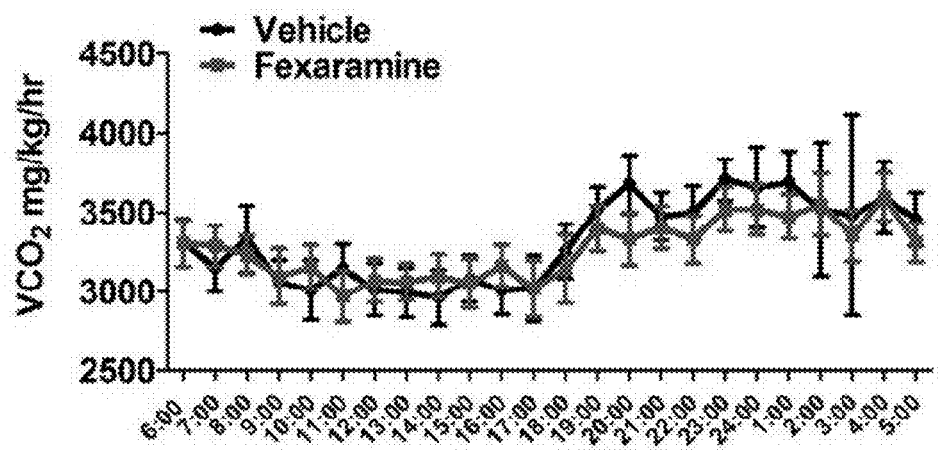
FIGS. 3A-3D are line graphs and a bar graph showing the effects of fexaramine administration in normal chow-fed mice. The mice were treated with vehicle or fexaramine (100 mg/kg) via PO for 5 weeks. Data represent the mean±STD. Statistical analysis as performed with the Student's t test ($*p<0.05$, $**p<0.01$).
Figure 3B:
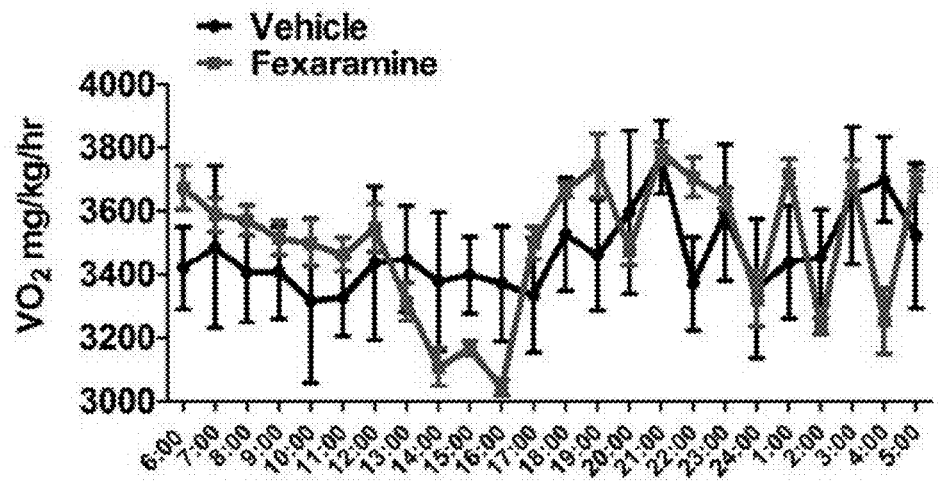
Figure 3C:
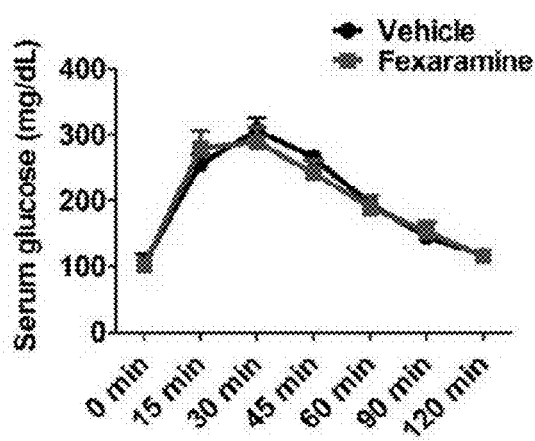
Figure 3D:
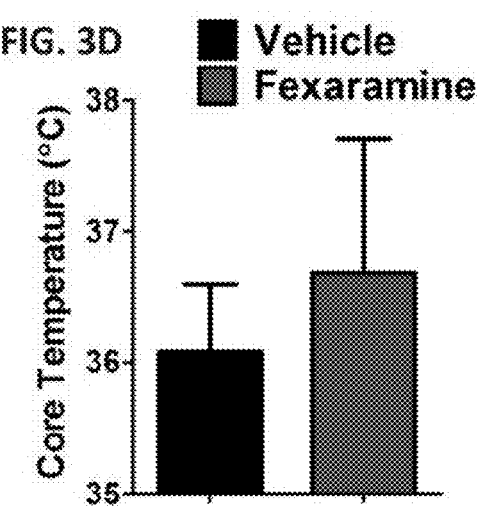

The reduction in fasting insulin levels also suggested improved glucose tolerance and insulin sensitivity in fexaramine-treated DIO mice. Therefore, glucose tolerance tests (GTTs) and insulin tolerance tests (ITTs) were performed to determine if glucose homeostasis was improved in fexaramine-treated DIO mice. Fex treatment induced dose-dependent improvements in glucose tolerance and insulin sensitivity in DIO mice (measured by glucose and insulin tolerance tests) (FIGS. 2F and 2G and 4C). In addition, while fexaramine improved glucose homeostasis in a dose-dependent manner in DIO mice, there were no effects observed in normal chow-fed mice across a range of doses. Notably, these Fex-induced changes in gene expression and improvements in metabolic homeostasis were abrogated in Fex-treated FXR null mice, establishing the FXR dependence of the observed effects (FIGS. 5A-5I).

Example 3

Fexaramine Enhances Energy Expenditure in Brown Adipose Tissue

Figure 6A:
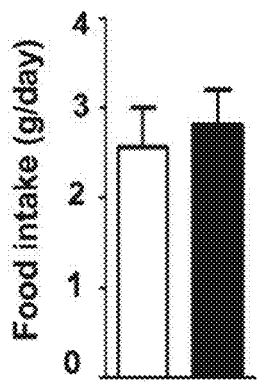
Figure 6B:
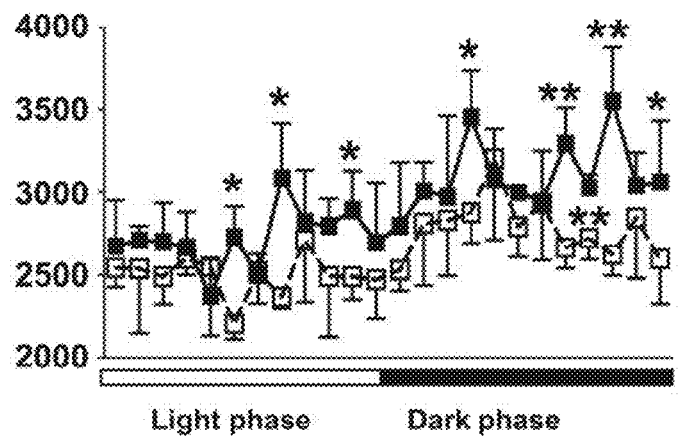
Figure 6C:
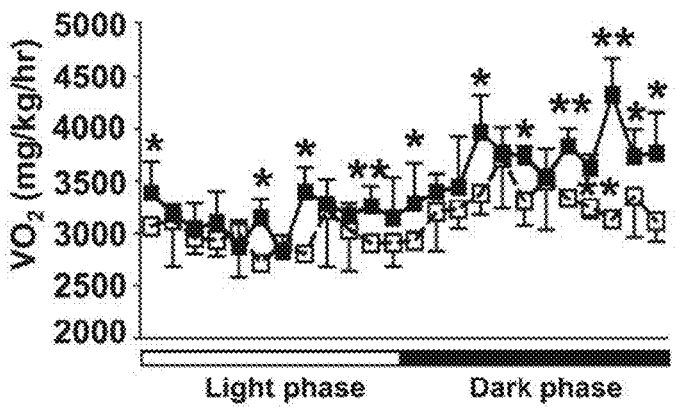
Figure 6D:
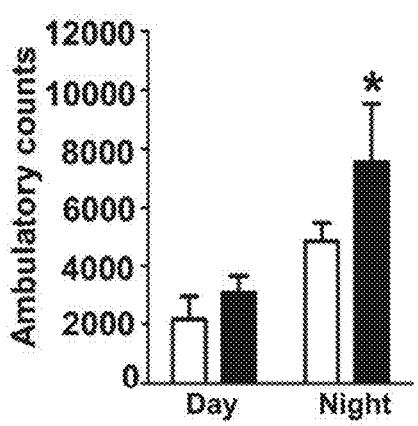

As the differential weight effect was not attributable to difference in food intake between vehicle-treated control mice and Fex-treated mice (FIG. 6A), the metabolic rates of weight-matched mice were compared. Fex-treated DIO mice had consistently higher oxygen consumption ($VO_2$) and exhaled more carbon dioxide ($VCO_2$) than vehicle-treated controls (FIGS. 6B-6C), but displayed similar respiratory exchange ratios, suggesting enhanced metabolism of both sugar and fat (FIG. 6M). Based on ambulatory counts, Fex-treated mice were more active than control mice, which can be a result of lower body weights supporting increased energy expenditure in treated mice (FIG. 6D).

Figure 6E:
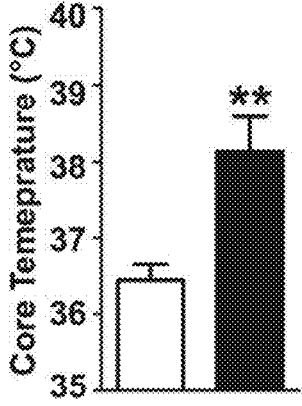
Figure 6F:
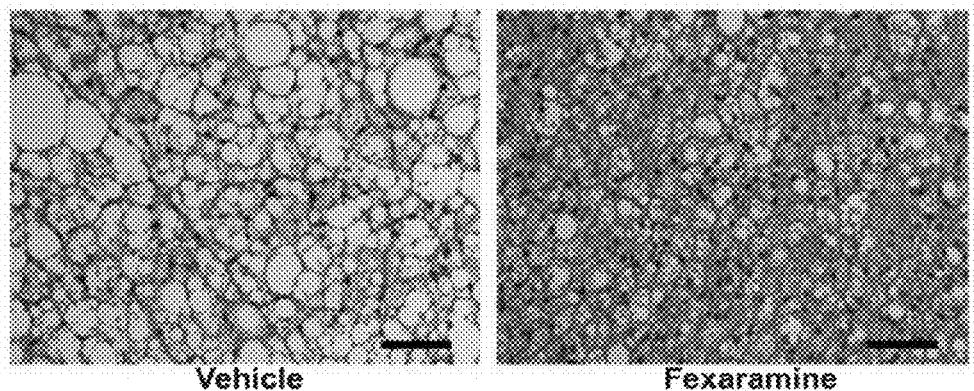
Figure 6G:
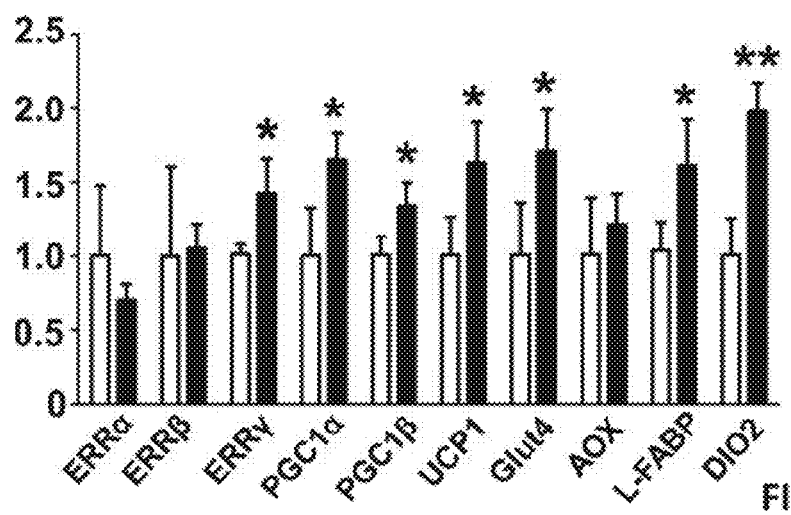
Figure 6H:
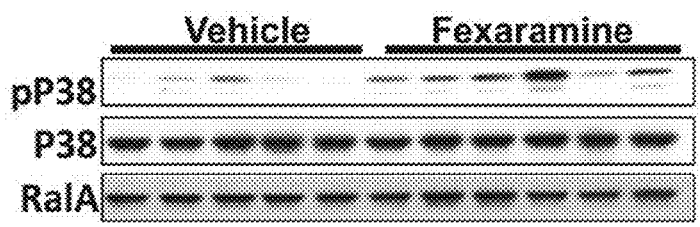
Figure 6I:
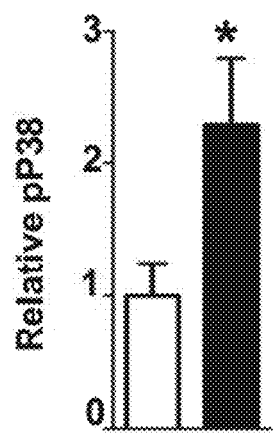

Consistent with increased energy expenditure, Fex treatment increased the core body temperature approximately 1.5° C. (FIG. 6E). In addition, the prominent accumulation of lipid vesicles in brown adipose tissue (BAT) of vehicle-treated DIO mice was markedly reduced in Fex-treated mice (FIG. 6F). Gene expression analysis confirmed the induction of ERRγ, PGC-1α, and PGC-10, as well as a number of their target genes involved in thermogenesis, mitochondrial biogenesis, and fatty acid oxidation in BAT (FIG. 6G). Moreover, Fex treatment increased the phosphorylation level of p38 (FIGS. 6H and 6I), previously shown to stabilize PGC-1α, a key coactivator of the thermogenic transcriptional program in BAT. A comparison of the transcriptional changes induced by Fex in inguinal, gonadal and brown adipose depots revealed coordinated changes that selectively enhance OXPHOS activity only in BAT, indicating that BAT is a key contributor to the increased energy expenditure and thermogenesis (FIG. 6J). Consistent with this conclusion, KEGG pathway analysis of Fex-induced transcriptional changes from RNA-sequence analysis in BAT identified oxidative phosphorylation as significantly changed (Table 1), and increased PKA activity was seen in Fex-treated mice (FIG. 6L).

TABLE 1

| KEGG pathway Term | p-value |
| --- | --- |
| Oxidative phosphorylation | 8.12E−07 |
| Chemokine signaling pathway | 2.21E−03 |
| Cytokine-cytokine receptor interaction | 4.40E−03 |
| Biosynthesis of unsaturated fatty acids | 7.04E−03 |
| PPAR signaling pathway | 7.53E−03 |

Furthermore, serum lactate levels were significantly reduced in Fex-treated DIO mice, suggesting that body-wide energy metabolism is shifted towards a more oxidative state (FIG. 6N). Thus, the marked reduction in lipids, increased PKA activity and p38 phosphorylation, and increased core body temperature indicate a coordinated activation of thermogenesis in BAT in Fex-treated DIO mice.

Example 4

Fexaramine Induces FGF15 and Alters Bile Acid Composition

RNA-Seq of intestinal tissues was used to explore the mechanisms through which Fex might contribute to systemic changes in energy expenditure and metabolic rate. Mice were fed on HFD for 14 weeks, and then subjected to daily oral injection of vehicle or fexaramine (100 mg/kg) for 5 weeks with HFD. KEGG pathway analysis revealed the induction of multiple cellular metabolic pathways including PPAR and adipocytokine signaling in both ileum and colon (Tables 2 and 3).

TABLE 2

| KEGG pathway (ileum) | |
| --- | --- |
| KEGG pathway Term | p-value |
| PPAR signaling pathway | 1.86E−05 |
| Adipocytokine signaling pathway | 2.91E−03 |
| Retinol metabolism | 3.03E−03 |
| Drug metabolism | 4.01E−03 |
| Arachidonic acid metabolism | 5.33E−03 |

TABLE 3

| KEGG pathway (colon) | |
| --- | --- |
| KEGG pathway Term | p-value |
| PPAR signaling pathway | 3.52E−11 |
| Adipocytokine signaling pathway | 8.90E−03 |
| Retinol metabolism | 7.06E−02 |

Overlap of Fex-induced expression changes with previously identified intestinal FXR binding sites identified a subset of genes as potential direct FXR target genes (FIG. 7A). Within this subset, FGF15 (corresponds to FGF19 in humans) was found to be dramatically upregulated by Fex. In addition to established FXR target genes such as Lp1, other genes exhibiting regulation by FXR were identified including Per1 (FIG. 7A).

Figure 7F:
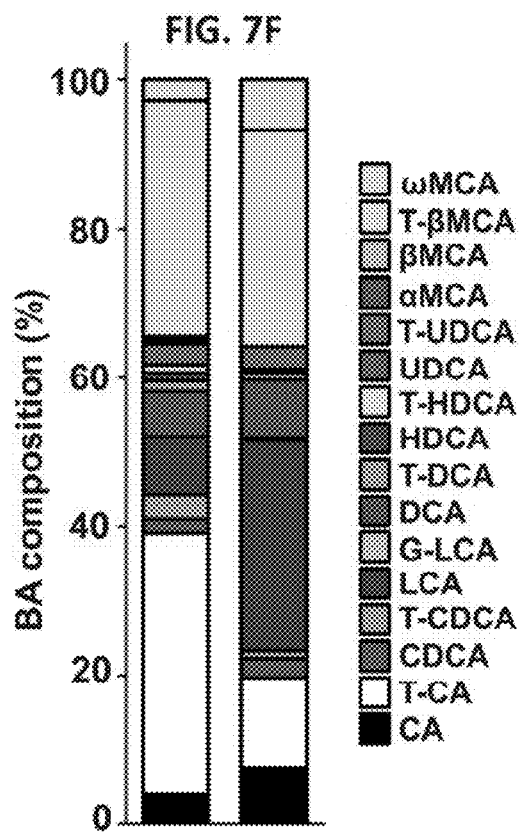
Figure 8:
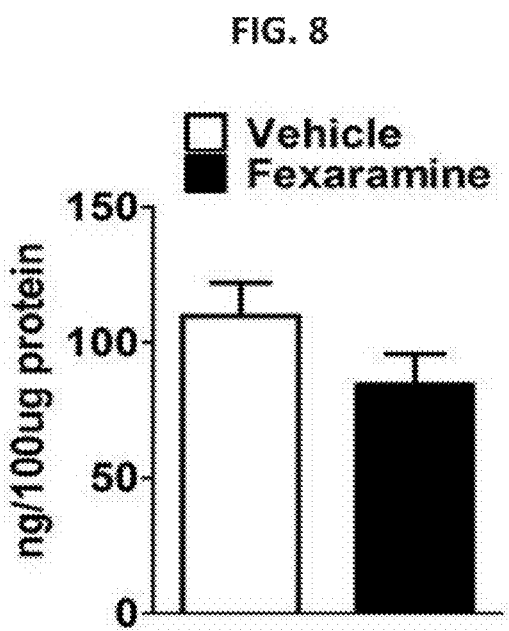
FIG. 8 is a bar graph showing hepatic Cyp7a1 levels determined by ELISA. Data represent the mean±SD. Statistical analysis was performed with the Student's t test. *p<0.05, **p<0.01.

As an intestinal endocrine hormone, FGF15 induction is of interest since it activates the thermogenic program in BAT, as well as negatively regulate BA synthesis through suppression of hepatic CYP7A1, the rate-limiting enzyme for BA synthesis. An increase in circulating FGF15 accompanied the increase in mRNA expression in ileum (FIGS. 7B and 7C) (such as an increase of at least 100%, at least 125%, or at least 150%). Consistent with an increase in serum FGF15, hepatic CYP7A1 expression was significantly repressed at both the mRNA and protein level after chronic Fex treatment, while the expression of CYP8B1 and CYP27A1 (enzymes not regulated by FGF15) were not affected (FIG. 7D and FIG. 8). In addition, expression of established liver FXR target genes SHP and BSEP were not altered, further demonstrating the absence of hepatic FXR activation after chronic Fex treatment (FIG. 7D) and indicating that other pathways, such as FGF15, mediate changes in hepatic gene expression.

Genetic activation of intestinal FXR has been previously shown to alter bile acid composition. This is relevant as dietary, microbial or hepatic stress can alter the pool and enhance the production of toxic and cholestatic BAs such as taurine-conjugated chenodeoxycholic acid (T-CDCA) and taurine-conjugated cholic acid (T-CA). Despite the apparent absence of hepatic FXR activation, Fex treatment produced striking changes in the composition of the BA pool. In addition to reducing the bile acid pool size, Fex treatment changed the relative proportions of circulating bile acids, most notably decreasing the fraction of taurocholic acid and increasing the fraction of the secondary bile acid, lithocholic acid (FIGS. 7E and 7F, Table 4). These changes are in keeping with increased intestinal FXR activation, including the effects of increased circulating FGF15 on bile acid synthesis in the liver. Indeed, decreased serum taurocholic acid has been previously reported in mice expressing a constitutively activated FXR transgene in intestine, as well as after injection of FGF19, the human analogue of FGF15 (Wu et al. *PloS one* 6, e17868, 2011). Furthermore, changes in bile acid synthesis away from cholic acid towards chenodeoxycholic acid and its derivatives, which includes lithocholic acid, were observed upon FGF19 treatment, consistent with a reduction in hepatic CYP7A1 and an increase in CYP7B1 expression.

TABLE 4

Fexaramine alters the serum bile acid composition

| | Bile Acid Composition (%) | |
| --- | --- | --- |
| | Vehicle | Fexaramine |
| CA | 4.08 | 7.51 |
| TCA | 34.96 | 12.23 |
| CDCA | 1.86 | 2.51 |
| TCDCA | 3.52 | 1.13 |
| LCA | 7.67 | 28.13 |
| GLCA | N.D. | 0.51 |
| DCA | 6.03 | 7.67 |
| TDCA | 1.42 | 1.02 |
| HDCA | 1.20 | 0.36 |
| T-HDCA | 0.99 | N.D |
| UDCA | 0.01 | 0.05 |
| T-UDCA | 2.85 | 3.07 |
| alpha MCA | 0.33 | N.D |
| beta MCA | 0.55 | N.D |
| T-beta MCA | 31.78 | 29.16 |
| omega MCA | 2.74 | 6.65 |

Mice fed a HFD for 14 weeks were maintained on a HFD and treated with vehicle or fexaramine (100 mg/kg/day per os for 5 week). Serum bile acid composition was determined by mass spectrometry. N.D not determined.

Figure 7G:
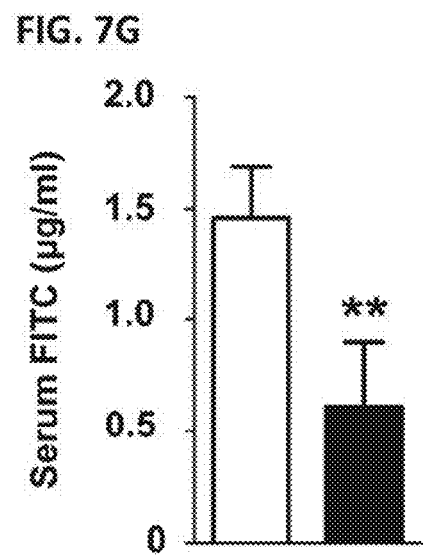
Figure 7H:
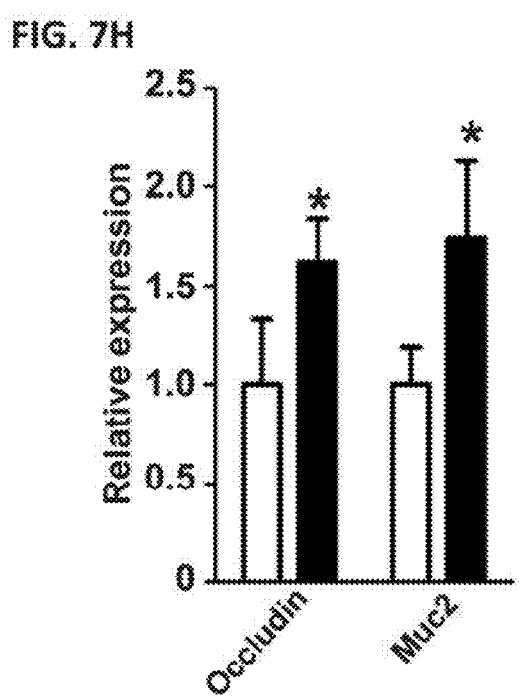

FXR activation has been reported to enhance mucosal defense gene expression and intestinal barrier function (Inagaki et al., *Proc Natl Acad Sci USA* 103:3920-3925, 2006; Gadaleta., et al. *Gut* 60:463-472, 2011). Consistent with these reports, mice showed reduced intestinal permeability, as measured by FITC-dextran leakage into the serum, and increased expression of mucosal defense genes Occludin and Muc2, after chronic Fex-treatment (FIGS. 7G and 7H).

Figure 9:
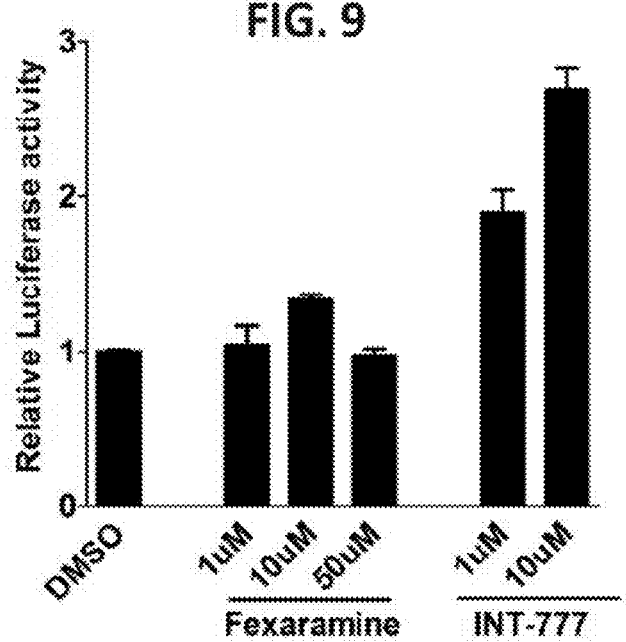
FIG. 9 is a bar graph showing that fexaramine fails to activate TGR5. HEK293 cells were transfected with expression vectors for cAMP-response element luciferase, β-galactosidase and human TGR5. 24 hours after transfection, cells were treated with fexaramine or INT-777 (a TGR5 agonist).
Figure 10A:
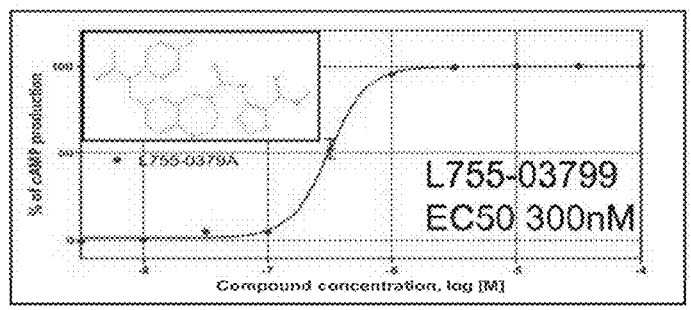
Figure 10B:
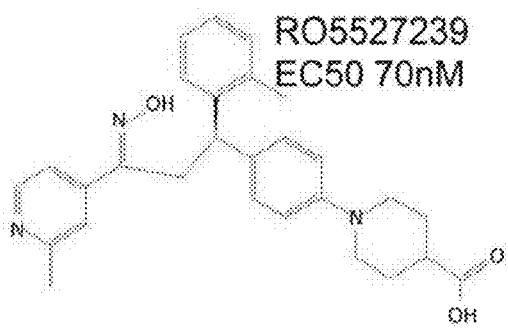
Figure 10C:
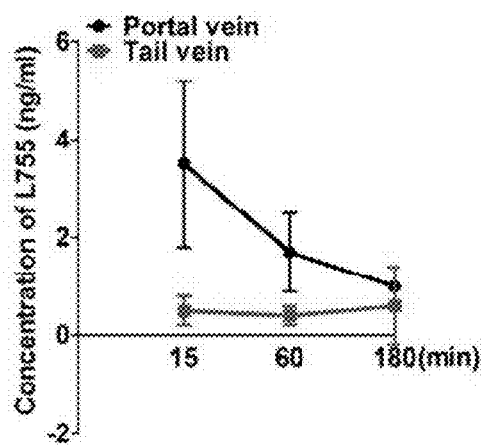
Figure 10D:
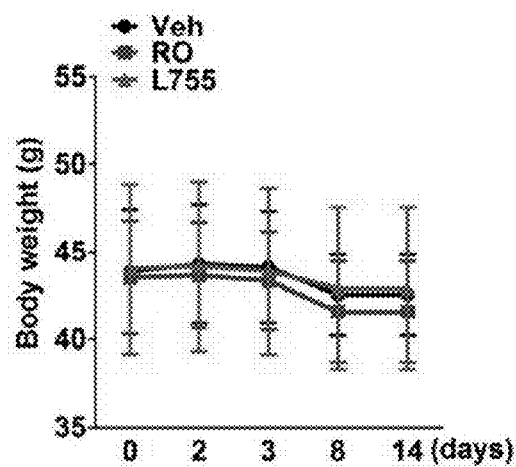
Figure 10E:
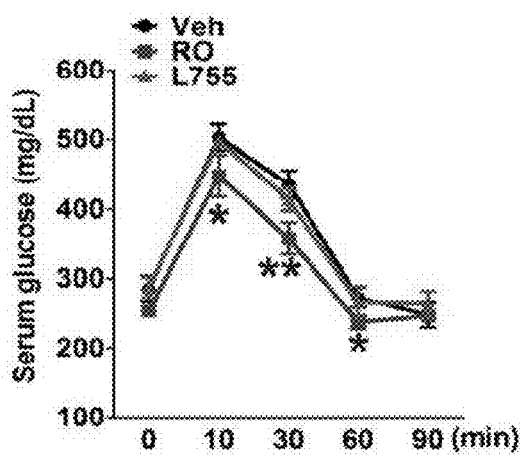
Figure 10F:
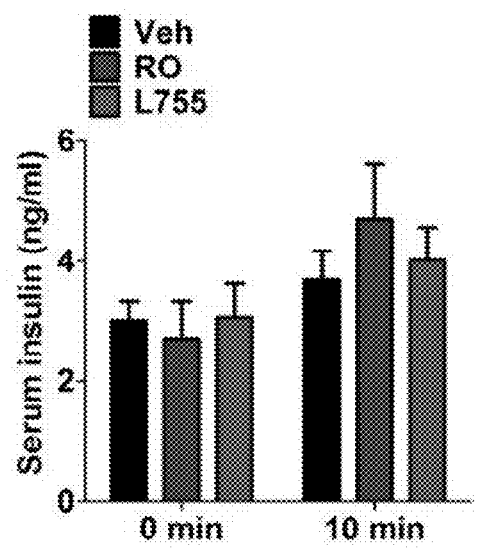

While Fex does not activate the G protein-coupled bile acid receptor, TGR5 (FIG. 9), the pronounced changes in BAs indicated that this pathway may contribute to the observed physiologic effects. Notably, treatment of HFD-fed mice with the intestinally-restricted TGR5 agonist, L7550379, failed to induce metabolic changes, while treatment with the systemic TGR5 agonist, RO5527239 improved glucose homeostasis, as measured by GTT and insulin secretion (FIGS. 10A-10F). These results indicated that TGR5 activation outside of the intestine may contribute to the beneficial effects of Fex treatment (FIGS. 10B, 10D, 10E and 10F).

Figure 11B:
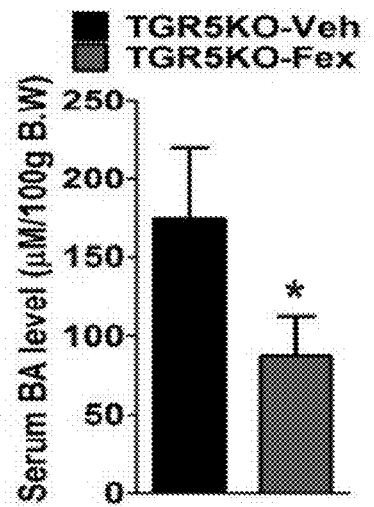
Figure 11C:
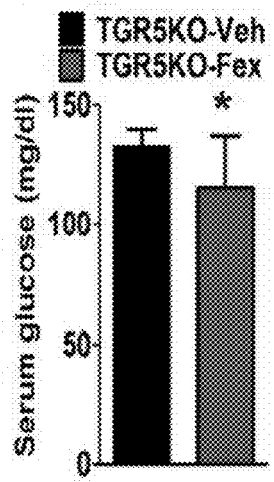
Figure 11D:
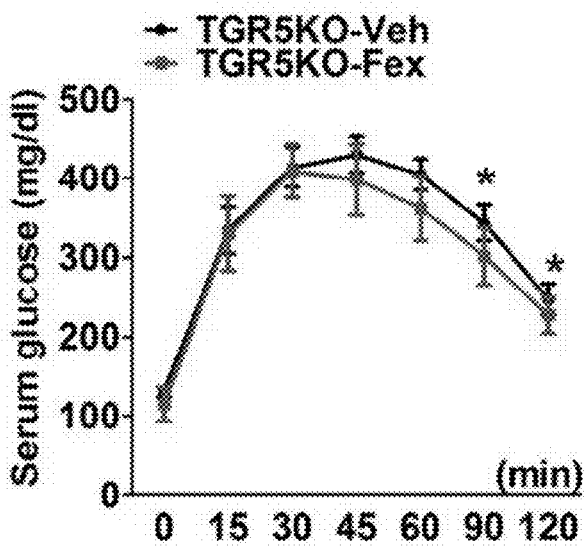
Figure 11E:
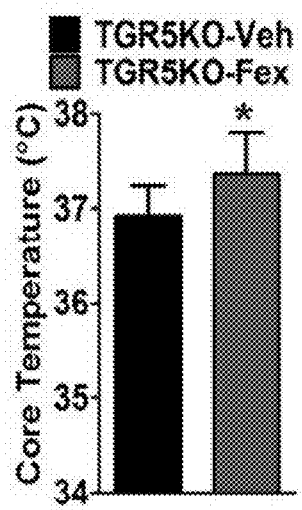
Figure 11F:
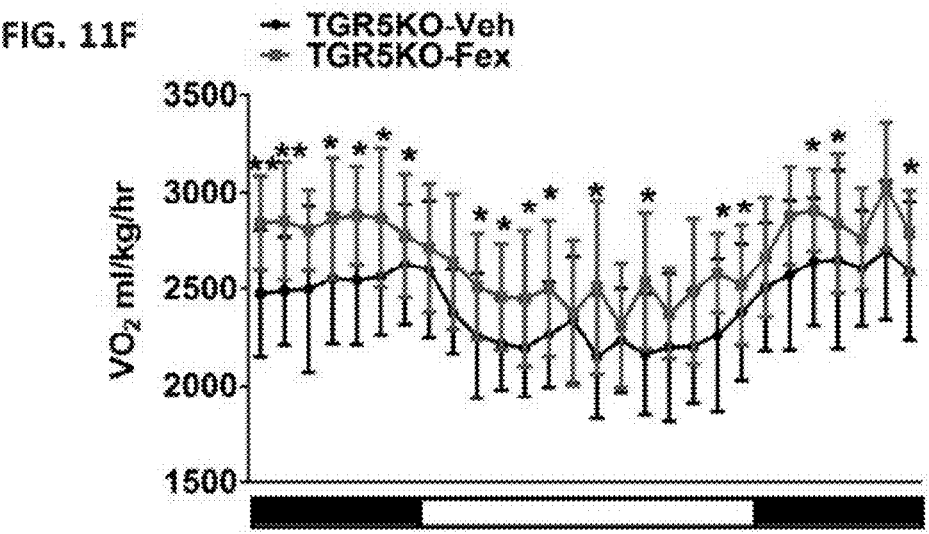
Figure 11G:
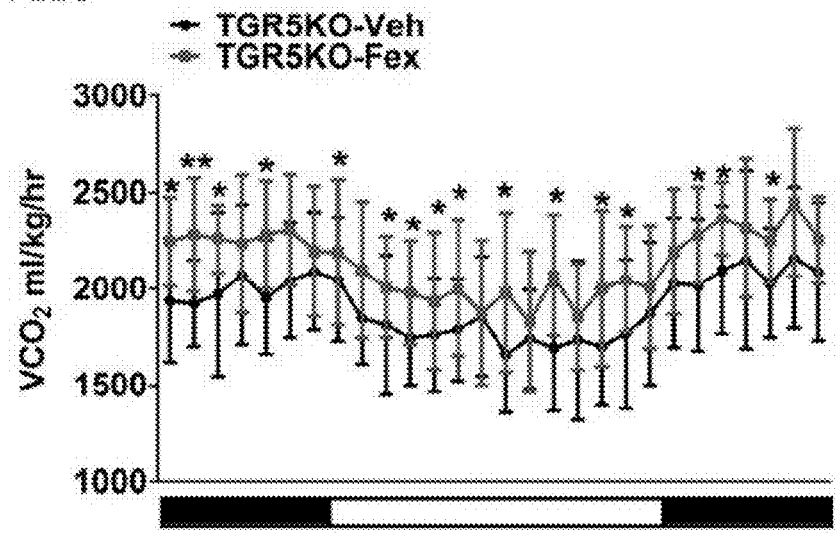
Figure 11H:
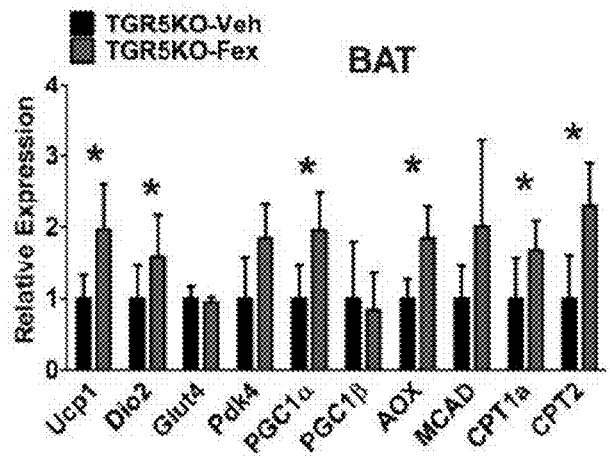
Figure 11I:
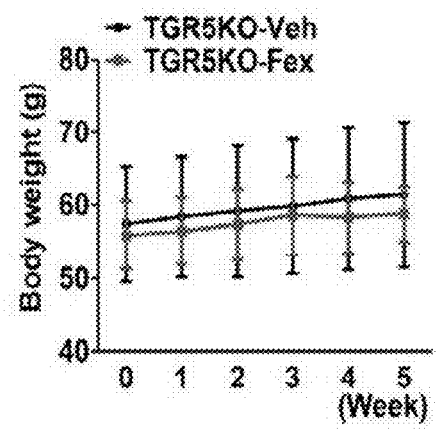
Figure 11J:
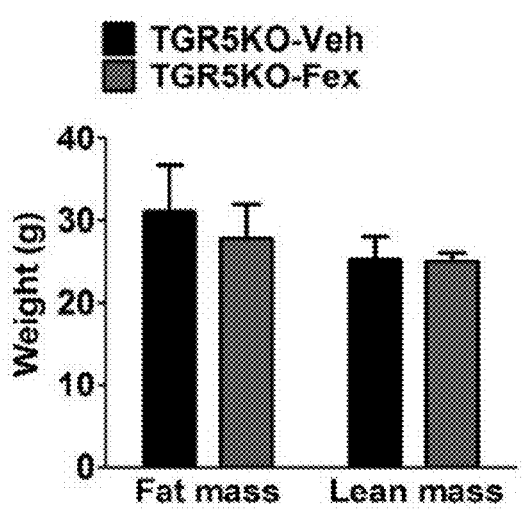
Figure 11K:
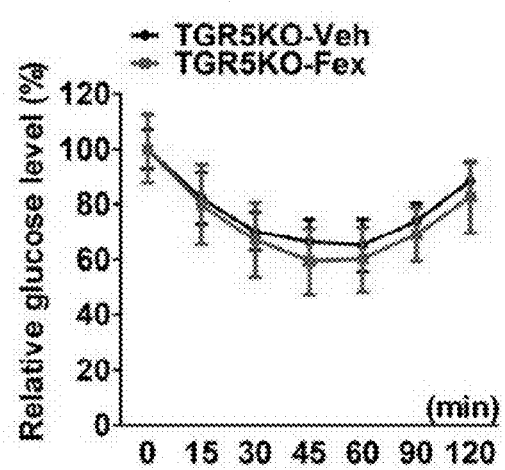
Figure 11L:
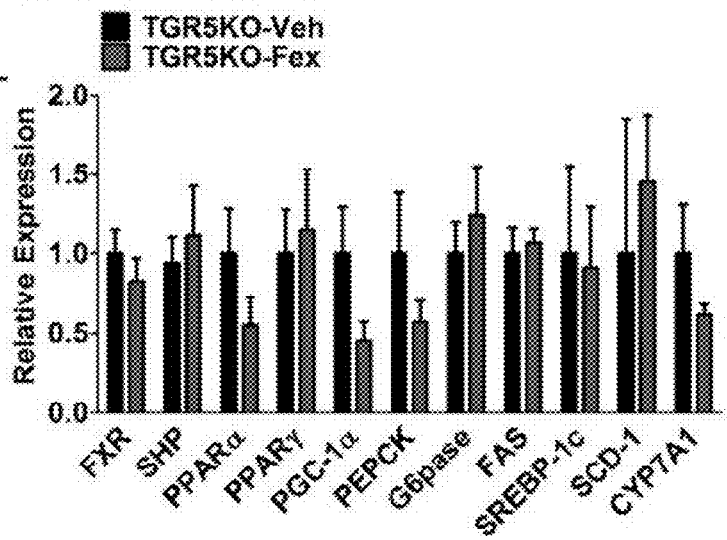

To address this possibility, HFD-fed TGR5 null mice were chronically treated with Fex (100 mg/kg/day PO for 5 weeks). As seen in wild type mice, Fex treatment induced multiple FXR target genes in the ileum of TGR5 null mice including FGF15, resulting in lowered serum BA levels (FIGS. 11A, 11B). In this TGR5 null background, Fex treatment induced moderate improvements in fasting glucose levels and glucose tolerance (FIGS. 11C, 11D). In addition, somewhat blunted increases in core body temperature and metabolic rate, correlating with the induction of thermogenic genes in BAT, were observed (FIGS. 11E-11H), indicating that these effects do not require TGR5 activation. In contrast to wild type mice, no significant changes in weight gain or insulin sensitivity were observed in Fex treated TGR5 null mice, and altered gene expression patterns were seen in the liver and muscle, indicating involvement of the TGR5 pathway (FIGS. 11I-11N). In particular, the anti-lipogenic effects of Fex in the liver appear to require TGR5 activation, as key hepatic lipogenic genes and liver triglyceride content were not affected by Fex treatment (FIGS. 11L, 11M).

Example 5

Fexaramine Induces Browning of White Adipose Tissue

During obesity, adipose tissue expands by hyperplastic and/or hypertrophic growth, is chronically inflamed, and produces inflammatory cytokines that ultimately contribute to systemic metabolic dysregulation. After chronic Fex-treatment, the cross-sectional area of adipocytes in visceral depots including gonadal and mesenteric was markedly reduced (FIG. 12A). Investigation of signaling pathways implicated in diet-induced inflammation identified reduced levels of IKK-ε and TANK-binding kinase 1 (TBK1) in Fex-treated DIO mice (FIGS. 12B, 13). These noncanonical IκB kinases were recently shown to play crucial roles in energy expenditure as a consequence of adipose tissue inflammation upon diet-induced obesity (Reilly et al., *Nat Med* 19:313-321, 2013). In addition, activation of the mammalian target of rapamycin complex1 (mTORC1) pathway, a key lipogenic pathway activated by high fat diet (HFD), was reduced in Fex-treated gonadal WAT, as evidenced by reduced S6K phosphorylation (FIG. 12B). Consistent with reduced adiposity, expression of the inflammatory cytokines TNFα, MCP-1 and IL-1α, as well as the macrophage marker F4/80, were reduced in visceral and brown adipose depots of Fex-treated mice (FIGS. 12C and 14).

Brown adipose-driven adaptive thermogenesis is fueled by mitochondrial oxidation of free fatty acids (FFAs) released from triglyceride stores into the circulation predominantly by the action of hormone-sensitive lipase (HSL). Low levels of HSL phosphorylation were seen in visceral and subcutaneous adipose depots from control mice, as expected, due to desensitization of the β-adrenergic pathway in WAT during obesity (Carmen & Victor, *Cell Signal* 18:401-408, 2006; Song et al. *Nature* 468:933-9, 2010). In contrast, a pronounced increase in HSL phosphorylation and serum levels of free fatty acids (FIGS. 12D and 12G), accompanied by increased serum catecholamine levels and β3-adrenergic receptor expression (FIGS. 12C, 12E and 12F), was observed after chronic Fex treatment. As β-adrenergic receptor activation has been shown to induce "brown fat-like" cells in inguinal adipose tissue, and these cells have been associated with resistance to diet-induced obesity and improved glucose metabolism (Tsukiyama-Kohara et al., *Nat Med* 7:1128-1132, 2001; Fisher et al., *Genes Dev* 26:271-281, 2012; Hansen et al., *Proc Natl Acad Sci USA* 101:4112-4117, 2004; Wang et al., *Mol Cell Biol* 28:2187-2200, 2008), UCP-1 expression was examined in inguinal adipose tissue. Immunohistochemistry revealed a substantial increase in the abundance of multi-locular, UCP1-expressing adipocytes in Fex-treated animals (FIG. 12H). Furthermore, Fex-treatment increased the expression of "brown fat-like" signature genes, as well as increased respiratory capacity in the stromal vascular fraction from inguinal adipose tissue (FIGS. 12I and 12J). These results indicate that Fexaramine, unlike systemic FXR ligands, induces a distinct coordinated metabolic response, enhancing β-adrenergic signaling to promote lipolysis, mobilizing fatty acids for oxidation in BAT and the "browning" of cells in white adipose tissue.

Example 6

Fexaramine Improves Insulin Sensitivity and Glucose Tolerance

To probe the mechanism through which chronic Fex treatment improved glucose homeostasis, hyperinsulinemic-euglycemic clamp studies were performed. No differences in basal hepatic glucose production (HGP), glucose disposal rate (GDR), insulin-stimulated GDR (IS-GDR), free fatty acid (FFA) suppression, and fasting insulin levels were observed between weight-matched cohorts (generated by treating initially heavier mice (2-3 grams) with Fex (FIGS. 15A-15C, FIGS. 15I and 15K)). However, Fex-treated mice displayed a marked increase in insulin-mediated suppression of HGP compared to control DIO mice (FIG. 15D). Thus, while the attenuated weight gain can contribute to improved glucose clearance in Fex-treated mice, this improvement in hepatic glucose suppression indicates enhanced liver insulin sensitivity after Fex treatment.

Liver insulin resistance has been linked to obesity-induced hepatic steatosis (Cohen et al., *Science* 332:1519-1523, 2011). Histological examination of liver tissue from Fex-treated DIO mice revealed a reduction in lipid droplets compared to controls indicating amelioration of hepatic steatosis (FIG. 15E). Consistent with this histology, a marked decrease in hepatic triglycerides (such as a reduction of at least 10%, or at least 20%) and reduced hepatic expression of gluconeogenic and lipogenic genes (such as a reduction of at least 20%, or at least 30%, or at least 50%)

were seen after chronic Fex treatment (FIGS. 15F and 15G). Furthermore, decreased serum alanine aminotransferase (ALT) levels were measured in Fex-treated mice, indicating reduced HFD-induced liver damage (FIG. 5H). Thus, in DIO mice Fex promotes hepatic insulin sensitization, reduced steatosis, improved metabolic markers, decreased ALT and enhanced BAT activity.

Example 7

FXR Activity Screen for Determining $EC_{50}$ Determination

Cell Culture and Transfection:

CV-1 cells were grown in DMEM+10% charcoal stripped FCS. Cells were seeded into 384-well plates the day before transfection to give a confluency of 50-80% at transfection. A total of 0.8 grams DNA containing 0.32 micrograms pCMX-hFXRfl, 0.32 micrograms pCMX-hRXRfl, 0.1 micrograms pCMX.beta.Gal, 0.08 micrograms pGLFXRE reporter and 0.02 micrograms pCMX empty vector was transfected per well using FuGene transfection reagent according to the manufacturer's instructions (Roche). Cells were allowed to express protein for 48 hours followed by addition of compound.

Plasmids:

Human FXR full length and RXR full length was obtained from Ronald Evans' laboratory and PCR amplification of the hFXR cDNA and the hRXR cDNA was performed. The amplified cDNAs was cloned into the vector pCMX generating the plasmids pCMX-hFXRfl and pCMX-hRXRfl. Ensuing fusions were verified by sequencing. The pCMXMH2004 luciferase reporter contains multiple copies of the GAL4 DNA response element under a minimal eukaryotic promoter (Hollenberg and Evans, 1988). pCMX.beta.Gal was generated in the Evans laboratory, Salk Institute.

Compounds:

All compounds were dissolved in DMSO and diluted 1:1000 upon addition to the cells. Compounds were tested in quadruple in concentrations ranging from 0.001 to 100 µM. Cells were treated with compound for 24 hours followed by luciferase assay. Each compound was tested in at least two separate experiments.

Luciferase Assay:

Medium including test compound was aspirated and washed with PBS. 50 µL PBS including 1 mM $Mg^{2+}$ and $Ca^{2+}$ were then added to each well. The luciferase assay was performed using the LucLite kit according to the manufacturer's instructions (Packard Instruments). Light emission was quantified by counting on a Perkin Elmer Envision reader. To measure 3-galactosidase activity 25 µL supernatant from each transfection lysate was transferred to a new 384 microplate. Beta-galactosidase assays were performed in the microwell plates using a kit from Promega and read in a Perkin Elmer Envision reader. The beta-galactosidase data were used to normalize (transfection efficiency, cell growth etc.) the luciferase data.

Statistical Methods:

The activity of a compound is calculated as fold induction compared to an untreated sample. For each compound the efficacy (maximal activity) is given as a relative activity compared to Fexaramine, a FXR agonist. The $EC_{50}$ is the concentration giving 50% of maximal observed activity. $EC_{50}$ values were calculated via non-linear regression using GraphPad PRISM (GraphPad Software, San Diego, Calif.). The $EC_{50}$ values for exemplary compounds are given in Table 5.

TABLE 5 purity, yields and activity data of exemplary fexaramine analogs

| Code number | Purity ELSD/UV | yield (mg) | 1st RND $EC_{50}$ | 2nd RND $EC_{50}$ | Fex $EC_{50}$ |
| --- | --- | --- | --- | --- | --- |
| NSSK00004 | 99.9 | 10.8 | 237 nM | 266.2 nM | 31.9/36 nM |
| NSSK00017 | 96.2 | 5.8 | 756 nM | 500 nM | 31.9/36 nM |
| NSSK00035 | 96.2 | 8.6 | 3.3 µM | 4.49 µM | 31.9/36 nM |
| NSSK00005 | 98.7 | 9 | 1.82 µM | 2.1 µM | 31.9/36 nM |
| NSSK00018 | 98.6 | 6.8 | 380.5 nM | 415.2 nM | 31.9/36 nM |
| NSSK00006 | 100.0 | 17 | 273.1 nM | 242.8 nM | 31.9/36 nM |
| NSSK00019 | 100.0 | 7.7 | 923 nM | 554 nM | 53.7/39 nM |
| NSSK00036 | 99.7 | 4.3 | 18.6 uM | 4.9 uM | 53.7/39 nM |
| NSSK00008 | 99.1 | 10.9 | 2.0 uM | 1.4 uM | 53.7/39 nM |
| NSSK00007 | 99.9 | 13.9 | 473 nM | 169.4 nM | 53.7/39 nM |
| NSSK00020 | 98.3 | 6.1 | 743 nM | 463.7 nM | 53.7/39 nM |
| NSSK00009 | 97.2 | 4.7 | 3.3 uM | 4.9 uM | 53.7/39 nM |
| NSSK00022 | 97.8 | 3 | 3.2 uM | 2.7 uM | 56/52.5 nM |
| NSSK00037 | 98.2 | 2.8 | 1.9 mM | 4.8 mM | 56/52.5 nM |
| NSSK00001 | 95.2 | 11.5 | 68.6 nM | 55.8 nM | 56/52.5 nM |
| NSSK00002 | 97.4 | 8.3 | 96.8 nM | 65.9 nM | 56/52.5 nM |
| NSSK00033 | 100.0 | 10 | 169.5 nM | 254.4 nM | 56/52.5 nM |
| NSSK00034 | 100.0 | 6.1 | 2.2 uM | 2.68 uM | 56/52.5 nM |
| NSSK00012 | 99.7 | 7.7 | 1.2 uM | 1.2 uM | 39.9/34 nM |
| NSSK00011 | 100.0 | 18.5 | 288.7 nM | 379 nM | 39.9/34 nM |
| NSSK00014 | 95.8 | 12.2 | 345.6 nM | 475.1 nM | 39.9/34 nM |
| NSSK00013 | 99.9 | 9.6 | 390.3 nM | 429.8 nM | 39.9/34 nM |
| NSSK00016 | 99.9 | 15.5 | 284.9 nM | 377.4 nM | 39.9/34 nM |
| NSSK00026 | 98.1 | 12.3 | 587.2 nM | 910.5 nM | 39.9/34 nM |
| NSSK00025 | 94.4 | 3.1 | 150.4 nM | 167.7 nM | 36.4/33 nM |
| NSSK00024 (Salk 00024) | 99.5 | 15.8 | 66.8 nM | 58.5 nM | 36.4/33 nM |
| NSSK00024 (retested) | | | 83 nM | | 63 nM |

TABLE 5-continued purity, yields and activity data of exemplary fexaramine analogs

| Code number | Purity ELSD/UV | yield (mg) | 1st RND EC$_{50}$ | 2nd RND EC$_{50}$ | Fex EC$_{50}$ |
|---|---|---|---|---|---|
| NSSK00027 (Salk 00027) | 96.8 | 19.4 | 48.9 nM | 46.6 nM | 36.4/33 nM |
| NSSK00027 (retested) | | | 118 nM | | 63 nM |
| NSSK00030 | 95.8 | 9.2 | 655.5 nM | 375 nM | 36.4/33 nM |
| NSSK00029 | 99.6 | 17.9 | 605 nM | 510 nM | 36.4/33 nM |
| NSSK00031 | 96.5 | 18.6 | 366 nM | 249 nM | 36.4/33 nM |
| NSSK00032 | 94.6 | 5.4 | 2.6 uM | 2.9 uM | 30/36.5 nM |
| NSSK00038 | 98.4 | 16.1 | 1.37 uM | 1.9 uM | 30/36.5 nM |
| NSSK00039 | 99.5 | 14.8 | 1.55 uM | 870 nM | 30/36.5 nM |
| NSSK00041 | 99.3 | 13.3 | 1.1 uM | 1.2 uM | 30/36.5 nM |
| NSSK00066 | 97.8 | 7.3 | 5.4 uM | 8.5 uM | 30/36.5 nM |
| NSSK00075 | 97.8 | 6.4 | 155 uM | 653 uM | 30/36.5 nM |
| NSSK00046 | 99.2 | 14.3 | 639 nM | 518.9 nM | 25.9/39.3 nM |
| NSSK00047 | 99.8 | 4.5 | 355 nM | 403.1 nM | 25.9/39.3 nM |
| NSSK00073 | 98.5 | 3.6 | 119M | 145.9M | 25.9/39.3 nM |
| NSSK00056 | 99.4 | 15.7 | 752 nM | 720 nM | 25.9/39.3 nM |
| NSSK00058 | 99.5 | 8.1 | 1.2 uM | 1.5 uM | 25.9/39.3 nM |
| NSSK00057 | 100.0 | 16.6 | 606 nM | 795 nM | 25.9/39.3 nM |
| NSSK00061 | 96.8 | 18 | 9.6 uM | 10.2 uM | 34/29.1 nM |
| NSSK00049 | 97.7 | 14.5 | 2.8 uM | 3.5 uM | 34/29.1 nM |
| NSSK00051 | 99.5 | 10.1 | 1.1 uM | 5.0 uM | 34/29.1 nM |
| NSSK00067 | 99.3 | 16.3 | 0.4M | 0.2M | 34/29.1 nM |
| NSSK00042 | 98.6 | 4.3 | 134.7 nM | 620.3 nM | 34/29.1 nM |
| NSSK00059 | 95.3 | 5.8 | 1.57 uM | 1.3 uM | 34/29.1 nM |
| NSSK00062 | 93.7 | 13 | 925.7 nM | 925.7 nM | 43/43 nM |
| NSSK00043 | 95.8 | 5.1 | 80.9 nM | 80.7 nM | 43/43 nM |
| NSSK00044 | 96.3 | 13.8 | 149 nM | 144.5 nM | 43/43 nM |
| NSSK00074 | 95.1 | 5.8 | 4.3 mM | 4.3 mM | 43/43 nM |
| NSSK00052 | 98.7 | 15.6 | 696.6 nM | 696.6 nM | 43/43 nM |
| NSSK00045 | 98.3 | 14.7 | 334 nM | 334 nM | 43/43 nM |
| NSSK00064 | 94.4 | 6 | 4.6 uM | 3.3 uM | 117/120 nM |
| NSSK00072 | 96.1 | 12.7 | 1.1 uM | 2.2 uM | 117/120 nM |
| NSSK00053 | 98.8 | 18.6 | 529.4 nM | 539 nM | 117/120 nM |
| NSSK00068 | 94.2 | 2.3 | 5.7 uM | 7.4 uM | 117/120 nM |
| NSSK00060 | 98.4 | 4.2 | 8.5 uM | 11.2 uM | 117/120 nM |
| NSSK00054 | 98.5 | 22.6 | 508.5 nM | 457 nM | 117/120 nM |
| NSSK00055 | 99.1 | 16.4 | 931 nM | 1.4 uM | 32/35 nM |
| NSSK00048 | 98.4 | 14.2 | 382 nM | 357 nM | 32/35 nM |
| NSSK00063 | 96.4 | 4.5 | 3 uM | 1.9 uM | 32/35 nM |
| NSSK00050 | 96.3 | 17.6 | 1.7 uM | 2.1 uM | 32/35 nM |
| NSSK00065 | 94.2 | 10 | 3.3 uM | 6.0 uM | 32/35 nM |
| NSSK00084 | 100.0 | 3 | 3.6 uM | 4.7 uM | 32/35 nM |
| NSSK00087 | 94.3 | 2.2 | 1.2 mM | 4.1 mM | 292/287 nM |
| NSSK00096 (Salk 00096) | 99.6 | 16.1 | 340 nM | 375 nM | 292/287 nM |
| NSSK00096 (retested) | | | 220 nM | | 63 nM |
| NSSK00088 | 97.8 | 6.7 | 64 mM | 34 mM | 292/287 nM |
| NSSK00089 (Salk 00089) | 100.0 | 16 | 383 nM | 406 nM | 292/287 nM |
| NSSK00089 (retested) | | | 366 nM | | 63 nM |
| NSSK00091 | 95.2 | 9.5 | 801 nM | 628 nM | 292/287 nM |
| NSSK00097 | 99.7 | 3 | 866 nM | 726 nM | 292/287 nM |
| NSSK00095 | 97.6 | 4 | 1.4 uM | 1.5 uM | 51/56 nM |
| NSSK00094 | 100.0 | 3.6 | 786 nM | 865 nM | 51/56 nM |
| NSSK00099 | 100.0 | 7.2 | 2.1 uM | 2.1 uM | 51/56 nM |
| NSSK00098 | 100.0 | 9.9 | 655 nM | 670 nM | 51/56 nM |
| NSSK00100 | 100.0 | 10.1 | 1.4 uM | 1.8 uM | 51/56 nM |
| NSSK00092 | 95.7 | 5.7 | 3.4 uM | 5.5 uM | 51/56 nM |
| NSSK00093 | 99.8 | 10.4 | 459 nM | 511 nM | 81/88 nM |
| NSSK00101 | 99.9 | 11.7 | 5.9 uM | 15.1 uM | 81/88 nM |
| NSSK00077 (Deuterated Fexaramine) | 96.5 | 12.5 | 177 nM | 150 nM | 81/88 nM |
| Deuterated Fexaramine (retested) | | | 98 nM | | 63 nM |
| NSSK00078 | 96.2 | 4.7 | 698.2 nM | 673 nM | 81/88 nM |
| NSSK00080 | 99.6 | 21.4 | 623 nM | 610 nM | 81/88 nM |
| NSSK00082 | 99.6 | 3.8 | 5.1 uM | 6.1 uM | 81/88 nM |
| NSSK00081 | 98.3 | 6.1 | 22.8 uM | 71 uM | 77/100 nM |
| NSSK00079 | 97.3 | 19.6 | 513 nM | 605 nM | 77/100 nM |
| NSSK00086 | 99.8 | 17.6 | 371 nM | 1.6 uM | 97/320 nM |

TABLE 5-continued purity, yields and activity data of exemplary fexaramine analogs

| Code number | Purity ELSD/UV | yield (mg) | 1st RND $EC_{50}$ | 2nd RND $EC_{50}$ | Fex $EC_{50}$ |
|---|---|---|---|---|---|
| NSSK00113 | 99.3 | 6.1 | 652 nM | 2.7 uM | 97/320 nM |
| NSSK00070 | 98.9 | 3.7 | 1.7 uM | 1.7 uM | 77/100 nM |
| NSSK00102 | 98.8 | 2.2 | 252 nM | 328 nM | 77/100 nM |
| NSSK00107 | 97.5 | 11.6 | 450 nM | 861 nM | 77/100 nM |
| NSSK00109 | 92.9 | 10.5 | 190 nM | 316 nM | 77/100 nM |
| NSSK00110 (Salk 00110) | 96.9 | 4 | 60.1 nM | 174 nM | 97/320 nM |
| NSSK00110 (retested) | | | 46 nM | | 63 nM |
| NSSK00104 | 95.5 | 7.3 | 227 nM | 547 nM | 97/320 nM |
| NSSK00103 | 97.7 | 5.9 | 308 nM | 1.0 uM | 97/320 nM |
| NSSK00114 | 92.7 | 12.2 | 264 nM | 614 nM | 97/320 nM |
| NSSK00108 | 93.7 | 19.5 | not converged | 497 nM | 1/39 nM |
| NSSK00118 | 97.2 | 1.4 | 7 uM | 55 uM | 1/39 nM |
| NSSK00119 | 98.3 | 1.9 | 798 nM | 65 uM | 1/39 nM |
| NSSK00115 | 98.4 | 5.4 | 1.4 mM | 2.0 uM | 1/39 nM |
| NSSK00117 | 94.2 | 3.1 | 983 nM | 1.3 uM | 1/39 nM |
| NSSK00116 | 98.9 | 16.2 | not converged | 8.6 uM | 1/39 nM |

FIGS. 16-28 provide dose-response curves for exemplary compounds indicating the relative activity and $EC_{50}$ values of the compounds.

Example 8

Synthesis of NSSK00110

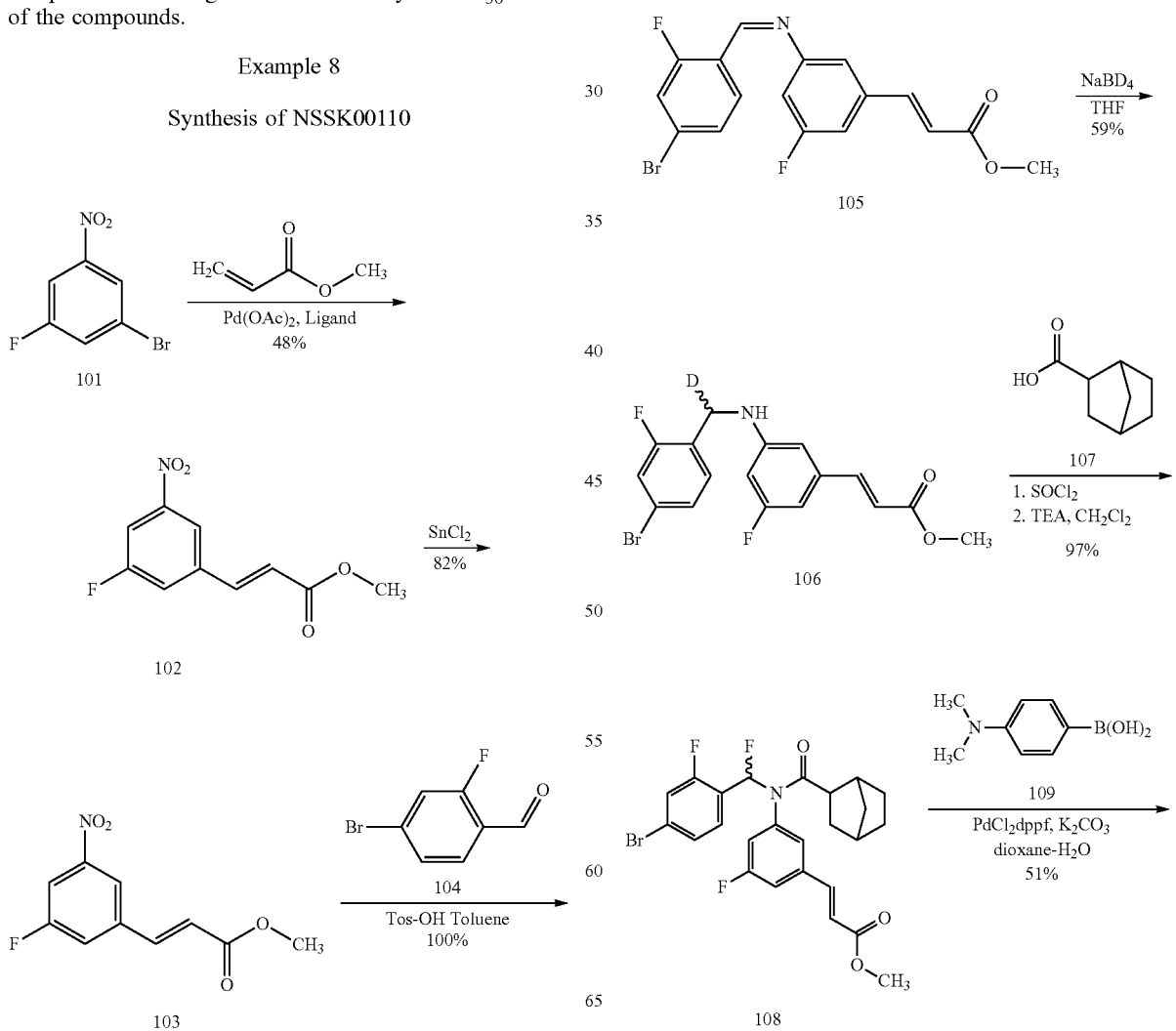

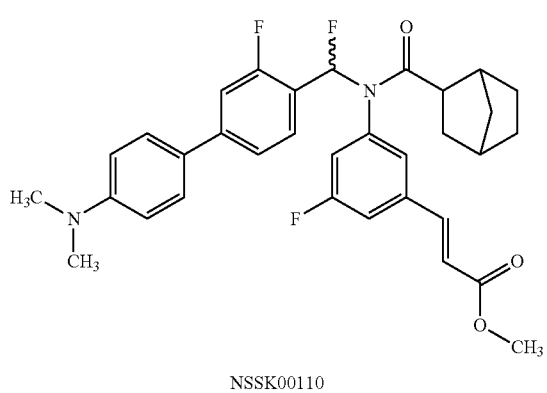

NSSK00110

8.1 General Procedure for Preparation of Compound 102

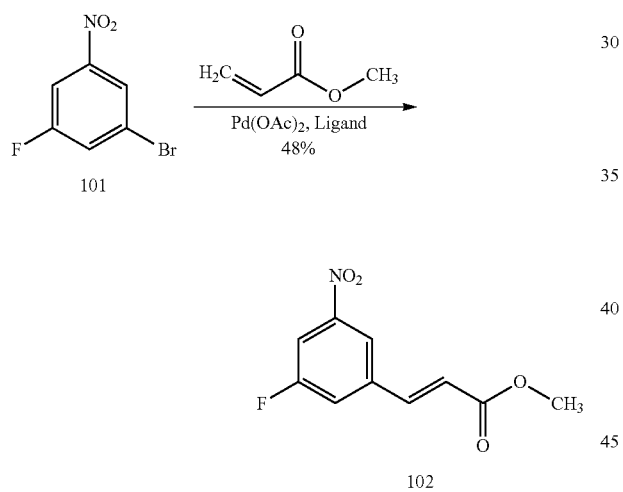

To the solution of compound 101 (13 g, 59.1 mmol) in triethylamine (TEA) (100 mL) was added methyl acrylate (54 mL, 591 mmol). Then the mixture was degassed with N₂ for 5 minutes, and Pd(OAc)₂ (2.6 g, 11.8 mmol) and tri(o-tolyl)phosphine (3.55 g, 11.8 mmol) were added and degassing was continued for another 5 minutes. The resulting solution was stirred at about 90 to 100° C. under N₂ overnight. The solution was extracted with EtOAc (3×200 mL) and the combined organic extracts were washed with brine (200 mL), dried over anhydrous Na₂SO₄, filtered, and concentrated in vacuo. The crude material was purified by Flash Chromatography (Petroleum ether/EtOAc=50:1) to give compound 102 (6.3 g, 48%) as a white solid.

$^1$H NMR: (CDCl₃, 400 MHz) δ 8.19 (s, 1H), 7.94 (dt, J=5.6 Hz, 2.4 Hz, 1H), 7.66 (d, J=16 Hz, 2H), 7.54 (dd, J=8.8 Hz, 2 Hz, 1H), 6.56 (d, J=16 Hz, 1H), 3.84 (s, 3H).

8.2 General Procedure for Preparation of Compound 103

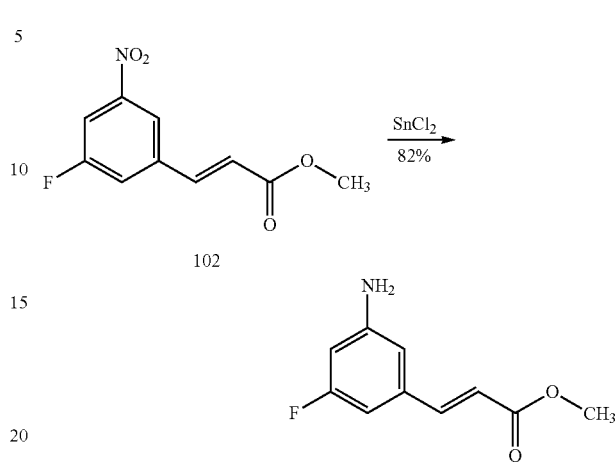

A mixture of compound 102 (9.8 g, 43.56 mmol) and SnCl₂.2H₂O (34 g, 148.09 mmol) in anhydrous EtOH (150 mL) was heated at 80° C. for 2.5 hours. Then the solvent was half removed under reduced pressure. The solution was poured into ice water and neutralized (pH=7) with saturated Na₂CO₃ solution, then filtered and the filtrate was extracted with ethyl acetate (3×200 mL). The combined organic extracts were washed with brine (200 mL), dried over anhydrous Na₂SO₄, filtered and concentrated in vacuo to give compound 103 (7 g, 82.%) as a yellow solid. The product was used directly in the next step without further purification.

$^1$H NMR: (CDCl₃, 400 MHz) δ7.52 (d, J=15.6 Hz, 1H), 6.62-6.50 (m, 2H), 6.40-6.33 (m, 2H), 3.86 (brs, 2H), 3.80 (s, 3H).

8.3 General Procedure for Preparation of Compound 105

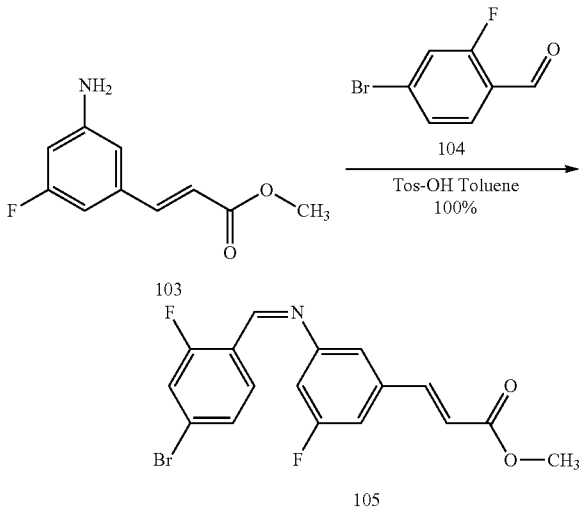

A 250 mL round-bottomed flask equipped with a Dean-Stark trap and reflux condenser was charged with compound 103 (2.5 g, 13 mmol), compound 104 (2.6 g, 13 mmol) and Tos-OH (300 mg, 1.7 mmol) in toluene (150 mL). The solution was refluxed at 130° C. for 48 hours until no more H₂O was collected in the Dean-Stark trap. The volatiles were removed under reduced pressure to yield compound 105 (5 g, 100%) as a red solid. The product was used directly in the next step without further purification.

TLC: Rf=0.5 (hexane/EtOAc:5/1)

8.4 General Procedure for Preparation of Compound 106

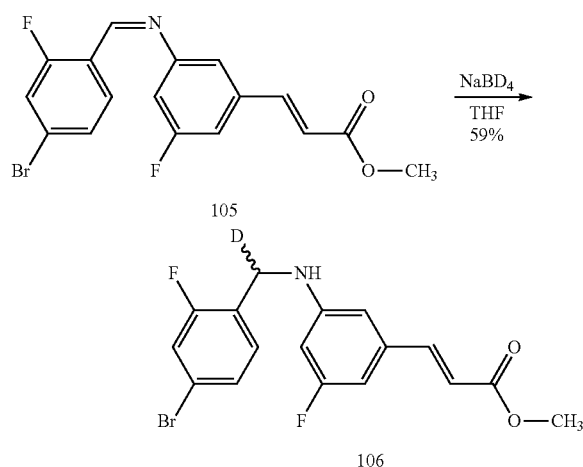

To a solution of compound 105 (5 g, 13 mmol) in THF (200 mL) was added NaBD₄ (1.1 g, 26 mmol). The mixture was stirred at room temperature for 16 hours. Then the mixture was quenched with saturated NH₄Cl solution, and the solution was extracted with ethyl acetate (3×100 mL) and the combined organic layers were washed with brine (100 mL), dried over anhydrous Na₂SO₄, filtered, and concentrated in vacuo. The material was purified by column chromatography on silica gel (petroleum ether/EtOAc=3/1) to give compound 106 (2.9 g, 59%) as a yellow solid.

¹H NMR: (DMSO-d₆, 400 MHz) δ7.54 (dd, J=9.6, 2 Hz, 1H), 7.48 (d, J=16 Hz, 1H), 7.42-7.37 (m, 1H), 7.36-7.30 (m, 1H), 6.77 (d, J=9.79 Hz, 1H), 6.73 (d, J=1.51 Hz, 1H), 6.65 (d, J=5.77 Hz, 1H), 6.58-6.51 (m, 1H), 6.42 (dt, J=11.67, 2.07 Hz, 1H), 4.35-4.28 (m, 1H), 3.71 (s, 3H).

8.5 General Procedure for Preparation of Compound 108

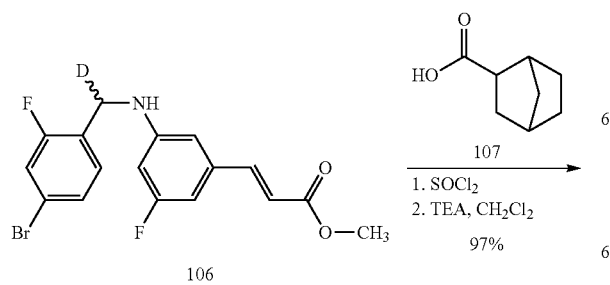

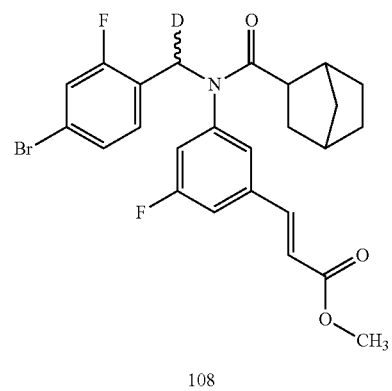

A solution of compound 107 (2.5 g, 14 mmol) in SOCl₂ (60 mL) was stirred at reflux for 3 hours under a nitrogen atmosphere. The mixture was concentrated in vacuo to give acid chloride as a yellow oil. To a solution of compound 106 (2.7 g, 7 mmol) in CH₂Cl₂ (60 mL) was added TEA (2.3 g, 21 mmol), followed by freshly-made acid chloride and DMAP (100 mg, 0.8 mmol). The mixture was stirred at room temperature for 16 hours. Then the mixture was washed with water (50 mL), the aqueous layer was extracted with CH₂Cl₂ (3×40 mL). The combined organic layers were washed with brine (50 mL), dried over anhydrous Na₂SO₄, filtered, and concentrated in vacuo. The material was purified by column chromatography on silica gel (petroleum ether/EtOAc=30/1) to give compound 108 (3.5 g, 97%) as a yellow solid.

¹H NMR: (DMSO-d₆, 400 MHz) δ7.68-7.52 (m, 3H), 7.44 (d, J=9.79 Hz, 1H), 7.37-7.22 (m, 3H), 6.76 (dd, J=16.19, 1.88 Hz, 1H), 5.04-4.70 (m, 1H), 3.72 (s, 3H), 2.78 (brs., 0.5H), 2.34 (brs., 0.5H), 2.25-2.05 (m, 1H), 1.89 (brs., 0.5H), 1.81-1.62 (m, 1H), 1.54 (brs., 0.5H), 1.48-1.15 (m, 5H), 1.15-1.01 (m, 2H), 0.98-0.62 (m, 1H).

8.6 General Procedure for Preparation of NSSK00110

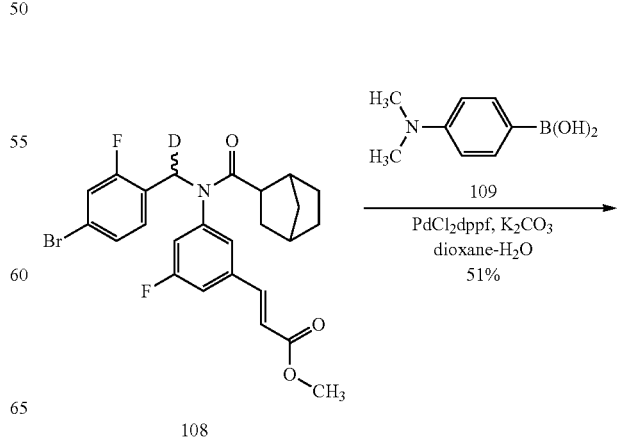

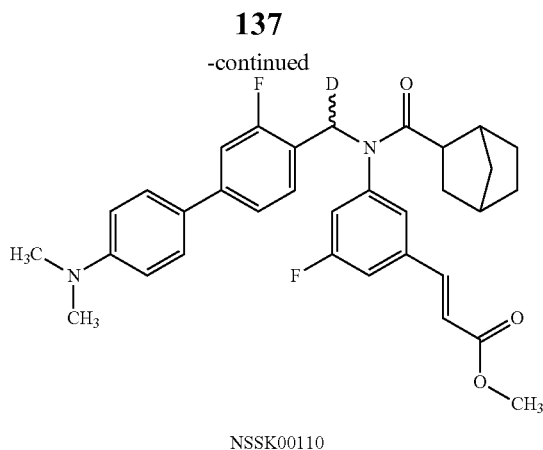

NSSK00110

To a solution of compound 108 (3.5 g, 6.9 mmol) in dioxane/H₂O (100 mL) was added K₂CO₃ (2.8 g, 17.3 mmol) and Pd(dppf)Cl₂ (500 mg, 0.7 mmol), followed by compound 109 (1.5 g, 9 mmol). The mixture was stirred at 80° C. for 4 hours under a nitrogen atmosphere. The mixture was washed with water (50 mL), the combined organic layers were washed with brine (10 mL), dried over anhydrous Na₂SO₄, filtered, and concentrated in vacuo. The material was purified by prep-HPLC to give compound NSSK00110 (1.9 g, 51%) as a yellow solid.

LCMS: MS (ESI) m/z 546 [M+H]⁺ (Purity: 100%)

¹H NMR: (DMSO-d₆, 400 MHz) δ7.68-7.57 (m, 2H), 7.56-7.48 (m, 3H), 7.34-7.28 (m, 2H), 7.25 (d, J=9.13 Hz, 1H), 6.78-6.70 (m, 3H), 5.00-4.84 (m, 1H), 3.71 (s, 3H), 2.92 (s, 6H), 2.80 (brs, 0.5H), 2.40 (brs, 0.5H), 2.27-2.09 (m, 2H), 1.91 (brs, 0.5H), 1.83-1.65 (m, 1H), 1.58 (brs, 0.5H), 1.49-1.19 (m, 3H), 1.07 (d, J=9.03 Hz, 2H), 0.94 (brs, 0.5H), 0.71 (brs, 0.5H).

Example 9

Synthesis of NSSK00024

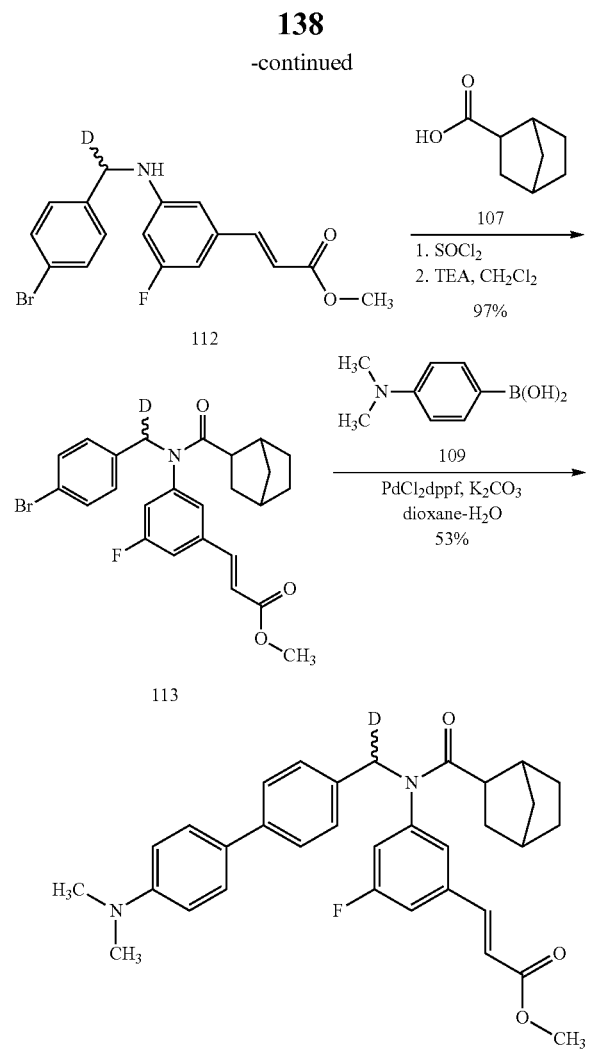

9.1 General Procedure for Preparation of Compound 111

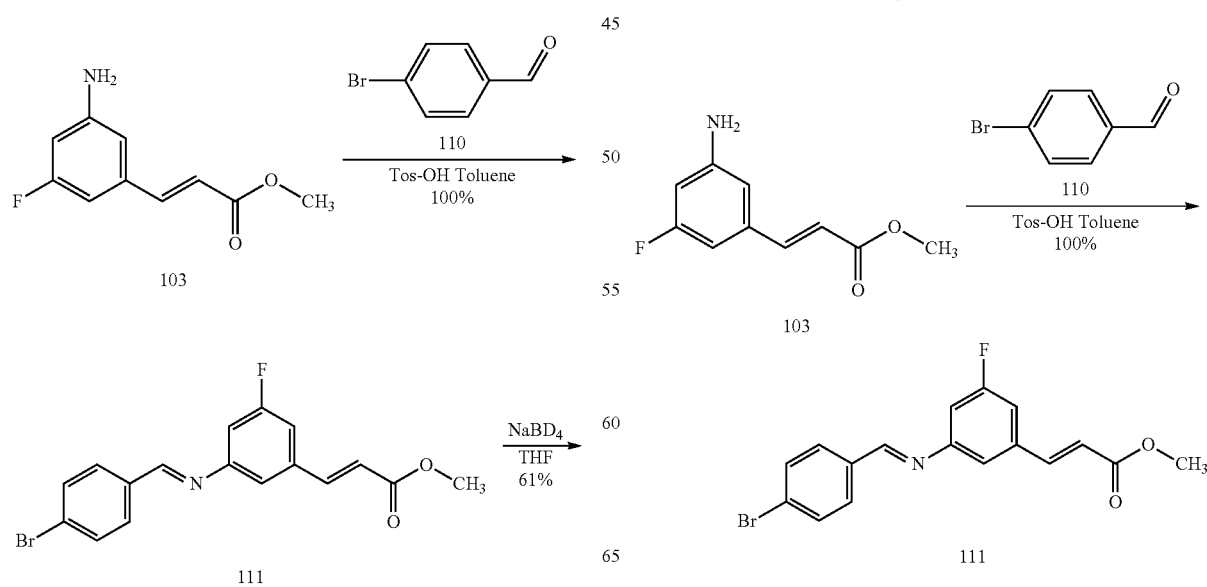

A 250 mL round-bottomed flask equipped with a Dean-Stark trap and reflux condenser was charged with compound 103 (5 g, 25 mmol), compound 110 (4.7 g, 25 mmol) and Tos-OH (600 mg, 3.4 mmol) in toluene (200 mL). The solution was refluxed at 130° C. for 48 hours until no more H₂O was collected in the Dean-Stark trap. The volatiles were removed under reduced pressure to yield compound 111 (9.7 g, 100%) as a red oil. The product was used directly in the next step without further purification.

TLC: Rf=0.5 (hexane/EtOAc:5/1)

9.2 General Procedure for Preparation of Compound 112

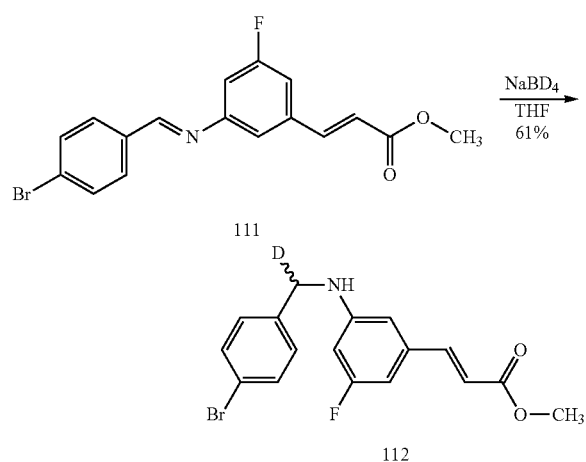

To a solution of compound 111 (9.7 g, 25 mmol) in THF (200 mL) was added NaBD₄ (2.2 g, 50 mmol), and the mixture was stirred at room temperature for 16 hours. Then the mixture was quenched with saturated NH₄Cl solution, and the solution was extracted with ethyl acetate (3×100 mL) and the combined organic layers were washed with brine (100 mL), dried over anhydrous Na₂SO₄, filtered, and concentrated in vacuo. The material was purified by column chromatography on silica gel (petroleum/EtOAc=3/1) to give compound 112 (5.6 g, 61%) as a yellow solid.

¹H NMR: (DMSO-d₆, 400 MHz) δ7.52 (d, J=6.4 Hz, 2H), 7.46 (d, J=16 Hz, 1H), 7.32 (d, J=8 Hz, 2H), 6.74-6.72 (m, 2H), 6.69 (s, 1H), 6.52 (d, J=16 Hz, 1H), 6.52 (d, J=12 Hz, 1H), 4.28-4.26 (m, 1H), 3.70 (s, 3H).

9.3 General Procedure for Preparation of Compound 113

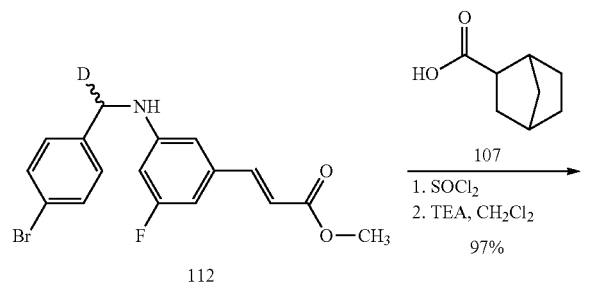

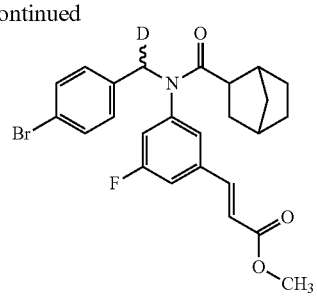

A solution of compound 107 (3.2 g, 20 mmol) in SOCl₂ (60 mL) was stirred at reflux for 3 hours under a nitrogen atmosphere. The mixture was concentrated in vacuo to give acid chloride as a yellow oil. To a solution of compound 112 (3 g, 8 mmol) in CH₂Cl₂ (60 mL) was added TEA (2.5 g, 24 mmol), followed by fleshly acid chloride and DMAP (100 mg, 0.8 mmol). The mixture was stirred at room temperature for 16 hours. Then the mixture was washed with water (50 mL), the aqueous layer was extracted with CH₂Cl₂ (3×40 mL). The combined organic layers were washed with brine (50 mL), dried over anhydrous Na₂SO₄, filtered, and concentrated in vacuo. The material was purified by column chromatography on silica gel (petroleum/EtOAc=30/1) to give compound 113 (3.5 g, 97%) as a yellow solid.

¹H NMR: (DMSO-d₆, 400 MHz) δ7.61-7.57 (m, 2H), 7.50-7.40 (m, 3H), 7.20-7.13 (m, 3H), 6.73 (d, J=16.4 Hz, 1H), 4.84-4.75 (m, 1H), 3.72 (s, 3H), 2.78 (brs, 0.5H), 2.34 (brs, 0.5H), 2.25-2.12 (m, 2H), 2.0-1.2 (m, 5H), 1.15-1.01 (m, 2H), 0.98-0.60 (m, 1H).

9.4 General Procedure for Preparation of NSSK00024

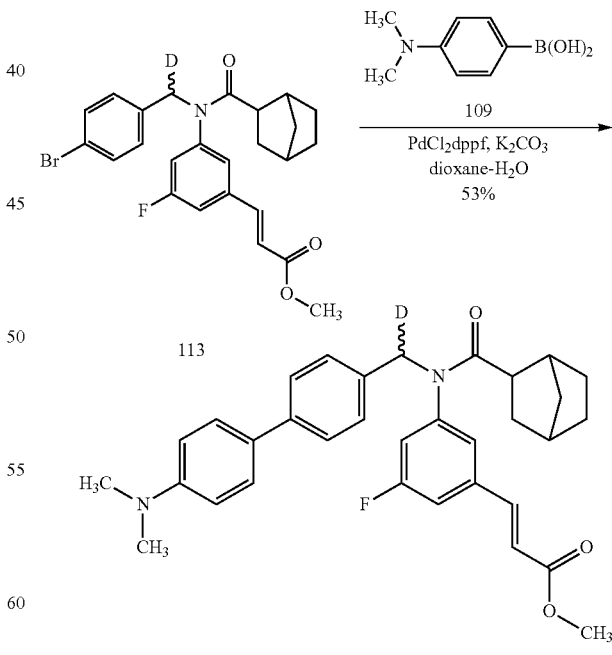

To a solution of compound 113 (3.5 g, 8.2 mmol) in dioxane/H₂O (100 mL) was added K₂CO₃ (3.4 g, 20.5 mmol) and Pd(dppf)Cl₂ (600 mg, 0.8 mmol), followed by compound 109 (1.7 g, 10.6 mmol). The mixture was stirred at 80° C. for 4 hours under a nitrogen atmosphere. The mixture was washed with water (50 mL), the combined organic layers were washed with brine (10 mL), dried over anhydrous $Na_2SO_4$, filtered, and concentrated in vacuo. The material was purified by prep-HPLC to give compound NSSK00024 (2.3 g, 53%) as a yellow solid.

LCMS: MS (ESI) m/z 528 [M+H]$^+$ (Purity: 99%)

$^1$H NMR: (DMSO-d$_6$, 400 MHz) δ7.61 (d, J=16.06 Hz, 2H), 7.48 (t, J=8.28 Hz, 5H), 7.19 (dd, J=8.78, 2.51 Hz, 3H), 6.79-6.69 (m, 3H), 5.00-4.77 (m, 1H), 3.71 (s, 3H), 2.91 (s, 6H), 2.86 (brs, 0.5H), 2.37 (brs., 0.5H), 2.30-2.09 (m, 2H), 1.92 (brs, 0.5H), 1.67-1.84 (m, 1H), 1.60 (brs, 0.5H), 1.52-1.19 (m, 3H), 1.08 (d, J=9.29 Hz, 2H), 0.95 (brs, 0.5H), 0.72 (brs, 0.5H).

Example 10

Synthesis of NSSK000027

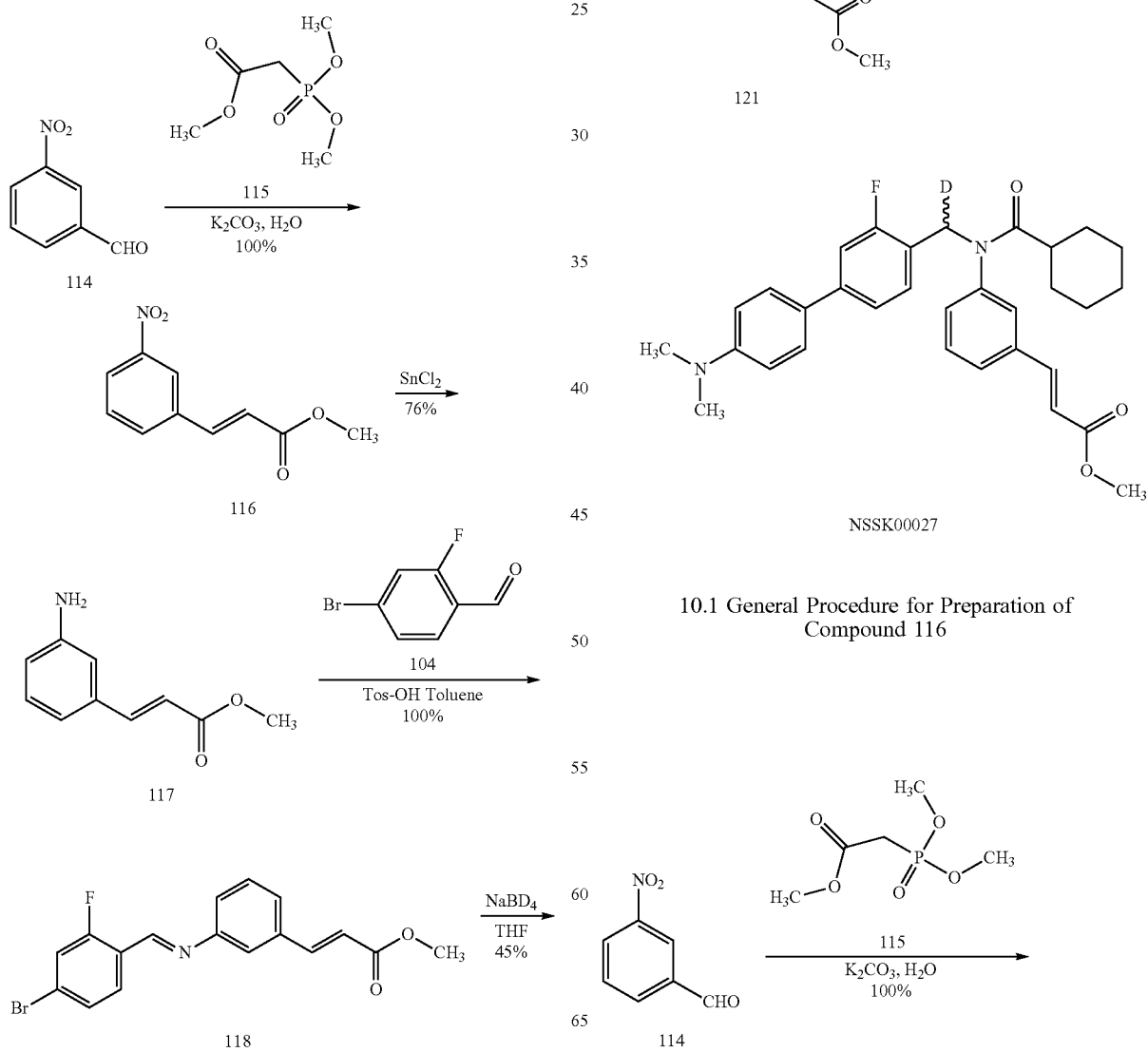

10.1 General Procedure for Preparation of Compound 116

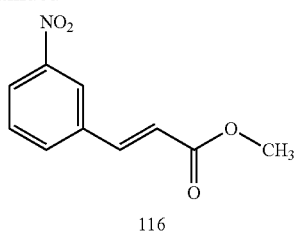

116

To a mixture of compound 115 (82.4 g, 452 mmol) and K₂CO₃ (96 g, 696 mmol) in H₂O (160 mL) was added compound 114 (52.4 g, 348 mmol). The reaction was stirred at room temperature for 1 hour. Then the solution was filtered and the filter cake was washed with 1 N HCl and water, and the solid was concentrated to give compound 116 (85 g, crude) as a white solid. The product was used directly in the next step without further purification.

¹H NMR: H20619-001-1Q1 (DMSO-d₆, 400 MHz) δ8.56 (s, 1H), 8.25-8.19 (m, 2H), 7.80 (d, J=16 Hz, 1H), 7.71 (t, J=8 Hz, 1H), 6.86 (d, J=16 Hz, 1H), 3.75 (s, 3H).

10.2 General Procedure for Preparation of Compound 117

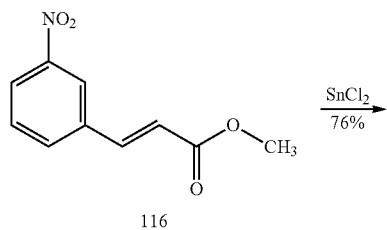

A mixture of compound 116 (50 g, 241.5 mmol) and SnCl₂.2H₂O (186.3 g, 820.7 mmol) in anhydrous EtOH (600 mL) was heated at 80° C. for 2.5 hours. Then the solvent was half removed under reduced pressure. Then the solution was poured into ice water and neutralized (pH=7) with saturated Na₂CO₃ solution, and the solution was extracted with ethyl acetate (3×500 mL) and the combined organic layers were washed with brine (500 mL), dried over anhydrous Na₂SO₄, filtered, and concentrated in vacuo to give compound 117 (32.3 g, 75.7%) as a yellow solid. The product was used directly in the next step without further purification.

¹H NMR: (CDCl₃, 400 MHz) δ7.60 (d, J=15.6 Hz, 1H), 7.17 (t, J=7.6 Hz, 1H), 6.93 (d, J=7.6 Hz, 1H), 6.82 (s, 1H), 6.71 (dd, J=8 Hz, 1.5 Hz, 1H), 6.38 (d, J=15.6 Hz, 1H), 3.80 (s, 3H), 3.76 (brs, 2H).

10.3 General Procedure for Preparation of Compound 118

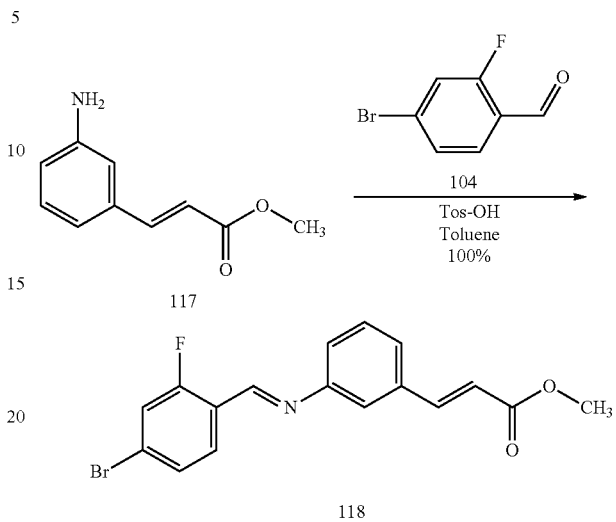

A 250 mL round-bottomed flask equipped with a Dean-Stark trap and reflux condenser was charged with compound 117 (5 g, 28.25 mmol), compound 104 (5.75 g, 28.25 mmol) and Tos-OH (600 mg, 0.58 mmol) in toluene (100 mL). The solution was refluxed at 110° C. for 24 hours until no more H₂O was collected in the Dean-Stark trap. The volatiles were removed under reduced pressure to yield compound 118 (10.2 g, 100%) as red oil, which was sent to next step directly without further purification.

TLC: Rf=0.8 (Petroleum ether/EtOAc=3/1)

10.4 General Procedure for Preparation of Compound 119

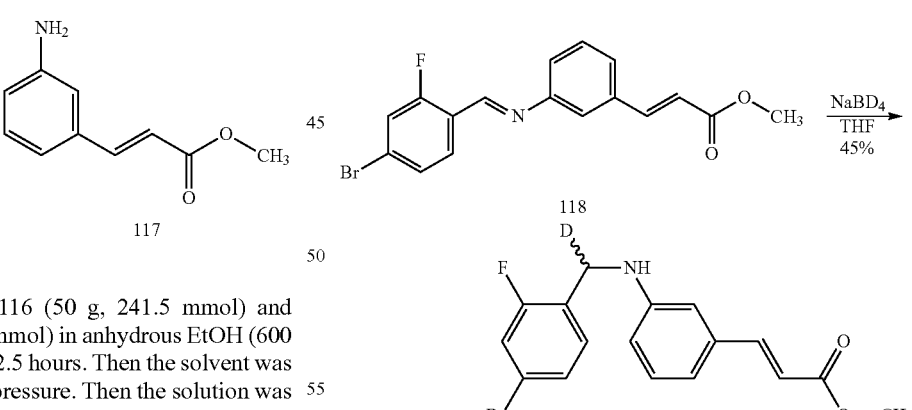

To a solution of compound 118 (10.2 g, 28.25 mmol) in THF (135 mL) was added NaBD₄ (2.37 g, 56.5 mmol), and the mixture was stirred at room temperature for 16 hours. The mixture was quenched with saturated NH₄Cl solution, and the solution was extracted with ethyl acetate (3×120 mL) and the combined organic layers were washed with brine (120 mL), dried over anhydrous Na₂SO₄, filtered, and concentrated in vacuo. The material was purified by Flash Chromatography (Petroleum ether:EtOAc=30:1) to give compound 119 (4.6 g, 45.1%) as a yellow solid. $^1$H NMR: (DMSO-d$_6$, 400 MHz) δ7.54-7.48 (m, 2H), 7.37-7.33 (m, 2H), 7.11 (t, J=7.6 Hz, 1H), 6.89-6.86 (m, 2H), 6.65 (dd, J=8 Hz, 1.6 Hz, 1H), 6.47 (d, J=16 Hz, 1H), 6.35 (d, J=6.4 Hz, 1H).

10.5 General Procedure for Preparation of Compound 121

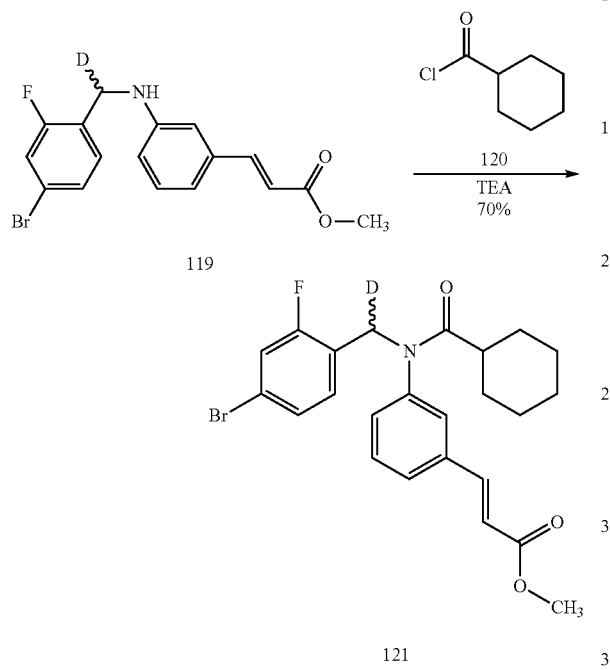

To a solution of compound 119 (5.6 g, 15.33 mmol) in CH$_2$Cl$_2$ (130 mL) was added compound 120 (4.5 g, 30.67 mmol), TEA (4.65 g, 45.99 mmol) and DMAP (280 mg, 2.30 mmol). The mixture was stirred at room temperature for 1 hour. Then the mixture was washed with water (3×100 mL), the combined organic layers were washed with brine (100 mL), dried over anhydrous Na$_2$SO$_4$, filtered, and concentrated in vacuo, then purified by pre-HPLC to give compound 121 (5.7 g, 70%) as a white solid.

$^1$H NMR: (DMSO-d$_6$, 400 MHz) δ7.71-7.61 (m, 3H), 7.44-7.40 (m, 2H), 7.35 (dd, J=8 Hz, 2 Hz, 1H), 7.26 (t, J=8 Hz, 1H), 7.19 (d, J=8 Hz, 1H), 4.84 (br. s., 1H) 3.72 (s, 3H), 2.20-2.08 (br. s., 1H), 1.69-1.55 (m, 4H), 1.50-1.47 (m, 1H) 1.42-1.30 (m, 2H), 1.15-1.03 (m, 1H), 0.94-0.80 (m, 2H).

10.6 General Procedure for Preparation of NSSK00027

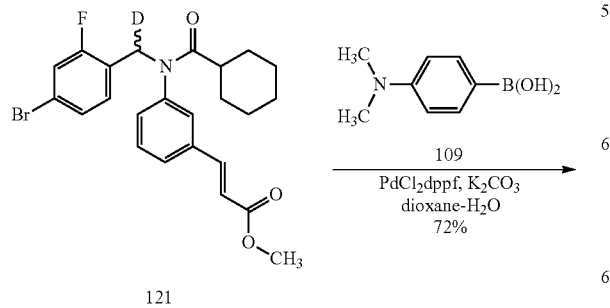

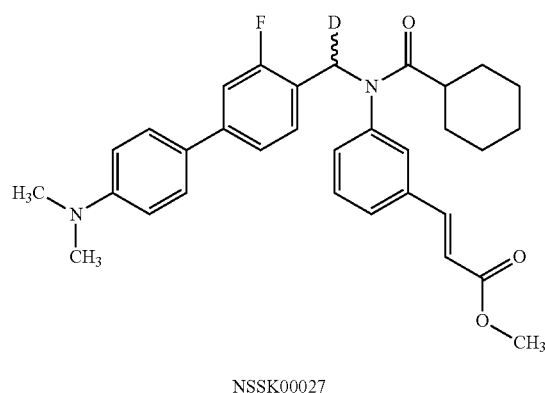

NSSK00027

To a solution of compound 121 (2.3 g, 4.84 mmol) in dioxane/H$_2$O (70 mL) was added K$_2$CO$_3$ (2 g, 14.52 mmol) and Pd(dppf)Cl$_2$ (357 mg, 0.48 mmol), followed by compound 109 (1.04 g, 6.29 mmol). The mixture was stirred at 80° C. for 4 hours under a nitrogen atmosphere. The reaction mixture was filtered and the filtrate was extracted with ethyl acetate (3×70 mL) and the combined organic layers were washed with brine (70 mL), dried over anhydrous Na$_2$SO$_4$, filtered, and concentrated in vacuo. The material was purified by Flash Chromatography (Petroleum ether:EtOAc=8:1) to give crude product. The crude material was purified by prep-HPLC to give NSSK00027 (1.8 g, 72%) as a green solid.

LCMS: MS (ESI) m/z=516 [M+H]$^+$ (Purity: 100%)

$^1$H NMR: (DMSO-d$_6$, 400 MHz) δ7.72-7.61 (m, 3H), 7.52 (d, J=8.8 Hz, 2H), 7.45-7.36 (m, 2H), 7.33-7.26 (m, 2H), 7.20 (d, J=7.9 Hz, 1H) 6.76 (d, J=8.8 Hz, 2H), 6.67 (d, J=16 Hz, 1H), 4.88 (brs, 1H), 3.71 (s, 3H), 2.93 (s, 6H), 2.22-2.10 (m, 1H) 1.71-1.57 (m, 4H), 1.54-1.46 (m, 1H) 1.45-1.33 (m, 2H), 1.16-1.06 (m, 1H), 0.96-0.80 (m, 2H).

Example 11

Synthesis of NSSK00089

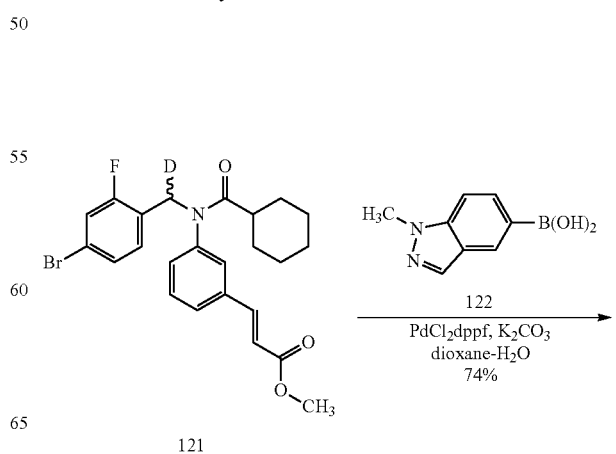

147

-continued

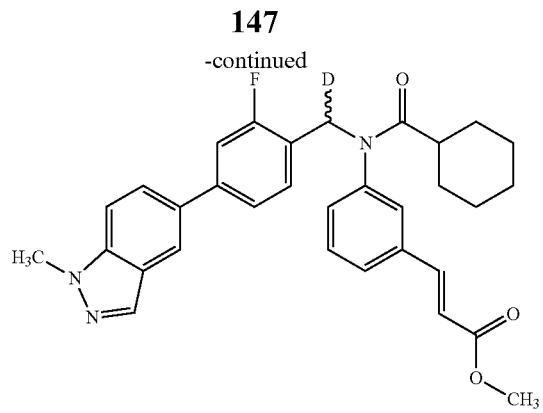

NSSK00089

To a solution of compound 121 (2.3 g, 4.84 mmol) in dioxane/H₂O (70 mL) was added K₂CO₃ (2 g, 14.52 mmol) and Pd(dppf)Cl₂ (357 mg, 0.48 mmol), followed by compound 122 (1.1 g, 6.29 mmol). The mixture was stirred at 80° C. for 4 hours under a nitrogen atmosphere. The reaction mixture was filtered and the filtrate was extracted with ethyl acetate (3×70 mL) and the combined organic layers were washed with brine (70 mL), dried over anhydrous Na₂SO₄, filtered, and concentrated in vacuo. The material was purified by Flash Chromatography (Petroleum ether:EtOAc=8:1) to give crude product. The crude material was purified by prep-HPLC to give NSSK00089 (1.9 g, 74%) as a white solid.

LCMS: MS (ESI) m/z=527 [M+H]⁺ (Purity: 99%)

¹H NMR: (DMSO-d₆, 400 MHz) δ8.06 (d, J=17.2 Hz, 2H), 7.76-7.59 (m, 5H), 7.53-7.35 (m, 4H), 7.24 (d, J=8 Hz, 1H), 6.67 (d, J=16 Hz, 1H), 4.93 (br. s., 1H) 4.06 (s, 3H), 3.70 (s, 3H), 2.23-2.12 (m, 1H), 1.74-1.56 (m, 4H), 1.54-1.34 (m, 3H), 1.18-1.03 (m, 1H), 0.98-0.79 (m, 2H).

Example 12

Synthesis of NSSK00096

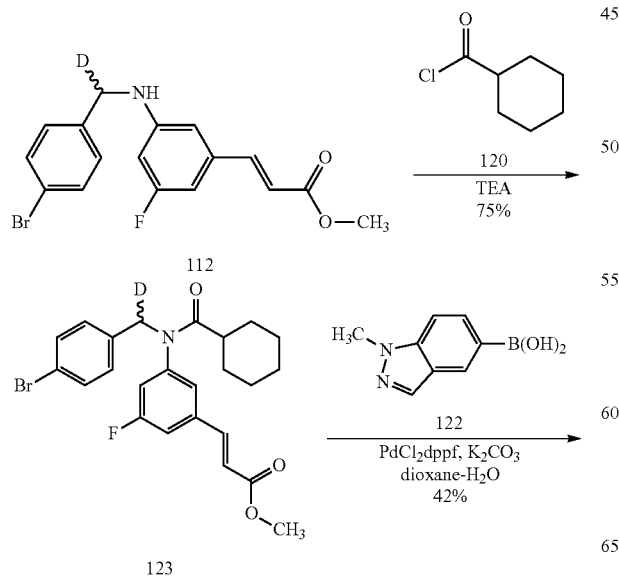

148

-continued

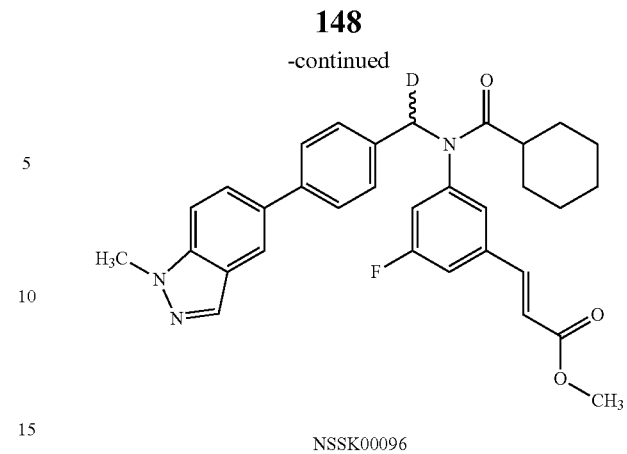

NSSK00096

12.1 General Procedure for Preparation of Compound 123

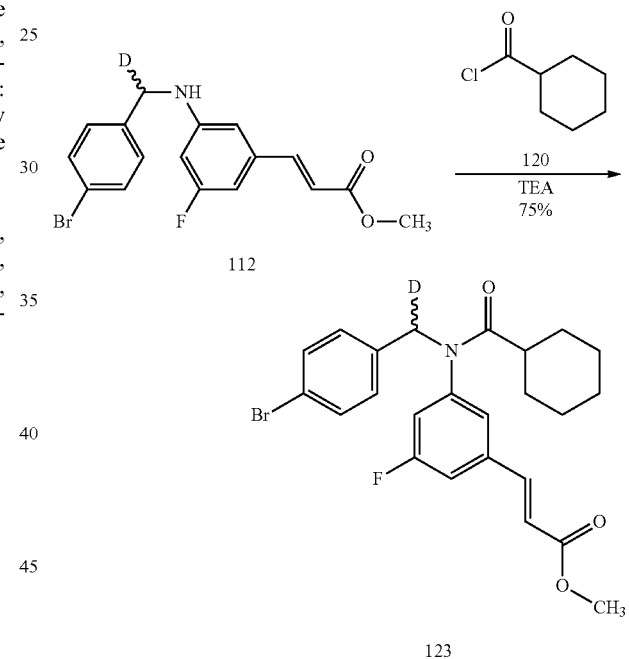

To a solution of compound 112 (2.5 g, 6.8 mmol) in CH₂Cl₂ (60 mL) was added TEA (2 g, 20.4 mmol), followed by compound 120 (2 g, 13.7 mmol), and DMAP (248 mg, 2 mmol). The mixture was stirred at room temperature for 3 hours. Then the mixture was washed with water (50 mL), the aqueous layer was extracted with CH₂Cl₂ (3×40 mL). The combined organic layers were washed with brine (50 mL), dried over anhydrous Na₂SO₄, filtered, and concentrated in vacuo. The material was purified by column chromatography on silica gel (petroleum/EtOAc=30/1) to give compound 123 (2.4 g, 75%) as a yellow solid.

¹H NMR: (DMSO-d₆, 400 MHz) δ7.66-7.58 (m, 2H), 7.47-7.45 (m, 3H), 7.18-7.12 (m, 3H), 6.74 (d, J=15.6 Hz, 1H), 4.81 (s., 1H), 3.72 (s, 3H), 2.20 (brs, 1H), 1.71-1.59 (m, 4H), 1.52-1.49 (m, 1H), 1.42-1.15 (m, 2H), 1.12-1.09 (m, 1H), 0.94-0.91 (m, 2H).

12.2 General Procedure for Preparation of NSSK00096

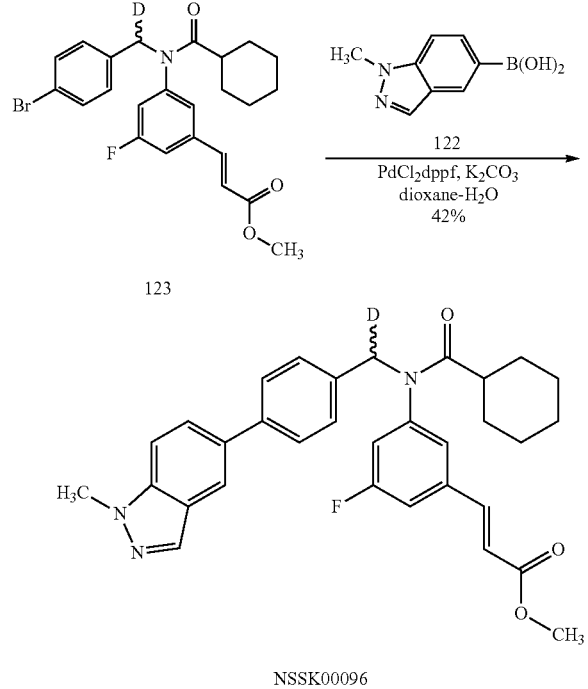

NSSK00096

To a solution of compound 123 (2.4 g, 5 mmol) in dioxane/H₂O (50 mL) was added K₂CO₃ (2 g, 12.5 mmol) and Pd(dppf)Cl₂ (366 mg, 0.5 mmol), followed by compound 122 (1.4 g, 6.5 mmol). The mixture was stirred at 80° C. for 4 hours under a nitrogen atmosphere. The mixture was washed with water (50 mL), the combined organic layers were washed with brine (10 mL), dried over anhydrous Na₂SO₄, filtered, and concentrated in vacuo. The material was purified by prep-HPLC to give compound NSSK00096 (1.1 g, 42%) as a yellow solid.

LCMS: MS (ESI) m/z=527 [M+H]⁺ (Purity: 100%)

¹H NMR: (DMSO-d₆, 400 MHz) δ8.07 (s, 1H), 7.97 (d, J=0.98 Hz, 1H), 7.72-7.58 (m, 6H), 7.50 (s, 1H), 7.26 (d, J=8.07 Hz, 2H), 7.20 (dd, J=9.41, 1.83 Hz, 1H), 6.73 (d, J=15.90 Hz, 1H), 4.90 (s., 1H), 4.05 (s, 3H), 3.71 (s, 3H), 2.24 (brs, 1H), 1.73 (d, J=11.74 Hz, 2H), 1.63 (d, J=12.72 Hz, 2H), 1.52 (d, J=11.74 Hz, 1H), 1.48-1.33 (m, 2H), 1.12 (q, J=12.72 Hz, 1H), 0.96 (brs, 2H).

Example 13

Synthesis of NSSK00077

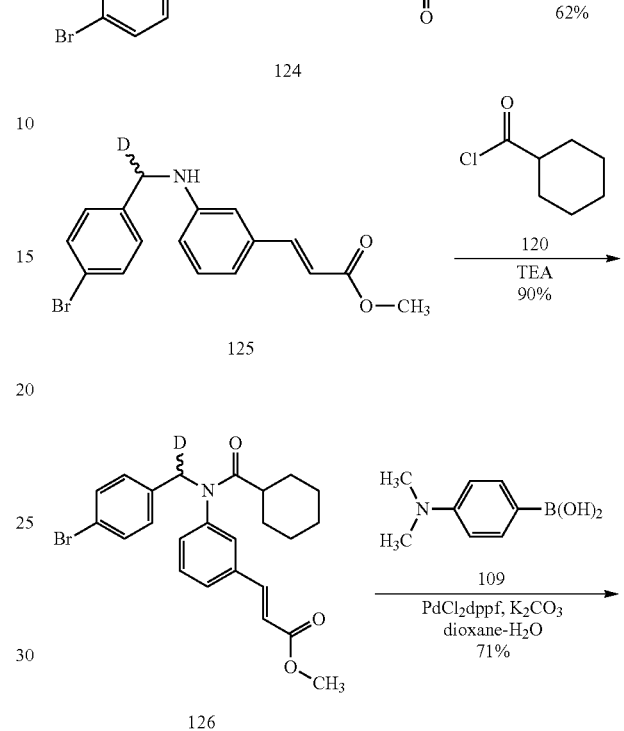

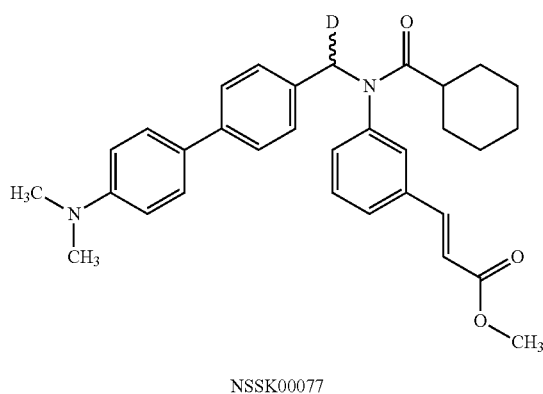

NSSK00077

13.1 General Procedure for Preparation of Compound 124

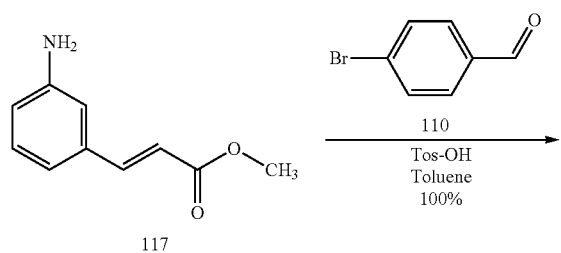

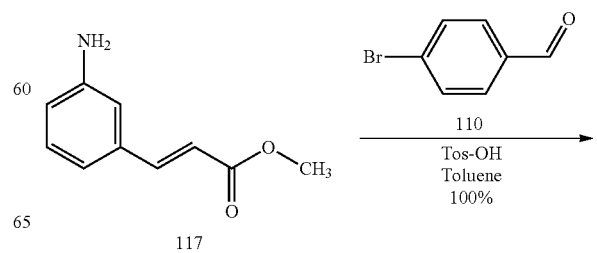

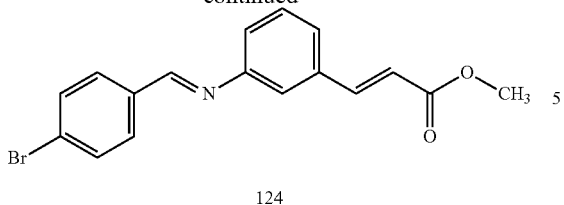

124

A 250 mL round-bottomed flask equipped with a Dean-Stark trap and reflux condenser was charged with compound 117 (3 g, 16.9 mmol), compound 110 (3.09 g, 16.9 mmol) and Tos-OH (348 mg, 2.02 mmol) in toluene (100 mL). The solution was refluxed at 110° C. for 24 hours until no more H₂O was collected in the Dean-Stark trap. The volatiles were removed under reduced pressure to yield compound 124 (5.8 g, 100%) as red oil, which was sent to next step directly without further purification.

TLC: Rf=0.8 (Petroleum ether/EtOAc=3/1)

13.2 General Procedure for Preparation of Compound 125

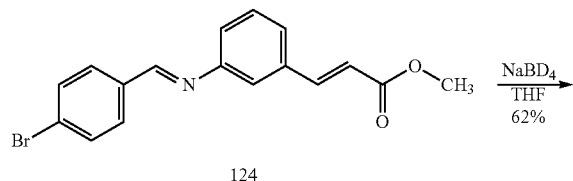

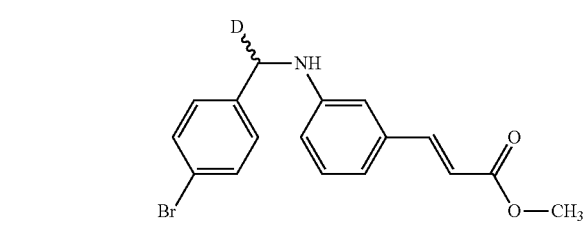

125

To a solution of compound 124 (5.8 g, 16.9 mmol) in THF (100 mL) was added NaBD₄ (1.42 g, 33.8 mmol). The mixture was stirred at room temperature for 16 hours. Then the mixture was quenched with saturated NH₄Cl solution, and the solution was extracted with ethyl acetate (3×100 mL) and the combined organic layers were washed with brine (100 mL), dried over anhydrous Na₂SO₄, filtered, and concentrated in vacuo. The material was purified by Flash Chromatography (Petroleum ether:EtOAc=30:1) to give compound 125 (3.6 g, 62.1%) as a yellow solid.

¹H NMR: (DMSO-d₆, 400 MHz) δ7.55-7.45 (m, 3H), 7.32 (d, J=8.4 Hz, 2H), 7.09 (t, J=7.6 Hz, 1H), 6.88-6.82 (m, 2H), 6.63 (d, J=8 Hz, 1H), 6.47-6.40 (m, 2H), 4.26 (d, J=6.36 Hz, 1H), 3.70 (s, 3H).

13.3 General Procedure for Preparation of Compound 126

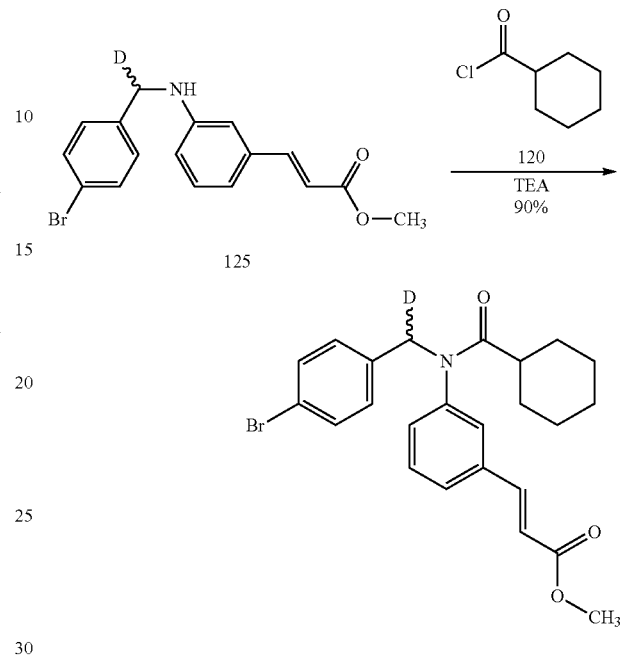

To a solution of compound 125 (3.6 g, 10.4 mmol) in CH₂Cl₂ (100 mL) was added compound 120 (3.16 g, 21.49 mmol), TEA (3.27 g, 32.34 mmol) and DMAP (197 mg, 1.62 mmol). The mixture was stirred at room temperature for 1 hour. Then the mixture was washed with water (3×100 mL), the combined organic layers were washed with brine (100 mL), dried over anhydrous Na₂SO₄, filtered, and concentrated in vacuo, then purified by pre-HPLC to give compound 126 (4.3 g, 90%) as a white solid.

¹H NMR: (DMSO-d₆, 400 MHz) δ7.73-7.60 (m, 3H), 7.50-7.38 (m, 3H), 7.17-7.08 (m, 3H), 6.68 (d, J=16.4 Hz, 1H), 4.80 (br. s., 1H), 3.72 (s, 3H), 2.20-2.08 (m, 1H), 1.72-1.56 (m, 4H), 1.54-1.46 (m, 1H), 1.45-1.31 (m, 2H), 1.17-1.04 (m, 1H) 0.95-0.82 (m, 2H).

13.4 General Procedure for Preparation of NSSK00077

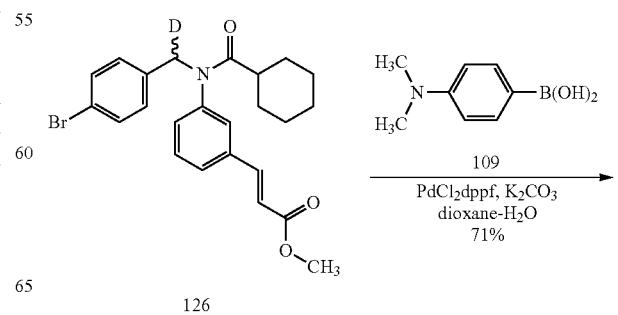

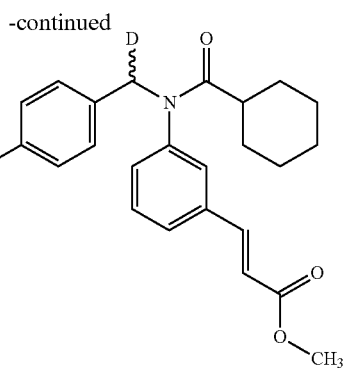

NSSK00077

To a solution of compound 126 (2.5 g, 5.47 mmol) in dioxane/H₂O (70 mL) was added K₂CO₃ (2.27 g, 16.41 mmol) and Pd(dppf)Cl₂ (412 mg, 0.55 mmol), followed by compound 109 (1.18 g, 7.12 mmol). The mixture was stirred at 80° C. for 4 hours under a nitrogen atmosphere. The mixture was then filtered and the filtrate was extracted with ethyl acetate (3×70 mL) and the combined organic layers were washed with brine (70 mL), dried over anhydrous Na₂SO₄, filtered, and concentrated in vacuo. The material was purified by Flash Chromatography (Petroleum ether: EtOAc=8:1) to give crude product. The crude material was purified by prep-HPLC to give NSSK00077 (1.9 g, 71%) as a yellow solid.

LCMS: MS (ESI) m/z=498 [M+H]⁺ (Purity: 99%)
¹H NMR: H20619-033-1H5 (DMSO-d₆, 400 MHz) δ7.72-7.59 (m, 3H), 7.53-7.44 (m, 4H), 7.41 (t, J=8 Hz, 1H), 7.16 (d, J=7.6 Hz, 2H), 6.77 (d, J=8.8 Hz, 2H), 6.66 (d, J=15.6 Hz, 1H), 4.84 (br. s., 1H), 3.71 (s, 3H), 2.91 (s, 6H), 2.24-2.12 (m., 1H), 1.73-1.57 (m, 4H), 1.55-1.34 (m, 3H), 1.17-1.04 (m, 1H), 0.97-0.79 (m, 2H).

Example 14

Effect of Fexaramine and Selectively-Deuterated Fexaramine Analogs In Vivo

An in vivo study of fexaramine and selectively-deuterated fexaramine compounds (FIG. 29A) was performed. Briefly, ob/ob mice were treated daily with vehicle, Fex, or deuterated analogs (50 mg kg⁻¹) by oral (PO) gavage for 2 weeks. Subsequently, body weight, body temperature, fasting blood glucose and insulin levels, insulin secretion, and GLP1 section were measured, and glucose tolerance tests (GTTs) performed.

As shown in FIGS. 29B-29C, treatment with fexaramine or a fexaramine analog treatment (2 weeks at 50 mg/kg) of ob/ob mice do not affect body weight, but did increase core body temperature. Fex-D treated was more effective at increasing core body temperature than Fex. Deuterated SALK110 (NSSK00110) showed superior activation compared to fexaramine.

As shown in FIG. 29D, while two weeks treatment with fexaramine does not significantly affect fasting blood glucose levels, FEX-D and SALK110 (NSSK00110) treatment significantly reduced fasting blood glucose levels.

Figure 29E:
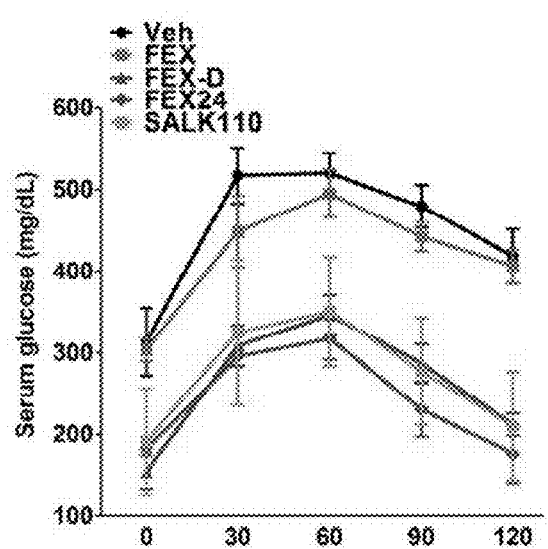

As shown in FIG. 29E, GTTs performed after two weeks of treatment with the indicated analogs demonstrated improved glucose tolerance with the deuterated analogs, but not with fexaramine, demonstrating superior activity with the deuterated analogs.

Figure 29F:
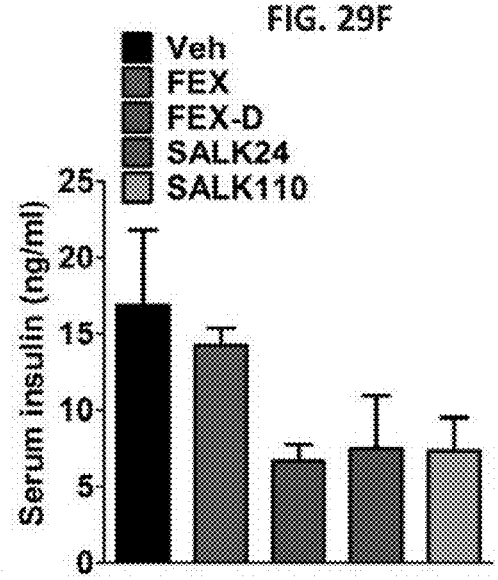

As shown in FIG. 29F, the deuterated fexaramine analogs were more active than fexaramine at lowering fasting insulin levels.

Figure 29G:
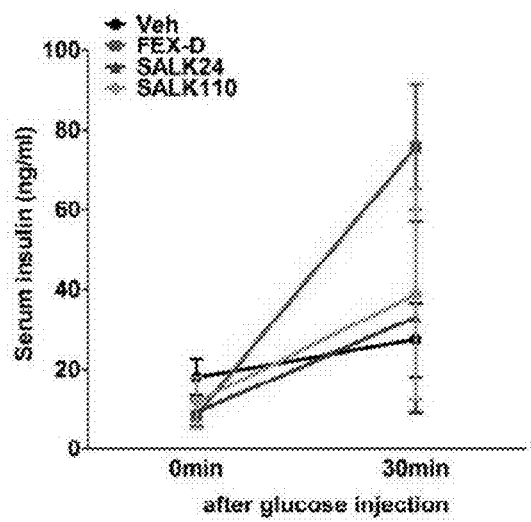

As shown in FIG. 29G, treatment with the deuterated fexaramine analogs increased insulin secretion in ob/ob mice in response to a glucose challenge, as measured during the GTT.

Figure 29H:
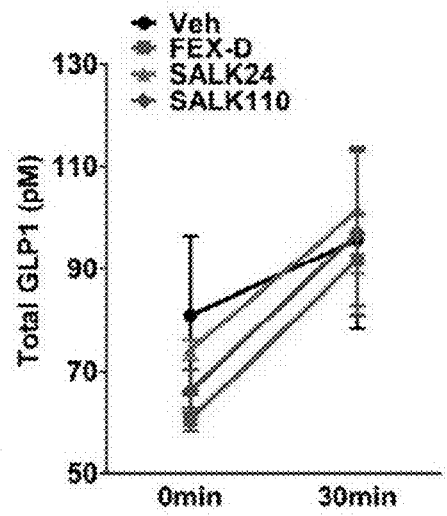

As shown in FIG. 29H, GLP1 secretion in ob/ob mice in response to a glucose challenge in mice treated with the deuterated fexaramine analogs, as measured during the GTT, increased GLP1 secretion which leads to increased insulin secretion.

Example 15

Orally Delivered Fexaramine Analogs are Intestinal-Specific FXR Agonists

Mice were treated daily with vehicle, FEX-D, or SALK110 (NSSK00110, 50 mg kg⁻¹) (see FIG. 29A) by oral (PO) gavage for 14 days, with tissues collected 1 hour after the final treatment. Gene expression changes in the liver were measured by QPCR.

As shown in FIG. 30, FEX-D and SALK110 (NSSK00110) fail to alter the expression of the canonical FXR target gene SHP and BSEP in the liver, indicating that both analogs are intestinal-specific (they do not enter the circulation when delivered orally). However, activation of FXR in the intestine induces the paracrine factor Fgf15, as demonstrated by reduced levels of Fgf15 target genes in the liver.

Example 16

Co-Upregulated Genes in Islets by Chronic Treatment of Fexaramine Analogs

Pancreatic islets were isolated from ob/ob mice after daily treatment by oral gavage with fexaramine (100 mg/kg for 5 weeks), FEX-D (50 mg/kg for 2 weeks) or SALK110 (NSSK00110, 50 mg/kg for 2 weeks). Changes in gene expression were determined by RNA-Seq.

As shown in FIG. 31 and Table 6, fexaramine and the deuterated analogs induce a common set of genes in islets that are involved in intracellular signaling, insulin secretion, and regulation of exocytosis. These gene changes are consistent with the increased insulin secretion seen in FIG. 29G.

TABLE 6

The functional annotation of common gene expression changes induced by fexaramine analogs, as determined by gene ontology.

| Gene Functions | P value |
| --- | --- |
| Intraceullular signaling casade | 3.2E−02 |
| Insulin secretion | 5.2E−02 |
| Regulation of exocytosis | 6.2E−02 |
| Peptide hormone secretion | 6.5E−02 |

Example 17

Intestinal Permeability Assay of Fexaramine Analogs

Standard Caco-2 cell permeability assays were performed on fexaramine and analogs as an in vitro evaluation of their intestinal permeability. The assays were performed as follows. Briefly, standard Caco-2 Culture Media DMEM FCS 10% L-Glutamine 1% PenStrep 1% (sterile-filtered) was placed in CacoReady 24 well transwell plate, obtained from ADMEcell (Alameda, Calif.). The plates were incubated in a 37° C., 5% $CO_2$ incubator for 4 hours. About 5 ml of 1000-fold diluted compound solution in transport buffer was prepared. The basal assay plate was prepared by adding 750 µl of transport buffer to A-B wells, and 780 µl of diluted compound solution to B-A wells. The basal assay plate was placed in the incubator. The CacoReady plate was put into a hood, apical section of plate lifted out and lowered onto empty basal plate. 200 µl of the Caco-2 media was removed from the apical wells and replaced with 200 µl of fresh transport media. This was repeated twice for a total of 3 washes. 200 µl of the media was removed from the apical wells and replaced with 200 µl of diluted compound (for A-B wells) or 200 µl of fresh transport buffer (for B-A wells). The basal plate was removed from the incubator and the apical section of plate transferred to the basal plate. Three replicate, 10 µl samples were collected from the apical and basal compartments for T0. The assay plate was covered and returned to the incubator. At T2 hrs, 3 replicate, 10 µl samples were collected from all apical compartments and B-A basal compartments; 3 replicate, 50 µl samples were collected from A-B basal compartments. 50 µl of all T0 and T2 hrs samples were mixed and transferred for bioanalysis.

Calculations: Analyte levels (peak area ratios) are measured on apical (A) and basolateral (B) sides at T0 and T2 hrs. A-to-B and B-to-A fluxes are calculated (mean of n=3 measurements). Apparent permeability (Papp, cm/sec) is calculated as dQ (flux)/(dt×Area×Concentration). The efflux ratio is (B-to-A)/(A-to-B) ratio [i.e., Papp(B-A)/Papp(B-A)]. A ratio >2 is evidence of efflux. PGP efflux can be confirmed by testing +/− pgp inhibitor (dosing solutions prepared with and without verapamil at a final assay concentration of 25 µM).

As shown in FIG. 32, all analogs are poorly transported, consistent with these molecules being intestinally restricted.

Example 18

Intestinal Activation of the Nuclear Receptor FXR Via Fexaramine Improves Tumor Burden in an APC$^{min}$ Colon Cancer Mice Model Background The lining of the mammalian intestine is comprised of a rapidly proliferating epithelial monolayer that undergoes continuous renewal. It provides two vital functions: absorbing nutrients and water, and serving as a physical barrier that separates the immune system from luminal bacteria, antigens, and toxins. Tissue homeostasis of the adult intestinal epithelium depends on cellular plasticity to enable self-renewal, proliferation, and apoptosis, and to ensure effective wound healing without promoting malignant outgrowth. These processes are regulated in part through Wnt-β-catenin signaling, which promotes proliferation of the epithelial stem cell compartment at the base of the intestinal crypt and is required for intestinal regeneration. Wnt ligands are secreted glycoproteins that activate the Frizzled family of G protein (heterotrimeric guanine nucleotide-binding protein)-coupled receptors and the co-receptors Lrp5 and Lrp6. Activation of Wnt receptor complexes leads to inhibition of a protein complex, which includes the tumor suppressor protein APC (adenomatous polyposis coli), which promotes ubiquitin-mediated degradation of the transcriptional coactivator β-catenin. In greater than 80% of sporadic and familial colorectal cancers (CRCs), mutations causing premature stop codons in APC induce constitutive accumulation and activation of β-catenin in the nucleus and drive tumor formation. Therefore, therapies designed to interfere with the Wnt-β-catenin pathway in CRC are of clinical use.

Methods

The farnesoid X receptor (FXR) is a bile acid activated nuclear receptor widely expressed through the body. The ability of the intestinal-specific FXR ligand fexaramine to inhibit the progression of colon cancer in mice with a heterozygote mutation for the Apc gene (ApcMin/+ mice on a C57B6 background obtained from Jackson Laboratories) was determined. Mice were maintained under temperature, air and light-controlled conditions and received food and water ad libitum; they did not receive any surgical or hormonal manipulation.

5 week old ApcMin/+ mice (13-15 males per group receiving a standard diet, a model for colorectal and intestinal cancer) were treated with vehicle (corn oil) or fexaramine (FEX, 100 mg/kg in corn oil) by oral gavage, three times a week for 23 weeks. Mice body weight and food-intake were measured daily. At the end of the treatment regimen, surviving animals were sacrificed by cervical dislocation and the entire intestinal tract was immediately removed and washed with cold phosphate-buffered saline.

Tumor Analysis, Histological Scores and Colonic Length

At the completion of the treatment, the colons were removed, flushed with PBS, fixed as "Swiss-rolls" in 4% paraformaldehyde at 4° C. overnight, and paraffin-embedded. Sections (5 µm) were cut stepwise (200 µm) through the complete block and stained with H&E. Tumor counts were performed blinded by a trained pathologist. To determine proliferation rates, mice were injected i.p. with 100 mg/kg of BrdU 2.5 hours prior to sacrifice and paraffin sections stained using a BrdU-in situ detection kit. The extent of apoptosis was determined by TUNEL assay using the ApoAlert DNA fragmentation assay kit. BrdU- and TUNEL-positive cells were counted by an investigator blinded to the genotype. For immunohistochemistry, antigen retrieval was performed (Vector Lab H3300) and then RTU Vectastain Universal Elite ABC Kit and NovaRED or VIP substrate (all from Vector Lab) were used, following the manufacturer's instructions.

Statistical Analysis

Statistical analysis were performed in collaboration with the Cancer Prevention-Biostatistics department at the University of California at San Diego Cancer Center. This is part of an ongoing collaboration and has previously been applied to the APC$^{Min}$ model of colorectal cancer as well as to several other cancer models including prostate and breast cancer. The volume of polyps was calculated considering them as hemispheres (½×¾ $\pi r^3$). All other evaluations were performed in the distal tract of the small intestine because ApcMin/+ mice develop the majority of tumors in the small intestine.

Results

As shown in FIG. 33A, fexaramine-treated mice are resistant to colon cancer-induced cachexia (weight loss). As shown in FIG. 33B, vehicle-treated mice lose ~10% body weight, while Fex-treated mice maintain their weight. As shown in FIG. 33C, a dramatic improvement in survival of Fex-treated mice compared to vehicle-treated (vehicle 20% survival at 25 weeks vs. 80% for Fex treated mice) was observed.

Figure 34A:
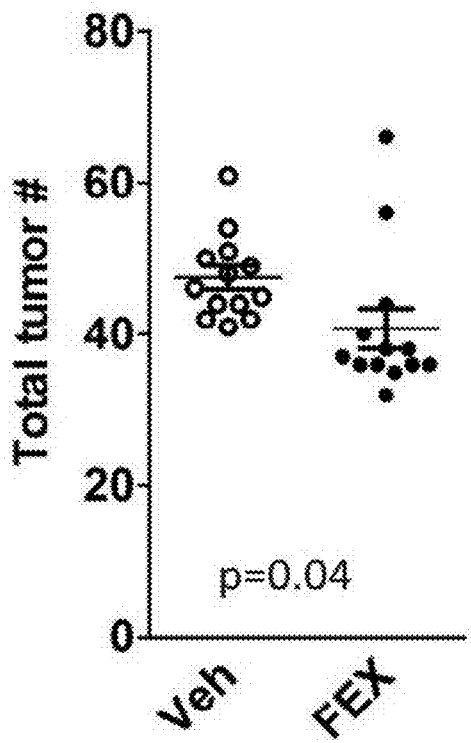
Figure 34B:
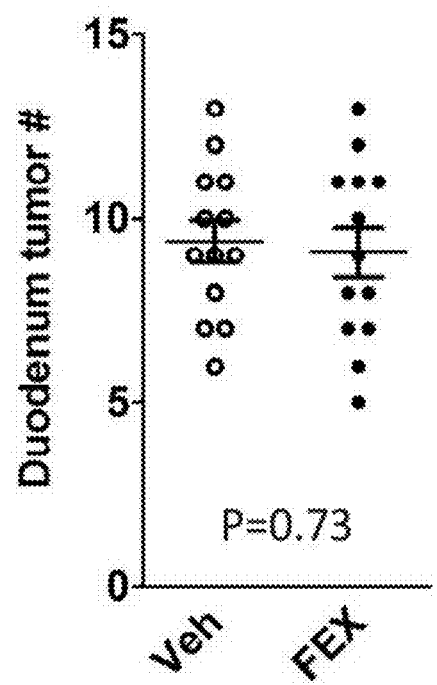
Figure 34C:
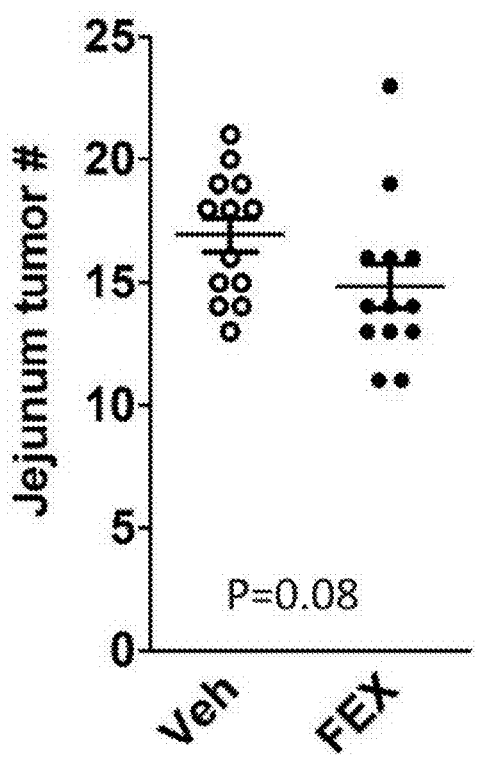
Figure 34D:
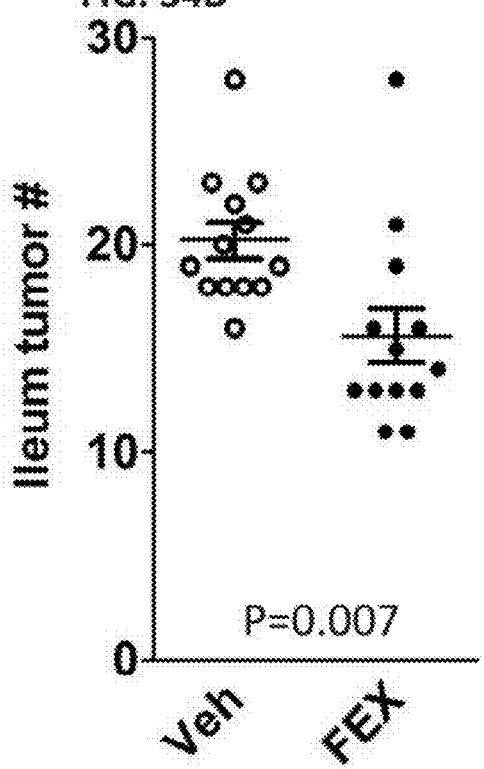
Figure 35A:
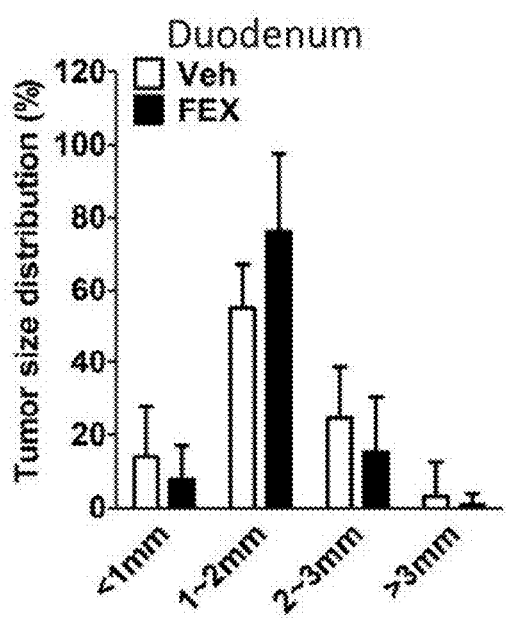
Figure 35B:
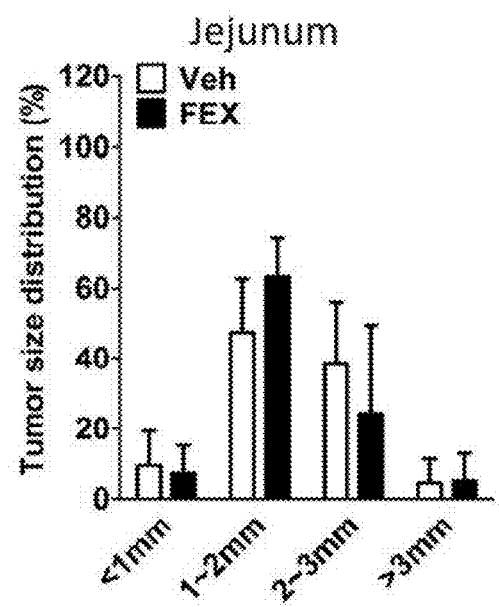
Figure 35C:
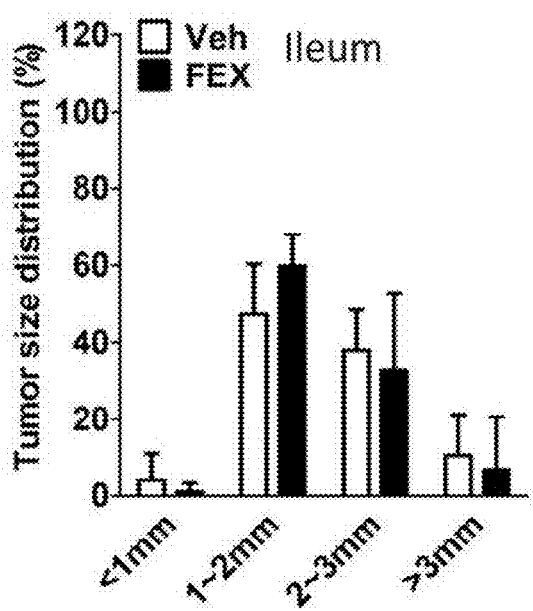
Figure 35D:
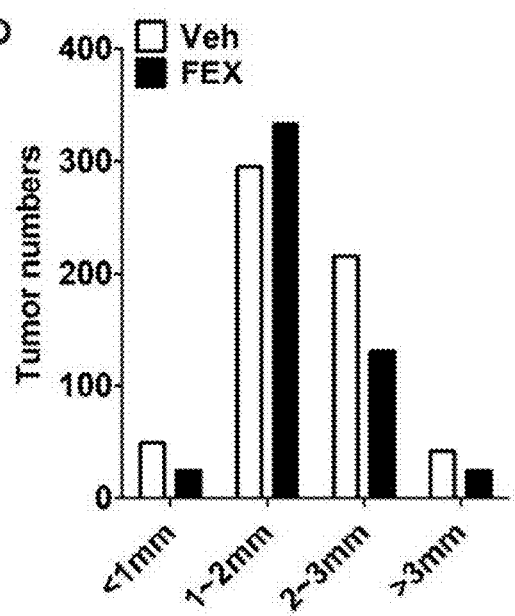

As shown in FIG. 34A, a dramatic reduction in tumor burden of Fex-treated versus vehicle-treated mice was observed after 23 weeks (20% reduction, p 0.04). As shown in FIG. 34B, no change in tumor burden of vehicle—versus FEX-treated mice was observed in the duodenum after 23 weeks (p 0.73). As shown in FIG. 34C, a dramatic reduction in tumor burden in Fex-treated versus vehicle-treated treated mice was observed in the jejunum after 23 weeks (11.75% reduction, p 0.08). As shown in FIG. 34D, a dramatic reduction in tumor burden in Fex-treated versus vehicle-treated treated mice was observed in the ileum after 23 weeks (25% reduction, p 0.08)

As shown in FIGS. 35A-35D, a dramatic reduction in tumor size in Fex-treated versus vehicle-treated treated mice was observed in the duodenum (FIG. 35A), the jejunum (FIG. 35B), the ileum (FIG. 35C), and throughout the intestine (FIG. 35D) after 23 weeks.

As shown in FIG. 36, serum total cholesterol and triglyceride levels in $APC^{min}$ mice after 23 weeks is reduced in fexaramine-treated, but not vehicle-treated mice. Very high triglycerides are dangerous. Levels above 500 mg/dL can cause fatty deposits in the skin and internal organs, which can damage the liver and pancreas.

As shown in FIGS. 37-40, respectively, duodenum, jejunum, ileum and colon paraformaldehyde fixed intestinal sections of $APC^{min}$ mice treated with fexaramine have reduced tumor size as compared to vehicle-treated mice.

In summary, fexaramine-treated $APC^{min}$ mice are resistant to cachexia, have an improved survival rate, have delayed tumor progression, and have reduced tumorigenesis (e.g., fewer tumor counts in ileum). In addition, the severe tumor burdens positively correlates with serum turbidity in vehicle group. Thus, use of fexaramine, or any of the fexaramine derivatives thereof provided herein, can be used to treat cancer, such as colon cancer for example by reducing one or more of cachexia, number of tumors, metastasis, and size of tumor(s), such as a reduction of at least 5%, at least 10%, at least 15%, at least 20%, or at least 50%, and/or increasing survival rate, such as an increase of at least 5%, at least 10%, at least 15%, at least 20%, or at least 50%.

Example 19

Administration of Fexaramine and Guggulsterone

Glucagon-like peptide 1 (GLP-1) is a gut-derived peptide secreted by intestinal L cells after a meal, where it functions to potentiate glucose-stimulated insulin secretion, enhance β-cell growth and survival, and inhibit gastric emptying and food intake. The demonstrated glucose-lowering effects of GLP-1 have lead to the approval of GLP-1 receptor agonists for the treatment of Type 2 diabetes. However, GLP-1 secretion is reduced in patients with type 2 diabetes, leading to interest in GLP-1 secretagogues as alternative therapies.

To examine the effects of FXR in the secretion of GLP-1, the metabolic changes induced in human L cells was measured by treatment with the FXR agonist, fexaramine and an FXR antagonist guggulsterone. Treatment of L cells with fexaramine (1 µM for 24 hours) lead to an increase in the oxygen consumption rate (OCR), consistent with increased mitochondrial activity and consequently, an increased energetic state (FIG. 41). The reverse effect was seen after treatment with the FXR antagonist, guggulsterone, with lower OCR after drug treatment. The ability of fexaramine to increase the energetic state of the L cells indicates that it can function as a GLP-1 secretagogue.

Example 20

Administration of Fexaramine Protects from Alcoholic Liver Disease

Patients with alcoholic hepatitis have a high mortality rate. In addition, patients with alcoholic liver disease show an overgrowth of intestinal bacteria.

The Tsukamoto-French mouse model, which involves continuous intragastric feeding of isocaloric diet or ethanol for 3 weeks, was used. C57BL/6J mice were co-administered vehicle or fexaramine by oral gavage (100 mg/kg/day). Mice were sacrificed after treatment and conjugated and unconjugated bile acid levels measured in serum and liver by liquid chromatography/mass spectrometry.

As shown in FIGS. 42A-42C, increased choloylglycine hydrolase activity is seen in the liver of alcoholic patients. Choloylglycine hydrolase is responsible for the deconjugation of bile acids. Ethanol treatment of mice leads to an increase in the level of deconjugated bile acids in serum, and an increase in the level of conjugated bile acids in the liver, as seen in human patients. In addition, there is a marked increase in the total bile acid levels. Consistent with this increase in total bile acid levels, ethanol treatment increased the expression of Cyp7a1, the enzyme that catalyzes the rate limiting step in the conversion of cholesterol to bile acids in the liver (FIGS. 43A and 43B).

As shown in FIG. 44A, co-administration of fexaramine to mice during the administration of ethanol protects them from alcoholic liver disease, by decreasing hepatic steatosis, as shown histologically (FIG. 44A) and quantified in FIG. 44C. Improved liver function is also indicated by decreased serum levels of alanine aminotransferase (ALT, FIG. 44B).

In view of the many possible embodiments to which the principles of the disclosure may be applied, it should be recognized that the illustrated embodiments are only examples of the disclosure and should not be taken as limiting the scope of the invention. Rather, the scope of the invention is defined by the following claims. We therefore claim as our invention all that comes within the scope and spirit of these claims.

We claim:

1. A compound, having a formula

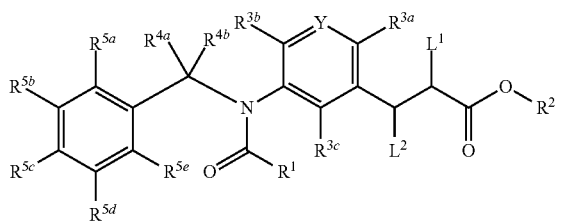

or a pharmaceutically acceptable salt, hydrate, solvate or prodrug thereof, wherein
- $R^1$ is selected from aryl, heteroaryl, heterocyclic, alkenyl, cycloalkyl, cycloalkenyl or polycyclic;
- $R^2$ is selected from alkyl, alkenyl, or cycloalkyl;
- Y is selected from N, N—O or C—$R^{3d}$;
- $R^{3a}$, $R^{3b}$, $R^{3c}$ and $R^{3d}$ are each independently selected from hydrogen, deuterium, halide, alkyl, alkenyl, alkoxy, alkylthio, amino, sulfonyl, aminosulfonyl, aminocarbonyl, acyl, hydroxyl or nitro;
- $R^{4a}$ and $R^{4b}$ are each independently selected from hydrogen, deuterium, halide or alkyl;
- $L^1$ and $L^2$ are independently selected from hydrogen, deuterium, alkyl, cycloalkyl, or together form a pi-bond; and
- $R^{5a}$, $R^{5b}$, $R^{5c}$, $R^{5d}$ and $R^{5e}$ are each independently selected from hydrogen, deuterium, halide, alkyl, alkenyl, alkoxy, alkylthio, amino, sulfonyl, aminosulfonyl, aminocarbonyl, acyl, aryl, heteroaryl, cycloalkyl, heterocyclyl, hydroxyl or nitro; or
- any two adjacent groups selected together form an aryl, heteroaryl, cycloalkyl or heterocyclic ring; and wherein
- none of $R^{5a}$, $R^{5b}$, $R^{5c}$, $R^{5d}$ or $R^{5e}$ are —$R^x$-$L^x$-$R^{x2}$, where $R^x$ is selected from O, $NR^{x3}$, sulfonyl or S;
  - $R^{x3}$ is selected from H, alkyl, alkenyl, alkynyl, cycloalkyl, cycloalkenyl, or aryl;
  - $L^x$ is selected from a bond, alkylene, alkenylene, alkynylene, cycloalkyl, cycloalkenyl, heterocyclic, aryl, heteroaryl or $CR^{x4}R^{x5}$;
  - $R^{x4}$ and $R^{x5}$ are each independently selected from H, D, halogen, alkyl, alkenyl, alkynyl, cycloalkyl, cycloalkenyl, —C(O)$OR^{x6}$, or —C(O)$NR^{x6}R^{x7}$;
  - $R^{x6}$ and $R^{x7}$ are each independently selected from H, alkyl, alkenyl, alkynyl, cycloalkyl or cycloalkenyl;
- $R^{x2}$ is selected from —C(O)$L^{x2}R^{x8}$ or a carboxyl bioisostere;
- $L^{x2}$ is a bond or $NR^{x3}$;
- $R^{x8}$ is H, alkyl, alkenyl, alkynyl, cycloalkyl, cycloalkenyl, —$OR^{x9}$, $N(R^{x9})_2$, —C(O)$R^{x9}$, —S(O)$_2R^{x9}$, —C(O)$OR^{x9}$, —S(O)$_2N(R^{x9})_2$ or C(O)$N(R^{x9})_2$; and
- each $R^{x9}$ is independently selected from H, alkyl, alkenyl, alkynyl, cycloalkyl or cycloalkenyl; and
- if $L^1$ and $L^2$ are both hydrogen or together form a pi-bond then
  - Y is N or C-halogen; or
  - $R^1$ is polycyclic; or
  - $R^{4a}$ is D; or
  - $R^{5a}$ is F, Cl or I; or
  - $R^{5d}$ and $R^{5e}$ together form an aryl, heteroaryl, cycloalkyl or heterocyclic ring; or
  - $R^{5b}$ and $R^{5c}$ together form an aryl, cycloalkyl, nitrogen-containing heterocyclic or nitrogen-containing heteroaryl ring; or
  - any combination thereof.

2. The compound of claim 1, the compound having a formula

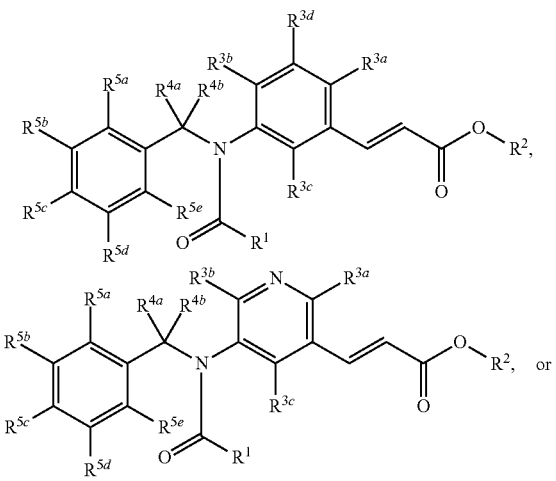

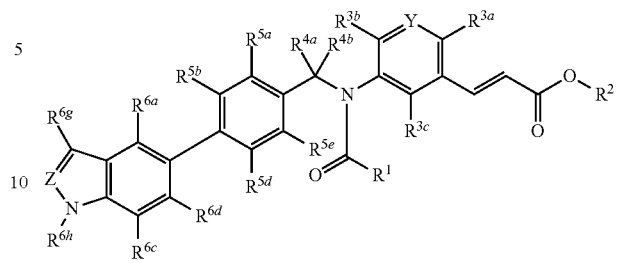

3. The compound of claim 1, wherein $R^{4a}$ is deuterium.

4. The compound of claim 2, wherein $R^{3d}$ or $R^{5a}$ or both are halogen.

5. The compound of claim 4, wherein $R^{3d}$ or $R^{5a}$ or both are F.

6. The compound of claim 1, wherein the polycyclic is selected from

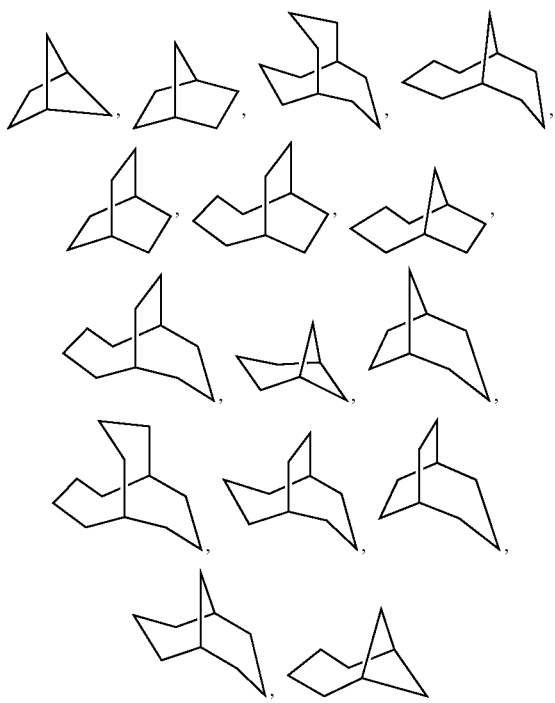

or adamantane.

7. The compound of claim 6, wherein the polycyclic is

8. The compound of claim 1, wherein $R^{5c}$ comprises a nitrogen-containing heteroaryl ring.

9. The compound of claim 8, wherein $R^{5c}$ is selected from pyridine, pyrazole, pyrrole, imidazole, oxazole, isoxazole, thiazole, isothiazole, triazole, pyrimidine, pyrazine, triazine, benzopyrazole, benzimidazole, indole, quinoline, indazole, purine, quinoxaline, or acridine.

10. The compound of claim 1, having the formula wherein Z is selected from N, CH, or C-alkyl;
$R^{6a}$, $R^{6c}$, $R^{6d}$ and $R^{6g}$ are each independently selected from H, D, halogen or alkyl; and
$R^{6h}$ is selected from H, D, alkyl, cycloalkyl, aryl or heteroaryl.

11. The compound of claim 10, wherein Z is N; $R^{6a}$, $R^{6c}$, $R^{6d}$ and $R^{6g}$ are all H; $R^{6h}$ is methyl; or a combination thereof.

12. The compound of claim 1, having a formula

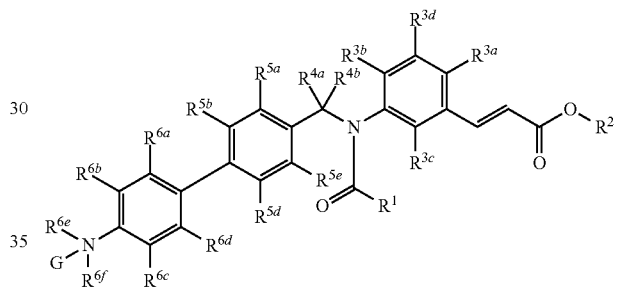

wherein $R^{6a}$, $R^{6b}$, $R^{6c}$, and $R^{6d}$ are each independently selected from H, D, halogen or alkyl;
G is a lone pair of electrons, or an oxygen;
$R^{6e}$ and $R^{6f}$ are each independently selected from alkyl, H or cycloalkyl; and
wherein $R^{3d}$ or $R^{5a}$ or both are halogen; or
$R^{4a}$ is D; or
$R^1$ is polycyclic; or
any combination thereof.

13. The compound of claim 12, wherein $R^{6e}$ and $R^{6f}$ are both methyl.

14. The compound of claim 1, wherein the compound is selected from

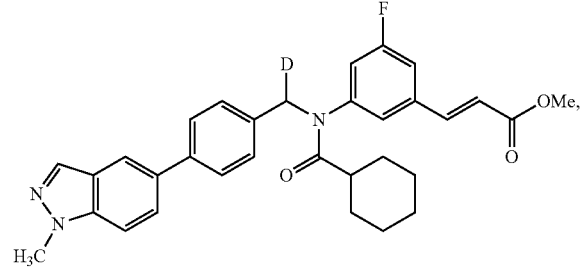

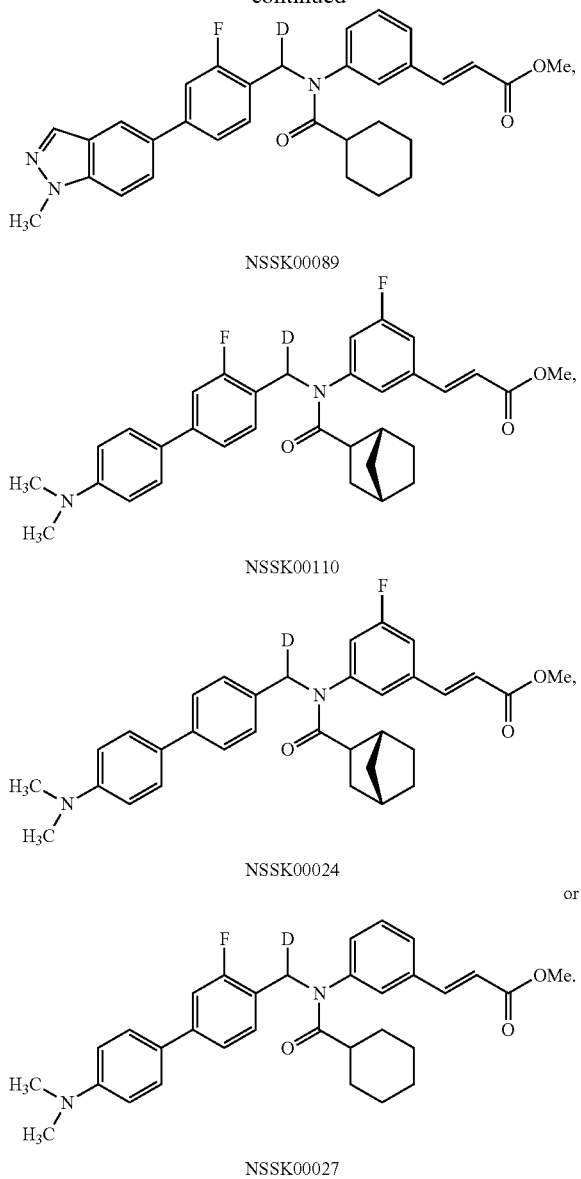

NSSK00089

NSSK00110

NSSK00024 or

NSSK00027

15. A method of making a compound of claim 1, the method comprising:
reacting an aldehyde with a first amine to form an imine;
reacting the imine with a reducing agent to form a second amine; and
reacting the second amine with an activated carboxylic acid derivative or a carboxylic acid to form an amide.

16. A composition, comprising a compound of claim 1 and an additional component.

17. A method of treating a disorder or disease in a subject, comprising administering to the subject a therapeutically effective amount of a compound of claim 1.

18. The method of claim 17, wherein the disorder or disease is selected from a metabolic disorder, inflammation in an intestinal region, a cell proliferation disease, alcoholic liver disease, non-alcoholic liver disease, a cholestatic disorder, an intestinal permeability disorder, a disease that causes or results from an altered intestinal microbiome, an inborn error of metabolism, a bile disorder, or an intestinal malabsorption disorder.

19. The method of claim 17, wherein the disorder or disease is selected from obesity, diabetes, insulin resistance, dyslipidemia, necrotizing enterocolitis, gastritis, ulcerative colitis, Crohn's disease, inflammatory bowel disease, irritable bowel syndrome, gastroenteritis, radiation induced enteritis, pseudomembranous colitis, chemotherapy induced enteritis, gastro-esophageal reflux disease (GERD), peptic ulcer, non-ulcer dyspepsia (NUD), celiac disease, intestinal celiac disease, colon cancer, post-surgical inflammation, gastric carcinogenesis, fatty liver (steatosis), cirrhosis, alcoholic hepatitis, nonalcoholic steatohepatitis (NASH), or nonalcoholic fatty liver disease (NAFLD), primary biliary cirrhosis (PBC), primary sclerosing cholangitis (PSC), cholestasis resulting from a drug, overlap syndrome (PBC plus autoimmune hepatitis), drug-induced cholestatic hepatitis, total parenteral nutrition (TPN)-induced cholestasis, ICU/sepsis-related cholestasis, obstetric cholestasis, graft vs. host disease, prolonged cholestasis due to hepatitis A, B or C infection, cholestasis due to cystic fibrosis, alcoholic hepatitis, progressive familial intrahepatic cholestasis (PFIC) syndromes, Alagille syndrome, biliary atresia, infectious colitis, type 1 diabetes, an intestinal permeability condition, an intestinal inflammation disorder, intestinal lesions, cirrhosis, cerebrotendinous xanthomatosis (CTX), benign biliary stricture, malignant biliary obstruction, bile acid diarrhea, short bowel syndrome, tropical sprue, environmental enteropathy, or volvulus.

20. A method of treating a disorder or disease in a subject, comprising administering to the subject a therapeutically effective amount of a composition of claim 16.

21. The method of claim 20, wherein the composition comprises an enteric coating.

22. The method of claim 17, wherein the disorder or disease is a cancer of the intestine.

23. The method of claim 22, wherein the cancer is colon cancer.

24. The method of claim 17, wherein the disorder or disease is type 1 diabetes or type 2 diabetes.

25. The compound of claim 1 having a structure

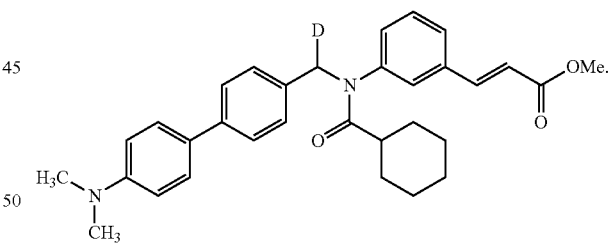

26. The method according to claim 17 comprising administering the compound to the gastrointestinal tract of the subject.

27. The method according to claim 17 comprising orally administering the compound to the subject.

28. The method according to claim 20 comprising administering the composition to the gastrointestinal tract of the subject.

29. The method according to claim 20 comprising orally administering the composition to the subject.

30. A method of treating a disorder or disease in a subject, comprising administering to the subject a therapeutically effective amount of a compound of claim 25.

31. The compound according to claim 1, selected from:
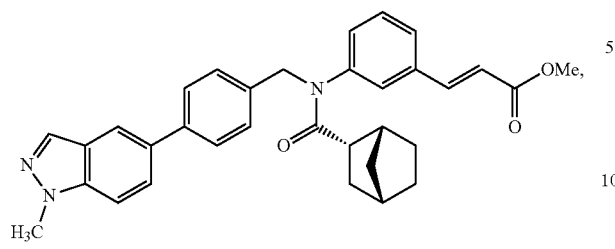
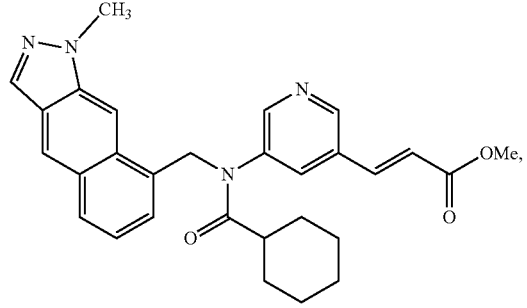
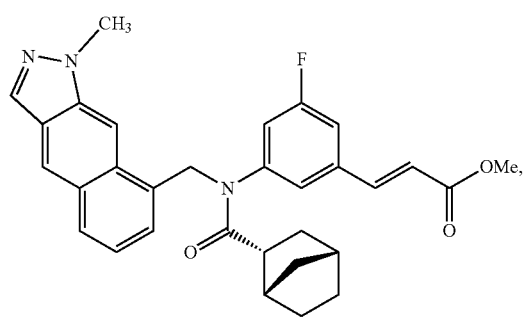
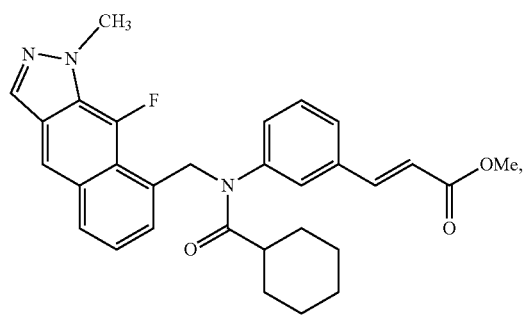
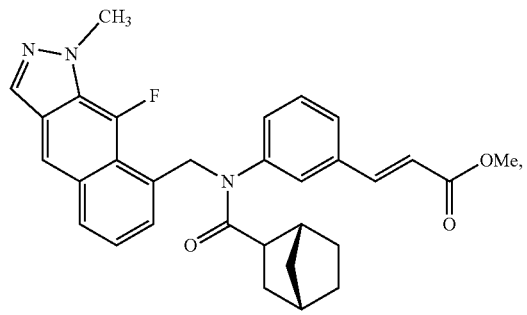
-continued
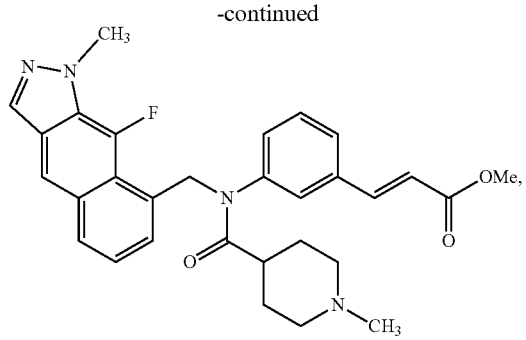
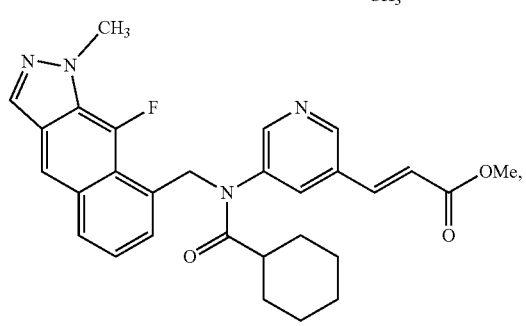
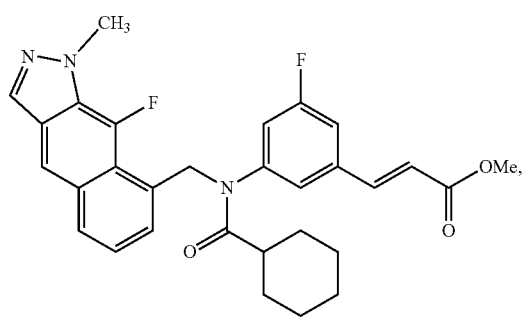
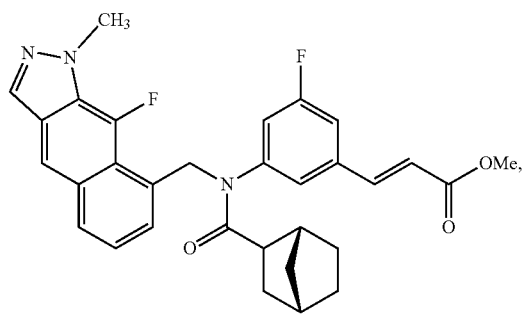
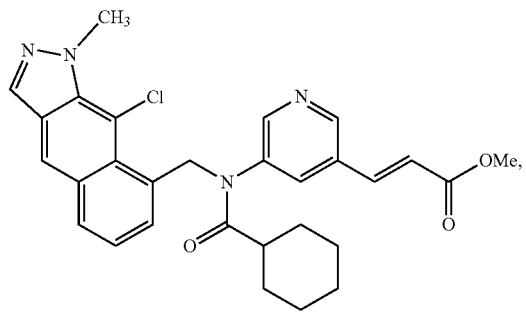

167
-continued
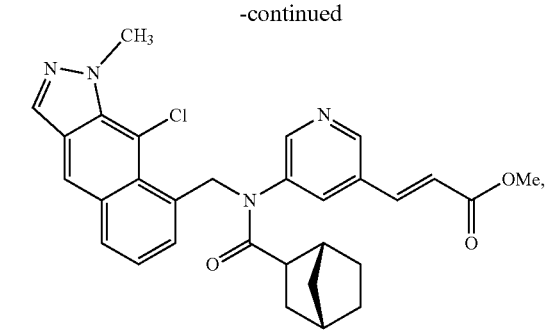
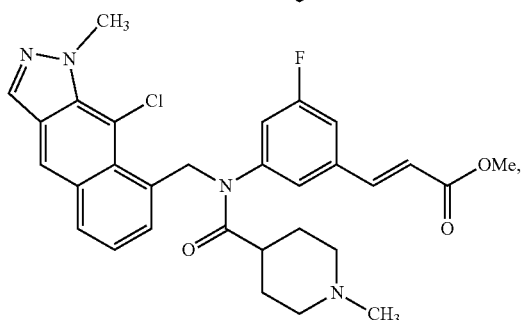
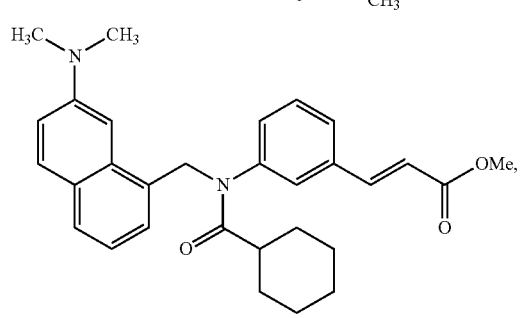
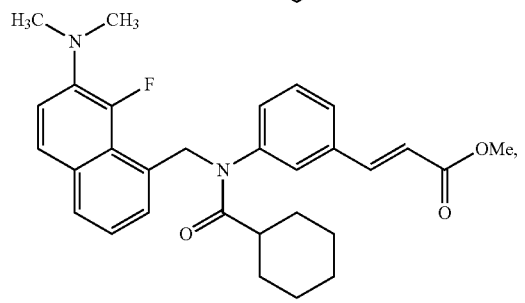
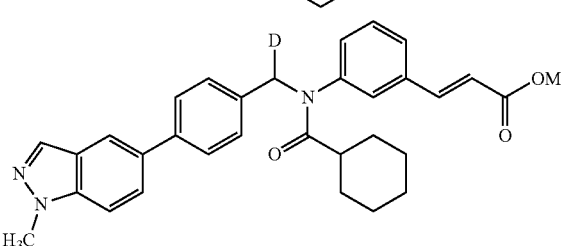
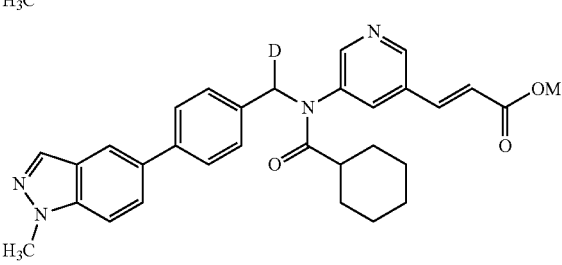
168
-continued
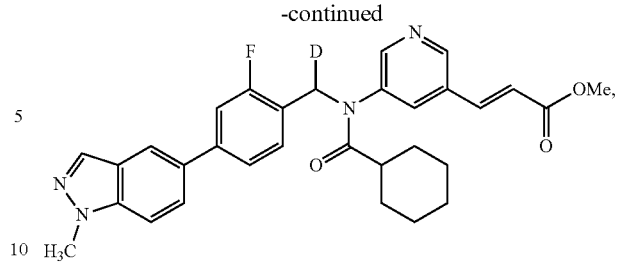
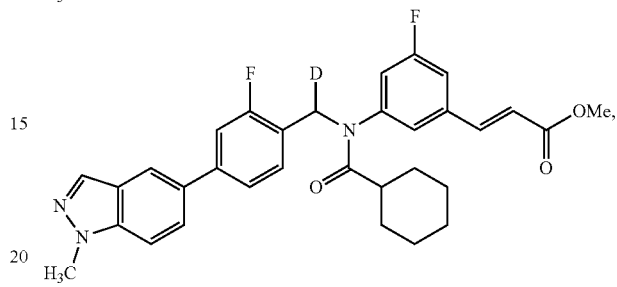
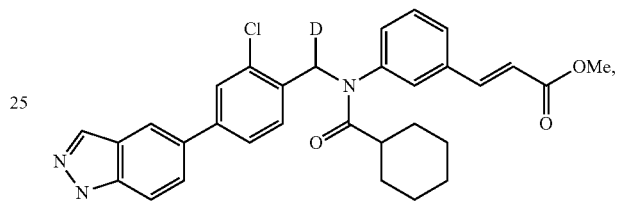
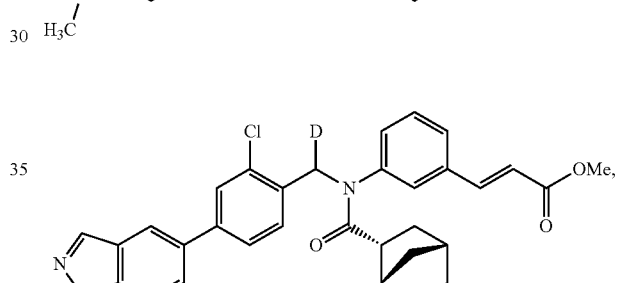
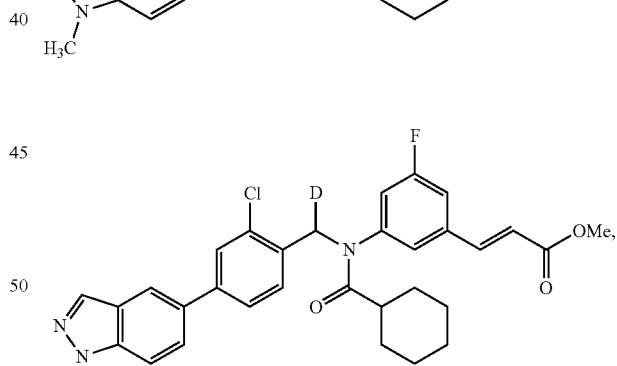
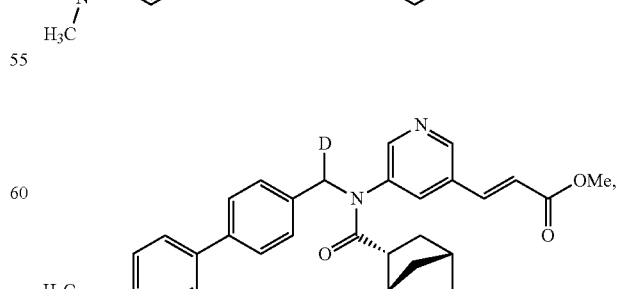

-continued
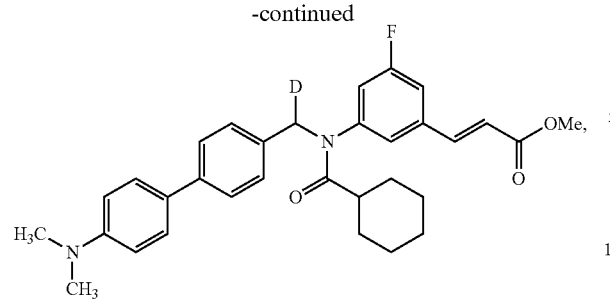
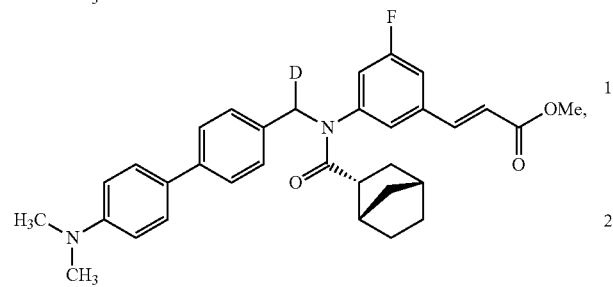
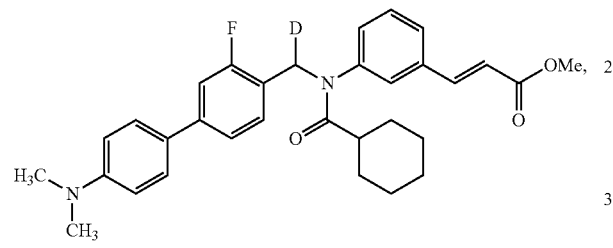
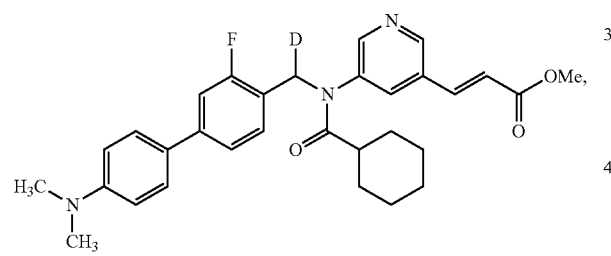
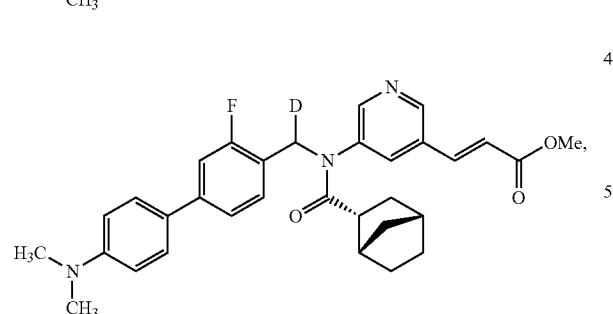
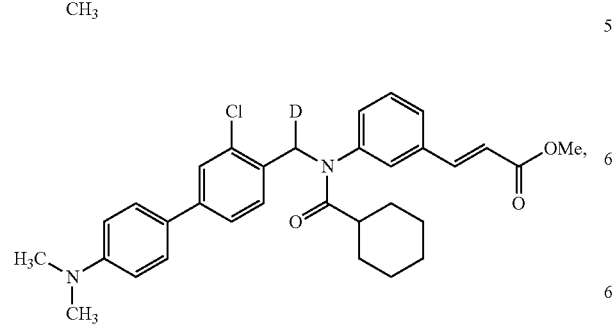
-continued
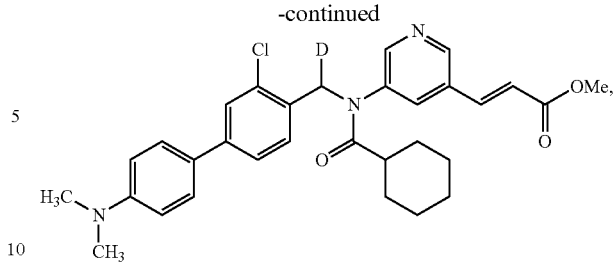
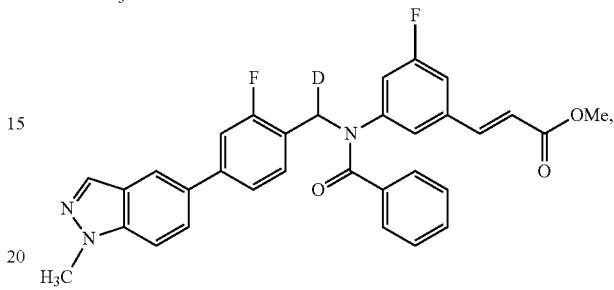
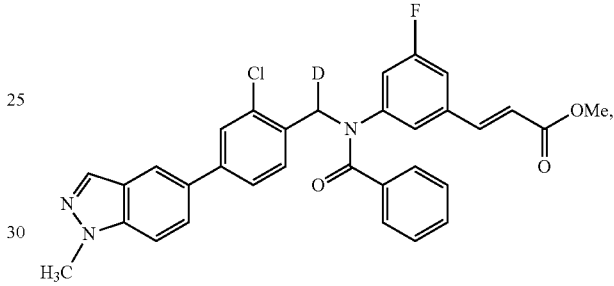
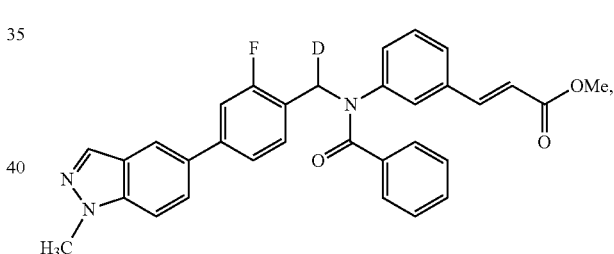
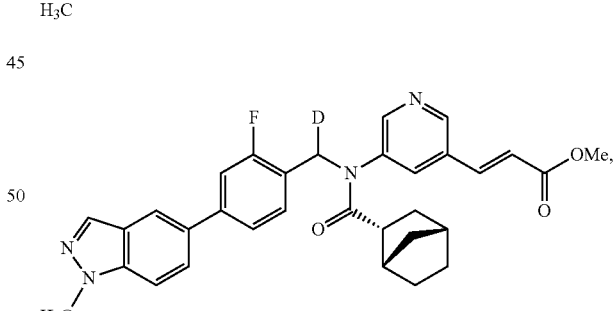
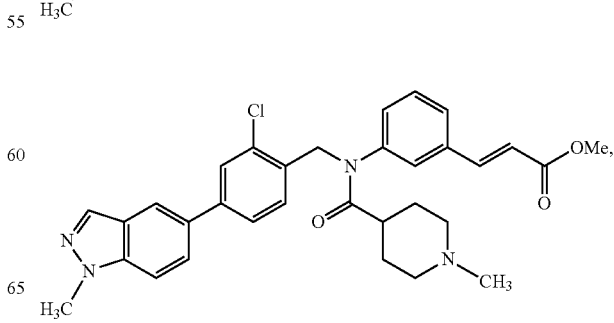

171
-continued
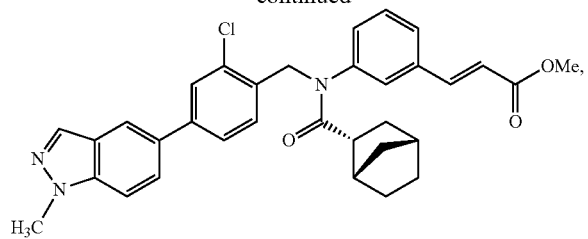
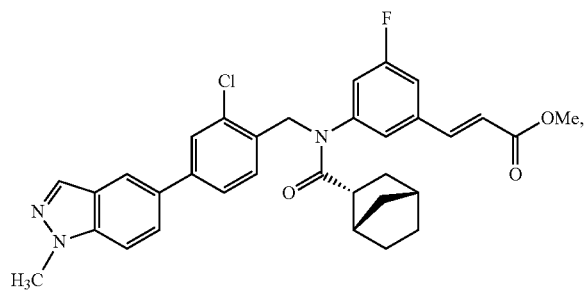
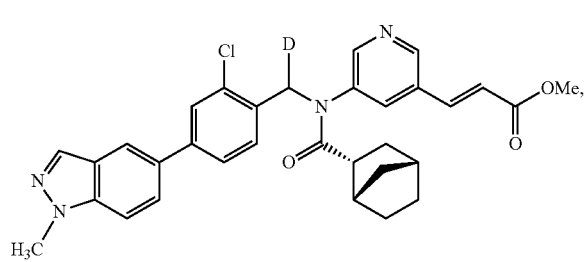
172
-continued
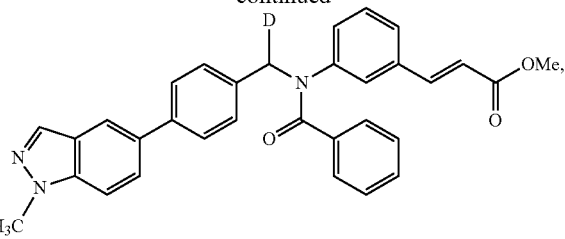
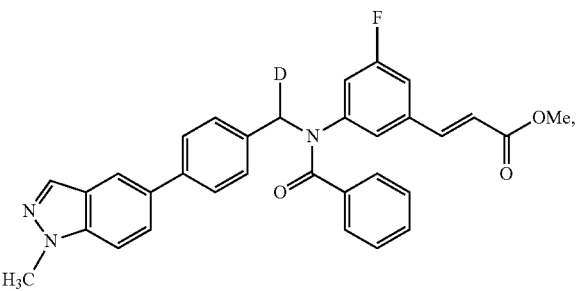
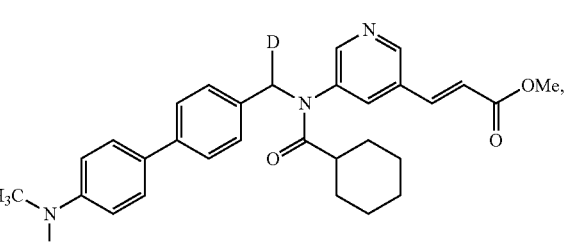
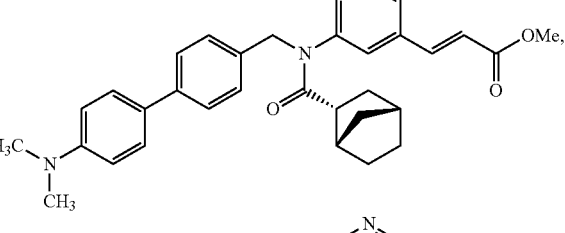
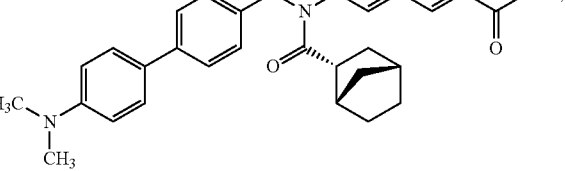
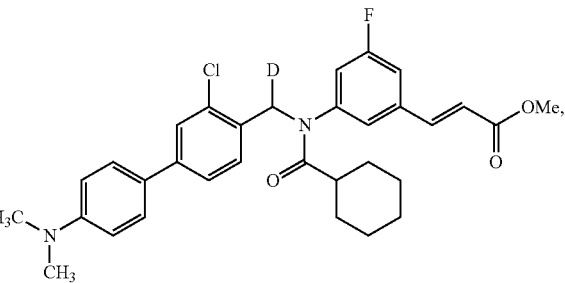

173
-continued
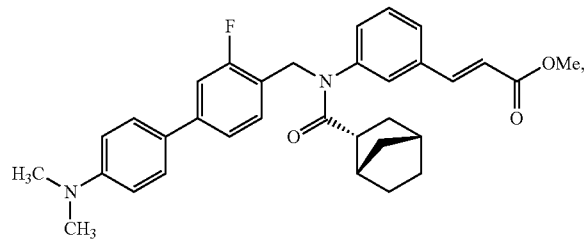
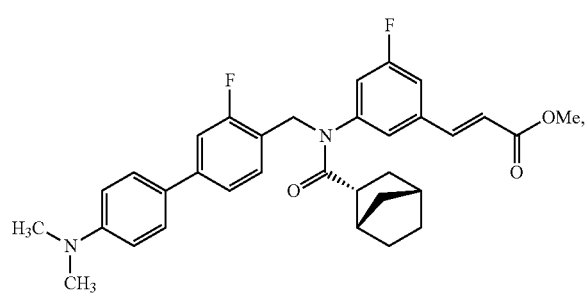
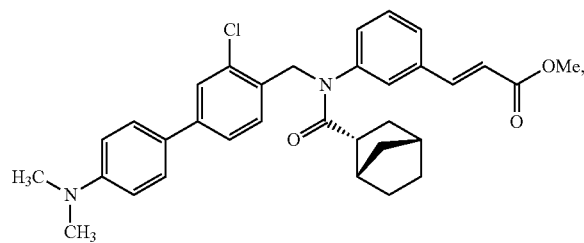
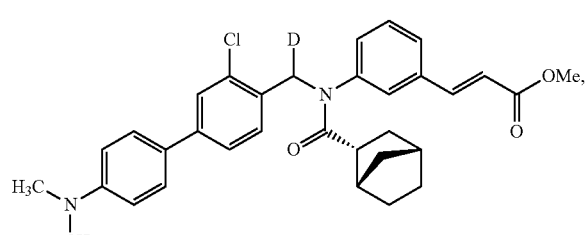
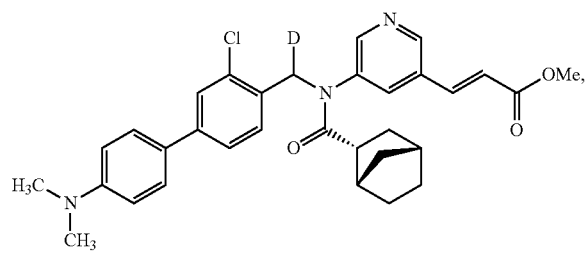
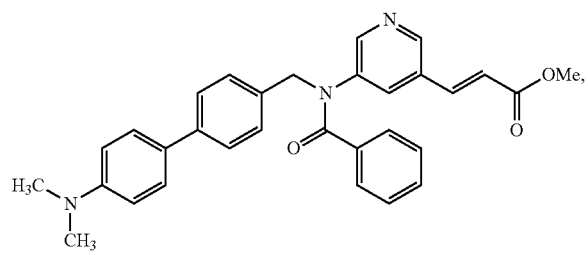
174
-continued
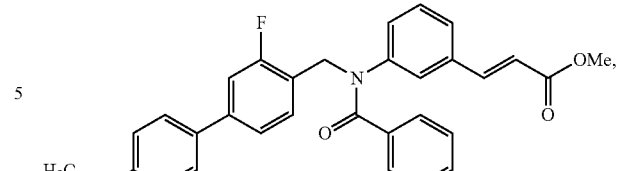
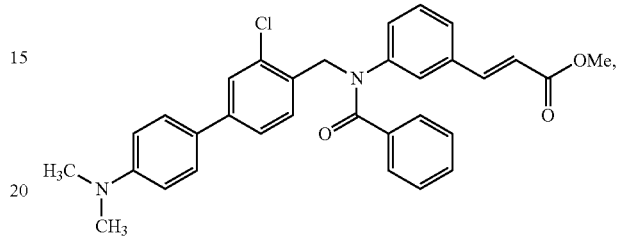
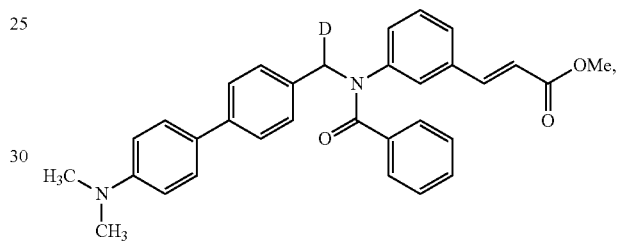
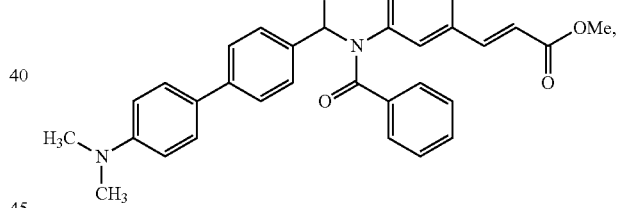
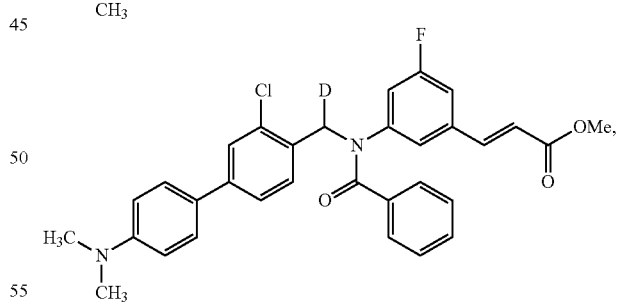
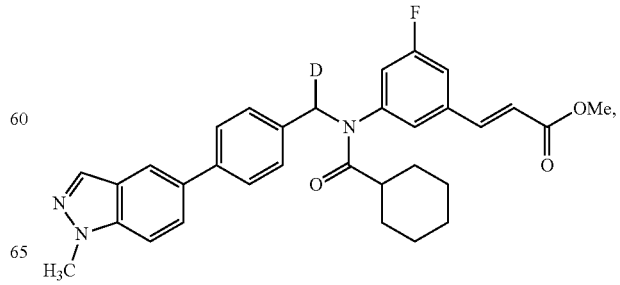

175
-continued
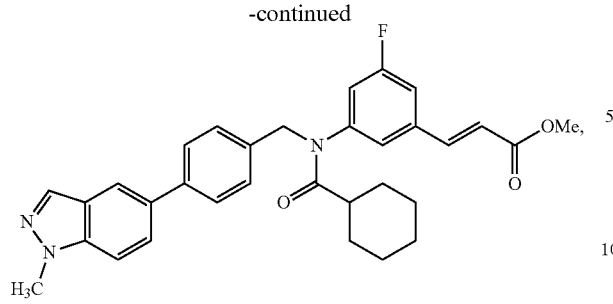
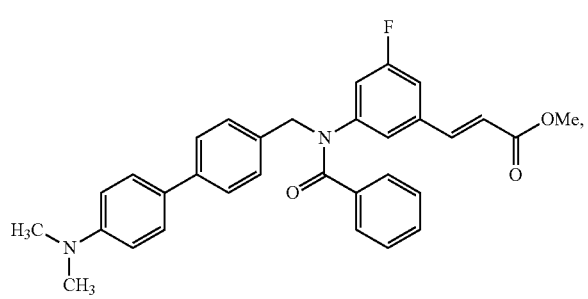
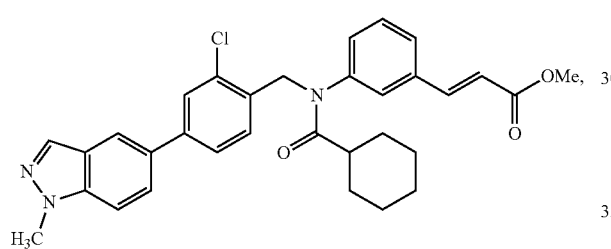
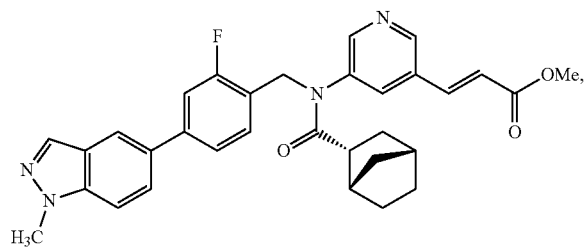
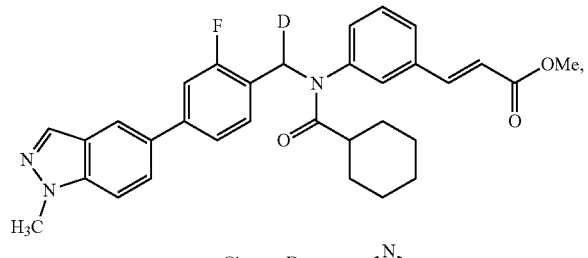
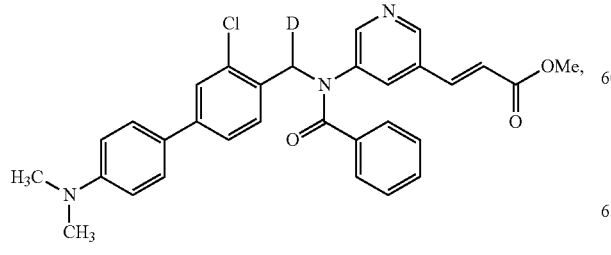
176
-continued
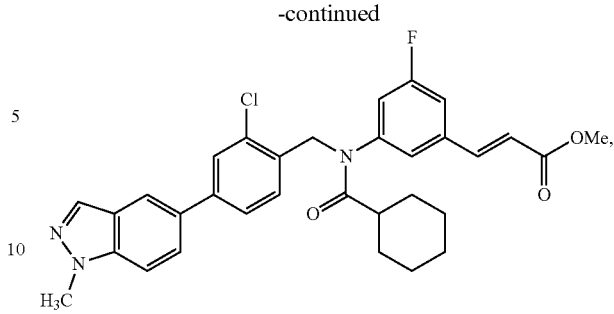
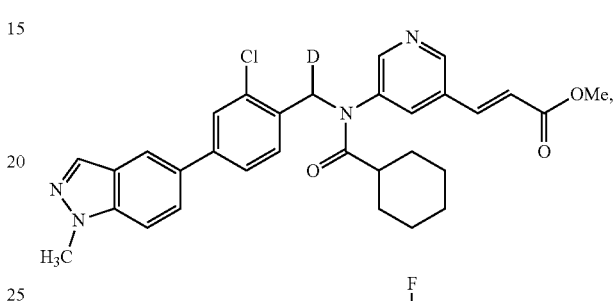
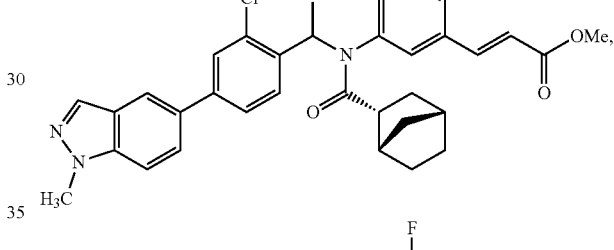
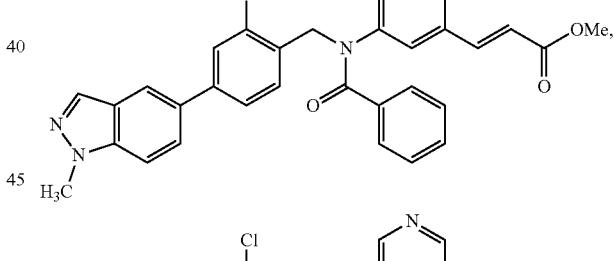
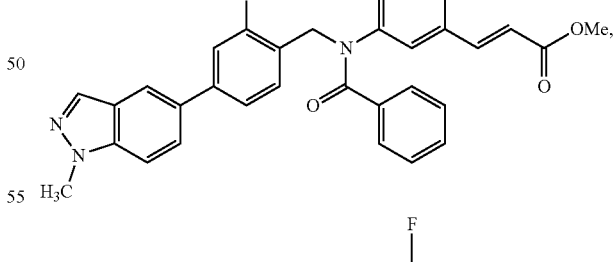
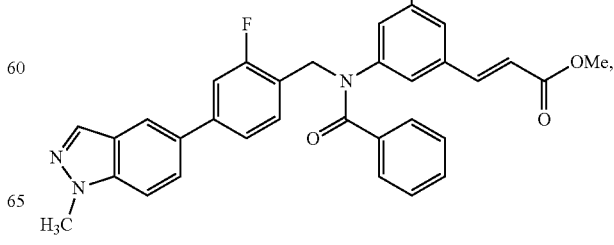

177
-continued
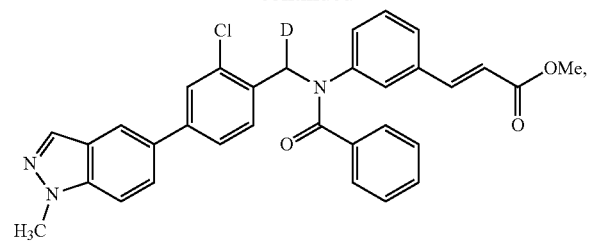
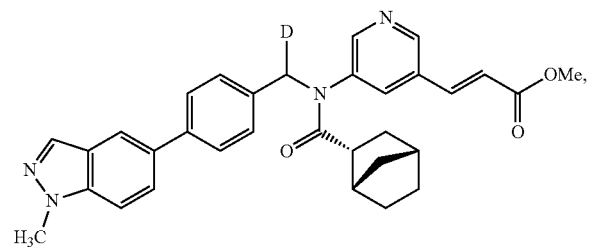
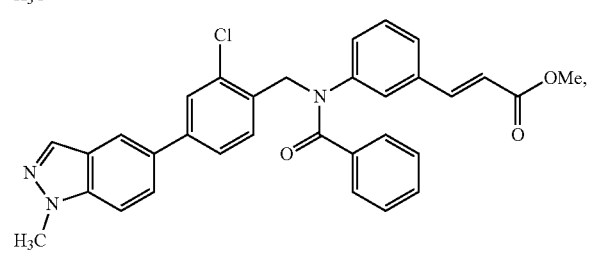
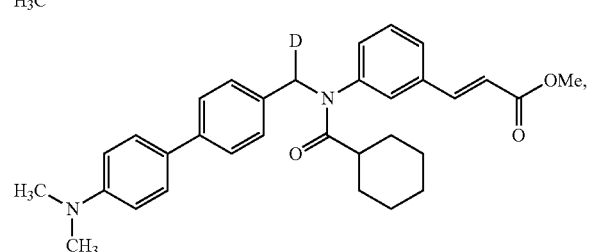
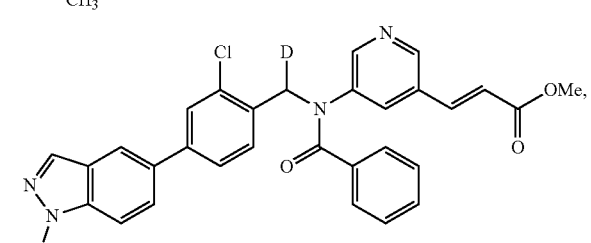
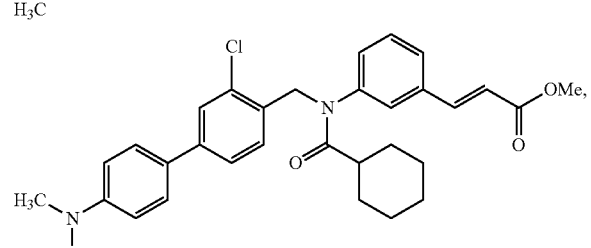
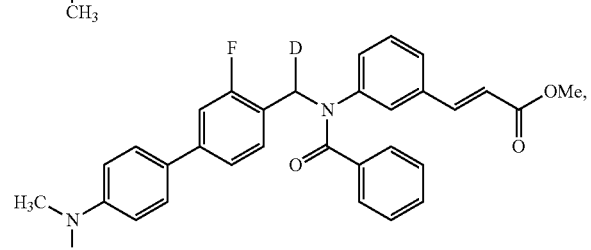
178
-continued
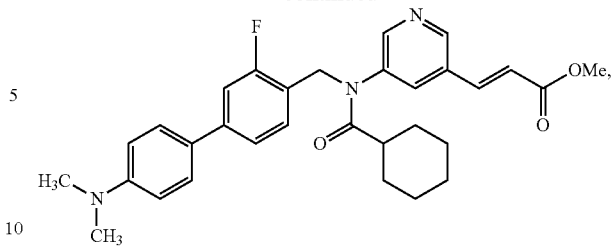
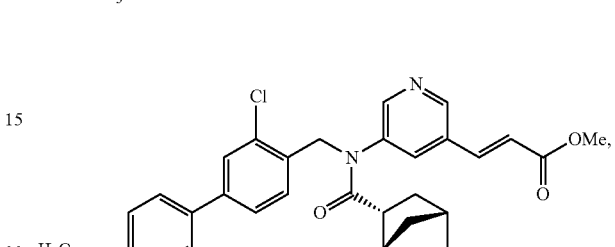
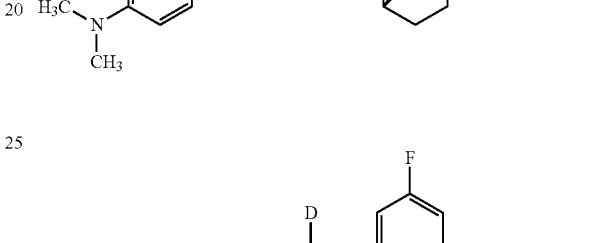
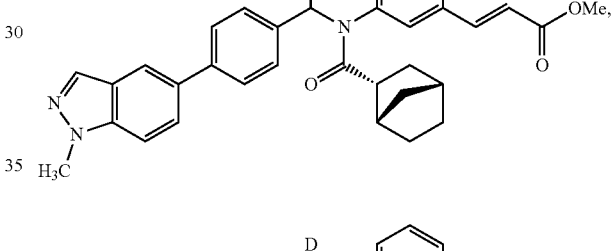
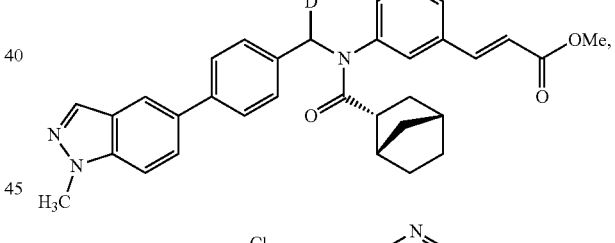
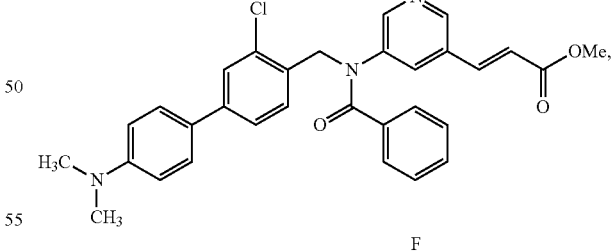
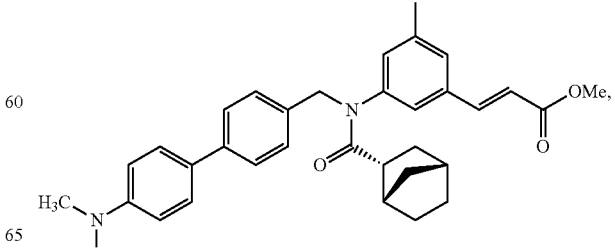

-continued
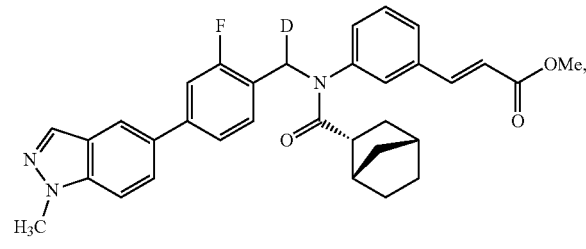
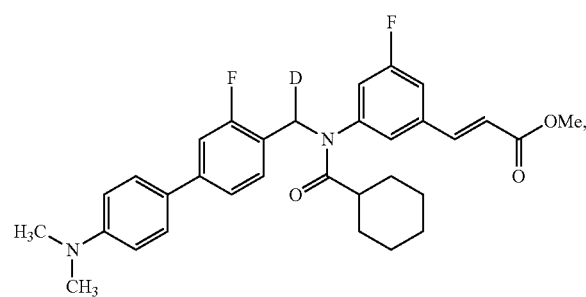
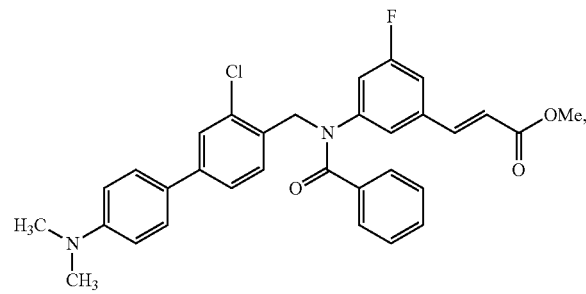
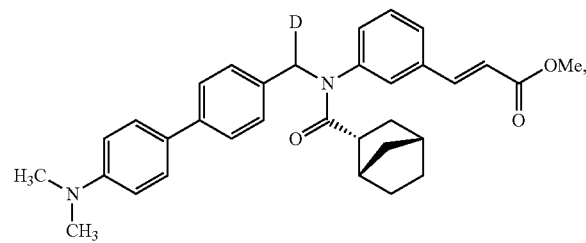
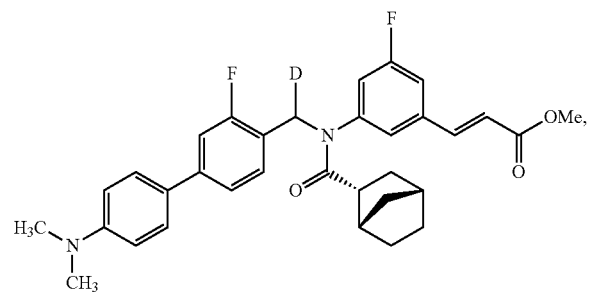
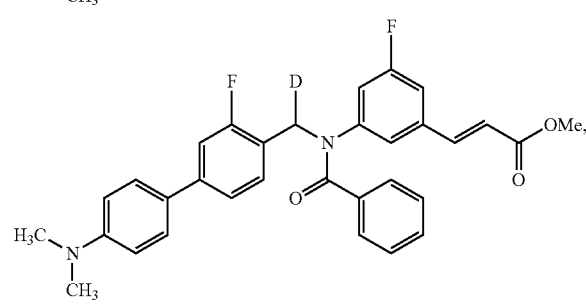
-continued
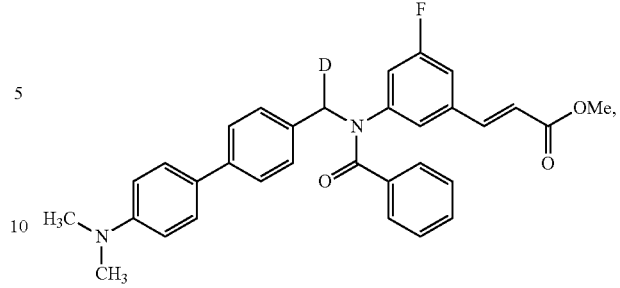
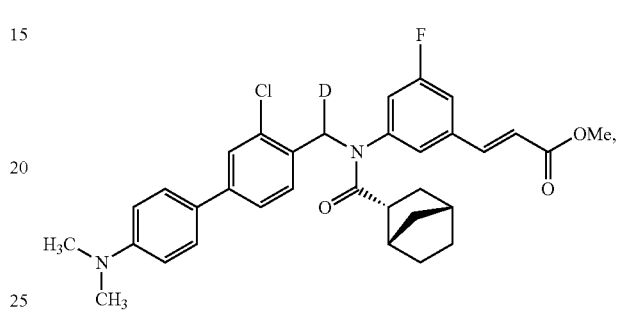
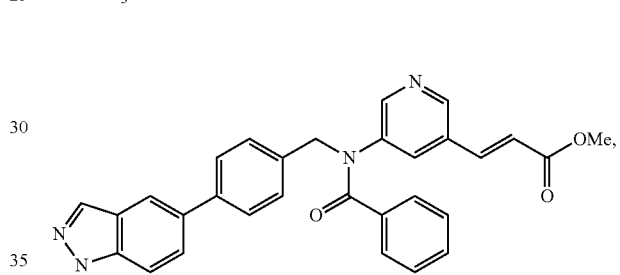
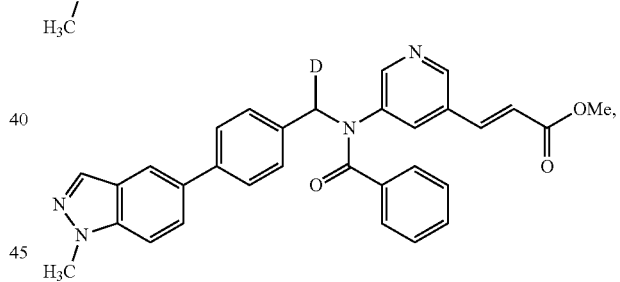
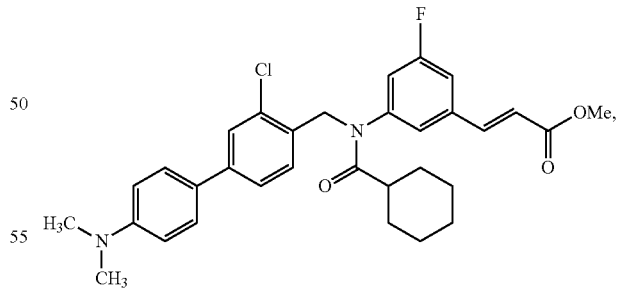
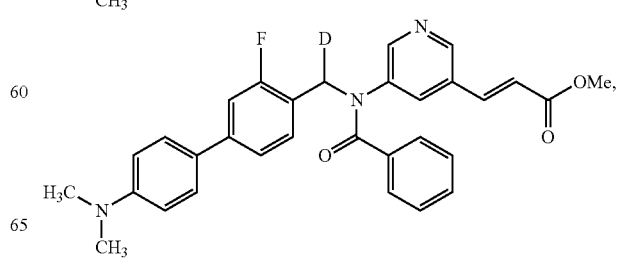

181
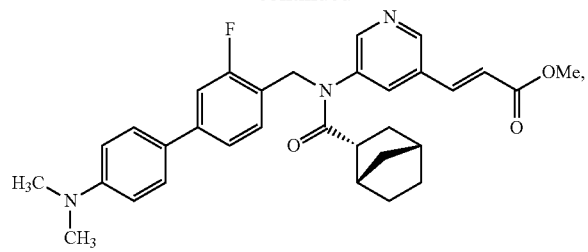
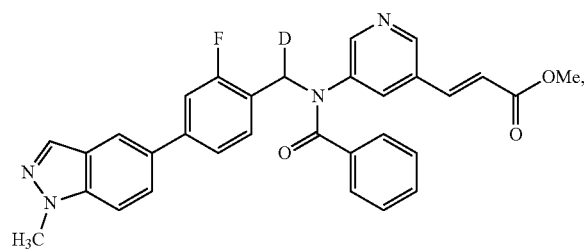
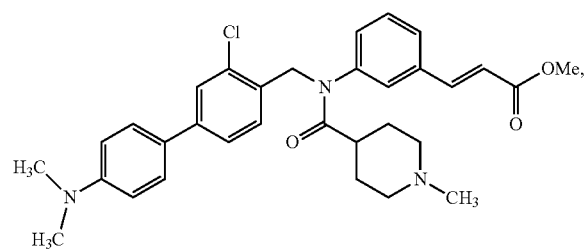
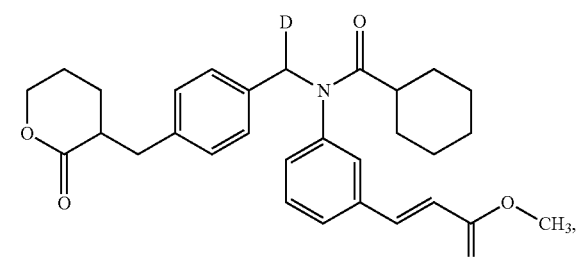
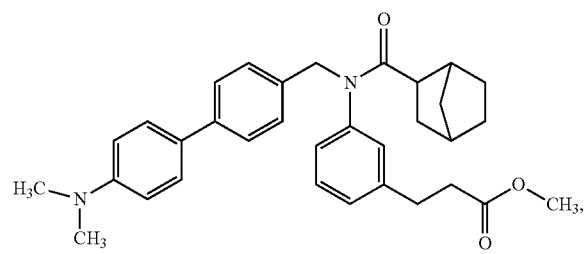
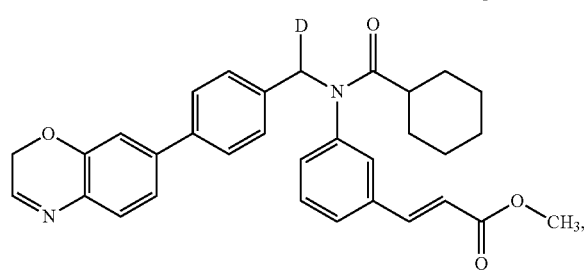
182
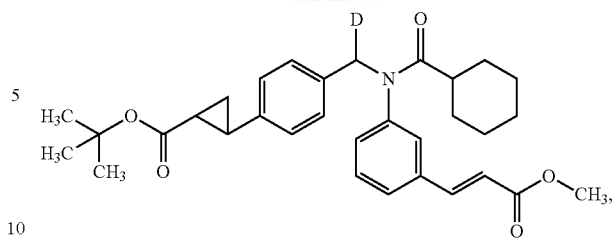
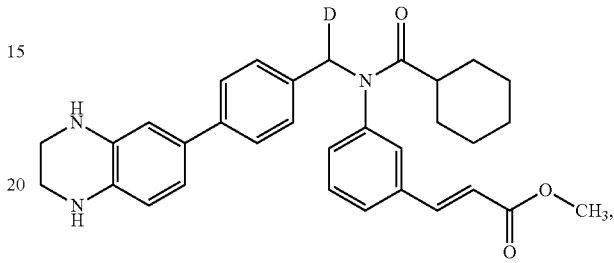
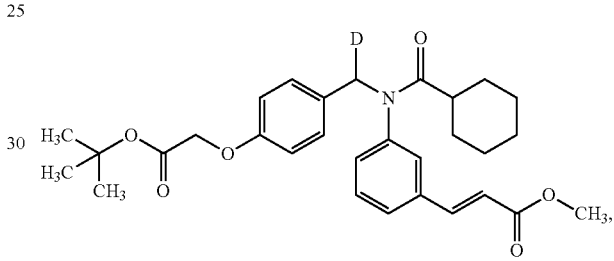
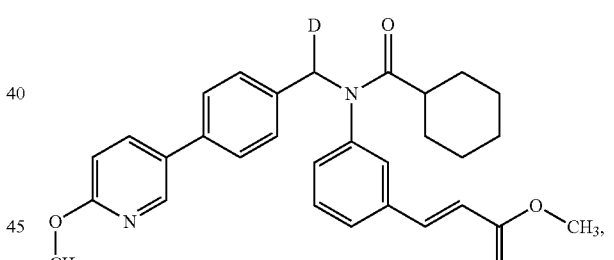
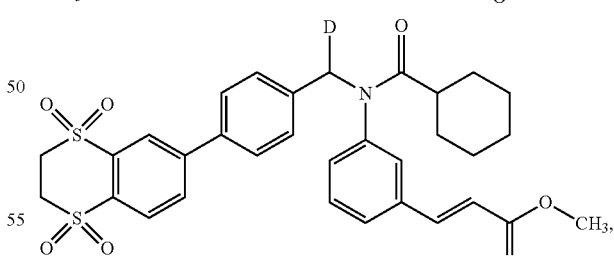
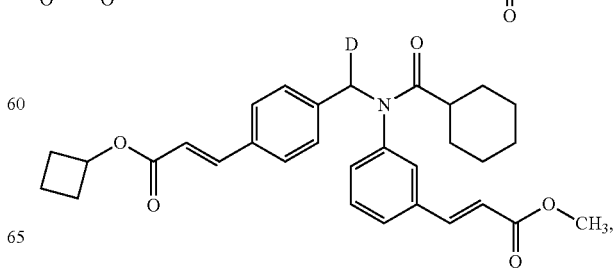

183
-continued
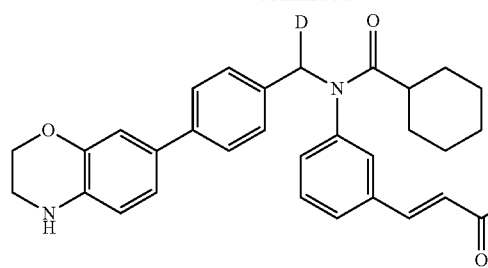
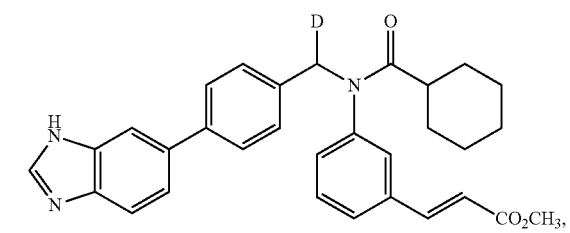
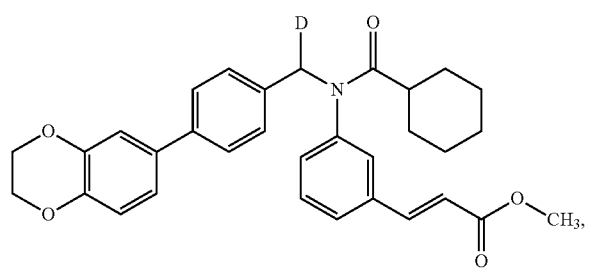
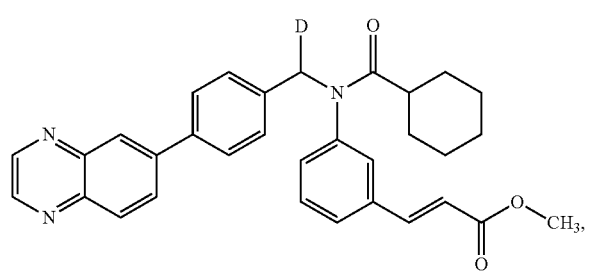
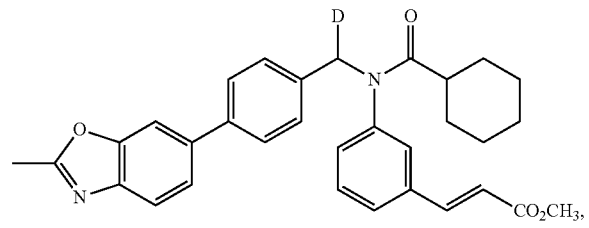
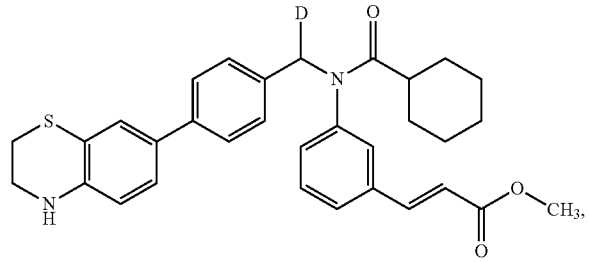
184
-continued
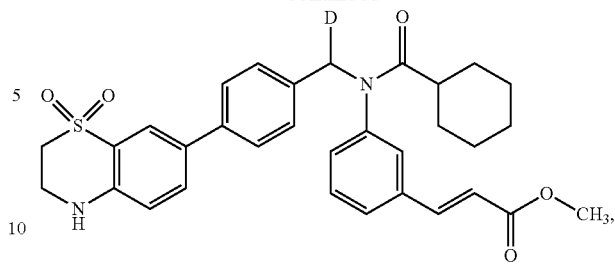
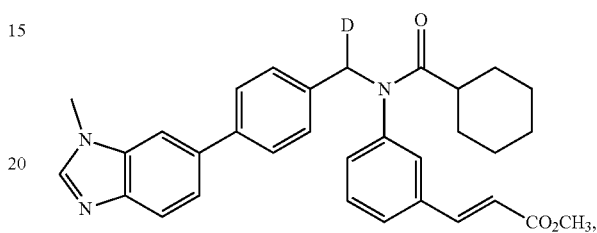
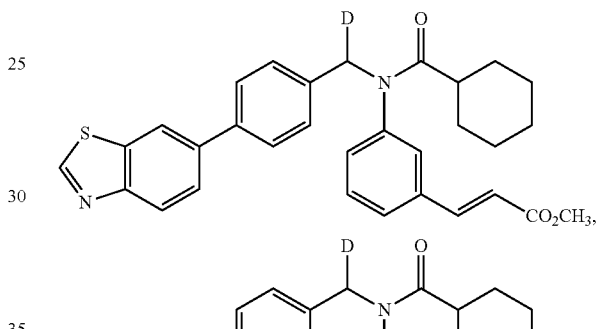
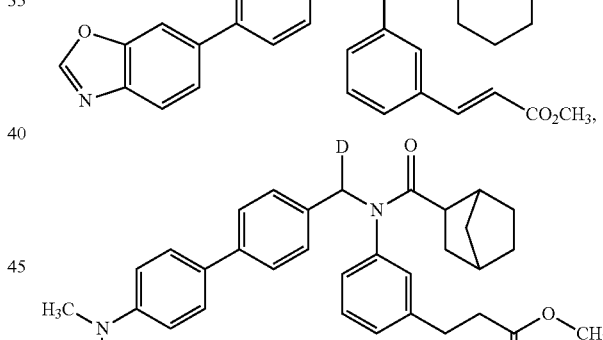
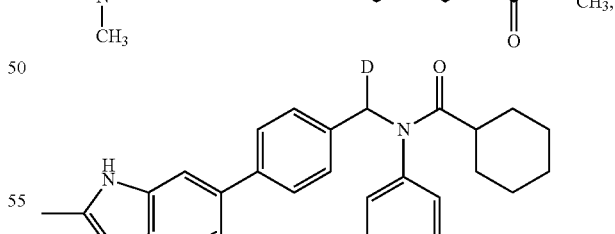
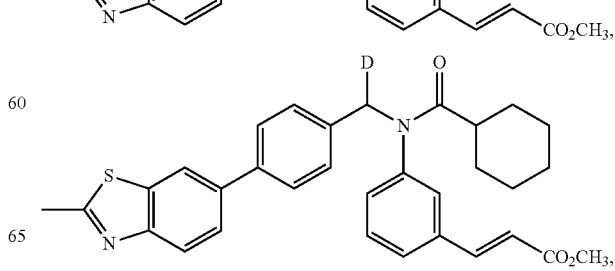

185
-continued
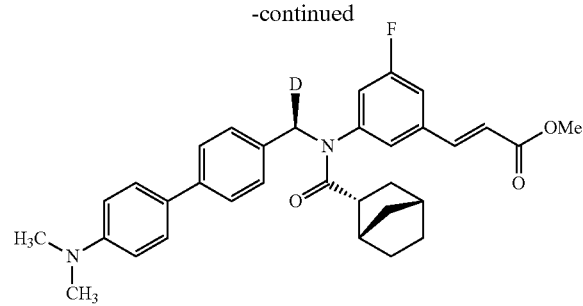
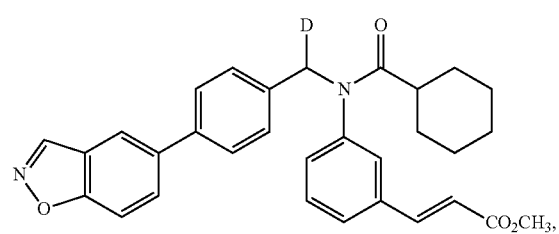
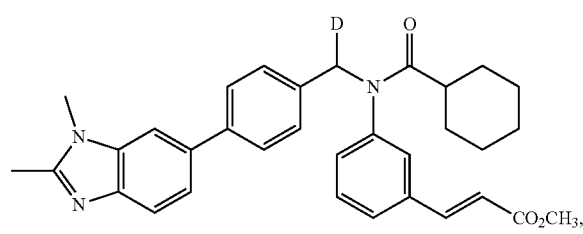
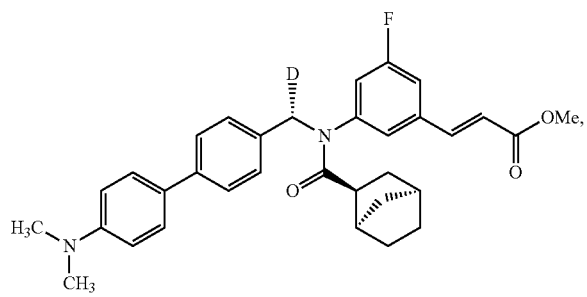
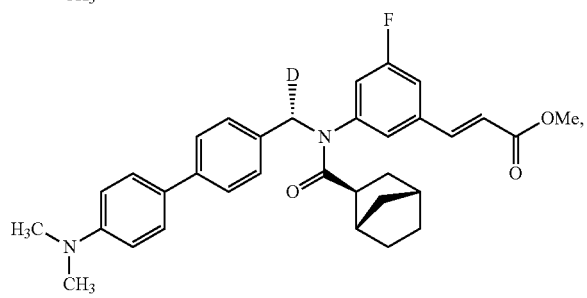
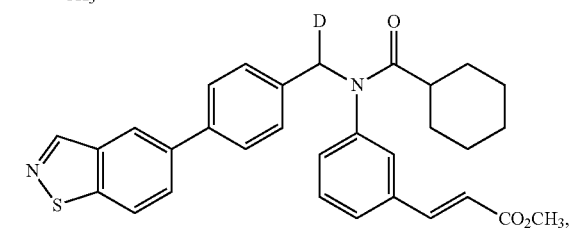
186
-continued
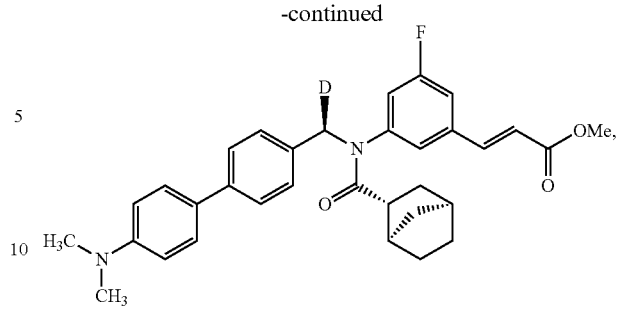
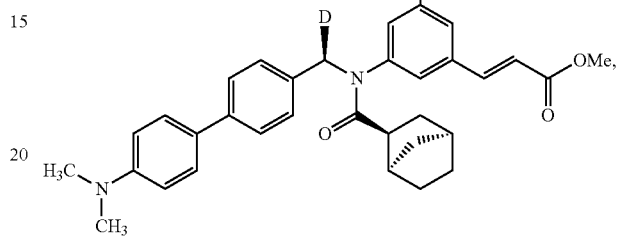
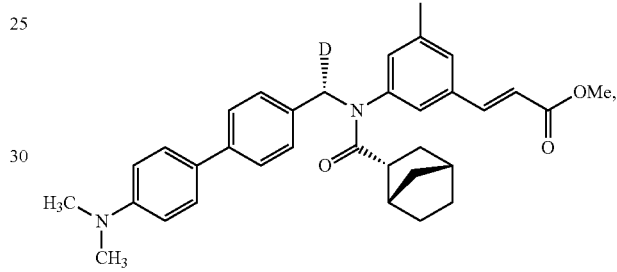
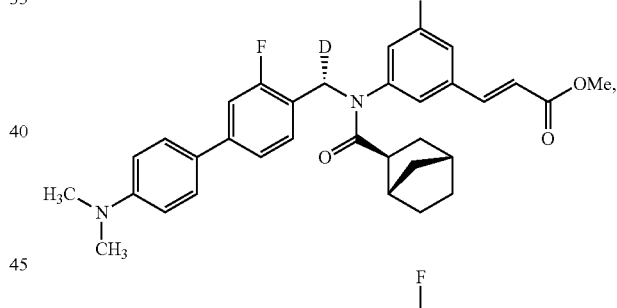
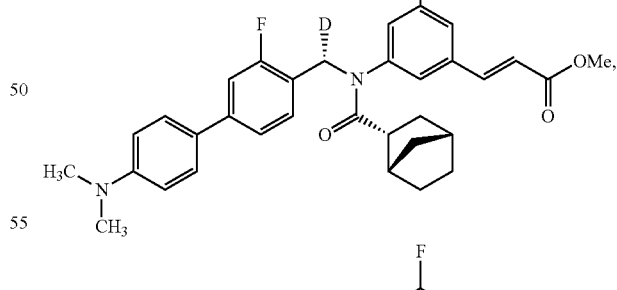
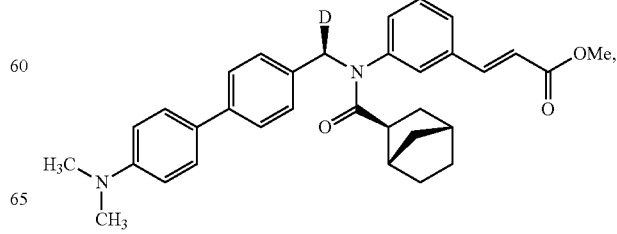

187
-continued
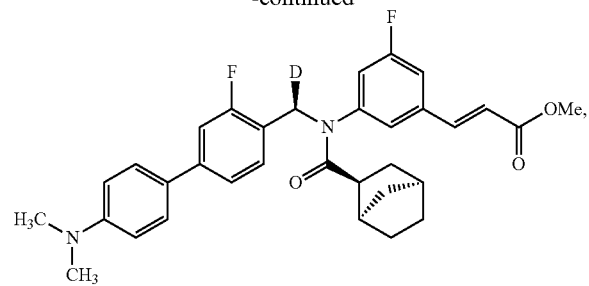
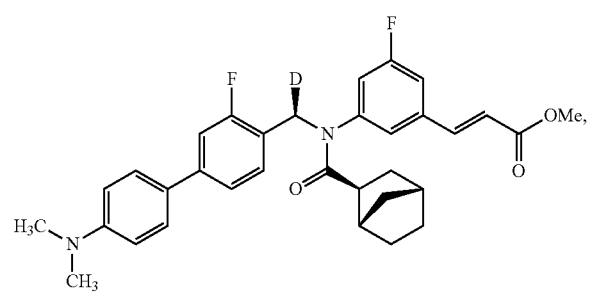
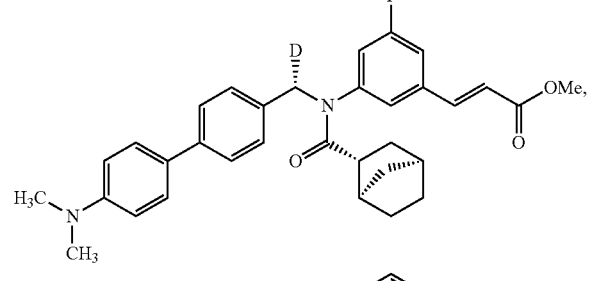
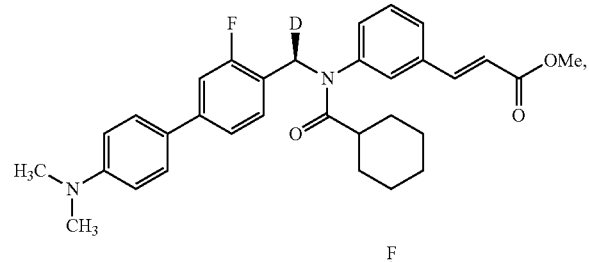
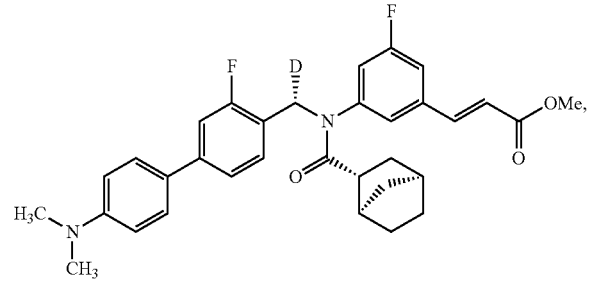
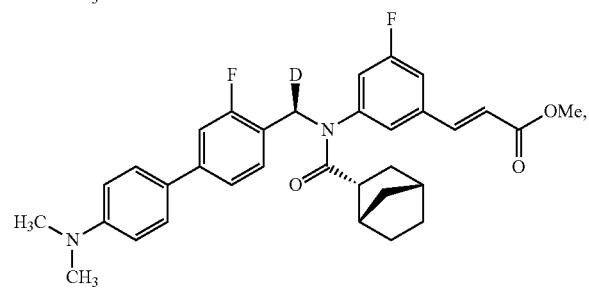
188
-continued
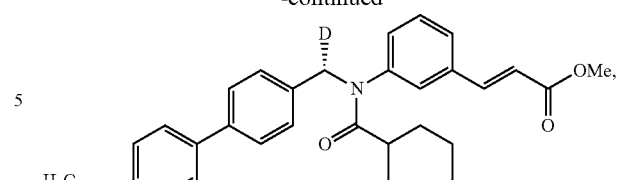
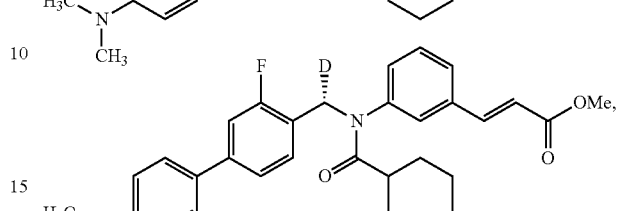
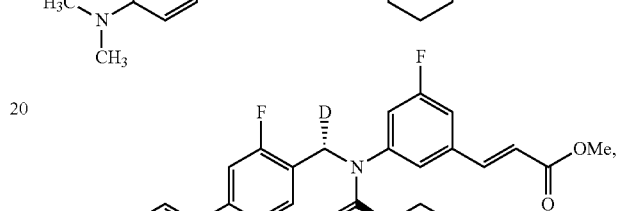
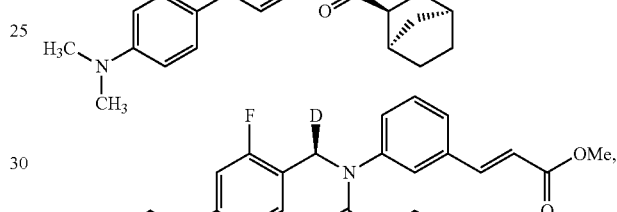
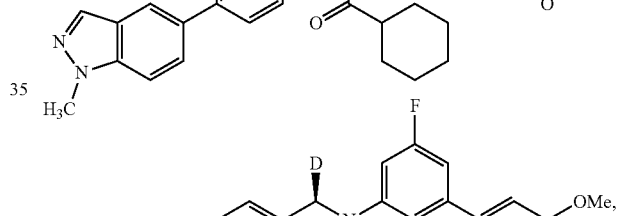
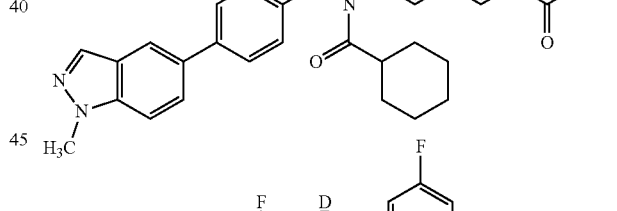
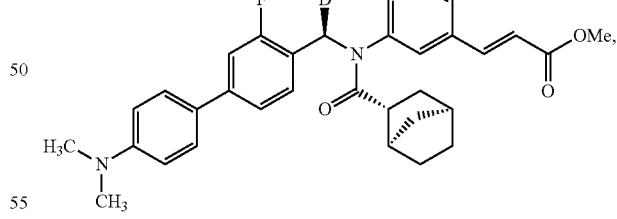
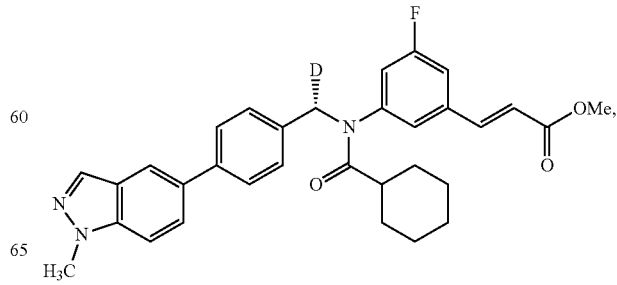

-continued
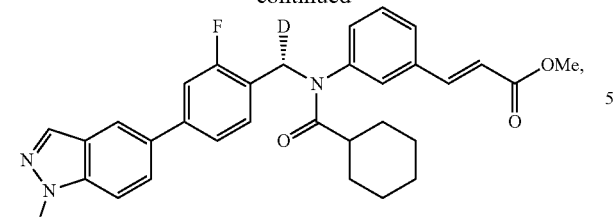
or
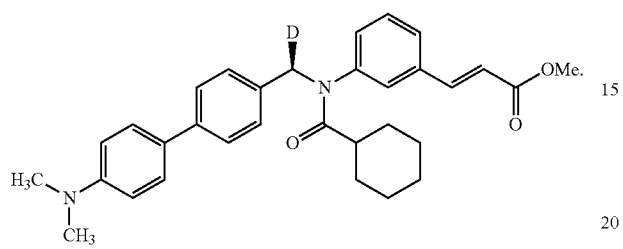
* * * * *

SEQUENCE LISTING

<160> NUMBER OF SEQ ID NOS: 2

<210> SEQ ID NO 1
<211> LENGTH: 30
<212> TYPE: PRT
<213> ORGANISM: Homo sapiens

<400> SEQUENCE: 1

```
His Ala Glu Gly Thr Phe Thr Ser Asp Val Ser Ser Tyr Leu Glu Gly
1               5                   10                  15

Gln Ala Ala Lys Glu Phe Ile Ala Trp Leu Val Lys Gly Arg
            20              25                  30

<210> SEQ ID NO 2
<211> LENGTH: 33
<212> TYPE: PRT
<213> ORGANISM: Homo sapiens

<400> SEQUENCE: 2

His Ala Asp Gly Ser Phe Ser Asp Glu Met Asn Thr Ile Leu Asp Asn
1               5                   10                  15

Leu Ala Ala Arg Asp Phe Ile Asn Trp Leu Ile Gln Thr Lys Ile Thr
            20              25                  30

Asp
```